US012161082B2

(12) United States Patent
Van Herwijnen et al.

(10) Patent No.: US 12,161,082 B2
(45) **Date of Patent: *Dec. 10, 2024**

(54) TOMATO PLANTS ALLOWING THE ESTABLISHMENT OF MITES

(71) Applicant: RIJK ZWAAN ZAADTEELT EN ZAADHANDEL B.V., De Lier (NL)

(72) Inventors: Zeger Otto Van Herwijnen, De Lier (NL); Dörthe Bettina Dräger, De Lier (NL); Karel Jozef Florent Bolckmans, De Lier (NL); Yvonne Maria Van Houten, De Lier (NL); Jasper De Joode, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/230,080

(22) Filed: Apr. 14, 2021

(65) Prior Publication Data

US 2021/0317164 A1 Oct. 14, 2021

Related U.S. Application Data

(63) Continuation of application No. 15/412,241, filed on Jan. 23, 2017, now Pat. No. 11,091,513, which is a continuation-in-part of application No. PCT/EP2015/068860, filed on Aug. 17, 2015.

(30) Foreign Application Priority Data

Aug. 18, 2014 (EP) .................................... 14181306

(51) Int. Cl.

| | |
|---|---|
| ***A01H 6/82*** | (2018.01) |
| ***A01H 5/08*** | (2018.01) |
| ***C07K 14/415*** | (2006.01) |
| *A01K 67/033* | (2006.01) |

(52) U.S. Cl.

CPC ............... *A01H 6/825* (2018.05); *A01H 5/08* (2013.01); *C07K 14/415* (2013.01); *A01K 67/033* (2013.01); *A01K 2227/70* (2013.01)

(58) Field of Classification Search

CPC ...................................................... A01H 6/825

See application file for complete search history.

(56) References Cited

U.S. PATENT DOCUMENTS

| | | | | |
|---|---|---|---|---|
| 11,091,513 | B2 * | 8/2021 | Van Herwijnen ........ | A01H 5/12 |
| 2014/0173771 | A1 | 6/2014 | Schuurink et al. | |
| 2015/0164014 | A1 | 6/2015 | Van Den Enden et al. | |

FOREIGN PATENT DOCUMENTS

| | | |
|---|---|---|
| EP | 2 700 301 | 2/2014 |
| WO | 2012/169893 | 12/2012 |

OTHER PUBLICATIONS

Yan et al (Role of Tomato Lipoxygenase D in Wound-Induced Jasmonate Biosynthesis and Plant Immunity to Insect Herbivores. PLOS Genetics. 1-16, 2013) (Year: 2013).*

Boter et al (Conserved MYC transcription factors play a key role in jasmonate signaling both in tomato and *Arabidopsis*. Genes & Development 18:1577-1591, 2004). (Year: 2004).*

Xu et al (SlMYC1 Regulates Type VI Glandular Trichome Formation and Terpene Biosynthesis in Tomato Glandular Cells. The Plant Cell, vol. 30: 2988-3005, Dec. 2018). (Year: 2018).*

Yan et al (Role of Tomato Lipoxygenase D in Wound-Induced Jasmonate Biosynthesis and Plant Immunity to Insect Herbivores. Plos Genomics. 7:1-16, 2013). (Year: 2013).*

Schmidt (Leaf structures affect predatory mites (*Acari: Phytoseiidae*) and biological control: a review. Exp Appl Acarol 62:1-17, published online Aug. 2013). (Year: 2013).*

Zhao et al (A Single Amino Acid Substitution in IIIf Subfamily of Basic Helix-Loop-Helix Transcription Factor AtMYC1 Leads to Trichome and Root Hair Patterning Defects by Abolishing Its Interaction with Partner Proteins in *Arabidopsis*. JBC. 287:14109-14121, 2012). (Year: 2012).*

Houten et al.(Herbivory-associated degradation of tomato trichomes and its impact on biological control of Aculops lycopersici. Exp Appl Acarol 60:127-138, 2013). (Year: 2013).*

Okabe et al (Tomato TILLING Technology: Development of a Reverse Genetics Tool for the Efficient Isolation of Mutants from Micro-Tom Mutant Libraries. Plant Cell Physiol. 52(11): 1994-2005, 2011). (Year: 2011).*

Spyropoulou et al (RNA sequencing on Solanum lycopersicum trichomes identifies transcription factors that activate terpene synthase promoters. BMC Genomics. 15:1-16, May 2014). (Year: 2014).*

Spyropoulou et al., RNA sequencing on Solanum lycopersicum trichomes identifies transcription factors that activate terpene synthase promoters, BMC Genomics (May 2014) 15(1):402.

Zhao, et al., A Single Amino Acid Substitution in IIIf Subfamily of Basic Helix-Loop-Helix Transcription Factor AtMYC1 Leads to Trichome and Root Hair Patterning Defects by Abolishing Its Interaction With Partner Proteins in Arabidopsis The Journal of Biological Chemistry (Apr. 2012) 287(17):14109-14121.

International Search Report and Written Opinion of the International Searching Authority dated Dec. 9, 2015, which issued during prosecution of International Application No. PCT/EP2015/068860.

GenBank: KF428776.1 (2013).

(Continued)

*Primary Examiner* — Charles Logsdon
*Assistant Examiner* — Wayne Zhong
(74) *Attorney, Agent, or Firm* — Duane Morris LLP; Thomas J. Kowalski

(57) ABSTRACT

The present invention relates to a modified Slmyc2 gene, which may comprise at least one modification as compared to the wild type sequence of SEQ ID No. 5, which modification leads to the reduction or absence of SlMYC2 protein activity, wherein the modified Slmyc2 gene is capable of conferring an aberrant glandular hair phenotype to a *Solanum lycopersicum* plant. The modification may be suitably selected from a modification that decreases the mRNA level of the Slmyc2 gene, a modification that decreases the level of the SlMYC2 protein and/or a modification that decreases the activity of the SlMYC2 protein, as compared to the wild type Slmyc2 gene of SEQ ID No. 5.

18 Claims, 22 Drawing Sheets

Specification includes a Sequence Listing.

(56) References Cited

OTHER PUBLICATIONS

Gupta, et al. BMC Plant Biology 2014, 14:38 (2014).
Hong, et al., The Plant Cell, vol. 24: 2635-2648 (Jun. 2012).
NCBI Reference Sequence: NM_001301178.2 (2014).
Dicke, Netherlands Journal of Zoology 38(2-4) 148-165 (1988).
Okabe, et al., Plant Cell Physiol. 52(11 ): 1994-2005 (2011).
Boter, et al., Conserved MYC transcription factors play a key role in jasmonate signaling both in tomato and *Arabidopsis*. Gen Es & DEVELOPMENT 18:1577-1591 (2004).
Xu, et al., S1MYC1 Regulates Type VI Glandular Trichome Formation and Terpene Biosynthesis in Tomato Glandular Cells. The Plant Cell, vol. 30: 2988-3005 (Dec. 2018).
Houten, et al., Herbivory-associated degradation of tomato trichomes and its impact on biological control of Aculops lycopersici. Exp Appl Acarol 60:127-138 (2013).
Liuhua Yan, et al., Role of Tomato Lipoxygenase D in Wound-Induced Jasmonate Biosynthesis and Plant Immunity to Insect Herbivores, PLOS Genetics (Dec. 2013) vol. 9, Issue 12, e1003964.
Bing Hua, et al., Mediation of JA signalling in glandular trichomes by the woolly/SIMYC1 regulatory module improves best resistance in tomato, Plant Biotechnology Journal (2021) 19: pp. 375-393.

* cited by examiner

FIG. 1A

SEQ ID No. 1:

>SlMYC2_genomic_SNP
attcaataattaattgtaattgtctggcattgttatggtggttcacatgtcaagttgctttatattatttgttattaaaataaaaatagaaaaatcaatgttat
tttcacgttcagcatccaccaaaacgtgctattaataatttaatgtctaaaacatatctacaaattatattatattagtataatatactttatgatatcttgaac
aaagacaattacaagtaggaccaatcaaaatgattccacaacgtgacgccaacgcgtacaaataaggattttcctttattataactttataataattaact
caccgtaattaatttgtatgattataatgaaatgactgaaactttttcgctcttaacaagaaatctcgatcgaactttagccatgaaataaaaataattgtgt
tgagagtagaatttccaaaaatagattttatagtgtgtaaaattatatttattaattttaatatgattatcaaaataccgaatcgaagaaagtaagtaaatt
ttaaggaatgtaatatgtatgtggtctcacccttacatgcattgaatatgtaaagagtgttttcgaaggacaaggatttttttgtttttactattaatgtatttt
aaaaacttaagacaaaattatttactcaaaatttacatgcgatattgtactaaaacgatttacaattattgtaggtaccttaattactctgatagtgcatggc
ctttaattacaagggataccaataacaaaaaagtccatatttgtgatgaatatgtcttatcacaaaaattgagaggaatattatgatagatttaatgaaaa
attttaatatggacaaaagaatattatgatagatttaaagaaaaaatttaatatggacaaaatttgtgatggactaataaatttactttttcattacgaatt
tttggagcctcacgttgaagatccaatgacttgttttcaaattagtttcaaagaatggctgagaatagtctttctaaaaaagcatcttcaatcgatggcttg
aatttaattattaaaagaattattatatttgataatgtattgattagatgcacgttatgaatttaaaatttcattttagacatgaacctaatatttaaatagac
accaacacaagtatatgacgcgaacaagtgatatttaagttatgagttcaaaatttatgaatcattagtcataactaaaaatgtgatactttaggggataa
ggatagaagagcaaatttaaattttacgtgaacctttttttatttaaatagaaaataatagagcgataaattcattatttatcgagtttcaaatcattaaaaat
acaatatataatatacgaattagatgtatatacacatttgaattcaatggtggactatataatttgatatttaagtaagcaaaagtagataaggagttcaa
gtttaaatttgtaaacatagaatttcctattttagagtttaaggtaaatttatgtatattttatcgtttggaatctcatttacgatgctacgctaaatattaga
aattgctaaaaataattgttgttattgtaatataatatcaaaatcaacatgatttcatttatttctttccatatatgaattatttccataaagcctacatgtag
gagatatgctaatttaatatttcctggaaatagttaacttagttgaaacattgaagtattagatattttattaatataagcactttaacaaatatggttataa
aaaaaaatcttcttcttttcaattcctttaacattcattgaaaatcttcttatttaacaatatttttccaattagttcaataactcgtcttcaatcatcgaagatat
ttaatgttactttttttgaagtaatgaaatttacttctaataatcttgtctttttttaaattggaaatgggaatagaaaatgataagacgaaattaaatcctc
acctacaagataaaagtttagataagttttgatagttaattaaatgaatttcaaattttttaatacttaaatacttctcattaataattgtaaagatatctactt
ttttcattcacttttacttcaaaaataaatcaaattatgtcacactttcactgtaataaattatatatatataataaaaaaaaagaaaaatcttctacctatat
aagtacgactctctaatggtgttaagtaaaaagaaaaatttagtataaagtcctaggtagttaaaaagtaaaaagtagaactaatgccggctttccttat
cctacgtataatttcccataaatcgcccaccttaatttttttttctgatttttcatttggcatcgaagcttatattagaatttaaacttacgttaaaatttttat
aatggcactaaatttttactaacataaataattatcccatcctaataaaaatttaaataaaaatatttgattaaaatacttaccgtttttctcggaaccct
cttctctttgtccactcactttcctcactcatttattttgagctcacaatatttttattatatatatatatatatccacaaaaatctctactctcatttctcacctaa
caaacaaaatctctcatttctgtttttgtaaaattcttcaatttaattgaatgacggactatagattatggagtaataccaatactactaatacatgtgatg
atactatgatgatggattctttttatcttccgatccatcctctttttggcctgcttccactcccaatcgtccgactccggtgaacggagtcggagaaacgat
gccgtttttcaatcaagagtcactacagcaaaggcttcaggctttaattgacggtgctcgtgaatcatgggcatatgctattttctggcaatcgtcagttgt
tgattttgcgagccaaactgtattgggttggggagatgggtattataaaggagaagaagataagaataaacggagagggtcgtctagttcagcagct
aattttgttgctgagcaagagcatagaaagaaggtgcttcgggagctgaattcattaatatccggtgtacaagcttccgccggaaacggaactgatgat
gcagtggatgaggaagtgacggatactgaatggtttttctgatttcaatgacccaatcgttgttaacggtaacgggcttccgggcttggcgatgtaca
gttcaagcccaatttgggttactggaacagagaaattagctgcttctcaatgtgaacgggccaggcaagcccaaggtttcgggcttcagacgattgtgt
gtattccttcagctaacggtgtagtggagcttggttcgactgagctgatattccaaagctcggatttgatgaacaaggttaagtatttgtttaacttcaata
ttgatatggggtctgttacaggctcaggttcgggctcaggctcttgtgctgtgcatcctgagcccgatccttcggccctttggcttacggatccatcttcctc
ggttgtggaacctaaggattcgttaattcatagtagtagtagggatgttcaacttgtgtatggaaatgagaattctgaaaatcagcagcagcattgtcaa
ggatttttcacaaaggagttgaatttttcgggttatggatttgatggaagtagtaataggaataaaactggaatttcttgtaagccggagtccagggaga
tattgaattttggtgatagtagtaagagattttcagggcaatcacagttgggtcctgggcctgggctcatggaggagaacaagaacaagaacaagaac
aagaaaaggtcacttggatcaaggggaaacaatgaagaaggaatgctttcgtttgtttcgggtgtgatcttgccaacttcaacaatggggaagtccgg
ggattctgatcactcagatctcgaagcctcagtggtgaaggaggccgttgtagaacctgaaaagaagccgaggaagcgagggaggaaaccagccaa
tggaagggaggagccattgaatcacgtggaagcggagagacagaggaggagaaattgaatcaaagattctacgcgctcagagccgtagtcccaa
atgtgtctaaaatggataaggcatcacttcttagagatgcaattgcatacatcaatgagttgaaatcaaaagttcaaaattcagatttagataaagagga
gttgaggagccaaattgaatgtttaaggaaggaattaaccaacaagggatcatcaaactattccgcctcccctccattgaatcaagatgtcaagattgtc
gatatggacattgacgttaaggtgattggatgggatgctatgattcgtatacaatgtagtaaaaagaaccatccagctgccaggctaatggcagccctc
aaggacttggacctagacgtgcaccacgctagtgtttccgtggtgaatgatttgatgatccaacaagccacagtcaaaatggggagccggctttatgct
caagaacagcttaggatagcattgacatcaaaaattgctgaatcgcgatgaaattatgtccctagtgagctatgtataatgttatcttctaatgagcgag
aattttcttctctgtatataaatgtgatgaaaccaatactagagatctcgagttgaggctttttagttcatgtaagattagatatatatatatgatgcagcttc
atccttttgtattcttcatccaggaaataaatgagaaaccaataattggtggctgatgatcaacttcatgttattactaattctcgttccctcttctttgggat
acaacacttgtcattttacattaggcaaattagaagaaaatactaagcatttttaattgaacgtaacatgtcatgtgtgaactagagtcacaagttcaatt
catgtaacaaacaatcacctttgcattttagtggagaaggatgcattgagtttcaacttgtacactaactagtcataagagattactttgttataaaaaaa
aaacaattttgaccttgttgtgtatataatatatgattcgagtttggacgaaagtttttatttaattatgatggatatattagttatggagtacacaattgcc tttactataaaacttattacttttaataataaatattttttaatgtaaatatataaatataatcaaaacttaatataaatggatgtattactaatcagttgctt
gttttagtctagaagaaagcaccaaacaaaggggtagggctgcattttcatttatagagaattcattgaatttggtcaaatcatagctgtattcattggac
taggaaatatttaaaaagtatatatattattgtttataataatataatgtcatgagtatcatttgagtttgaagtgacacaagccctttaaatgcagttgattt
aggcacaaactttgttattattcccgccgtccaaatagttgttacatttggcttcctaaaaattaatttaactaatttttaaatttaattttatattttgaaaaat
taaagtttataaatacaaaaattattttaatttcttacatataattaaaaaatatatataaaatttatataatttagcgctggaaaattattttgaaaacagag
gaagtattattattattttggtcttatgaattgtgtgataaacagtttatatctgttaatcaaatagacagagattgatagatgtgacaaagattcgtttttttg
tttgaggttttataaaaggaaaattgtataaaatagcaaactaataacttaaattaaatggaatagctagggtttgatttaattgtgctccatagcaaacg
ttggcaaaaatttaccagaagtctcgctcgccactctcccattctcgcctctctcgctttatacatagaagtgtataatttatgtttctgttttgtataaagcg
agagaaaattgtatatacacatgcaaaaatgtatatctttgtgttatacacttaattatataatttacaaacattttacttcaaatattgcagcgaaaaaggc
caaagaattatacaatcgtgaattatataattgcagtgaaatacaatttttctagctttatacaacagaagtgtatatattgtatttctgtttttgtataaag
cgagaaaaacatatatcttcttgctatacacttataattatgcaatatacatacattttaattcgattaaactgtatacaaaactaattatacaattgcagcg
aaatggcgaattatacaatttaggccagcgaattatacacttttatatgtatagcgaattatacagtttttatatttgctatggagcgcatatattatacaaa
tatgatttttttgtttgctatatgtgaaagttgccctttttataaaagcttttatgtatagtttgatttgtttttttaaaaaataaaatatgacaactttagtatcaa
aatagattaaatttatatacaataaatagttatattttacagccagccatttatctttctttttttttcaagccacaaaatcaccttgtagaaagttattttgttcg
atattttattgctaatatataaaaatattattataaaaagcatgtaatatatatataaaaaatttgatttcaaagaatactttgatcattataatgatatgttaat
ataaataataattattatagattaatctgatcgtatattttcagtatacattaatatatacatctaaaatatgactgtattaaatatgaacaaaatcatttacat
caccctatatataatattttaattaaaaagatgtataaagaagaataaaaaacgctgaagtttaaagcgaatgttattgaccagatcaaattgacttgaaga
ccaaaattgaattgttgaatacaattaattaatttaaaaatgaccatgttttacatgtgaaattcatttatatatatatatatatatcatatattattatagtatt
cacattttgttgtttacactgatggttccgttaagtgttcacatttctttgtttaacactaaactttggagggaaggatgtgaaaataaaaaatttgggtaga
aaattaatcgataatttaatattgtctaatttatcttatgtatattatgatcattactcccttattatctttgtatttttttaatcttgattatcatattatttagtatt
tttttatccttaattttgatatgttttacttgagtcaaaaatctatagaaaataatttttctatttttacaagataagggtaaagatgtgcgaacacaacttttttt
gaagccccacttatgaaattacactgaacatattgttgtagtaactgtacgaactctttttttctttctatataaacaaatgtataactaaagtatttagtaaaa
taaaaatataattctatttagttcatgaatgagaccacaatatgaatgtatagagctggggatatttttttgtttttgtgtagatggatattaatcgaagatgt
attggttcttaatagtaagaataacaatagccattaccctaaagattgattcacctttattttagggtataaaccaaaaaagaatggacattattaacacga
gacctttagcatttccaaaaaaaaatgggagaattttgttatttatttaaaaagaaaaaaaaaaagaacacacccttaacctcaatatcctcaaaaattcaa
ccatcaatatcattattttattttcatatcctatgcatttttttattagcttgtaaacttttaattttcttcctattcttttatacaacaatgactctcaattgtttaacc
tgccaagctctaaaaagaacagattcacatgaggaactaagggaaacactgaatcatgttaatgataagtcgaattttcgtctttttttcagtgggaatgg
agaggaactggtcagggaacttggttgaaagacggaaatatgaaaaaacgaggggtcgaaccataatgggaaaagaaaataat

SEQ ID No. 2:

>SlMYC2_CDS_SNP
atgacggactatagattatggagtaataccaatactactaatacatgtgatgatactatgatgatggattctttttttatcttccgatccatcctctttttggcc
tgcttccactcccaatcgtccgactccggtgaacggagtcggagaaacgatgccgtttttcaatcaagagtcactacagcaaaggcttcaggctttaatt
gacggtgctcgtgaatcatgggcatatgctattttctggcaatcgtcagttgttgattttgcgagccaaactgtattgggttggggagatgggtattataa
aggagaagaagataagaataaacggagagggtcgtctagttcagcagctaattttgttgctgagcaagagcatagaaagaaggtgcttcgggagctg
aattcattaatatccggtgtacaagcttccgccggaaacggaactgatgatgcagtggatgaggaagtgacggatactgaatggtttttttctgatttcaa
tgacccaatcgtttgttaacggtaacgggcttccgggcttggcgatgtacagttcaagcccaatttgggttactggaacagagaaattagctgcttctca
atgtgaacgggccaggcaagcccaaggtttcgggcttcagacgattgtgtgtattccttcagctaacggtgtagtggagcttggttcgactgagctgat
attccaaagctcggatttgatgaacaaggttaagtatttgtttaacttcaatattgatatggggtctgttacaggctcaggttcgggctcaggctcttgtgc
tgtgcatcctgagcccgatccttcggccctttggcttacggatccatcttcctcggttgtggaacctaaggattcgttaattcatagtagtagtagggatgt
tcaacttgtgtatggaaatgagaattctgaaaatcagcagcagcattgtcaaggatttttcacaaaggagttgaatttttcgggttatggatttgatggaa
gtagtaataggaataaaactggaatttcttgtaagccggagtccagggagatattgaattttggtgatagtagtaagagattttcagggcaatcacagtt
gggtcctgggcctgggctcatggaggagaacaagaacaagaacaagaacaagaaaaggtcacttggatcaaggggaaacaatgaagaaggaatg
ctttcgtttgtttcgggtgtgatcttgccaacttcaacaatggggaagtccggggattctgatcactcagatctcgaagcctcagtggtgaaggaggccg
ttgtagaacctgaaaagaagccgaggaagcgagggaggaaaccagccaatggaagggaggagccattgaatcacgtggaagcggagagacaga
ggagggagaaattgaatcaaagattctacgcgctcagagccgtagtcccaaatgtgtctaaaatggataaggcatcactttcttagagatgcaattgcat
acatcaatgagttgaaatcaaaagttcaaaattcagatttagataaagaggagttgaggagccaaattgaatgtttaaggaaggaattaaccaacaag
ggatcatcaaactattccgcctcccctccattgaatcaagatgtcaagattgtcgatatggacattgacgttaaggtgattggatgggatgctatgattcg
tatacaatgtagtaaaaagaaccatccagctgccaggctaatggcagccctcaaggacttggacctagacgtgcaccacgctagtgtttccgtggtgaa
tgatttgatgatccaacaagccacagtcaaaatggggagccggctttatgctcaagaacagcttaggatagcattgacatcaaaaattgctgaatcgcg
atga

FIG. 1B

SEQ ID No. 3:

>SlMYC2_AA_STOP
MTDYRLWSNTNTTNTCDDTMMMDSFLSSDPSSFWPASTPNRPTPVNGVGETMPFFNQESLQQRLQALIDGARE
SWAYAIFWQSSVVDFASQTVLGWGDGYYKGEEDKNKRRGSSSSAANFVAEQEHRKKVLRELNSLISGVQASAGN
GTDDAVDEEVTDTEWFFLISMTQSFVNGNGLPGLAMYSSSPIWVTGTEKLAASQCERARQAQGFGLQTIVCIPSA
NGVVELGSTELIFQSSDLMNKVKYLFNFNIDMGSVTGSGSGSGSCAVHPEPDPSALWLTDPSSSVVEPKDSLIHSS
SRDVQLVYGNENSENQQQHCQGFFTKELNFSGYGFDGSSNRNKTGISCKPESREILNFGDSSKRFSGQSQLGPGP
GLMEENKNKNKNKKRSLGSRGNNEEGMLSFVSGVILPTSTMGKSGDSDHSDLEASVVKEAVVEPEKKPRKRGRKP
ANGREEPLNHVEAERQRREKLNQRFYALRAVVPNVSKMDKASLL*DAIAYINELKSKVQNSDLDKEELRSQIECLR
KELTNKGSSNYSASPPLNQDVKIVDMDIDVKVIGWDAMIRIQCSKKNHPAARLMAALKDLDLDVHHASVSVVNDL
MIQQATVKMGSRLYAQEQLRIALTSKIAESR

SEQ ID No. 4:

>SL06992
ggaagcggagagacagaggagggagaaattgaatcaaagattctacgcgctcagagccgtagtcccaaatgtgtctaaaatggataa
ggcatcacttctttgagatgcaattgcatacatcaatgagttgaaatcaaaagttcaaaattcagatttagataaagaggagttgaggag
ccaaattgaatgtttaaggaagga

FIG. 1C

SEQ ID No. 5:

>SlMYC2_genomic_WT
attcaataattaattgtaattgtctggcattgttatggtggttcacatgtcaagttgcttttatattatttgttattaaaataaaaatagaaaaatcaatgttat
tttcacgttcagcatccaccaaaacgtgctattaataatttaatgtctaaaacatatctacaaattatattatattagtataatatactttatgatatcttgaac
aaagacaattacaagtaggaccaatcaaaatgattccacaacgtgacgccaacgcgtacaaataaggattttcctttattataactttataataattaact
caccgtaattaatttgtatgattataatgaaatgactgaaactttttcgctcttaacaagaaatctcgatcgaactttagccatgaaataaaaataattgtgt
tgagagtagaatttccaaaaatagattttatagtgtgtaaaattatatttattaatttttaatatgattatcaaaataccgaatcgaagaaagtaagtaaatt
ttaaggaatgtaatatgtatgtggtctcacccttacatgcattgaatatgtaaagagtgttttcgaaggacaaggatttttttgtttttactattaatgtatttt
aaaaacttaagacaaaattatttactcaaaatttacatgcgatattgtactaaaacgatttacaattattgtaggtaccttaattactctgatagtgcatggc
ctttaattacaagggataccaataacaaaaaagtccatatttgtgatgaatatgtcttatcacaaaaattgagaggaatattatgatagatttaatgaaaa
attttaatatggacaaaagaatattatgatagatttaaagaaaaaatttaatatggacaaaattgtgatggactaataaatttactttttcattacgaatt
tttggagcctcacgttgaagatccaatgacttgttttcaaattagtttcaaagaatggctgagaatagtctttctaaaaaagcatcttcaatcgatggcttg
aatttaattattaaaagaattattatatttgataatgtattgattagatgcacgttatgaatttaaaatttcattttagacatgaacctaatatttaaatagac
accaacacaagtatatgacgcgaacaagtgatatttaagttatgagttcaaaatttatgaatcattagtcataactaaaaatgtgatactttaggggataa
ggatagaagagcaaatttaaattttacgtgaacctttttatttaaatagaaaataatagagcgataaattcattatttatcgagtttcaaatcattaaaaat
acaatatataatatacgaattagatgtatatacacatttgaattcaatggtggactatataatttgatatttaagtaagcaaaagtagataaggagttcaa
gtttaaatttgtaaacatagaatttcctatttagagtttaaggtaaatttatgtatattttatcgtttggaatctcattttacgatgctacgctaaatattaga
aattgctaaaaataattgttgttattgtaatataatatcaaaatcaacatgatttcatttatttctttccatatatgaattatttccataaagcctacatgtag
gagatatgctaatttaatatttcctggaaatagttaacttagttgaaacattgaagtattagatattttattaatataagcactttaacaaatatggttataa
aaaaaaatcttcttcttttcaattcctttaacattcattgaaaatcttcttatttaacaatatttttccaattagttcaataactcgtcttcaatcatcgaagatat
ttaatgttactttttttgaagtaatgaaatttacttctaataatcttgtctttttttaaattggaaatgggaatagaaaatgataagacgaaattaaatcctc
acctacaagataaaagtttagataagttttgatagttaattaaatgaatttcaaatttttaatacttaaatacttctcattaataattgtaaagatatctactt
ttttcattcactttttacttcaaaaataaatcaaattatgtcacactttcactgtaataaattatatatatataataaaaaaaaagaaaaatcttctacctatat
aagtacgactctctaatggtgttaagtaaaaagaaaaatttagtataaagtcctaggtagttaaaaagtaaaaagtagaactaatgccggctttccttat
cctacgtataattttcccataaatcgcccaccttaattttttttttctgatttttcatttggcatcgaagcttatattagaatttaaacttacgttaaaatttttat
aatggcactaaaatttttactaacataaataattatcccatcctaataaaaatttaaataaaaaatatttgattaaaaatacttaccgtttttctcggaaccct
cttctctttgtccactcactttcctcactcatttatttttgagctcacaatatttttattatatatatatatatatccacaaaaatctctactctcatttctcaccta
caaacaaaatctctcatttctgtttttttgtaaaattcttcaatttaattgaatgacggactatagattatggagtaataccaatactactaatacatgtgatg
atactatgatgatggattctttttatcttccgatccatcctctttttggcctgcttccactcccaatcgtccgactccggtgaacggagtcggagaaacgat
gccgtttttcaatcaagagtcactacagcaaaggcttcaggctttaattgacggtgctcgtgaatcatgggcatatgctattttctggcaatcgtcagttgt
tgattttgcgagccaaactgtattgggttggggagatgggtattataaaggagaagaagataagaataaacggagagggtcgtctagttcagcagct
aattttgttgctgagcaagagcatagaaagaaggtgcttcgggagctgaattcattaatatccggtgtacaagcttccgccggaaacggaactgatgat
gcagtggatgaggaagtgacggatactgaatggtttttctgatttcaatgacccaatcgtttgttaacggtaacgggcttccgggcttggcgatgtaca
gttcaagcccaatttgggttactggaacagagaaattagctgcttctcaatgtgaacgggccaggcaagcccaaggtttcgggcttcagacgattgtgt
gtattccttcagctaacggtgtagtggagcttggttcgactgagctgatattccaaagctcggatttgatgaacaaggttaagtatttgtttaacttcaata
ttgatatggggtctgttacaggctcaggttcgggctcaggctcttgtgctgtgcatcctgagcccgatccttcggccctttggcttacggatccatcttcctc
ggttgtggaacctaaggattcgttaattcatagtagtagtagggatgttcaacttgtgtatggaaatgagaattctgaaaatcagcagcagcattgtcaa
ggatttttcacaaaggagttgaatttttcgggttatggatttgatggaagtagtaataggaataaaactggaatttcttgtaagccggagtccagggaga
tattgaatttggtgatagtagtaagagattttcagggcaatcacagttgggtcctgggcctgggctcatggaggagaacaagaacaagaacaagaac
aagaaaaggtcacttggatcaaggggaaacaatgaagaaggaatgctttcgtttgtttcgggtgtgatcttgccaacttcaacaatggggaagtccgg
ggattctgatcactcagatctcgaagcctcagtggtgaaggaggccgttgtagaacctgaaaagaagccgaggaagcgagggaggaaaccagccaa
tggaagggaggagccattgaatcacgtggaagcggagagacagaggaggagaaattgaatcaaagattctacgcgctcagagccgtagtcccaa
atgtgtctaaaatggataaggcatcacttcttggagatgcaattgcatacatcaatgagttgaaatcaaaagttcaaaattcagatttagataaagagga
gttgaggagccaaattgaatgtttaaggaaggaattaaccaacaagggatcatcaaactattccgcctcccctccattgaatcaagatgtcaagattgtc
gatatggacattgacgttaaggtgattggatgggatgctatgattcgtatacaatgtagtaaaaagaaccatccagctgccaggctaatggcagccctc
aaggacttggacctagacgtgcaccacgctagtgtttccgtggtgaatgatttgatgatccaacaagccacagtcaaaatggggagccggctttatgct
caagaacagcttaggatagcattgacatcaaaaattgctgaatcgcgatgaaattatgtccctagtgagctatgtataatgttatcttctaatgagcgag
aattttcttctctgtatataaatgtgatgaaaccaatactagagatctcgagttgaggctttttagttcatgtaagattagatatatatatatgatgcagcttc
atcctttgtattcttcatccaggaaataaatgagaaaccaataattggtggctgatgatcaacttcatgttattactaattctcgttccctcttcttttgggat
acaacacttgtcatttacattaggcaaattagaagaaaatactaagcatttttaattgaacgtaacatgtcatgtgtgaactagagtcacaagttcaatt
catgtaacaaacaatcacctttgcattttagtggagaaggatgcattgagtttcaacttgtacactaactagtcataagagattactttgttataaaaaaaa

FIG. 2A aaacaattttgaccttgttgtgtatataatatatgattcgagtttggacgaaagtttttatttaattatgatggatatattagttatggagtacacaattgcc
tttactataaaacttattacttttaataataaatattttttaatgtaaatatataaatataatcaaaacttaatataaatggatgtattactaatcagttgctt
gttttagtctagaagaaagcaccaaacaaaggggtagggctgcattttcatttatagagaattcattgaatttggtcaaatcatagctgtattcattggac
taggaaatatttaaaaagtatatatattattgtttataataatataatgtcatgagtatcatttgagtttgaagtgacacaagccctttaaatgcagttgattt
aggcacaaactttgttattattcccgccgtccaaatagttgttacatttggcttcctaaaaattaatttaactaatttttaaatttaattttatattttgaaaaat
taaagtttataaatacaaaaattattttaatttcttacatataattaaaaaatatatataaaatttatataatttagcgctggaaaattattttgaaaacagag
gaagtattattattattttggtcttatgaattgtgtgataaacagtttatatctgttaatcaaatagacagagattgatagatgtgacaaagattcgtttttg
tttgaggttttataaaaggaaaattgtataaaatagcaaactaataacttaaattaaatggaatagctagggtttgatttaattgtgctccatagcaaacg
ttggcaaaaatttaccagaagtctcgctcgccactctcccattctcgcctctctcgctttatacatagaagtgtataatttatgtttctgttttgtataaagcg
agagaaaattgtatatacacatgcaaaaatgtatatctttgtgttatacacttaattatataatttacaaacatttacttcaaatattgcagcgaaaaaggc
caaagaattatacaatcgtgaattatataattgcagtgaaatacaatttttctagctttatacaacagaagtgtatatattgtatttctgtttttgtataaag
cgagaaaaacatatatcttcttgctatacacttataattatgcaatatacatacattttaattcgattaaactgtatacaaaactaattatacaattgcagcg
aaatggcgaattatacaatttaggccagcgaattatacacttttatatgtatagcgaattatacagttttatatttgctatggagcgcatatattatacaaa
tatgatttttttgtttgctatatgtgaaagttgccctttataaaagcttttatgtatagtttgatttgtttttttaaaaaataaaatatgacaactttagtatcaa
aatagattaaatttatatacaataaatagttatattttacagccagccatttatctttctttttttcaagccacaaaatcaccttgtagaaagttattttgttcg
atattttattgctaatatataaaaatattattataaaaagcatgtaatatatatataaaaatttgatttcaaagaatactttgatcattataatgatatgttaat
ataaataataattattatagattaatctgatcgtatattttcagtatacattaatatatacatctaaaatatgactgtattaaatatgaacaaaatcatttacat
caccctatataatattttaattaaaaagatgtataaagaagaataaaaaacgctgaagtttaaagcgaatgttattgaccagatcaaattgacttgaaga
ccaaaattgaattgttgaatacaattaattaatttaaaaatgaccatgttttacatgtgaaattcatttatatatatatatatatcatatattattatagtatt
cacattttgttgtttacactgatggttccgttaagtgttcacatttctttgtttaacactaaactttggagggaaggatgtgaaaataaaaaatttgggtaga
aaattaatcgataatttaatattgtctaatttatcttatgtatattatgatcattactcccttattatctttgtattttttttaatcttgattatcatattatttagtatt
tttttatccttaattttgatatgttttacttgagtcaaaaatctatagaaaataatttttctatttttacaagataagggtaaagatgtgcgaacacaactttttt
gaagccccacttatgaaattacactgaacatattgttgtagtaactgtacgaactcttttttctttctatataaacaaatgtataactaaagtatttagtaaaa
taaaaatataattctatttagttcatgaatgagaccacaatatgaatgtatagagctggggatatttttttgtttttgtgtagatggatattaatcgaagatgt
attggttcttaatagtaagaataacaatagccattaccctaaagattgattcacctttattttagggtataaaccaaaaaagaatggacattattaacacga
gacctttagcatttccaaaaaaaaatgggagaattttgttatttatttaaaaagaaaaaaaaaaagaacacacccttaacctcaatatcctcaaaaattcaa
ccatcaatatcattattttattttcatatcctatgcatttttttattagcttgtaaacttttaattttcttcctattcttttatacaacaatgactctcaattgtttaacc
tgccaagctctaaaaagaacagattcacatgaggaactaagggaaacactgaatcatgttaatgataagtcgaattttcgtctttttttcagtgggaatgg
agaggaactggtcagggaacttggttgaaagacggaaatatgaaaaaacgaggggtcgaaccataatgggaaaagaaaataat

SEQ ID No. 6:

>SIMYC2_CDS_WT
atgacggactatagattatggagtaataccaatactactaatacatgtgatgatactatgatgatggattctttttttatcttccgatccatcctctttttggcc
tgcttccactcccaatcgtccgactccggtgaacggagtcggagaaacgatgccgtttttcaatcaagagtcactacagcaaaggcttcaggctttaatt
gacggtgctcgtgaatcatgggcatatgctattttctggcaatcgtcagttgttgattttgcgagccaaactgtattgggttggggagatgggtattataa
aggagaagaagataagaataaacggagagggtcgtctagttcagcagctaattttgttgctgagcaagagcatagaaagaaggtgcttcgggagctg
aattcattaatatccggtgtacaagcttccgccggaaacggaactgatgatgcagtggatgaggaagtgacggatactgaatggtttttttctgatttcaa
tgacccaatcgtttgttaacggtaacgggcttccgggcttggcgatgtacagttcaagcccaatttgggttactggaacagagaaattagctgcttctca
atgtgaacgggccaggcaagcccaaggtttcgggcttcagacgattgtgtgtattccttcagctaacggtgtagtggagcttggttcgactgagctgat
attccaaagctcggatttgatgaacaaggttaagtatttgtttaacttcaatattgatatggggtctgttacaggctcaggttcgggctcaggctcttgtgc
tgtgcatcctgagcccgatccttcggccctttggcttacggatccatcttcctcggttgtggaacctaaggattcgttaattcatagtagtagtagggatgt
tcaacttgtgtatggaaatgagaattctgaaaatcagcagcagcattgtcaaggatttttcacaaaggagttgaatttttcgggttatggatttgatggaa
gtagtaataggaataaaactggaatttcttgtaagccggagtccagggagatattgaattttggtgatagtagtaagagattttcagggcaatcacagtt
gggtcctgggcctgggctcatggaggagaacaagaacaagaacaagaacaagaaaaggtcacttggatcaaggggaaacaatgaagaaggaatg
ctttcgtttgtttcgggtgtgatcttgccaacttcaacaatggggaagtccggggattctgatcactcagatctcgaagcctcagtggtgaaggaggccg
ttgtagaacctgaaaagaagccgaggaagcgagggaggaaaccagccaatggaagggaggagccattgaatcacgtggaagcggagagacaga
ggagggagaaattgaatcaaagattctacgcgctcagagccgtagtcccaaatgtgtctaaaatggataaggcatcacttcttggagatgcaattgcat
acatcaatgagttgaaatcaaaagttcaaaattcagatttagataaagaggagttgaggagccaaattgaatgtttaaggaaggaattaaccaacaag
ggatcatcaaactattccgcctcccctccattgaatcaagatgtcaagattgtcgatatggacattgacgttaaggtgattggatgggatgctatgattcg
tatacaatgtagtaaaaagaaccatccagctgccaggctaatggcagccctcaaggacttggacctagacgtgcaccacgctagtgtttccgtggtgaa
tgatttgatgatccaacaagccacagtcaaaatggggagccggctttatgctcaagaacagcttaggatagcattgacatcaaaaattgctgaatcgcg
atga

FIG. 2B

SEQ ID No. 7:

>SlMYC2_AA_WT
MTDYRLWSNTNTTNTCDDTMMMDSFLSSDPSSFWPASTPNRPTPVNGVGETMPFFNQESLQQRLQALIDGARE
SWAYAIFWQSSVVDFASQTVLGWGDGYYKGEEDKNKRRGSSSSAANFVAEQEHRKKVLRELNSLISGVQASAGN
GTDDAVDEEVTDTEWFFLISMTQSFVNGNGLPGLAMYSSSPIWVTGTEKLAASQCERARQAQGFGLQTIVCIPSA
NGVVELGSTELIFQSSDLMNKVKYLFNFNIDMGSVTGSGSGSGSCAVHPEPDPSALWLTDPSSSVVEPKDSLIHSS
SRDVQLVYGNENSENQQQHCQGFFTKELNFSGYGFDGSSNRNKTGISCKPESREILNFGDSSKRFSGQSQLGPGP
GLMEENKNKNKNKKRSLGSRGNNEEGMLSFVSGVILPTSTMGKSGDSDHSDLEASVVKEAVVEPEKKPRKRGRKP
ANGREEPLNHVEAERQRREKLNQRFYALRAVVPNVSKMDKASLLGDAIAYINELKSKVQNSDLDKEELRSQIECLR
KELTNKGSSNYSASPPLNQDVKIVDMDIDVKVIGWDAMIRIQCSKKNHPAARLMAALKDLDLDVHHASVSVVNDL
MIQQATVKMGSRLYAQEQLRIALTSKIAESR

SEQ ID No. 8:

>SL06992
ggaagcggagagacagaggagggagaaattgaatcaaagattctacgcgctcagagccgtagtcccaaatgtgtctaaaatggataaggcatcactt
cttggagatgcaattgcatacatcaatgagttgaaatcaaaagttcaaaattcagatttagataaagaggagttgaggagccaaattgaatgtttaagg
aagga

| Sample ID | cis-3-hexenal | α-pinene | verbanene | myrcene | carene | α-phellandrene | p-cymene | limonene | β-phellandrene' | δ-elemene | β-caryophyllene | α-humulene' |
|---|---|---|---|---|---|---|---|---|---|---|---|---|
| Mo14/001 | 46 | <0.1 | <0.1 | <0.1 | <0.1 | <0.1 | <0.1 | <0.1 | <0.1 | <0.1 | <0.1 | <0.1 |
| Mo14/002 | 52 | <0.1 | <0.1 | <0.1 | <0.1 | <0.1 | <0.1 | <0.1 | <0.1 | <0.1 | <0.1 | <0.1 |
| Mo14/003 | 45 | <0.1 | <0.1 | <0.1 | <0.1 | <0.1 | <0.1 | <0.1 | <0.1 | <0.1 | <0.1 | <0.1 |
| Mo14/004 | 39 | <0.1 | <0.1 | <0.1 | <0.1 | <0.1 | <0.1 | <0.1 | <0.1 | <0.1 | <0.1 | <0.1 |
| Mo14/005 | 46 | <0.1 | <0.1 | <0.1 | <0.1 | <0.1 | <0.1 | <0.1 | <0.1 | <0.1 | <0.1 | <0.1 |
| Mo14/006 | 36 | <0.1 | <0.1 | <0.1 | <0.1 | <0.1 | <0.1 | <0.1 | <0.1 | <0.1 | <0.1 | <0.1 |
| Mo14/007 | 29 | 27 | 6 | 8 | 94 | 11 | 4 | 34 | 410 | 8 | 48 | 26 |
| Mo14/008 | 29 | 42 | 12 | 13 | 204 | 15 | 8 | 69 | 954 | 7 | 47 | 25 |
| Mo14/009 | 41 | 17 | 6 | 9 | 70 | 5 | 5 | 24 | 285 | 7 | 80 | 40 |
| Mo14/010 | 63 | 33 | 6 | 22 | 120 | 11 | 6 | 47 | 533 | 8 | 62 | 32 |
| Mo14/011 | 54 | 10 | <0.1 | 13 | 35 | <0.1 | <0.1 | 13 | 137 | 9 | 80 | 40 |
| Mo14/012 | 77 | 7 | <0.1 | 8 | 19 | <0.1 | <0.1 | 8 | 91 | 7 | 58 | 32 |
| Mo14/013 | 15 | 63 | 35 | 13 | 186 | 32 | 9 | 95 | 1227 | 10 | 28 | 16 |
| Mo14/014 | 19 | 47 | 21 | 12 | 123 | 12 | 8 | 66 | 823 | 10 | 27 | 14 |
| Mo14/015 | 27 | 70 | 33 | 19 | 206 | 30 | 12 | 103 | 1413 | 15 | 49 | 26 |
| Mo14/016 | 35 | 63 | 17 | 16 | 290 | 40 | 9 | 114 | 1492 | 11 | 18 | 11 |
| Mo14/017 | 34 | 62 | 21 | 23 | 254 | 29 | 10 | 92 | 1328 | 21 | 51 | 28 |
| Mo14/018 | 35 | 54 | 15 | 21 | 208 | 25 | 9 | 79 | 1073 | 15 | 45 | 23 |

FIG. 4B

| | cis-3-hexenal | α-pinene | verbenene | myrcene | carene | α-phellandrene | p-cymene | limonene | β-phellandrene* | δ-elemene | β-caryophyllene | α-humulene* |
|---|---|---|---|---|---|---|---|---|---|---|---|---|
| Average Mo14/ 007-012 | 48,8 | 22,8 | 7,5 | 12,1 | 90,3 | 10,4 | 5,8 | 32,5 | 401,6 | 7,7 | 62,5 | 32,5 |
| SD | 19,3 | 13,6 | 3,2 | 5,5 | 66,9 | 4,3 | 1,9 | 22,8 | 317,2 | 0,7 | 14,8 | 6,4 |
| Average Mo14/ 013-018 | 27,5 | 59,8 | 23.7 | 17,5 | 211,1 | 28,1 | 9,5 | 91,4 | 1226,0 | 13,7 | 36,2 | 19,6 |
| SD | 8,5 | 8,0 | 8,3 | 4,5 | 57,4 | 9,3 | 1,3 | 17,2 | 245,5 | 4,3 | 13,6 | 7,1 |
| P-value | 0,03 | 0,00 | 0,01 | 0,09 | 0,01 | 0.01 | 0,01 | 0,00 | 0,00 | 0,01 | 0,01 | 0.01 |

SEQ ID No. 9:

>c_annuum_gDNA ctctaaatatgtaaaatgaattaggaataaatgcacatattttccttcgcagaaagagatagcaacatggacctcaaacagcctcttggcatattatttact
taactatcaaaatggttaaatgtgtattttataataactaaaagcttaaacaataaagtaataaatcttattagtatattttatttctatctgtatcatcgactc
cttcatatgtctataattaatactttttgctaaacataacattatttctttttataagttgaaacactgaattatcacactttcatattatataaactcgtaactg
aaaatgtttcaaaaatagttatagataatatcttttcaattcctaaattcaactcctcaacccaaggaaagaatggaaatggattcatatacgttgatttctc
attctttttctatcatttcatttaccttcctattgagagggaaatggaatcaagaaaatgatcaaccacattattagatactcacttcgttagtgttatttgtta
aatattgacttgatacactgcacctttgggtgtggttgagttggtttgaggggtgactttcaaagcgaaggtcgcggtatcaattccctctaatgctttttc
aatctagctcgtcacactaggtttacctagtgcggtttacatctcctgtgtggtttacgagtgattatacagtgaggggtttacccaatacacacaaagtgc
tcacccgaagggcagaggctagtggctgggtaaacccgaagggcagaggctagtggctgcggggtttacccagtgcgcacaaagtgctcacccgac
tttcctgaagtttcaaaaaatatatatatatatatatattgacttgatacatttcttaaagagcaaaataaattaaaaattaaataataactcaactctacatt
ttcttaattgaacagaaaaataagtaactatgttttggtacagtgaataaatagaagtggtcgaaaaagtattttctccattctagaagtacaccaagctt
ctaataagagtcaacacacctaagtttaaacgtaattcaaacatcaatttcttagtttttaaaactaaattatggatattaaaaaattataagaaaaacaaa
tgatactccttacaatttatttggttatcagattacaactgattcgacttgtcaaataataatgattgaaatatatgataggatatgtcgcagtaagagattt
gaatcataataggtgaggataaacgctattgcaaaaaaagtttttaatttcaccaaatattgggaaactacttcaaatatactccatcaatttacatttaa
agaataaataattaatattaaggataaaagatttttttttaatcttatttttgatatatcaaaatgataagtataaataaaaattcaattaaagaaataatg
taacgtaaaagtgaacagagggaatcctttttagtagacatttatatttagttgaagtttaaaaatcccaaataattcaaattaaagttgactttcataaac
acttattaaaaaaatcagccaaagataatacatttataaaaatgtaattttcaaatgaattaactagacgtaaattttttttttttcaaaagtaatttttaata
agttattttaataaaaaagcttctcaaaataagaatttttatagccacttgaccaaacaagtctcccaaacatgaatttgaattaatttttaaaaaaatttc
gcaagtaaaaactaaaaagacttcttaaaatgtgtttttcaaaatttaaattctattcaagtttgatattatcctaaaattattgaccatattagaaatgtttg
attgaaattatttcttgaaaattagaaaaaaaatgaggttctttgatatttttttgaagcagtggtatggccatataagaatacactcattatatgttattga
ttggttgctgattaaagaagttcgtcttttttaattttttattcgatatttatattgaaactttgattaccttactgtaagatgtgacatttctaacaaaattatatt
tatattaaaaattttaaaattaaaacatttaattaagggtgagccagatccactaccgcaccgtagccgcgacccatatggtacaagaggagtagtagtg
atgttggcgattaattggcgggtccttcgtggaacccgccagtctctttcctcattctcccaaattcagctcaaattcacctcaaataaaacccaaactcaa
attccactcttattaaccaaacccaatatttctctctcatttttctccgccacacccctctatcctcattctctctctctacacaccattttcacctgttttctgct
gtgtgttttatggaatgactgattacagcttgcccaccatgaatctctggaataacagtactactgatgacaacgtttctatgatggaggcttttatgtcttc
cgatctttctttttggggtggtactactacttctagtgctactgctactgctgctgctcttgctaatcccaattatacttcaactgtttaccctcctcctggcgct
tcttgtgcatcttccgtaacggctacagctgctgctgtgactgttgatgcgtcaaaaaccatgccatttttcaaccaggagacgctacagcagcgtcttca
gaccctaatagacggtgctcgtgagacgtggacgtatgctatcttctggcagtcgtctgatttagatttctcgagtccgtctgtgttgggttggggtgatg
gttattacaaaggggaggaggataaaaacaagaggaaattatctgtttcttctccggcttatattgctgagcaggaacatcggaagaaggttcttagag
agctgaattcgttgatttcagggacacaaactggtacagacgatgctgttgatgaagaagttaccgataccgaatggttctttcttatctccatgactcaa
tcttttgtcaacgggaacgggcttccgggccaggctatgtgcagttccagcccgatttgggttgccggagtagagaaattggctgcttctcactgtgaac
gggctcggcaggcccaagggttcgggcttcagacgatggtgtgtatcccttcagctaacggtgttgttgaattgggttcgacggagttgattatccaga
gttctgatctgatgaataaggttagagtactgttcaatttcaataatgatttggggtcaggttcatgggctgtgcagccggagagcgatccgtcagcgct
ttggttgacggagccatcttcctcaggtatggaagttagagagtctttaaatacagttcaaacaagttcaattccatcaagtaatagtaataagcaaattg
cgtatggaaatgagaacaatgatcatccatctggaaatgggaatggtcatagttcttataatcagcagcatcctcatcaacaaacacaaggatttttcac
gaaggagttaaacttttcggactttgggttcgatggaagtagtaataggaacgggaattcatcgctctcttgcaagcctgagtctggggaaatcttgaat
tttggtgatagtacgaagaaaagtgcttgtagtgcaaatgggaacttgttttcgggccattcccaatttggggcaggtgaggagaacaagaacaagac
caagaaaaggtcagctacttccaggggaagcaatgaagaaggaatgctttcatttgtttcgggtacagttttgccttcttccggtatgaagtcaggcgga
ggcgaagactctgaccattcagatcttgaagcttcggtggtgaaagaagctgatagtagtagagttgtagaaccggaaaagaagccaaggaagcga
ggaaggaagcctgctaatggaagggaggaacctttgaatcatgttgaggcagagaggcaaaggagggagaaattgaaccaaagattctacgcgctt
agagctgttgtaccgaatgtgtctaagatggacaaggcatcacttcttggagatgcaatttcatacataaatgagttgaaatcgaagcttcacaatacag
agtcagataaagaagacttgaagagccaaatagaggatttgaagaaagaattagctagtaaagaatcaaggcgccctggtcaaccaccaccaaacca
agatctcaagatgtctagccacaccggaaccaagattgtagacgcggagatagacattaagataatgggatgggatgttatgattcgtgtacaatctaa
taaaaagaatcatccagccgcaaggtttatggcggccctcatggaactagacctagatgtgaaccatgccagtgtttcattggtgaacgagttgatgatc
cagcaagccacagtgaaaatgagtagccgtcattacactgaagagcagcttaggatagcattgatgtcaagaattgctgaaacgcgctaaaaagacc

FIG. 6A ctagaaagtagatagaactcaaagaaagcatgtgggctttgatggcgctctggttgctgcagctctatgtaatgtttttgttatgaattagagatttcatc
aggctatcttcgtgttatttttcgaacttgtaccttaggtggttgtcgaaatattcttgtacataaatgttattacccgaaaactcaacataatcgggctttag
ctcatgtaattaaacatatattccaactccgtcttgtctgttagattgcatctatcattatgtattctttgtccatgcataaatgaagaaatttgatggcaggt
gaatttgattttgaagcaaatgtgatttactgtcgtgctgcttattcttatacccaatttttgagctgcattaggattgtgtgaagtactttaagctattcattc
atgagaaaaatgtgaaagagatcatcatttcagaaatatgcactatttctccaattcaaacttcatgttcaaattgtattaaataattgtattggaggtcatt
gcttacgacctttatgcatcacattttgactaaaaacaataacggattatttcatgagaatatttggatttacatatacacctcagaaaaactatcatctttc
atttgagtttttaatgtcatactccatccgactcaatttaatttgcgccgaagaatgccaaaaaagtttcacatttatggtcaatagatgagtaatctcctta
taaggcttggattatcctctttcctaatgctcaaaaggtgtaagtttagccatgacctaattttatatatactttttttttgacatttctttaatcttaattttcat
acgacatatttaagattataaattaaataatattttaatacattctatcttgtgtcaagttaaatgagacaaacaaattataacaaaggaagcatcaaata
aaataggaaagaaggaaaaagggatttcgtaaaagagcgataagataaggtgatagtttgatagactagattggactagatgcaacagcaaaatag
aacaggaaactacaaggaactagtccatttattcatttggctgcttgctcgtttatattgtgaattgtatatctccacatatttattctaataaagatatcag
gaagaaggcatgtgtcttattatttcctttaggagaatacactgaacttggttcttcttttggtccctattgtctactatagaccaatgtatattttccataat
agtattggcataacatgctaaagtattttccataatagtattggcaagaaacgccatgaatatcatgtaggttgaaactgacagcaacgtttcaaattcac
ttcatttgaactttcacttcacccaagtacagtctccccgtccgaagcaggattttcatcaaagagatgcaacatttaccataaataaattttctcccccca
tccctctctctctatatattagtaactttggatccagatgaacccttttccgcctcacaagtttcacccaagttccaagtatatgttactctagaagttttaact
ttctttttagtaattctttgttaatatgttgtccctatactagtatctggacatgccactactgaaaaattcaaaatttaccttcattctttaaggtaatttacaa
ttcaatctttaaggtttttatattgaccttattatattttaaagttatgaatttatatttattattattactttctatatttttaaataagtgacattttagtcttttca
ttttatttctaaataacttggtgttttagataattaagaagatattaatgatgttattataagtttaccacttttaaataaagaaagttttacatgacttaagg
agtactaagaattacatcatttccaaagaaatattaagaataagttggtaaaaatactatttatttaaaaataaaaaaaaataattttaacaaactaataca
tataaatttatatttcctattgaaaatacaattcatactaatctcaacgccgctcggtaaaattagatccgcttcactttaactgctaattattgaataaagtg
tagggacaaatttgatgtaaataaaatcatctactccactaatatattaatttgtttttaatttaatatatattttcatacactagacaacaaagaattgtga
cgtgacgcaaatttggtggaagtggacatgcagacaaaaaagatcatgtgttac

SEQ ID No. 10:

>c_annuum_CDS
atgactgattacagcttgcccaccatgaatctctggaataacagtactactgatgacaacgtttctatgatggaggcttttatgtcttccgatctttcttttg
gggtggtactactacttctagtgctactgctactgctgctgctcttgctaatcccaattatacttcaactgtttaccctcctcctggcgcttcttgtgcatcttc
cgtaacggctacagctgctgctgtgactgttgatgcgtcaaaaaccatgccatttttcaaccaggagacgctacagcagcgtcttcagaccctaatagac
ggtgctcgtgagacgtggacgtatgctatcttctggcagtcgtctgatttagatttctcgagtccgtctgtgttgggttggggtgatggttattacaaagg
ggaggaggataaaaacaagaggaaattatctgtttcttctccggcttatattgctgagcaggaacatcggaagaaggttcttagagagctgaattcgtt
gatttcagggacacaaactggtacagacgatgctgttgatgaagaagttaccgataccgaatggttctttcttatctccatgactcaatctttttgtcaacgg
gaacgggcttccgggccaggctatgtgcagttccagcccgatttgggttgccggagtagagaaattggctgcttctcactgtgaacgggctcggcagg
cccaagggttcgggcttcagacgatggtgtgtatcccttcagctaacggtgttgttgaattgggttcgacggagttgattatccagagttctgatctgatg
aataaggttagagtactgttcaatttcaataatgatttggggtcaggttcatgggctgtgcagccggagagcgatccgtcagcgctttggttgacggag
ccatcttcctcaggtatggaagttagagagtctttaaatacagttcaaacaagttcaattccatcaagtaatagtaataagcaaattgcgtatggaaatga
gaacaatgatcatccatctggaaatgggaatggtcatagttcttataatcagcagcatcctcatcaacaaacacaaggatttttcacgaaggagttaaac
ttttcggactttgggttcgatggaagtagtaataggaacgggaattcatcgctctcttgcaagcctgagtctggggaaatcttgaatttggtgatagtac
gaagaaaagtgcttgtagtgcaaatgggaacttgttttcgggccattcccaatttggggcaggtgaggagaacaagaacaagaccaagaaaaggtca
gctacttccaggggaagcaatgaagaaggaatgctttcatttgtttcgggtacagttttgccttcttccggtatgaagtcaggcggaggcgaagactctg
accattcagatcttgaagcttcggtggtgaaagaagctgatagtagtagagttgtagaaccggaaaagaagccaaggaagcgaggaaggaagcctg
ctaatggaagggaggaacctttgaatcatgttgaggcagagaggcaaaggagggagaaattgaaccaaagattctacgcgcttagagctgttgtacc
gaatgtgtctaagatggacaaggcatcacttcttggagatgcaatttcatacataaatgagttgaaatcgaagcttcacaatacagagtcagataaaga
agacttgaagagccaaatagaggatttgaagaaagaattagctagtaaagaatcaaggcgccctggtcaaccaccaccaaaccaagatctcaagatg
tctagccacaccggaaccaagattgtagacgcggagatagacattaagataatgggatgggatgttatgattcgtgtacaatctaataaaaagaatcat
ccagccgcaaggtttatggcggccctcatggaactagacctagatgtgaaccatgccagtgtttcattggtgaacgagttgatgatccagcaagccaca
gtgaaaatgagtagccgtcattacactgaagagcagcttaggatagcattgatgtcaagaattgctgaaacgcgctaa

FIG. 6B

SEQ ID No. 11:

>c_annuum_AA
MTDYSLPTMNLWNNSTTDDNVSMMEAFMSSDLSFWGGTTTSSATATAAALANPNYTSTVYPPPGASCASSVTA
TAAAVTVDASKTMPFFNQETLQQRLQTLIDGARETWTYAIFWQSSDLDFSSPSVLGWGDGYYKGEEDKNKRKLS
VSSPAYIAEQEHRKKVLRELNSLISGTQTGTDDAVDEEVTDTEWFFLISMTQSFVNGNGLPGQAMCSSSPIWVAGV
EKLAASHCERARQAQGFGLQTMVCIPSANGVVELGSTELIIQSSDLMNKVRVLFNFNNDLGSGSWAVQPESDPSA
LWLTEPSSSGMEVRESLNTVQTSSIPSSNSNKQIAYGNENNDHPSGNGNGHSSYNQQHPHQQTQGFFTKELNFS
DFGFDGSSNRNGNSSLSCKPESGEILNFGDSTKKSACSANGNLFSGHSQFGAGEENKNKTKKRSATSRGSNEEGM
LSFVSGTVLPSSGMKSGGGEDSDHSDLEASVVKEADSSRVVEPEKKPRKRGRKPANGREEPLNHVEAERQRREKL
NQRFYALRAVVPNVSKMDKASLLGDAISYINELKSKLHNTESDKEDLKSQIEDLKKELASKESRRPGQPPPNQDLK
MSSHTGTKIVDAEIDIKIMGWDVMIRVQSNKKNHPAARFMAALMELDLDVNHASVSLVNELMIQQATVKMSSRH
YTEEQLRIALMSRIAETR

SEQ ID No. 12:

> c_sativus _gDNA
ttttaaatttgaggcgtcataaagttagtttatatgtgagaggtatcttgttgaatttttaagtttttaaaatttttattcaataaagttctaaatttgctct
atttttttctgtttggcatccaactgtagacatactttttcaaaatttaacactcggtttggtatttgaatttaattaaataaagctatactcaacaaaaaa
tatattgtttttaaagtagttaattaagttggttaataccataaagtaagcacaaagcaatatgtgacaaataagtgataaataagtaatttgtcttacgg
gtatttgtgacaaataagtttataaggataactcaaccatcttagacaacctatcaacatcaacttgcctaaggtgaatgttaatattgattgttaggggtg
agtgtcacttgccattgaagttgattatcaaaggtgattttcattgcagtttatcatataagcagtagttggagtctgaaattgaaggtggttatcgaagtt
gataatcaaaaagtgattttctcaaagtttgtagtcatagcttggaattcatcgtgtaaacgtggtcatcaaagttggctttttttggagtttcctattggag
atagttaccatagcccaaaattagttgttggaggtggtcacataaaggtatctagtcgttaggtcagtttgtcatcgaaggtggttgccagaccttgaaat
cgatcatcaaagttggttatctgagtgtggtaatggtaattgatcgttgaatctattagaaaaactggagagagcttcatcaacctataaagttagtgga
ccaaagagaactcaaactcaacttatattttgatgtgttaactcccctaaaataaaacaaacgaaacaaaaaaaaaaatcataaagacaaaaatgaaa
aaatggagtaccatcattgtactaaaaaaatatattttaacaaaagaaaaaatcaatgactacaaataaattttaaaacactagatttaaaaaaaaaat
caaagaacaaaaatagaagatatttatatatatatatatttaaaaaagaaaattaatagatattataatgaggcttagtattttcaaaatcctgttttaggg
caaaaaaaagaggggaaaaataaaacaacttccgtctttgattcacaaacaagagacgtgtcatgttctcattagctaaaaccggaaaaaaagcgatg
agtaaaaaagtcataaaaacggttaaccctcaacgcctctcaagggttcttcacgtgccagtcacgtggaaggaagggaagcgaaccgggtctaaga
aaaccgcactatctggggtaagtactattagtataattgtactataagcgcggagttgagaaagacgccggctttttgaacgatttaatcggcgatctaa
agaagaagcctcttggttccttcttctcctcttcgcttctctgttaaatgttcatcacaaataaatcccataccaatcgcccgacatttctctcactccacaatc
ggagaccaaagattattcctttttcccatttctatttcttccaatctcaatcgcatgacggattatcgtttgtcgacgatgaatctctggactgacgagaac
gcgtcggttatggacgctttcatgaattccgatctgtcttcctactgggctccgtcagccgcctcctctcactctcttcaccacccaccgccacctcagtcctc
cgcctccacatccactcccccgccggacgcacctaagtccctccccgttttcaatcaggagactctgcagcagcggctccaggcgctgatcgacggtgct
agggagagttggacttatgcgatttttctggcagtcgtcttatgattatttctggtgggtctgttttggggtggggtgatgggtattacaaaggagaggaa
gataaaggaaagggaaaagcgaaaatggtgtcgtcagcggcggagcaggctcaccggaagaaggttttacgggagcttaactctttgatttctggct
ctgccgccggacctgacgatgcggtggatgaggaggttacggatacggagtggttctttttggtttcgatgactcagtcgtttgttaatggtgttgggtt
accgagtcaagcgttttaccactcgacgccgatttgggtctctggtgccgatcggctgtcggcgtctgcctgtgaacgagctagacaggggagggttttt
gggttacagacgatggtctgtattccatcgcctaacggtgttgtggaaatgggttcgacggaattgattcatcgaacgtcggatttgatgaataaggtca
agattctgttcaatttcaacaatctcgaaacgagttcttggatttcgggaactaccgccgccgcatccgctgccgacgaaggggaaaacgacccgtcgtc
gatgtggatcagtgagccatcgagtacaatcgagatgaaggattcaatcaccaccactgttccttccagcaacgttccggcaaagccaatccgttcgga
aaatcccagtacaagtagcttaacggaaaatatgagcacgattcaacaatcccatcataaacagagccaaagcttcttaaatttctccgattacggcttc
gaatcaaatcccacaaagaacaccaccgctaccgccaccgcaaccaccagcaccaccccatcattcaagccggaatccggcgggatgctgaatttcgg
caacgggagcctcttctccggccattcacagtacgtaacaaacgaacagaacgagaaaaagagatcccctgcttctcgaagtagcaacgacgaaggg
atcctctctttcacctccggcgtgatcttaccctcttccggtaaggtaaaatccggtgattcagaccattcagatctcgaagcatcagcgatcagagaagt

FIG. 6C ggatagctgtacaaaatcattagaacccgaaaaacgtccaagaaaaagaggtagaaaaccagcaaacggaagagaagagccattgaatcacgtaga
agcagagagacaacggcgagagaaattaaaccagaaattctacgctctccgagctgtagttccaaacgtatctaagatggacaaagcctcactactag
gtgacgcggtttcgtacataaacgagctcaaatcgaagctccaaatggcagaatcggagaaaacagatatgggaaaacatctagaattgctgaagaa
ggagatgggaggaaaagatttaggatgttactcaaacccaaatgatgaagatctgaaaacagggaaaagaaaggtaatggatatggagattgaagt
taaaatcatgggttgggatgcgatgataaggattcaaagcaacaagaagaatcatccggcggcgaggttgatgacggcgtttaaggatttggatttag
aaatgcttcacgcgagtgtttctgtagtgaatgatttgatgattcaacaagcaacagtgaagatggggagcagatttacacacaagagcagcttaaaa
tggctcttgtcgcccgagtcggcggtggtggaagtggaggcggcggtggaatcatgtaaatggggttaggggacattttgaagctcccaattagtag
agtttagttgagggaatctgatttagtattgtgtaatataaatgttggtaaattatttttgataattctcttgttgttcatcttttgttgttagagtaatttggga
gttcttctatatgtagtttttgtttattaaatatgaaatctaatagaagtaaagatcaaagaccttcaaactttgtgtttgatcatttcaattctccttctttcctt
ttttttttttttttgttttgttttgttttagggtttgtttgaactagtaggtctagtttagggaaaatctaggtttgatcggaaattaaggactaacctta
acctttcttggtacaaactttagttaaacctacatgtcaatagacttaaaagatttagtattaaggtccaaactttcccacggttgagatcgaaagcccctg
atataagaacaactcataaaatttgacatttgattaggttattaagtggatttcaatggggatcgagacctactctcttaggtcaacatttttcataaataca
taagttggttagtctagatttgtaaattttaattgggtttagttgtttatgtatggagataggtaattgaacttctcatattgagttatatactcctacaagta
aagggagaaactcccaatagatattggttgtgttggaaaggttatgaatcgattaataagtcaattaccattatcttgattttgaacgccaatgcatcaca
tgcatatatatatatatatattgtcggctagtacacgaccaattaatgtttggataaagttctttccagaatcatcctatttcaagactcactaaaatccttc
agatatatggttccacaattggtcctatgtacaacagtgtattgaactacttcaacacgatgttcgtacaacaatacccacaactcattttgcactccatag
caaaaaataatatattatgttaaggacaaccccttaggtaaattgctttgaatgagttaatcaatcatttatccttgtggatctaacattaatcctctcatacc
tactaattggtatgcttgagatgcattttctcgagcacctatagaagacgttatatatagactggattaaagggacactcatcctaaaattaggattcatt
tcttgtagcaaatattcacttgtagcatacgatatctaaagggactggcgtaagttttctactgcgggtacgtttccataatgatggtgtcttttcaatatca
aactttactgttcaccatcttgaactagccatcctttagagagtattgttaaaagatatcaattcctaatgaaatggatgtcgcagtggcccactaaaagtc
tttaattgatattacaatctttatgctagttgagctatgctcgatttatcattttgtatacaataagctctaacaagttagttaggttccatcctttatatatagt
ttgtacacattattattttagatgcatgccacatgcctaaaccttcaaatgattggttactatattggagagtttaagctacctctcatacatagaaatgtta
agtagattcaatgaagtttagaaattttaattttgaaaat SEQ ID No. 13:

> c_sativus _CDS atgacggattatcgtttgtcgacgatgaatctctggactgacgagaacgcgtcggttatggacgctttcatgaattccgatctgtcttcctactgggctcc
gtcagccgcctcctctcactctcttcaccacccaccgccacctcagtcctccgcctccacatccactcccccgccggacgcacctaagtccctccccgttttc
aatcaggagactctgcagcagcggctccaggcgctgatcgacggtgctagggagagttggacttatgcgattttctggcagtcgtcttatgattattctg
gtgggtctgttttggggtggggtgatgggtattacaaaggagaggaagataaaggaaagggaaaagcgaaaatggtgtcgtcagcggcggagcag
gctcaccggaagaaggttttacgggagcttaactctttgatttctggctctgccgccggacctgacgatgcggtggatgaggaggttacggatacgga
gtggttcttttggtttcgatgactcagtcgtttgttaatggtgttgggttaccgagtcaagcgttttaccactcgacgccgatttgggtctctggtgccgat
cggctgtcggcgtctgcctgtgaacgagctagacaggggagggtttttgggttacagacgatggtctgtattccatcgcctaacggtgttgtggaaatg
ggttcgacggaattgattcatcgaacgtcggatttgatgaataaggtcaagattctgttcaatttcaacaatctcgaaacgagttcttggatttcgggaac
taccgccgccgcatccgctgccgacgaaggggaaaacgacccgtcgtcgatgtggatcagtgagccatcgagtacaatcgagatgaaggattcaatc
accaccactgttccttccagcaacgttccggcaaagccaatccgttcggaaaatcccagtacaagtagcttaacggaaaatatgagcacgattcaacaat
cccatcataaacagagccaaagcttcttaaatttctccgattacggcttcgaatcaaatcccacaaagaacaccaccgctaccgccaccgcaaccaccag
caccaccccatcattcaagccggaatccggcgggatgctgaatttcggcaacgggagcctcttctccggccattcacagtacgtaacaaacgaacagaa
cgagaaaaagagatcccctgcttctcgaagtagcaacgacgaagggatcctctctttcacctccggcgtgatcttaccctcttccggtaaggtaaaatcc
ggtgattcagaccattcagatctcgaagcatcagcgatcagagaagtggatagctgtacaaaatcattagaacccgaaaaacgtccaagaaaaagag
gtagaaaaccagcaaacggaagagaagagccattgaatcacgtagaagcagagagacaacggcgagagaaattaaaccagaaattctacgctctcc
gagctgtagttccaaacgtatctaagatggacaaagcctcactactaggtgacgcggtttcgtacataaacgagctcaaatcgaagctccaaatggcag
aatcggagaaaacagatatgggaaaacatctagaattgctgaagaaggagatgggaggaaaagatttaggatgttactcaaacccaaatgatgaag
atctgaaaacagggaaaagaaaggtaatggatatggagattgaagttaaaatcatgggttgggatgcgatgataaggattcaaagcaacaagaaga
atcatccggcggcgaggttgatgacggcgtttaaggatttggatttagaaatgcttcacgcgagtgtttctgtagtgaatgatttgatgattcaacaagc

FIG. 6D aacagtgaagatggggagcagattttacacacaagagcagcttaaaatggctcttgtcgcccgagtcggcggtggtggaagtggaggcggcggtgg
aatcatgtaa

SEQ ID No. 14:

>c_sativus_AA
MTDYRLSTMNLWTDENASVMDAFMNSDLSSYWAPSAASSHSLHHPPPPQSSASTSTPPPDAPKSLPVFNQETL
QQRLQALIDGARESWTYAIFWQSSYDYSGGSVLGWGDGYYKGEEDKGKGKAKMVSSAAEQAHRKKVLRELNSLI
SGSAAGPDDAVDEEVTDTEWFFLVSMTQSFVNGVGLPSQAFYHSTPIWVSGADRLSASACERARQGRVFGLQTM
VCIPSPNGVVEMGSTELIHRTSDLMNKVKILFNFNNLETSSWISGTTAAASAADEGENDPSSMWISEPSSTIEMKDSI
TTTVPSSNVPAKPIRSENPSTSSLTENMSTIQQSHHKQSQSFLNFSDYGFESNPTKNTTATATATTSTTPSFKPESG
GMLNFGNGSLFSGHSQYVTNEQNEKKRSPASRSSNDEGILSFTSGVILPSSGKVKSGDSDHSDLEASAIREVDSCT
KSLEPEKRPRKRGRKPANGREEPLNHVEAERQRREKLNQKFYALRAVVPNVSKMDKASLLGDAVSYINELKSKLQ
MAESEKTDMGKHLELLKKEMGGKDLGCYSNPNDEDLKTGKRKVMDMEIEVKIMGWDAMIRIQSNKKNHPAARL
MTAFKDLDLEMLHASVSVVNDLMIQQATVKMGSRFYTQEQLKMALVARVGGGGSGGGGIM

SEQ ID No. 15:

>c_melo_gDNA
ttcctgtcctaaggttgcagtaattttagattttactttgagataaaaattgtaaaaattaaatgggtttagtattacaataatcgatttaactataaaattctt
aaataataaattaatatatttaattatattatgtaagttaggctttgtaagttatttattctcttacattaattatagtatgtgtttttttatatgatttgaatttc
aattcatttattgtatttaaattatctgataaaagtttaggatttttaatcaaaattaaatcaattactatagaagattaaaaatattttaatttaaaaatgag
ttattttgaaaaaagaaataaaggatatatatatatacatattgaaataagtgagagtattactttattttgagtaaagtgggaaaataaatttttgcgtag
aaaatttgctaactttcaaaaaagcatttgtcgtcttttctctttcttctatttttgtaattttgttgtttttttccctctcattccttaatcattttattgcaatgttt
ttcccttaaaaagaagcatagctcaatttttaaatattttgataatgtgtagaattgaataatcaaatctctaatattcatgctaaccattttaactattttttg
atagggttgaaagtatgttaggtttttatgagtatttactatatattaacaattgggctcaatttttataaatttgtaatttgatggtttgagttttaaaagga
aagaaatggttggaatgttaataatcaatatggtttagattaaagtaatcgatttcacaaaagttggagttgagctagggatatgacatgcattcaaccc
acctaggcttgaggggagacgagagtttggaccaaatgtccaaatatgaaccgatcaatttttaccttggtcgagacatacccacactttgattaaata
ggcatgttaaacgtgtaggacaacatattgagtttgagaaaaagcctaatctaactccaaaaccctaatttaaatgtcttaggtcataagtaagttaacta
tatcatccaaactcttgcgagttgcgacaacttaaagagtttaattagttacaatcattattgtaattttttaaatttgaggcatcatatgttgttactcgatg
aggctgtttagggcgttgagttgatgtagggtgttgttaagaagcaaagtaatatgtcttatggatacttgtgacaaataagtttataaggatgatccaa
ccaatcttagacaacttctcaacatcaaattgccttaggtgaatgttagtatatattgattgttagaggtagttgtcactatttgtcattgaagttgattatca
aaggtgattctcgttgaagtttatcatagaggtgggttgttggagcccaaagttaaaggtggttttcgaagttgataatcaaaggcgattttcgctaaag
tttgtagtcatagcttggaattcatcgcatggacgtagtcatcaaagttggctttcgttggatttgttatcagagatgattacaggctcgaaattagtggtt
ggaggtggtcgtgcaaaggtaatctagttgtcatagtttttcatcgaaggtggttgtaggaccctgaaatcgattgtcaaagttggaggtgtgaaagtg
gctgttgtcggagtcggatcctagagtttggtaatgggtaattgtcataatggtaatcgatcgtcgaatccattgaaaacattggaaagaactccaccaa
catgtaaagttggtaggccaaacgaaactcaaacccatcttatattgatgtgcaaaacatctctaggataaaacaaaccaaactaataaatcataaagac
aaaaatgaaaaatgagagtaccaaaaaaaaaaaaaaaagagcaataacttcaaataagtttaaaacactagatttaaaaaaaaatcaaagaacaa
aaatagaagatatttttaatctctacaaaaaaaaaaaaaaagaaaaaaagaaaattatagatattaataattgtaatgaggcttagtattttcaaaatcctc
atttagaggaaaaaaaaagggagaaaataaactaacttccgtctttgtttcacaaacaagacacgcgtcatattctcattagctaaaaccgcaaaaaaa
gcaatcagtcaaaaagtcttaaaaacggttaacactctaaacgcctctcaagaattcttcacgtgtcagtcacatggaaaagaaaccggccgaaccggg
tcgaagtaaaccgcgttatctggcgaagtacaaagtataatagtactataaccgcggagttgaaaaagacgccggctttttgaacgattaaatcggcga
tctaaagaagaaggctcttggttccttcttcctctgtgttcgctcctttcttaaatgttcatcacaaataaatcccaatccaatcgcccgacatttctctcactc
cacaatcggagacagaagattattcctttttccgatttctgtttcttccaatctcaatcgcatgacggattatcgtttgtcgacgatgaatctctggactgac
gagaacgcgtcggtgatggacgctttcatgaattccgatctctcttcctactgggctccatcagccgcctcctctcactctcttcaccatccaccaccacctc
agtcctccgcctcaacgtccactcccccgccggacccacctaagtccctccccgttttcaatcaggagactctgcagcagcggctccaggcgctgattga
cggtgctagggagagttggacttatgcgatttttctggcagtcatcttatgattattccggtgggtctgttttggggtggggtgatgggtattacaaagga
gaggaagataaaggaaaggggaaagcgaaaatggtgtcgtcagcggcagagcaggctcaccggaagaaggttttacgggagcttaactctttgatt

FIG. 6E tctggctctgccgctggaccggacgatgcggtggatgaggaggttacggatacagagtggttctttttggtttcgatgactcagtcgtttgttaatggtgt
tgggttaccgagtcaggcgttttaccactcgacgccgatttgggtctctggtgccgatcggctgtcggcgtctgcctgtgaacgagctagacaggggag
ggtttttgggttacagacgatggtctgtattccatcgcctaacggtgttgtggaaatgggttcgacggaattgattcatcgaacatcggatttgatgaata
aggtcaaaattctgttcaatttcaacaatctcgagacgagttcttggatttcgggaactaccgccgccgcatccgctgcagacgaaggggaaaacgacc
cgtcgtcgatgtggatcagtgagccatctagtacaatcgagatgaaggattcaattaccaccaccgtcccttccagcaacgttccggcaaagccaatccg
atccgaaaatcccagttcaagtagcttaacggaaaatatgagcacgattcaacaatcccatcataaacagagccaaagcttcttaaatttctccgattacg
gcttcgagtcaaatccctcaaagaacaccaccgccaccgccaccgtaaccaccagcaccactccatcattcaagccggaatccggcgggatgctgaatt
ttggaaacggaagcctcttctccggccattcacagtacgtaacaaacgaacagaacgaagaaaagagatcccctgcttctcgaagtagcaacgacgaa
gggatcctctctttcacctccggcgtgatcttaccctcttccggtaaggtaaaatcaggcgattcggaccactcagatctcgaagcatcagtgatcagaga
agtagatagctgtacaaaatcattagaacccgaaaaacgtccaagaaaaagaggtagaaaaccagcaaacggaagagaagagccattgaatcacgt
agaagcagagagacaacggcgagagaaattaaaccagaaattctacgctctacgagctgtagttccaaacgtatctaaaatggacaaagcctcactac
tcggtgacgccgtttcgtacataaacgagctgaaatcgaagctccaaatggcagaatcggagaaaacagatatgggaaaacatctagaattgctgaa
gaaggagatgggagggaaagatgtaggatgttacacaaacccaaatgatgaagatctgaaaatagggaaaagaaaggtaatggatatggagattg
aagttaaaatcatgggttgggatgcgatgatcagaattcaaagcaacaagaagaatcatccggcggcgaggttgatgacggcgtttaaggatttggat
ttagaaatgcttcacgccagtgtttctgtagtgaatgatttgatgattcaacaagcaacagtgaagatggggagcagattttacacacaagagcagctta
aaatggctcttgtggcccgagtcggtggtggtggaggcggaagcggcggtggaatgatgtaaatggggttaggggacatttttgaagctcccaa
gtagtagagattagttgagggaatataaatctgatttagtattgtgtaatattaatgttggtaaattattttgataattttgttgttcatctttgttgttaga
gtaatttgggagttcttcttctatatatatgtagtttttgttgattaaatatcaaatctaatagaagtgaagatcaaagaccttcaaactttgtgtttgatgat
ttcagttctctttccttgtttttagggttttgtttgaagtaaaaatctaggtttgattggaaatttaggactaaccttaacctcccagctcagtacaaacctta
gttaaacctaaatgtcaatggacctaagatttggtattgggtccacatttcgtgtggttgagatagaaaccccaactttcatataagaacaacccatata
aaattcgtcatttgattaggttattcgataagtggatttcaaaagggatcgggagaataactagtctcttaagtcaacatttttcatatatacataagttgg
tcgatctagatttctaaattttaagttgggtttagttgtttttgtacaatagggaacgtgcgtgtgcgtgtgcgcgtgcgtgtgtgtgtggttgtgtgtgtgt
gtgtgtcgctagttgtgtgtgtgtgtgtggttcgctaatacannnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnntcaatggactgacgtatttatttactaggtcataatgatggtgtttttccaaaatcaaac
tttgctgttcaatatcttagactagccatcctttagaggagattgttaaaaatcatcaattactaataaaaaaagactattgcagtggcccactggaagt
ctttagttgatactacaatctttatgctagttaagctacgctcaatttgtccgtttgtatacaatgaactctagcaaattagcttacatcatttatacatacttt
aaatgattggttactgtctatcggggagagtttaacctagctcttatacatagaaattttaagcaggtttaacgaaagttgaagtttagaaaatttaatttt
gaaaataatcatataaacatgcatgtcacacatgtttattgatatgctaagtcaatgagctatagagagttaggttcatagccacataaataaaacctata
actcttagttttatgttttcgaaatttatggccgtttcttactatttaaacttttctaaaagaaaaaatttgaactcattaaattctaacaacaaaaacatgtttt
tgaaaacgaaataaaaatagataataaaacacaaaaaacttatagatgaaaatagtgtttataaggttacttaaaaaaaaaccaaacaatcatcaaata
cgaagtttttgaaatttgatttagatttattcgatgtgtggttaataattgggatgtagaaagataagctatggatgatagtgaagaattgaaggtgacct
tacactttcatatatggacataaaaaaggaccattttcatagaatcttcaagaagatattgatggagataattttctctctttttgtgaccccttcttcatataa
agtaattccattgttgaagttaaatggtaaaaaagaaaaaaaaaaagaactttttattattgtataaaacaatgatttagattttgaattttatttgtgaca
atttggtcattttgaatatctaaactacgttggttattttatcgtcac

SEQ ID No. 16:

>c_melo_CDS
atgacggattatcgtttgtcgacgatgaatctctggactgacgagaacgcgtcggtgatggacgctttcatgaattccgatctctcttcctactgggctcc
atcagccgcctcctctcactctcttcaccatccaccaccacctcagtcctccgcctcaacgtccactcccccgccggacccacctaagtccctccccgtttc
aatcaggagactctgcagcagcggctccaggcgctgattgacggtgctagggagagttggacttatgcgattttctggcagtcatcttatgattattccg
gtgggtctgttttggggtggggtgatgggtattacaaaggagaggaagataaaggaaaggggaaagcgaaaatggtgtcgtcagcggcagagcag
gctcaccggaagaaggttttacgggagcttaactctttgatttctggctctgccgctggaccggacgatgcggtggatgaggaggttacggatacaga
gtggttctttttggtttcgatgactcagtcgtttgttaatggtgttgggttaccgagtcaggcgttttaccactcgacgccgatttgggtctctggtgccgat

FIG. 6F cggctgtcggcgtctgcctgtgaacgagctagacaggggagggtttttgggttacagacgatggtctgtattccatcgcctaacggtgttgtggaaatg
ggttcgacggaattgattcatcgaacatcggatttgatgaataaggtcaaaattctgttcaatttcaacaatctcgagacgagttcttggatttcgggaac
taccgccgccgcatccgctgcagacgaaggggaaaacgacccgtcgtcgatgtggatcagtgagccatctagtacaatcgagatgaaggattcaatta
ccaccaccgtcccttccagcaacgttccggcaaagccaatccgatccgaaaatcccagttcaagtagcttaacggaaaatatgagcacgattcaacaat
cccatcataaacagagccaaagcttcttaaatttctccgattacggcttcgagtcaaatccctcaaagaacaccaccgccaccgccaccgtaaccaccag
caccactccatcattcaagccggaatccggcgggatgctgaattttggaaacggaagcctcttctccggccattcacagtacgtaacaaacgaacagaa
cgaagaaaagagatcccctgcttctcgaagtagcaacgacgaagggatcctctctttcacctccggcgtgatcttaccctcttccggtaaggtaaaatca
ggcgattcggaccactcagatctcgaagcatcagtgatcagagaagtagatagctgtacaaaatcattagaacccgaaaaacgtccaagaaaaagag
gtagaaaaccagcaaacggaagagaagagccattgaatcacgtagaagcagagagacaacggcgagagaaattaaaccagaaattctacgctctac
gagctgtagttccaaacgtatctaaaatggacaaagcctcactactcggtgacgccgtttcgtacataaacgagctgaaatcgaagctccaaatggcag
aatcggagaaaacagatatgggaaaacatctagaattgctgaagaaggagatgggagggaaagatgtaggatgttacacaaacccaaatgatgaa
gatctgaaaatagggaaaagaaaggtaatggatatggagattgaagttaaaatcatgggttgggatgcgatgatcagaattcaaagcaacaagaag
aatcatccggcggcgaggttgatgacggcgtttaaggatttggatttagaaatgcttcacgccagtgtttctgtagtgaatgatttgatgattcaacaag
caacagtgaagatggggagcagatttacacacaagagcagcttaaaatggctcttgtggcccgagtcggtggtggtggtggaggcggaagcggcg
gtggaatgatgtaa SEQ ID No. 17:

>c_melo_AA
MTDYRLSTMNLWTDENASVMDAFMNSDLSSYWAPSAASSHSLHHPPPPQSSASTSTPPPDPPKSLPVFNQETL
QQRLQALIDGARESWTYAIFWQSSYDYSGGSVLGWGDGYYKGEEDKGKGKAKMVSSAAEQAHRKKVLRELNSLI
SGSAAGPDDAVDEEVTDTEWFFLVSMTQSFVNGVGLPSQAFYHSTPIWVSGADRLSASACERARQGRVFGLQTM
VCIPSPNGVVEMGSTELIHRTSDLMNKVKILFNFNNLETSSWISGTTAAASAADEGENDPSSMWISEPSSTIEMKDSI
TTTVPSSNVPAKPIRSENPSSSSLTENMSTIQQSHHKQSQSFLNFSDYGFESNPSKNTTATATVTTSTTPSFKPESG
GMLNFGNGSLFSGHSQYVTNEQNEEKRSPASRSSNDEGILSFTSGVILPSSGKVKSGDSDHSDLEASVIREVDSCTK
SLEPEKRPRKRGRKPANGREEPLNHVEAERQRREKLNQKFYALRAVVPNVSKMDKASLLGDAVSYINELKSKLQM
AESEKTDMGKHLELLKKEMGGKDVGCYTNPNDEDLKIGKRKVMDMEIEVKIMGWDAMIRIQSNKKNHPAARLMT
AFKDLDLEMLHASVSVVNDLMIQQATVKMGSRFYTQEQLKMALVARVGGGGGGGSGGGMM SEQ ID No. 18:

>c_lanatus_gDNA
ttttatataaatactaaattgttataaattaaactacgttattactttgtttttatttcatctgcaaacattcaaaattgaaatccttctagtcacaagttaaaaa
aattgggagactataccaggtgtacagtgaaaggaaaattacaaggagtaaaaaaattaatattgaatttataaactatcttaacattttattttttatttt
ttattttgccaactacaacaaataagagaaattatgttaaattgcaaaactgctaaaaatatttaaaatcaatagcaaaatacaccgtctacatgcgaatg
tgggatcaaatctcccctgtttgaagtgaaaaaagttaaaggagcatttgactaaattaacaaagaaatttttgttttcaaccaaaacaaatgttactctgt
tactttgttttgagtgaattgtgaaagtaagctaatgtgtagaaaatgtgataactttcaaaaaagcattcgtcgccttttatatttctacaatattgtttcgt
ttcatttttttatttttatttttttcatcccctcctttcctttaatatataactattgcaaatttcttaaatgagtttaacaacctttcaatgcaagttttttcttttttttttttt
tacaatctgtgaagttgaaaaaattgatactatcaccttatattggcagtattaaccttatgccatatgagttatatttatttttgataaatacttacaatatgtt
aatgattaagttcaattttatgtagtgtaaatttaaatttttaaatttaatttaatgaatattctgcttcctgaaacaacatgttggtcccacgggtggtatca
ggtggaggttgtctttggattgacaagcattggaagatttaaaagctcttcgttttccattcgggattgtcattctgtcacttttggtggaatctgattatgtt
gaagtgatcacgtccctttgcaagattgatagtgatctttcgaatattacatttgtttttttgttgtgttttaaagctagatgaagaatttgggaacatccattt
tgctaagtgttcgaggtttagtaattatttggctgcacactcgctagctagattggttgtgtctcctttttttgaattcttttttaggctcgaatttgactttcctcc
tccttggaaaggttttaattttagttcatggggttctaatgtccctaagttgttagttgctgttattggtgaggttgattgtcagttggggaaaaaaaatttt
aatagtttagacctagttttacacctcatttggtaactatttggttttttttgaatgattttgctggttgagagagataagtgaaatttttatatatttgtaaata
gtttgatatttttttcatttataataatttctcttcaaaattcaatcaaatttttaaagtataaattaaaagaaagggatcataacaaatcactcatccatttga
aatacaaaaataaattttgcactatatatatataaactcaacatctcttataagataaagcaaaataactaaataaaataaattgttttcaaatataagaaa
atgaacaaaaacatttataactacaatcaaattttactgtctatttgcgatagatctcgatctattgtagatagattgtaatattttgttattttttttaaatatat

FIG. 6G tctgcaactttatcatttaaaataatttttcaaataaaaatttagaaacaaaattgttgattgcaagtaagtacatagactaaaaatatttgttaacaaaaaa
aaaaaaaaaaaaacaatcaaagactttaaataatttttaaaataaaaattgcagagagattagaaaaaaaatcaaagaacagaaatggtagatattttt
agctttttttaaaaaaagaaaaataatagatattttaatatggcgtagtattttcaaaagcgatttatttggagcaaaaaaaggaaagaataaaaccactt
cagtctttgattaacaaatcagacacgtgtcaacctctcattagtggaaaatgcaaacaaaccgatcagtcaaaagtcttaaaaacggttacccccaaa
gctcacaaacgaaacgcccccgatgatccttcacgtgcccgtcacgtggaaagaaacgaaccgaaccgggtctaaatgagccgcactctctggcagga
gtactagtatagtactacaagcgcggagttgaaaacgacgccggcttttgaacgattaaatcggcgatccaaagaagaagcctcttggttccttcttcc
cctgttcgctcctctgtaaatgttcatcacaaataaatcccaatccaatcgcccgacatttctctcactccacaattggagacccagaattattctctttttccc
attctgtttcttctcgaatcccaatcgcatgacggattatcgtttgtcgacgatgaatctctggactgacgaaaacgcgtcggtgatggacgctttcatgaa
ctccgatctgtcctcttactgggctccatctgccgcctcctctcactctcttcaccacccaccgccgcctcagtcctccgcctccacctccactcccccaccgg
acccgcccaagtccctgcctgttttcaatcaggagactctgcagcagcggctccaggcgctgatcgatggcgctagggagagttggacttacgcgattt
tctggcagtcgtcctatgattattccggtgcgtcggttttagggtggggagatgggtattacaaaggggaggaggataaagggaagggaaaagcga
aaatggtgtcgtcggcggcagagcaggctcatcggaagaaggttttacgggagcttaactctttaatttctggctccgctgccggaccggacgatgcg
gtggatgaggaggttacggatacggagtggttctttttggtttcgatgactcagtcttttgataatggagtttggttaccgagtcaggcgttttacaactc
gacgccgatttgggtttctggcgccgatcggctgtcggcgtctgcctgtgaacgggccagacaggggagggtttttgggttacagacgatggtctgtat
tccatcgccaaacggagttgtggaaatgggttcgacggaattgattcatcgaacgtcggatttgatgaacaaggtcaagattctgttcaatttcaacaat
ctcgaaacgagttcttggatatcgggaaccaccgccgccgatgaaggggaaaacgacccgtcgtcgatgtggatcagtgagccgtcgagtactatcg
agatgaaggattccattaccaccaccgtcccttccggcaacgtcccggcaaagccaatccattcggaaaatcccagttccagcagcttaacggaaaata
tcagcgcgatccaacaaccatcccatcaaaaacaaagccaaagcttcttaaatttctccgattacggcttcgaatcaaatccctcaaagaacaccaccgc
ggccgcaacaaccaccaccgccaccccatcattcaagccggaatccggcgggatgctgaatttcggcaacggaaacctcttctctagccattcacagta
tgtaacaaacgaacagaacgagaaaagagatcccctgcttctcggagtagcaacgacgaagggatcctctctttcacctctggcgtgatcttaccctcc
tccggtaaggtaaaatccggggactcagaccactcagatctcgaagcatcggtgatcagagaagtggatagctgtacaaaatcattagaacccgaaaa
acgtccaagaaaaagaggtagaaaaccagcaaacggaagagaagagccattgaatcatgtagaagcagagagacaacggcgagagaagttgaac
cagaaattctacgctctccgagctgtagttccaaacgtatctaaaatggacaaggcctcactactgggagacgcggtttcttacatcaacgagctcaaat
caaagctccaaatagcggaaacggagaaaacagagatgggaaaacatttagaattgctgaagaaggagatgggagggaaagatttcgggaattac
ccgaacccaaatgatgaagatctgaaaatagggaaaagaaaggtaatggatatggagatcgaagttaaaatcatgggttgggatgcgatgataagg
attcaaagcagcaagaaaaatcatccggcggcaaggctgatggcggcgtttaaggatttagatttagaaatgcttcatgcgagtgtttctgtagtgaat
gatttgatgattcaacaggcaacggtgaagatggggagcagatttacacacaggagcagcttaaaatggctctcgtcgcccgagtcgggggcggcg
gcggcagcagccatggaatgatgtaaatgggttgtgtaattacaagtgggaggggacatttttgagggctcccaagtagagattagctgagggaatct
gattagtatgtgtaagataaaatgttggtaaattatttgatcattttgttgttgtttcatctttttttggttgttagagtaatttgggaagttctttgtgtagttt
ttgttaaatatcaaatctaatagaacagaagatgaaagaccttcaaactttgtgatgggttgctgtcttcaaaaatacccattgcgtttctctctttttggta
gaagtttagtcggtaggtacttcttccactaaaccttaacctcacatagtatccacacgagttaagtctagagttctcaatagccatgagttgggcccaaa
ggccgagaagcccaactttcgtatctcaaatcagattaggtttaagacttaagtcatcctcaatttgtctgtttgtataataatatctatctattatgcttatt
aatgagctattataaggtaaggtaggttacatcatttatatttatagttagataatcactcaaagttaattttagatgcatgccgcacgtctaaacttgcaa
atgattggttaccatatttgggaggagttcataaaaatgttaaagtgaaaatatcatatacaacatgttgatgccacatgtttgtttcatatgctaattcagt
gtgagctatggtcagtttggttgagagttacactttataaaaactattttttaaggcagtgtcttataacaaatttcattttaattttatgatttttcaaattt
ttgaaatttatttccttctaattctaatttttctattatggtgttcacatgtctacatgaaactcttgaattccttgtcaaattctaataacaaaaacatgttttg
gaaactacatatttttagtttttttttctttaacaaaacatggaaacttaggatgaaagtagtgtttataaggttatttttcaaaaacaaaatatcaaatgattat
caaatgagaccttaattcttaaaatttggctacgattttgaaatattattaaaaagtatataacaaaacaaaaacaaagaatgtcacgagtaaattttgttt
ctataaatttaaattaaaaaaaatttaaaaatagagatcaaataatcataaaaagagcctatgtgtgattggcatgtaaaaagataaggttttgagcc
attgatgatagtggaagcttgtgaagaattaaagatgaccttacacttcatgtatggacataaaatgtcatcttcatagaatattcaagaagatttgata
aatataatttttcactctttgtgacttctataaagtagttcaattgttgaagtaaaatggcaaaaaatggttttatgaactttcataaaattgataatcctcac
cccaattccatttgtttgtttttagtttttttaaaattaaacctatttttctatttcttgtaatgatttacatctttcttaggtgtaatcgttgaattcgtagtcaaat
tctaaaatgaaaaactaatttttttagtttcaaaatttggcttgactttaaaccattggtaaaaaaattagataacaaaggcaaaaatttggaattggaa
gtagtctctataaacttaattttcaaaaacaaaaaaaagaccaaaaaccaaatggttaccaaacgggatagtaatttttgaattgatttgtacaatttagtt
cttctttttgtaataattaagtgtgtcaattcttaatacgtaataactaacttaatatttgtagctaataaaataatattttttgtctttaattagtttataagatgt

FIG. 6H gactgtaagaaattctattaaatgttttttttcaccatagaagttaaattgttaaataattgaaagtttatggattaaactttacataattgtttaaaaattaa
attattacaaaactagaaaatttagaggttaaaagtgtttttttttttttttttttaacttaaaaggttttatttgga

SEQ ID No. 19:

>c_lanatus_CDS
atgacggattatcgtttgtcgacgatgaatctctggactgacgaaaacgcgtcggtgatggacgctttcatgaactccgatctgtcctcttactgggctcc
atctgccgcctcctctcactctcttcaccacccaccgccgcctcagtcctccgcctccacctccactcccccaccggacccgcccaagtccctgcctgttttc
aatcaggagactctgcagcagcggctccaggcgctgatcgatggcgctagggagagttggacttacgcgatttctggcagtcgtcctatgattattcc
ggtgcgtcggttttagggtggggagatgggtattacaaaggggaggaggataaagggaagggaaaagcgaaaatggtgtcgtcggcggcagagc
aggctcatcggaagaaggttttacgggagcttaactctttaatttctggctccgctgccggaccggacgatgcggtggatgaggaggttacggatacg
gagtggttctttttggtttcgatgactcagtcttttgataatggagtttggttaccgagtcaggcgttttacaactcgacgccgatttgggtttctggcgccg
atcggctgtcggcgtctgcctgtgaacgggccagacaggggagggtttttgggttacagacgatggtctgtattccatcgccaaacggagttgtggaa
atgggttcgacggaattgattcatcgaacgtcggatttgatgaacaaggtcaagattctgttcaatttcaacaatctcgaaacgagttcttggatatcggg
aaccaccgccgccgatgaaggggaaaacgacccgtcgtcgatgtggatcagtgagccgtcgagtactatcgagatgaaggattccattaccaccacc
gtcccttccggcaacgtcccggcaaagccaatccattcggaaaatcccagttccagcagcttaacggaaaatatcagcgcgatccaacaaccatcccat
caaaaacaaagccaaagcttcttaaatttctccgattacggcttcgaatcaaatccctcaaagaacaccaccgcggccgcaacaaccaccaccgccacc
ccatcattcaagccggaatccggcgggatgctgaatttcggcaacggaaacctcttctctagccattcacagtatgtaacaaacgaacagaacgagaaa
aagagatcccctgcttctcggagtagcaacgacgaagggatcctctctttcacctctggcgtgatcttaccctcctccggtaaggtaaaatccggggact
cagaccactcagatctcgaagcatcggtgatcagagaagtggatagctgtacaaaatcattagaacccgaaaaacgtccaagaaaaagaggtagaaa
accagcaaacggaagagaagagccattgaatcatgtagaagcagagagacaacggcgagagaagttgaaccagaaattctacgctctccgagctgt
agttccaaacgtatctaaaatggacaaggcctcactactgggagacgcggtttcttacatcaacgagctcaaatcaaagctccaaatagcggaaacgg
agaaaacagagatgggaaaacatttagaattgctgaagaaggagatgggagggaaagatttcgggaattacccgaacccaaatgatgaagatctga
aaatagggaaaagaaaggtaatggatatggagatcgaagttaaaatcatgggttgggatgcgatgataaggattcaaagcagcaagaaaaatcatc
cggcggcaaggctgatggcggcgtttaaggatttagatttagaaatgcttcatgcgagtgtttctgtagtgaatgatttgatgattcaacaggcaacggt
gaagatggggagcagattttacacacaggagcagcttaaaatggctctcgtcgcccgagtcgggggcggcggcggcagcagccatggaatgatgta
a

SEQ ID No. 20:

>c_lanatus_AA
MTDYRLSTMNLWTDENASVMDAFMNSDLSSYWAPSAASSHSLHHPPPPQSSASTSTPPPDPPKSLPVFNQETL
QQRLQALIDGARESWTYAIFWQSSYDYSGASVLGWGDGYYKGEEDKGKGKAKMVSSAAEQAHRKKVLRELNSLI
SGSAAGPDDAVDEEVTDTEWFFLVSMTQSFDNGVWLPSQAFYNSTPIWVSGADRLSASACERARQGRVFGLQT
MVCIPSPNGVVEMGSTELIHRTSDLMNKVKILFNFNNLETSSWISGTTAADEGENDPSSMWISEPSSTIEMKDSITTT
VPSGNVPAKPIHSENPSSSSLTENISAIQQPSHQKQSQSFLNFSDYGFESNPSKNTTAAATTTTATPSFKPESGGML
NFGNGNLFSSHSQYVTNEQNEKKRSPASRSSNDEGILSFTSGVILPSSGKVKSGDSDHSDLEASVIREVDSCTKSLE
PEKRPRKRGRKPANGREEPLNHVEAERQRREKLNQKFYALRAVVPNVSKMDKASLLGDAVSYINELKSKLQIAETE
KTEMGKHLELLKKEMGGKDFGNYPNPNDEDLKIGKRKVMDMEIEVKIMGWDAMIRIQSSKKNHPAARLMAAFKD
LDLEMLHASVSVVNDLMIQQATVKMGSRFYTQEQLKMALVARVGGGGGSSHGMM

FIG. 6I

FIG. 8
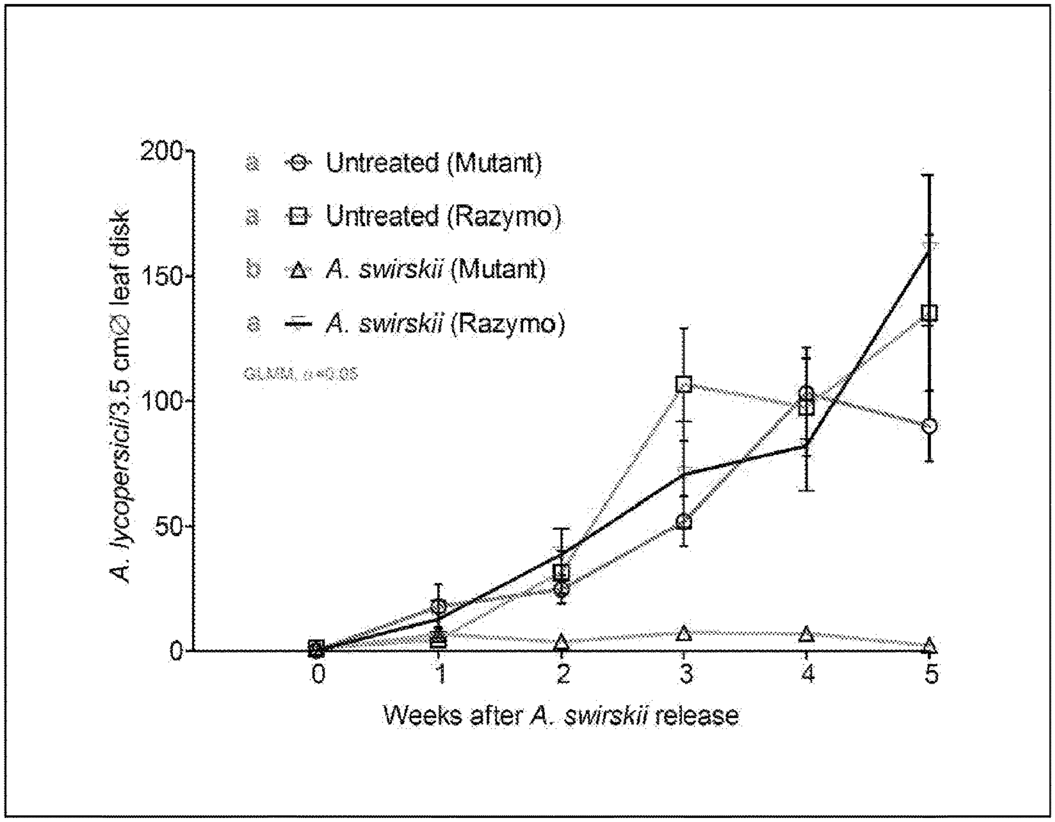
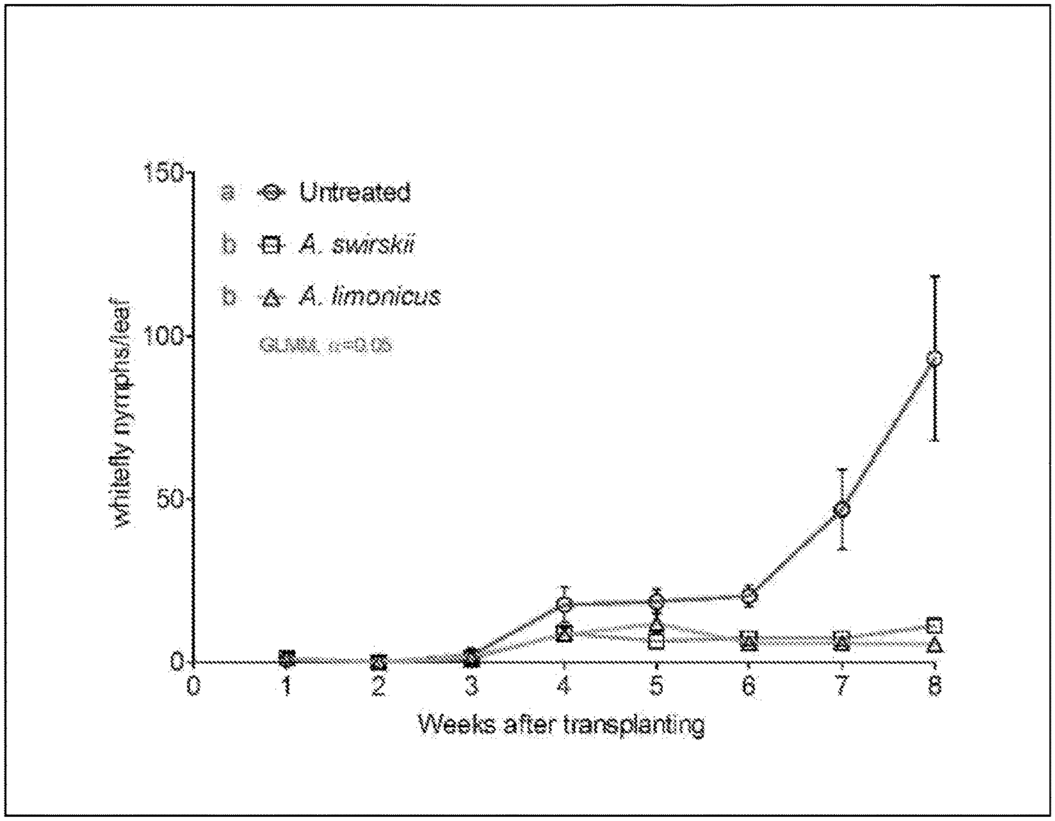
FIG. 9

TOMATO PLANTS ALLOWING THE ESTABLISHMENT OF MITES

RELATED APPLICATIONS AND INCORPORATION BY REFERENCE

This application is continuation of application Ser. No. 15/412,241 filed Jan. 23, 2017, now allowed, which is a continuation-in-part application of international patent application Serial No. PCT/EP2015/068860 filed Aug. 17, 2015, which published as PCT Publication No. WO 2016/026816 on Feb. 25, 2016, which claims benefit of European patent application Serial No. EP 14181306.3 filed Aug. 18, 2014.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 14, 2019, is named Y7954_01294SL.txt and is 101 kbytes in size.

FIELD OF THE INVENTION

The present invention relates to a *Solanum lycopersicum* plant that has an aberrant glandular hair phenotype. The invention also relates to the seeds and progeny of such plants and to propagation material for obtaining such plants. Furthermore, the invention relates to the use of the plants, seeds and propagation material for conferring the aberrant glandular hair phenotype to tomato plants. The invention also relates to sequences and the use of sequences for identifying the aberrant glandular hair phenotype.

BACKGROUND OF THE INVENTION

Plants of the species *Solanum lycopersicum* (tomato) belong to the nightshade family, also known as Solanaceae. Within this family it is nowadays grouped in the genus *Solanum*, which does not only harbor tomato, but also the important food crops potato and eggplant. It is a perennial, herbaceous, flowering plant species which is native to South America.

Other species that are related to tomato within the *Solanum* genus are for example *Solanum pimpinellifolium, Solanum chilense, Solanum peruvianum* and *Solanum habrochaites*. Although it is known that crossing can be considerably difficult, these species are used to obtain traits that are valuable in growing tomato plants. In the recent history, advancement in tomato breeding has led to tomato varieties having, for example higher yield, higher disease resistance and increased shelf life.

Commercial vegetable production, including the production of tomato, is affected by many conditions. The choice of the grower for a certain variety is a determining factor, and forms the genetic basis for the result that can be achieved. In addition, there are many external factors that influence the outcome. Growing conditions like climate, soil, and the use of inputs like fertilizer play a major role. There are various ways of cultivating tomatoes and other crops, among which, the most common are: open field, greenhouse and shade house production. Although the species can be grown under a wide range of climatic conditions, it performs most successfully under dry and warm conditions. In addition to this, the presence of pests and diseases also affects the total yield that can be reached.

Pest and disease management in the production of tomato and other crops can, depending on the way the plants are grown, be done in several ways. On the one hand, breeding focuses on the addition of resistances to pests and diseases to the trait portfolio of plants. Wild relatives of certain species often form a useful source of such resistant germplasm. Alternatively, the growing conditions can be modified in such a way that temperature, humidity levels or light intensity are selected to create less favourable settings for the development of diseases and pests. Often the temperatures that are favourable for the successful production of plants and/or fruits, are also favourable for important pest such as whiteflies. Thirdly, herbicides or pesticides can be used to eradicate weeds and pests, respectively. However, the use of such chemical compounds is under discussion as it might leave residues on plants and fruits that could be compromising to the health of consumers when said plants and/or fruits are consumed.

When vegetables are grown in greenhouses, a fourth pest management alternative is available to growers, which is known as biological pest control. By releasing living organisms that exert their predacious, parasitical and/or herbivorous capacity together with an active human management role, natural enemies can be used to control certain pests. There are various insects known in the art that are commercially reared for use in greenhouses. One of the important insect families in this respect is formed by the Phytoseiidae that is widely used in the biological control of whiteflies, spider mites and thrips.

In addition, WO06/057552 describes a method for biological pest control by making use of the phytoseiid predatory mite *Amblyseius swirskii*. However, these mites are not able to establish themselves on tomato plants, meaning that they are not able to live and reproduce. This makes them unsuitable for use as an efficient biological pest control. Tomato growers can be blocked by the absence of such biological pest controls, because good resistances aimed at insects especially for whitefly, are not yet present in tomato varieties. If a greenhouse is infested by whiteflies, a complete batch of plants might become useless for high yield and high quality vegetable production as the plants might be severely affected. The same applies to the phytoseiid predatory mite *Amblydromalus limonicus*, that is also not capable to establish on tomato plants.

For the predatory mite *Phytoseiulus persimilis*, it is known that it can be used to combat *Tetranychus urticae* (red spider mite) on tomato plants, but this predator exclusively feeds on *Tetranychus* species and thus cannot be deployed to combat infestations of other species. For another predatory mite, *Neoseiulus californicus*, a very low performance on tomato plants has been shown in the control of a *Tetranychus* species infestation.

Citation or identification of any document in this application is not an admission that such document is available as prior art to the present invention.

SUMMARY OF THE INVENTION

Thus, there exists a need for tomato plants that allow for application of biological pest control by the proper establishment of mites, in particular the predatory mites *Amblyseius swirskii* and/or *Amblydromalus limonicus*. Upon successful establishment, the mites can perform their desired role: function as a biological pest control in fighting infestation by whitefly as well as thrips.

In the research that led to the present invention, novel tomato plants were developed, which may comprise a modified Slmyc2 gene that is capable of conferring an aberrant glandular hair phenotype, allowing for the establishment of mites, in particular the predatory mites *Amblyseius swirskii* and/or *Amblydromalus limonicus*. More in detail, it was determined that the predatory mites are hampered by the presence and/or appearance of a specific type of trichomes or glandular hairs that are present on the stems and leaves of tomato plants and/or by volatiles that are produced in the glandular hair cells.

The present invention relates to a modified Slmyc2 gene, which may comprise at least one modification as compared to the wild type sequence of SEQ ID No. 5, which modification leads to the reduction or absence of SlMYC2 protein activity, wherein the modified Slmyc2 gene is capable of conferring an aberrant glandular hair phenotype to a *Solanum lycopersicum* plant. The modification may be suitably selected from a modification that decreases the mRNA level of the Slmyc2 gene, a modification that decreases the level of the SlMYC2 protein and/or a modification that decreases the activity of the SlMYC2 protein, as compared to the wild type Slmyc2 gene of SEQ ID No. 5.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as “comprises”, “comprised”, “comprising” and the like can have the meaning attributed to it in U.S. Patent law; e.g., they can mean “includes”, “included”, “including”, and the like; and that terms such as “consisting essentially of” and “consists essentially of” have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

Representative seeds of *Solanum lycopersicum* with the modified Slmyc2 gene of the invention, capable of conferring an aberrant glandular hair phenotype, that allows for the establishment of mites, in particular the predatory mites *Amblyseius swirskii* and/or *Amblydromalus limonicus*, were deposited under accession number NCIMB 42222 on Feb. 24, 2014 with NCIMB Ltd. (Ferguson Building, Craibstone Estate, Bucksburn, Aberdeen, AB21 9YA). All seeds of the deposit comprise the modified Slmyc2 gene homozygously. Plants grown from these seeds thus allow the establishment of mites, in particular the predatory mites *Amblyseius swirskii* and/or *Amblydromalus limonicus*.

The deposited seeds do not meet the DUS criteria which are required for obtaining plant variety protection, and can therefore not be considered to be a plant variety.

The Deposits with NCIMB Ltd. (Ferguson Building, Craibstone Estate, Bucksburn, Aberdeen, AB21 9YA), under deposit accession number NCIMB 42222 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIGS. 1A-1C: Sequences of the modified Slmyc2 gene of the invention. SEQ ID No. 1 depicts the genomic DNA sequence. In SEQ ID No. 1, the first base pair (bp) of the start codon is located at position 2648. The last bp of the stop codon is located at position 4540 of SEQ ID No. 1. SEQ ID No. 2 reflects the coding sequence (CDS). SEQ ID No. 3 depicts the protein sequence. SEQ ID No. 4 depicts the mutant sequence of the in-gene marker SL06992.

FIGS. 2A-2C: Sequences of the wild type Slmyc2 gene. SEQ ID No. 5 depicts the genomic DNA sequence. In SEQ ID No. 5, the first base pair (bp) of the start codon is located at position 2648. The last bp of the stop codon is located at position 4540 of SEQ ID No. 5. SEQ ID No. 6 reflects the coding sequence (CDS). SEQ ID No. 7 depicts the protein sequence. SEQ ID No. 8 depicts the wild type sequence of the in-gene marker SL06992.

FIG. 4A: Table showing the level of selected volatiles in arbitrary units (A.U.) for plants comprising the mutation homozygously (Mo14/001-006), plants comprising the mutation heterozygously (Mo14/007-012) and for wild type plants (Mo14/013-018).

Aldehyde: cis-3-hexenal

Monos: α-pinene, mycrene, carene, α- and β-phellandrene, p-cymene, limonene. Sesquiterpenes: δ-elemene, β-caryophyllene, α-humulene. Monoterpenoid: verbenene †: corrected for limonene ‡: also known as α-caryophyllene FIG. 4B: Table_showing the average levels of selected volatiles as measured in arbitrary units (A.U.) for plants comprising the mutation heterozygously (Mo14/007-012) and for wild type plants (Mo14/013-018)); the P-values were calculated with a Student's t-test and indicate whether the difference between the heterozygous and wild type plants is significant (P<0.05).

Figure 5A:
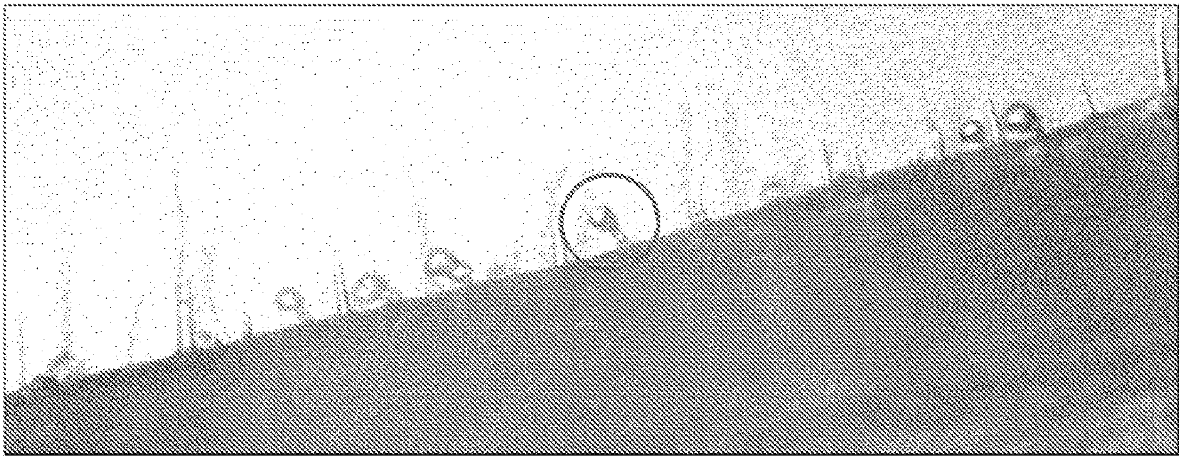
Figure 5B:
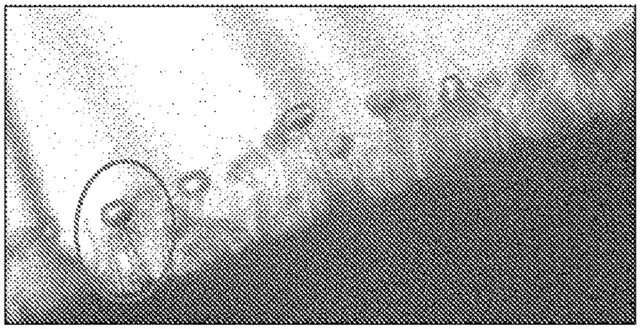

FIGS. 5A-5B: Pictures of glandular hair phenotypes. In FIG. 5A, a type VI trichome as found on tomato plants of the invention, is indicated with the circle. In FIG. 5B, a type VI trichome as found on non-mutant background tomato plants, is indicated with the circle.

FIGS. 6A-6I: MYC2 amino acid sequences of other plant species. SEQ ID No. 9 to 11 respectively depict the genomic DNA sequence, the coding DNA sequence and the amino acid sequence of *Capsicum annuum*. In SEQ ID No. 9, the first basepair (bp) of the start codon is located at position 2387. The last bp of the stop codon is located at position 4459 of SEQ ID No. 9. SEQ ID No. 12 to 14 respectively depict the genomic DNA sequence, the coding DNA sequence and the amino acid sequence of *Cucumis sativus*. In SEQ ID No. 12, the first basepair (bp) of the start codon is located at position 1578. The last bp of the stop codon is located at position 3563 of SEQ ID No. 12. SEQ ID No. 15 to 17 respectively depict the genomic DNA sequence, the coding DNA sequence and the amino acid sequence of *Cucumis melo*. In SEQ ID No. 15, the first basepair (bp) of the start codon is located at position 2515. The last bp of the stop codon is located at position 4503 of SEQ ID No. 15. SEQ ID No. 18 to 20 respectively depict the genomic DNA sequence, the coding DNA sequence and the amino acid sequence of *Citrillus lanatus*. In SEQ ID No. 18, the first basepair (bp) of the start codon is located at position 2408. The last bp of the stop codon is located at position 4378 of SEQ ID No. 18

Figure 7:
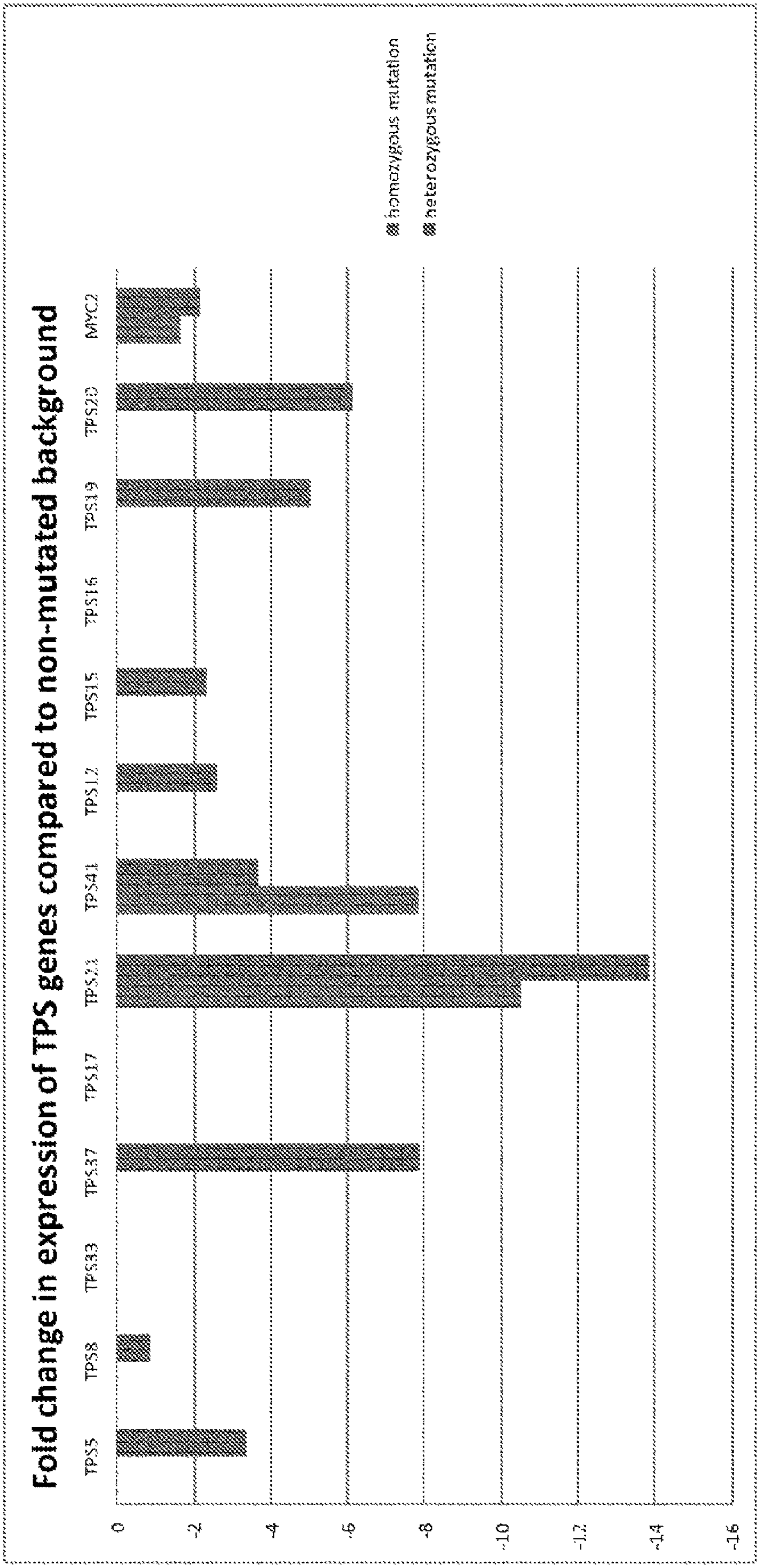

FIG. 7: Expression of terpene synthase genes in the homo- and heterozygous plants of the invention and the non-mutant background plants.

FIG. 8: Average density (number±SE) of *Aculops lycopersici* per 3.5 cm 0 leaflet per week on plants comprising the modified Slmyc2 gene (Mutant) and Razymo, respectively. Evaluations started just before the *A. swirskii* release (week 0), which was released four weeks after *A. lycopersici*. Legends with the same letter are not significantly different (GLMM, P>0.05)

FIG. 9: Average density (number±SE) of *Bemisia tabaci* nymphs per leaf of plants comprising the modified Slmyc2 gene during the experiment. Legends with the same letter are not significantly different (GLMM, P>0.05)

Figure 10B:
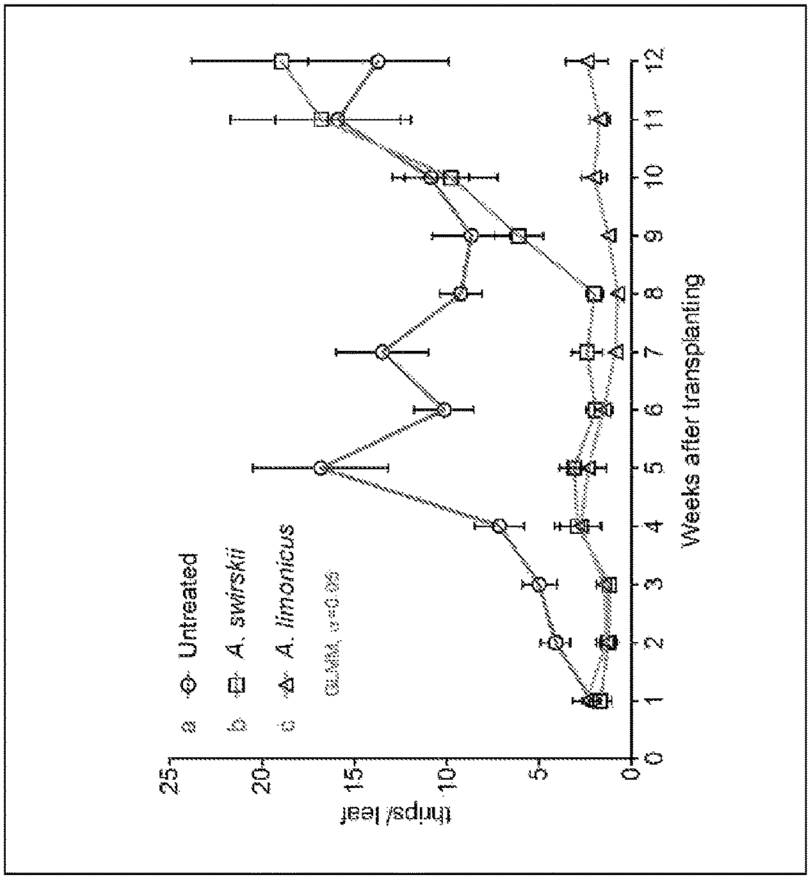
Figure 10A:
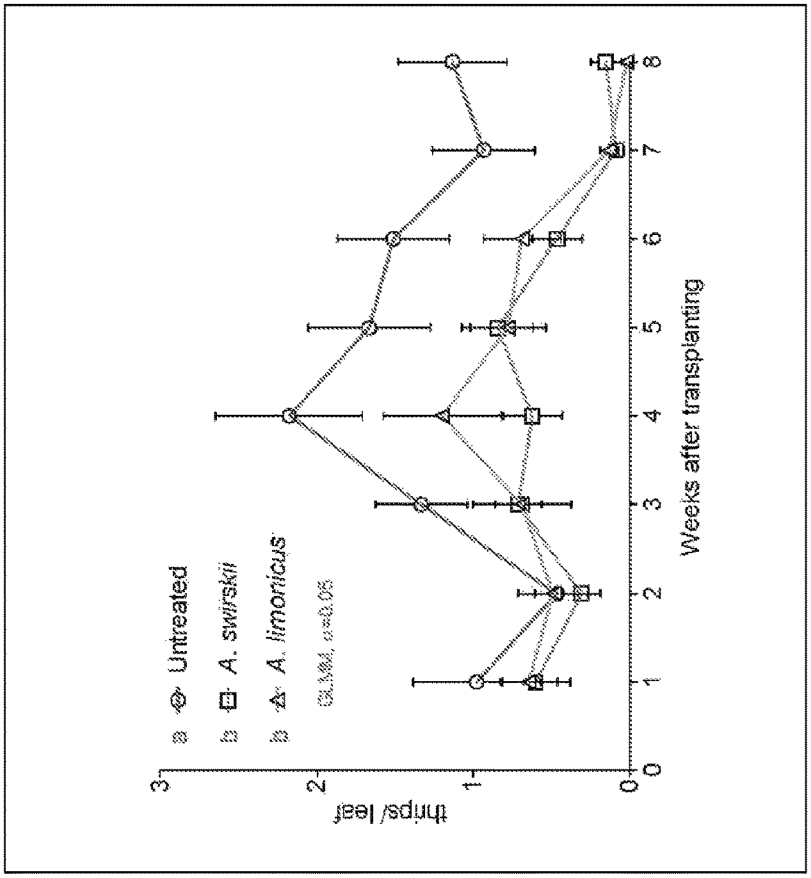

FIG. 10A: Average density (number±SE) of *Frankliniella occidentalis* per leaf of plants comprising the modified Slmyc2 during the summer experiment. Legends with the same letter are not significantly different (GLMM, P>0.05).

FIG. 10B: Average density (number±SE) of *Frankliniella occidentalis* per leaf of plants comprising the modified Slmyc2 during the winter experiment. Legends with the same letter are not significantly different (GLMM, P>0.05).

DETAILED DESCRIPTION OF THE INVENTION

The surface of the various plant parts of tomato and other crops is covered with trichomes, both non-glandular and glandular. Non-glandular trichomes are usually regarded as 'hairs' and do not produce, store, or secrete specific biochemical compounds.

A glandular trichome typically consists of a stalk, made up of one or more cells, and one or more glandular cells at the tip of the stalk that form the glandular head. Four different types of glandular trichomes are identified in tomato and related *Solanum* species, namely types I, IV, VI, and VII. These types differ in size and length of the stalks, and in number of secretory cells that form the glandular head. A variety of biochemical compounds in tomato are produced in glandular trichomes. (McDowell et al., Plant Physiology Vol. 155, 524-539 (2011)).

Biochemical compounds that are produced by the various glandular trichomes in tomato may comprise terpenes, terpenoids, flavonoids, fatty acids, alkaloids, and acyl sugars such as acyl glucoses and acyl sucroses. These compounds are known to play important roles in attracting and repelling various insects and in determining susceptibility to certain diseases. However, many aspects of the roles of these metabolites are still unclear, and extensive research is ongoing to determine more precisely the functionality of glandular trichomes and the substances they excrete.

The invention thus relates to a modified Slmyc2 gene, which may comprise at least one modification as compared to the wild type genomic sequence of SEQ ID No. 5, which modification leads to reduction or absence of Slmyc2 protein activity, wherein the modified Slmyc2 gene is capable of conferring an aberrant glandular hair phenotype to a *Solanum lycopersicum* plant.

The modified slmyc2 gene is also referred to herein as "the gene of the invention", or "the modified slmyc2 gene of the invention". These terms are used interchangeably herein.

In an embodiment, the modification leading to the modified Slmyc2 gene, is selected from a modification that decreases the mRNA level of the Slmyc2 gene; a modification that decreases the level of the Slmyc2 protein; and/or a modification that decreases the activity of the Slmyc2 protein, as compared to the wild type Slmyc2 gene.

In a further embodiment, the modification leading to the modified Slmyc2 gene, results in the presence of a premature stop codon within the coding sequence.

In a preferred embodiment, the modification leading to the modified Slmyc2 gene, results in the presence of a premature stop codon within the coding sequence, in particular the modification which may comprise a single nucleotide polymorphism (SNP) on position 1477 of SEQ ID No. 2, being the coding sequence (CDS). The CDS is that portion of a gene, composed of exons, that codes for protein. SEQ ID No.2 may comprise the presence of a SNP from nucleotide G (wild type) to T. This SNP is the same as the SNP on position 4124 of SEQ ID No. 1, which is the corresponding genomic sequence. This SNP results in a stop codon at amino acid position 493 of SEQ ID No. 3, whereas the wild type amino acid sequence (SEQ ID No. 7) may comprise a Glycine residue at this position. This SNP, resulting in a modified Slmyc2 gene can be found in plants grown from seed of which a representative sample was deposited with the NCIMB under accession number NCIMB 42222.

In another embodiment, the modified Slmyc2 gene of the invention relates to any SNP occurring in SEQ ID No. 6, which is the wild type CDS, that results in the presence of a premature stop codon within that coding sequence. Such a SNP is referred to as a nonsense mutation. Any such a SNP will thus result in a premature stop codon in SEQ ID No. 6. Preferably, the modified Slmyc2 gene of the invention relates to any SNP occurring before position 1477 of SEQ ID No. 6 that results in the presence of a premature stop codon within that coding sequence. Any such SNP will thus result in a premature stop codon before amino acid position 493 of SEQ ID No. 7.

A SNP might also be a mutation in the coding sequence that codes for a different amino acid, instead of a stop codon. Such a SNP is referred to as a missense mutation. The invention also relates to missense mutations resulting in a modified Slmyc2 gene of in the invention.

Modifications in the coding sequence other than SNP's that might result in the modified Slmyc2 gene of the invention include insertions and/or deletions. Insertion of one or more nucleotides might affect proper mRNA splicing or result in a shift in the reading frame. These events can result in a decreased level of SlMYC2 protein and/or in a decreased level of SlMYC2 protein activity. Deletion of one or more nucleotides might, like insertions, result in a shift in the reading frame. This event can result in a decreased level of SlMYC2 protein and/or in a decreased level of SlMYC2 protein activity.

The invention also relates to modifications in the non-coding genomic sequence of Slmyc2, represented by SEQ ID No. 5. Modifications in the non-coding sequence include mutations in the intron sequence, the upstream and/or downstream sequence. The upstream sequence, the sequence before the start codon of the gene of the invention, may comprise the promoter and the 5'-untranslated region (5'-UTR), also called the leader sequence. Since these regions are involved in the regulation of the gene transcription to mRNA and the subsequent translation, and therefore in gene expression, suitable modification can lead to a decrease of the expression through a decrease of the Slmyc2 mRNA level and/or a decrease in the level of the SlMYC2 protein.

The aberrant glandular hair phenotype caused by the gene of the invention was intensively studied. It was determined that the aberrant glandular hair phenotype is particularly observed for type VI trichomes, but might also extend to other types of glandular hairs. Remarkably, the aberrant glandular hair phenotype for type VI glandular hairs on plants of the invention is characterized by the reduction and preferably absence of both mono- and sesquiterpenes, in particular α-pinene, myrcene, carene, α-phellandrene, β-phellandrene, p-cymene, limonene, δ-elemene, β-caryophyllene and/or α-humulene, and/or is characterized by deformed glandular hairs. The aberrant glandular hair phenotype of the invention is further characterized by the reduction and preferable absence of monoterpenoid compounds, in particular verbenene. Other volatiles, such as an aldehyde, were found to be present in aberrant type VI glandular hairs on plants of the invention as well as in the non-mutant background plants (see Example 5).

Of type VI glandular hairs found on plants of the invention, both the stalk cell as well as the head consisting of four glandular cells appear shrunken, less developed and/or dried when compared to the same cells of non-mutated type VI glandular hairs. These deformed type VI glandular hairs also appear to be smaller than non-mutated type VI glandular hairs. This reduction in size might be the direct result from the shrunken, less-developed and/or dried character (see FIGS. 5A-B).

The aberrant glandular hair phenotype does not attract the predatory mites, but it enables and facilitates the mites to roam freely on the plants. 'Predatory mites' or 'mites' as referred to herein, belong to the Phytoseiidae family. The invention relates to this complete family, which may comprise the species *Amblyseius swirskii, Amblydromalus limonicus, Phytoseiulus persimilis* and *Neoseiulus californicus.*

Thus, the invention relates to a modified Slmyc2 gene, which may comprise at least one modification as compared to the wild type genomic sequence of SEQ ID No. 5, which modification leads to reduction or absence of Slmyc2 protein activity, wherein the modified Slmyc2 gene is capable of conferring an aberrant glandular hair phenotype to a *Solanum lycopersicum* plant, wherein the aberrant glandular hair phenotype is further characterized by the reduction and preferably absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs. The aberrant glandular hair phenotype, or the trait of the invention, allows for the establishment of predatory mites, in particular *Amblyseius swirskii* and/or *Amblydromalus limonicus*, on a *Solanum lycopersicum* plant. The aberrant glandular hair phenotype, or the aberrant glandular hair phenotype which allows for the establishment of predatory mites, in particular *Amblyseius swirskii* and/or *Amblydromalus limonicus*, is also referred to herein as "the trait" or "the trait of the invention". These terms are used interchangeably herein.

The said aberrant glandular hair phenotype of the invention is conferred by a modified Slmyc2 gene, the inheritance of which is consistent with that of a monogenic trait. Preferably, said inheritance is consistent with that of a monogenic intermediate trait. In this context, the term "intermediate" is to mean that the aberrant glandular hair phenotype is observable in plants which may comprise the modified Slmyc2 gene in homozygous as well as in heterozygous state.

An example of the modified Slmyc2 gene can be found in plants grown from seed of which a representative sample was deposited with the NCIMB under accession number NCIMB 42222.

In an embodiment, the invention relates to a *Solanum lycopersicum* plant which may comprise the modified Slmyc2 gene of the invention.

The invention relates to a *Solanum lycopersicum* plant that may comprise a modified Slmyc2 gene, wherein said modified Slmyc2 gene results in an aberrant glandular hair phenotype that allows for the establishment of predatory mites, in particular *Amblyseius swirskii* and/or *Amblydromalus limonicus*, on said tomato plant. This plant is also referred to herein as a plant of the invention.

In a preferred embodiment, a plant of the invention may comprise the modified Slmyc2 gene in homozygous state. When a plant comprises the modified Slmyc2 gene in homozygous state, the trait of the invention is characterized by the reduction and preferably absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

In an embodiment, a plant of the invention may comprise the modified Slmyc2 gene in heterozygous state. When a plant comprises the modified Slmyc2 gene in heterozygous state, the trait of the invention is characterized by the reduction of terpenes, in particular α-pinene, myrcene, carene, α-phellandrene, β-phellandrene, p-cymene, limonene and/or δ-elemene, and/or is characterized by deformed glandular hairs. In this context, the term "reduction of terpenes" is to mean that the level of terpenes is reduced but not completely absent when compared to plants which may comprise the wild type Slmyc2 gene homozygously. The level of terpenes is, in increasing order of preference, 10%, 20%, 30%, 40%, 50%, 60%, 70%, 80%, 90% reduced when compared with the level of terpenes in a plant which may comprise the wild type Slmyc2 gene homozygously.

The present invention also relates to a *Solanum lycopersicum* plant, wherein the modified Slmyc2 gene of the invention is the same as or equivalent to the modified Slmyc2 gene that is found in or obtainable from the genome of *Solanum lycopersicum* plants grown from seeds of which a representative sample was deposited with the NCIMB under accession number NCIMB 42222. With the same or equivalent, it is meant that no segregation for the trait of the invention is observed in the F2 resulting from a cross that is part of an allelism test as described herein. With the same or equivalent, reference is also made to a myc2 gene that is obtained from a wild relative of *Solanum lycopersicum* and modified to confer the same aberrant glandular hair phenotype. In this respect, wild relatives of *Solanum lycopersicum* include: *S. arcanum, S. chmielewskii, S. neorickii, S. cheesmaniae, S. galapagense, S. pimpinellifolium, S. chilense, S. corneliomulleri, S. habrochaites, S. huaylasense, S. sisymbriifolium, S. peruvianum*, and *S. pennellii.*

The invention further relates to a *Solanum lycopersicum* plant which may comprise the modified Slmyc2 gene homozygously or heterozygously, and which is causative of an aberrant glandular hair phenotype, that allows for the establishment of mites, in particular the predatory mites *Amblyseius swirskii* and/or *Amblydromalus limonicus* on said tomato plant, when compared to a *Solanum lycopersicum* plant not carrying said modified Slmyc2 gene.

In one embodiment, the invention provides a *Solanum lycopersicum* plant exhibiting the trait of the invention, conferred by a modified Slmyc2 gene, which *Solanum lycopersicum* plant is obtainable by crossing a *Solanum lycopersicum* plant which may comprise said modified Slmyc2 gene of which a representative sample of seed was deposited under NCIMB accession number NCIMB 42222 with another *Solanum lycopersicum* plant to produce an F1, subsequently selfing said F1 to obtain an F2, and selecting a *Solanum lycopersicum* plant of the invention.

Furthermore, it was found during the research leading to the present invention that the modified Slmyc2 gene of the invention is located on chromosome 8 of *Solanum lycopersicum.*

More in particular, in the deposit NCIMB 42222 the modified Slmyc2 gene of the invention, the genomic sequence of which is represented by SEQ ID No. 1, is located on chromosome 8 of *Solanum lycopersicum.*

The invention also relates to a *Solanum lycopersicum* plant, which may comprise the modified Slmyc2 gene of the invention, wherein said modified Slmyc2 gene is obtainable by introgression from a *Solanum lycopersicum* plant grown from seeds of which a representative sample was deposited under NCIMB accession number NCIMB 42222, and wherein said modified Slmyc2 gene, the genomic sequence of which is represented by SEQ ID No. 1, in the seeds of the seed deposit number NCIMB 42222 is positioned on chromosome 8 of *Solanum lycopersicum.*

A *Solanum lycopersicum* plant of the invention can be suitably identified amongst descendants from a cross between a *Solanum lycopersicum* plant not allowing the establishment of predatory mites, in particular *Amblyseius swirskii* and/or *Amblydromalus limonicus*, and a plant that carries the modified Slmyc2 gene, preferably in the homozygous state, by growing F2 plants from seeds that are the result of the initial cross and a selfing step, and selecting plants expressing the aberrant glandular hair phenotype. Plants can be selected on the basis of determining the phenotype through a bioassay as described in Example 2, or through the identification of the modified Slmyc2 gene, for example by comparison with SEQ ID No. 5 or SEQ ID No. 6 or using markers that are disclosed herein.

In order to determine equivalence of genetic determinants that cause a particular phenotypic trait the well-known allelism test, more specifically designated as complementation test, can be used. To determine whether a plant shows the same aberrant glandular hair phenotype as plants of the invention, an allelism test can be performed in which a tester plant which is homozygous for the modified Slmyc2 gene of the invention is crossed with material to be tested that is also homozygous for its genetic determinant. When no segregation for aberrant glandular hair phenotype is present in the F2 of the cross, the genetic determinants have been proven to be equivalent or the same and the plant is thus a plant of the invention.

The tester plant is suitably a plant of deposit NCIMB 42222, or a progeny plant of the deposit showing an aberrant glandular hair phenotype that allows for the establishment of mites, in particular the predatory mites *Amblyseius swirskii* and/or *Amblydromalus limonicus* on said *Solanum lycopersicum* plant.

The *Solanum lycopersicum* plant of the invention can be any one of the types of cultivated tomato from the following group: cherry, plum, cocktail, truss, beefsteak, round, grape, etc.

In another embodiment, the invention relates to a *Solanum lycopersicum* seed which may comprise the modified Slmyc2 gene of the invention.

This seed is also referred to herein as a seed of the invention.

In a further embodiment, the plant grown from seed of the invention allows for the establishment of mites, in particular the predatory mites *Amblyseius swirskii* and/or *Amblydromalus limonicus*, when the modified Slmyc2 gene is present in heterozygous, preferably in the homozygous state.

The invention further relates to a *Solanum lycopersicum* seed which may comprise said modified Slmyc2 gene, which seed is capable of growing into a plant that exhibits the trait of the invention.

The invention also relates to progeny of the *Solanum lycopersicum* plants, cells, tissues, and seeds of the invention, wherein the progeny plants, cells, tissues, and seeds may comprise the modified Slmyc2 gene. Such progeny can in itself be plants, cells, tissues, or seeds.

The term "progeny" as used herein is intended to mean the first and all subsequent descendants from a cross with a plant of the invention that may comprise the said modified Slmyc2 gene. "Progeny" also encompasses plants that carry the modified Slmyc2 gene of the invention in homozygous or heterozygous state and are obtained from other plants or progeny of plants of the invention by vegetative propagation or multiplication.

The invention relates to a progeny plant of a *Solanum lycopersicum* plant which may comprise the modified Slmyc2 gene of the invention in homozygous or heterozygous state.

The invention also relates to a progeny plant of *Solanum lycopersicum* plant of the invention that exhibits the aberrant glandular hair phenotype, allowing for the establishment of mites, in particular the predatory mites *Amblyseius swirskii* and/or *Amblydromalus limonicus*, on said progeny plant. This progeny plant thus may comprise the modified Slmyc2 gene in the heterozygous, preferably homozygous state.

According to a further aspect thereof, the invention relates to propagation material capable of developing into and/or being derived from a *Solanum lycopersicum* plant which may comprise the modified Slmyc2 gene of the invention in homozygous or heterozygous state.

This propagation material is also referred to herein as propagation material of the invention.

In one embodiment, such propagation material is formed by a seed of the *Solanum lycopersicum* plant of the invention, wherein the seed is capable of developing into a plant that may comprise the modified Slmyc2 gene of the invention in homozygous or heterozygous state.

In a further embodiment, the propagation material of the invention is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts and cells.

In an additional embodiment, the invention relates to tissue culture of propagation material of the invention.

In another embodiment, the plant developed out of the propagation material may comprise a modified Slmyc2 gene as found in *Solanum lycopersicum* plants grown from seeds of which representative seed was deposited under NCIMB accession number NCIMB 42222.

The invention also relates to the harvested part of the *Solanum lycopersicum* plant which may comprise the modified Slmyc2 gene of the invention.

Moreover, the invention relates to a food product which may comprise one or more harvested parts of a *Solanum lycopersicum* plant which may comprise the modified Slmyc2 gene of the invention. The harvested part or food product can be, or may comprise the fruits of a *Solanum lycopersicum* plant. A preferred food product which may comprise a fruit—or parts thereof—of the *Solanum lycopersicum* plant of the invention is a salad, wherein the fruit may optionally be mixed with leaves of for example lettuce, spinach, endive, chicory, beet, Swiss chard, etc. The food product or harvested part may have undergone one or more processing steps. Such a processing step might comprise, but is not limited to any one of the following treatments or combinations thereof: cutting, washing, cooking, steaming, baking, frying, pasteurizing, freezing, grinding, extracting oil, pickling, or fermenting. The processed form that is obtained is also part of this invention.

Yet another aspect of the invention relates to the use of the modified Slmyc2 gene of the invention for the development of a *Solanum lycopersicum* plant on which predatory mites, in particular *Amblyseius swirskii* and/or *Amblydromalus limonicus* can establish.

In an embodiment, the invention relates to the use of the modified Slmyc2 gene of the invention for the development of a *Solanum lycopersicum* plant on which predatory mites, in particular *Amblyseius swirskii* and/or *Amblydromalus limonicus* can establish, wherein the establishment of said mites is allowed by an aberrant glandular hair phenotype.

In yet another embodiment, the invention relates to the use of the modified Slmyc2 gene of the invention for the development of a *Solanum lycopersicum* plant, wherein the modified Slmyc2 gene of the invention is capable of conferring an aberrant glandular hair phenotype to said *Solanum lycopersicum* plant, wherein the aberrant glandular hair phenotype is characterized by the absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

In another embodiment, the invention relates to the use of a plant of the invention in combination with the predatory mite *Amblyseius swirskii* for the control of a plant pest, in particular *Aculops lycopersici, Bemisia tabaci* and/or *Frankliniella occidentalis.*

In another embodiment, the invention relates to the use of a plant of the invention in combination with the predatory mite *Amblydromalus limonicus* for the control of a plant pest, in particular *Aculops lycopersici, Bemisia tabaci* and/or *Frankliniella occidentalis.*

In another embodiment, the invention relates to the use of a plant of the invention in combination with the predatory mites *Amblyseius swirskii* and *Amblyseius swirskii* for the control of a plant pest, in particular *Aculops lycopersici, Bemisia tabaci* and/or *Frankliniella occidentalis.*

In another embodiment, the invention relates to the use of a plant of the invention in combination with the predatory mite *Phytoseiulus persimilis* for the control of a plant pest, in particular *Tetranychus urticae.*

In another embodiment, the invention relates to the use of a plant of the invention in combination with the predatory mite *Neoseiulus californicus* for the control of a plant pest, in particular *Tetranychus urticae.*

In another embodiment, the invention relates to the use of a plant of the invention in combination with the predatory mite *Phytoseiulus persimilis* and *Neoseiulus californicus* for the control of a plant pest, in particular *Tetranychus urticae.*

The trait of the invention may be identified by, for instance, using suitable markers.

The skilled person knows how to develop new markers linked to a trait using already known genes, markers, QTLs, alleles or other DNA molecules that are associated with a certain trait, and sequences thereof.

The term "genetic determinant" as used herein encompasses one or more QTLs, genes, or alleles. These terms are used interchangeably. A genetic determinant can be identified by the position on a genetic map, or by indication of the location on a linkage group or chromosome. When a genetic determinant is no longer linked to a specific molecular marker, but its position on a chromosome as defined on a genetic map is unaltered, this genetic determinant is still the same as when it was linked to the molecular marker. The trait that it confers is therefore also still the same.

The invention further relates to a cell of a *Solanum lycopersicum* plant of the invention, which cell may comprise the modified Slmyc2 gene of the invention. The said cell thus may comprise the genetic information encoding the said aberrant glandular hair phenotype, in particular genetic information which is substantially identical, preferably completely identical to the genetic information encoding the said aberrant glandular hair phenotype, wherein the said genetic information is the modified Slmyc2 gene, which may comprise at least one modification as compared to the wild type sequence of SEQ ID No. 5. Preferably, the cell of the invention is part of a plant or plant part, but the cell may also be in isolated form.

The invention also relates to a cell of a *Solanum lycopersicum* plant, which cell may comprise the modified Slmyc2 gene of the invention, and which plant is obtained or obtainable by transferring the trait of the invention into an agronomically valuable *Solanum lycopersicum* plant. The trait of the invention is caused by the modified Slmyc2 gene of the invention which is as found in seeds of which a representative sample was deposited under NCIMB accession number NCIMB 42222.

The invention further relates to the use of seeds of a *Solanum lycopersicum* plant, which seed may comprise the modified Slmyc2 gene of the invention for transferring the modified Slmyc2 gene into another agronomically valuable *Solanum lycopersicum* plant.

The invention also relates to the use of seeds of which a representative sample was deposited under NCIMB accession number NCIMB 42222 for transferring the modified Slmyc2 gene of the invention into another agronomically valuable *Solanum lycopersicum* plant.

The invention also relates to the use of a *Solanum lycopersicum* plant of the invention for the cultivation and preservation of predatory mites or a colony therefrom, with the aim of controlling an insect pest.

The invention also relates to the use of a *Solanum lycopersicum* plant which may comprise the modified Slmyc2 gene of the invention, as a crop.

The invention also relates to the use of a *Solanum lycopersicum* plant which may comprise the modified Slmyc2 gene of the invention as a source of seed.

The invention also relates to the use of a *Solanum lycopersicum* plant which may comprise the modified Slmyc2 gene of the invention as a source of propagating material.

The invention also relates to the use of a *Solanum lycopersicum* plant which may comprise the modified Slmyc2 gene for consumption.

In plant species other than *Solanum lycopersicum*, the homolog of Slmyc2 might influence the glandular hair phenotype. Therefore, the invention also relates to a modified myc2 gene capable of conferring an aberrant glandular hair phenotype to a plant, which modification leads to reduction or absence of MYC2 protein activity, and wherein the modification may be selected from a modification that decreases the mRNA level of the myc2 gene; a modification that decreases the level of the MYC2 protein; and/or a modification that decreases the activity of the MYC2 protein, as compared to a non-modified wild type myc2 gene.

The invention also relates to a modified myc2 gene that leads to the reduction and/or absence of terpenes in a plant. The modified myc2 gene can be present in heterozygous or homozygous state. The myc2 gene can be modified in the same or equivalent way as the Slmyc2 gene, as described herein.

The aberrant glandular hair phenotype conferred by modified myc2 gene is characterized by the absence and/or reduction of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs. In this respect, absence of terpenes is a level of terpenes that is not detectable by currently available measurement techniques and/or is at least, in increasing order of preference, 95%, 96%, 97%, 98%, 99% or 100% lower than the level of terpenes in a plant which may comprise the wildtype myc2 gene homozygously. The term "reduction of terpenes" is to mean in this context that the level of terpenes is reduced but not completely absent when compared to plants which may comprise the wild type myc2 gene homozygously. The level of terpenes is, in increasing order of preference, 10%, 20%, 30%, 40%, 50%, 60%, 70%, 80%, 90% reduced when compared with the level of terpenes in a plant which may comprise the wild type myc2 gene homozygously.

In an embodiment, a plant of the invention which may comprise the modified myc2 gene exhibits the aberrant glandular hair phenotype of the invention, allowing for the establishment of predatory mites, in particular *Amblyseius swirskii* and/or *Amblydromalus limonicus* on said plant.

In a preferred embodiment, a plant of the invention may comprise the modified myc2 gene in homozygous state. When a plant comprises the modified myc2 gene in homozygous state, the aberrant glandular hair phenotype allowing for the establishment of predatory mites, in particular *Amblyseius swirskii* and/or *Amblydromalus limonicus* on said plant, is characterized by the absence and/or reduction of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.

In an embodiment, a plant of the invention may comprise the modified myc2 gene in heterozygous state. When a plant comprises the modified myc2 gene in heterozygous state, the aberrant glandular hair phenotype allowing for the establishment of predatory mites, in particular *Amblyseius swirskii* and/or *Amblydromalus limonicus* on said plant, is characterized by the reduction of terpenes, in particular α-pinene, myrcene, carene, α-phellandrene, β-phellandrene, p-cymene, limonene, δ-elemene, β-caryophyllene and/or α-humulene. The term "reduction of terpenes" is defined above.

The invention further relates to the use of such a modified myc2 gene for the development of a plant that may comprise a reduced level of terpenes or a plant showing absence of terpenes.

The invention further relates to the use of such a modified myc2 gene for the development of a plant that exhibits an aberrant glandular hair phenotype, wherein said aberrant glandular phenotype is caused by the reduction or absence of MYC2 protein activity as compared to non-modified wild type MYC2 protein activity.

One way in which the modified myc2 gene can be used is by reducing its expression. The reduced expression can be achieved by a decrease in the mRNA level of the myc2 gene; a decrease in the level of MYC2 protein; and/or a decrease in the activity of the MYC2 protein, as compared to the mRNA level, protein level or protein activity of a non-modified wild type myc2 gene.

The modified myc2 gene of the invention can be used to confer an aberrant glandular phenotype to a plant, wherein the plant is selected from any of the species *Capsicum anuum, Cucumis melo, Cucumis sativus* and *Citrullus lanatus*. Also, the modified myc2 gene can be used for reducing or eliminating terpenes in those plant species. The wild type genomic sequence, the wild type CDS and the wild type amino acid sequence for myc2 of *Capsicum annuum* are depicted with SEQ ID No. 9, 10 and 11 respectively. The wild type genomic sequence, the wild type CDS and the wild type amino acid sequence for myc2 of *Cucumis sativus* are depicted with SEQ ID No. 12, 13 and 14 respectively. The wild type genomic sequence, the wild type CDS and the wild type amino acid sequence for myc2 of *Cucumis melo* are depicted with SEQ ID No. 15, 16 and 17 respectively. The wild type genomic sequence, the wild type CDS and the wild type amino acid sequence for myc2 of *Citrullus lanatus* are depicted with SEQ ID No. 18, 19 and 20 respectively.

Both the Slmyc2 as the myc2 genes can be modified by means of mutagenesis. Mutagenesis may comprise the random introduction of at least one modification by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements.

Mutagenesis also may comprise the more specific, targeted introduction of at least one modification by means of homologous recombination, oligonucleotide-based mutation induction, zinc-finger nucleases (ZFNs), transcription activator-like effector nucleases (TALENs) or Clustered Regularly Interspaced Short Palindromic Repeat (CRISPR) systems.

A modified Slmyc2 or myc2 gene of the invention can alternatively be introduced into a plant using genetic modification. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

In one embodiment the modified Slmyc2 or myc2 gene is an exogenous Slmyc2 or myc2 gene which can be introduced into a plant by a transgenic method or a cisgenic method.

The invention also relates to a modified recombinant Slmyc2 or myc2 gene, wherein the expression of said modified recombinant Slmyc2 or myc2 gene is driven by a strong promoter, which promoter is operably linked to a Slmyc2 or myc2 gene sequence, which gene sequence includes the 5'-UTR, the CDS, and/or the 3'-UTR. Many examples of strong constitutive promoters are known in the art; some of the most commonly used ones are e.g. the cauliflower mosaic virus 35S-promoter (pCaMV 35S) and modified versions thereof, ubiquitin promoters from various plant species, actin promoters from various plant species, and the promoter of Elongation Factor 1 alpha (EIF1$\alpha$).

In one embodiment the invention relates to a gene construct, which gene construct may comprise a selectable marker, a promoter sequence, a Slmyc2 or myc2 gene sequence, and a terminator sequence.

In one aspect the invention relates to a method for producing a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which may comprise a) crossing a plant which may comprise the modified Slmyc2 gene with another plant;
b) selfing the resulting F1 plants to obtain F2 plants;
c) selecting plants that exhibit the aberrant glandular hair phenotype and/or may comprise the modified Slmyc2 gene in the F2;
d) optionally performing one or more additional rounds of selfing or crossing, and subsequently selecting a plant which may comprise the trait or modified gene of the invention.

The word "trait" in the context of this application refers to the phenotype of the plant. In particular, the word "trait" refers to the trait of the invention, more in particular to the aberrant glandular hair phenotype that allows for the establishment of mites, in particular the predatory mites *Amblyseius swirskii* and/or *Amblydromalus limonicus* as a result of the presence of a modified Slmyc2 gene. The term "genetic determinant" is used for the genetic information in the genome of the plant that confers the trait of the invention, the genetic information being the modified Slmyc2 gene. When a plant exhibits the trait of the invention, its genome may comprise the genetic determinant conferring the trait of the invention. The plant thus has the genetic determinant of the invention. According to the invention, the genetic determinant may comprise the modified Slmyc2 gene.

It is clear that the parent plant that provides the trait of the invention is not necessarily a plant grown directly from the deposited seeds. The parent plant can also be a progeny plant from seed that is identified to comprise the trait of the invention by other means.

In one aspect, the invention relates to a method for producing a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which may comprise a) crossing a plant which may comprise the modified Slmyc2 gene with another plant;
b) optionally backcrossing the resulting F1 plants with the preferred parent plant;
c) selecting for plants that exhibit an aberrant glandular hair phenotype and/or may comprise the modified Slmyc2 gene in the F2;
d) optionally performing one or more additional rounds of selfing or crossing, and subsequently selecting a plant exhibiting an aberrant glandular hair phenotype as a plant which may comprise the modified Slmyc2 gene.

The invention additionally provides a method of introducing another desired trait into a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which may comprise:

a) crossing a *Solanum lycopersicum* plant which may comprise a modified Slmyc2 gene, representative seed of which were deposited under deposit number NCIMB 4222, with a second *Solanum lycopersicum* plant that exhibits a desired trait to produce F1 progeny;
b) selecting an F1 progeny that exhibits said aberrant glandular hair phenotype and/or may comprise the modified Slmyc2 gene and the desired trait;
c) crossing the selected F1 progeny with either parent plant, to produce backcross progeny;
d) selecting backcross progeny exhibiting the desired trait and an aberrant glandular hair phenotype and/or which may comprise the modified Slmyc2 gene; and
e) optionally repeating steps c) and d) one or more times in succession to produce selected fourth or higher backcross progeny that exhibits the desired trait and the aberrant glandular hair phenotype. The invention includes a *Solanum lycopersicum* plant produced by this method.

In one embodiment selection for plants exhibiting the aberrant glandular hair phenotype of the invention is performed in the F1 or any further generation, preferably by using SEQ ID No. 1 or 2. In another aspect selection for the trait of the invention is started in the F2 of a cross or alternatively of a backcross. Selection of plants in the F2 can be performed phenotypically as well as by using the said sequences which directly or indirectly detect the genetic determinant underlying the trait.

In one embodiment selection for plants exhibiting the aberrant glandular hair phenotype is started in the F3 or a later generation.

In one embodiment the plant which may comprise the genetic determinant is a plant of an inbred line, a hybrid, a doubled haploid, or of a segregating population.

The invention further provides a method for the production of a *Solanum lycopersicum* plant which may comprise the modified Slmyc2 gene of the invention by using a doubled haploid generation technique to generate a doubled haploid line which may comprise the modified Slmyc2 gene.

The invention furthermore relates to hybrid seed that can be grown into a *Solanum lycopersicum* plant which may comprise the modified Slmyc2 gene of the invention, and to a method for producing such hybrid seed which may comprise crossing a first parent plant with a second parent plant and harvesting the resultant hybrid seed, wherein said first parent plant and/or said second parent plant is a plant of the invention.

In one embodiment, the invention relates to a method for producing a hybrid *Solanum lycopersicum* plant which may comprise the modified Slmyc2 gene of the invention, which may comprise crossing a first parent *Solanum lycopersicum* plant with a second parent *Solanum lycopersicum* plant and harvesting the resultant hybrid seed, of which the first parent plant and/or the second parent plant may comprise the modified Slmyc2 gene of the invention, and growing said hybrid seeds into hybrid plants.

The invention also relates to a method for the production of a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus* by using a seed that may comprise the modified Slmyc2 gene of the invention for growing the said *Solanum lycopersicum* plant. The seeds are suitably seeds of which a representative sample was deposited with the NCIMB under deposit number NCIMB 42222.

The invention also relates to a method for obtaining a *Solanum lycopersicum* plant which exhibits an aberrant glandular hair phenotype, that allows for the establishment of mites, in particular the predatory mites *Amblyseius swirskii* and/or *Amblydromalus limonicus*, which may comprise reducing the endogenous level of SlMYC2 protein in the plant by mutation of the Slmyc2 gene of the plant.

The invention also relates to a method for seed production which may comprise growing *Solanum lycopersicum* plants from seeds of which a representative sample was deposited with the NCIMB under deposit number NCIMB 42222, allowing the plants to produce seeds, and harvesting those seeds. Production of the seeds is suitably done by crossing or selfing.

In one embodiment, the invention relates to a method for producing a *Solanum lycopersicum* plant which may comprise the modified Slmyc2 gene of the invention by using tissue culture.

The invention furthermore relates to a method for producing of a *Solanum lycopersicum* plant which may comprise the modified Slmyc2 gene of the invention by using vegetative reproduction.

In one embodiment, the invention relates to a method for producing a *Solanum lycopersicum* plant which may comprise the modified Slmyc2 gene of the invention by using a method for genetic modification to introgress said modified Slmyc2 gene into the *Solanum lycopersicum* plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for developing *Solanum lycopersicum* plants which may comprise the modified Slmyc2 gene of the invention, wherein germplasm which may comprise said modified Slmyc2 gene of the invention is used. Representative seed of said plant which may comprise the modified Slmyc2 gene of the invention and being representative for the germplasm was deposited with the NCIMB under deposit number NCIMB 42222.

In a further embodiment the invention relates to a method for producing a *Solanum lycopersicum* plant which may comprise the modified Slmyc2 gene of the invention, wherein progeny or propagation material of a plant which may comprise the modified Slmyc2 gene conferring the trait of the invention is used as a source to introgress the said trait into another *Solanum lycopersicum* plant. Representative seed of a plant which may comprise the modified Slmyc2 gene of the invention was deposited with the NCIMB under deposit number NCIMB 42222.

The invention provides preferably a *Solanum lycopersicum* plant which may comprise a modified Slmyc2 gene, capable of conferring an aberrant glandular hair phenotype, that allows for the establishment of mites, in particular the predatory mites *Amblyseius swirskii* and/or *Amblydromalus limonicus*, which plant is obtainable by any of the methods herein described and/or familiar to the skilled person.

The aberrant glandular hair phenotype conferred by the modified Slmyc2 gene of the invention enables the establishment on the plant of predatory mites that do normally not establish on tomato plants with a non-aberrant glandular hair phenotype and thus allows biological pest control by means of these mites.

The present invention will be elucidated in the following examples. These examples are for illustrative purposes only and are not to be construed as limiting the present invention in any way.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Creation of *Solanum lycopersicum* Plants of the Invention

Seeds of two *Solanum lycopersicum* breeding lines, TR306 and T029, were treated with ems (ethyl methane sulfonate) by submergence of approximately 10.000 seeds into an aerated solution of 0.5% (w/v) ems during 24 hours at room temperature.

The treated seeds were germinated and the resulting plants were grown in a greenhouse to produce M2 seeds.

After maturation, M2 seeds were harvested and bulked in one pool. The resulting pool of M2 seeds was used as starting material to identify individual M2 plants that showed an aberrant glandular hair phenotype.

The efficacy of the genetic modification procedure was assessed by determining the occurrence of bleached plants, which is indicative for chlorophyll loss due to modifications in genes directly or indirectly involved in the formation or accumulation of chlorophyll. The type VI trichome phenotype is depicted in FIGS. 5A-B.

Example 2

Identification of a *Solanum lycopersicum* Plant that Allows for the Establishment the Predatory Mite *Amblyseius swirskii*

Two breeding lines (TR306 and T029), a commercially available hybrid and three mutants resulting from the experiment as described in Example 1 were used in a bioassay to investigate whether the predatory mite *Amblyseius swirskii* is able to establish on these *Solanum lycopersicum* plants. As a positive control, *Capsicum annuum* variety Compas RZ was also included in this experiment.

In Table 1, an overview of the lines and varieties is given. The bioassay took place in a multi-tunnel greenhouse in Spain under Mediterranean growing conditions. This greenhouse was divided into 4 compartments and one of them was divided into 40 walk-in cages of 5×3.5×4 meter (l×w×h), of which five were used during the experiment. Treatments were compared in a complete randomized block design with five replicates of seven plant species: six tomato varieties (5 selected+1 commercial [negative control]) and 1 sweet pepper (positive control).

Each replicate consisted of two potted plants of each line or variety which were isolated using sticky bands on the pot and the overhead thread used to train the plants to avoid movement of predatory mites between adjacent replicates. One replicate of each plant species was allocated in each block (cage). Seeds of these plants were sown at the end of July 2012 and placed as duplicate of each tested line/variety into a total of 6 cages.

*A. swirskii* predatory mites were released onto 6 week old plants, by sprinkling the carrying material that comprised the mites over all plants at a rate of 100 predatory mites/plant. Quantity of mites per gram of carrying material was used to estimate the amount to release.

The predatory mites were initially fed by adding pollen ad libitum and additions started after predator release and continued weekly for three weeks thereafter. Plants were sampled biweekly for 6 weeks, beginning one week after the release of the predatory mites. In each sampling, five plants were randomly selected in each experimental cage and five leaves were sampled from each of these five randomly selected plants. Leaves were selected at random along the plant. On each leaf, immature stages (larvae, protonymphs, and deutonymphs) and adults of phytoseiid mites were counted.

Figure 3:
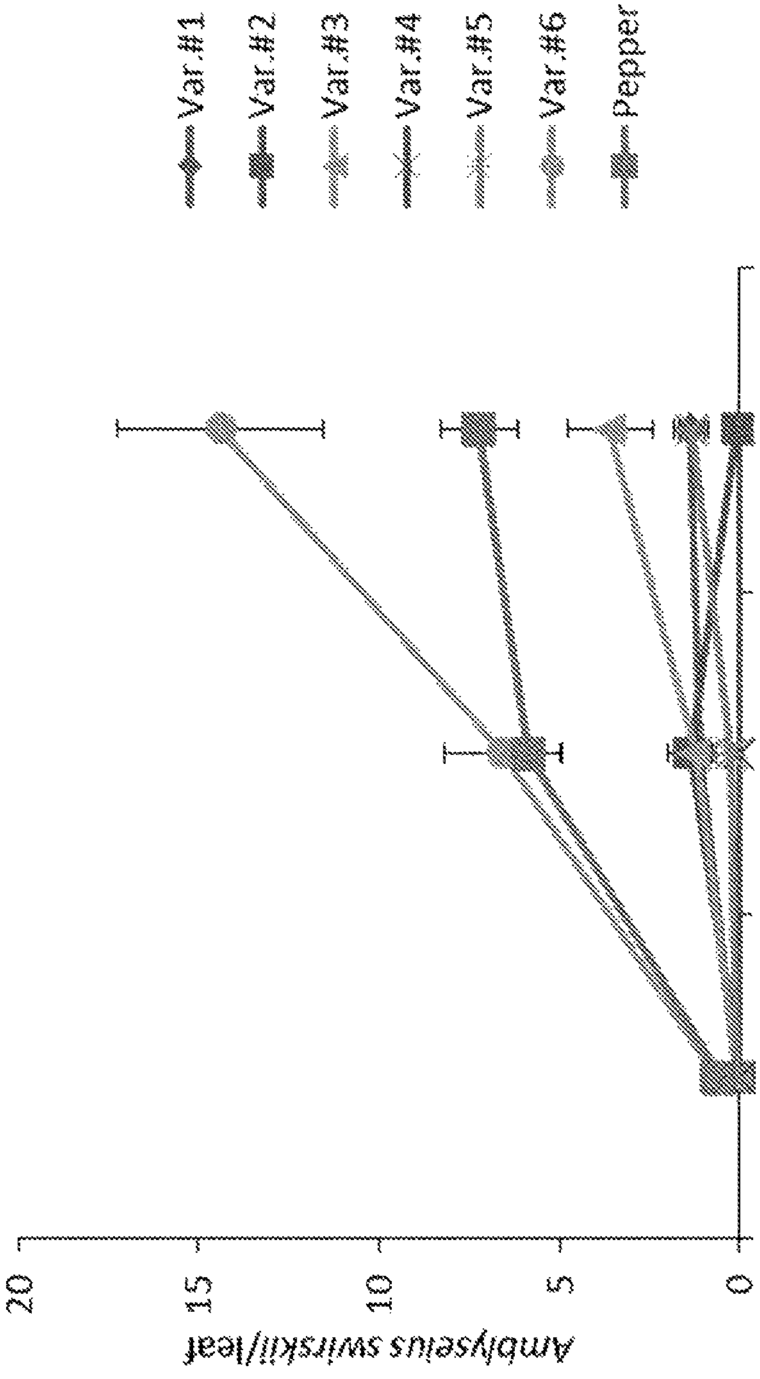
FIG. 3: Average density (number±SE) of *Amblyseius swirskii* per leaf per week for several tomato varieties and for the sweet pepper control.

The results are displayed in FIG. 3. It becomes clear that line #6, comprising the modified Slmyc2 gene of the invention, showed the establishment of the largest number of mites. It is significantly larger than the number found on leaves of the *Capsicum annuum* control plant.

TABLE 1

| Number | Description | Accession |
|---|---|---|
| Line #1 | Hybrid | Mecano |
| Line #2 | Breeding line | TR306 |
| Line #3 | EMS mutant | 302 |
| Line #4 | EMS mutant | 304 |
| Line #5 | Breeding line | T029 |
| Line #6 | EMS mutant | 305 |
| Pepper | Pepper | Compas RZ |

Example 3

QTL Mapping

The *Solanum lycopersicum* mutant comprising the modified Slmyc2 gene of the invention was crossed with parent line TR306. From this cross, a F2 mapping population was generated, which was used for population-specific genetic map construction and QTL-mapping.

In total, 940 markers were used to analyze the 86 offspring individuals. Of these, 241 were polymorphic, informative (enough segregation) and useful (not many U-scores).

The F2 individuals were scored in two classes: hl (having the trait of the invention), wt (wild type phenotype, including unclear phenotypes).

As the trait was being considered (monogenic) recessive, this should result in a 3:1 segregation of the trait. Indeed, the trait distribution in this translation is wt:hl 61:25, which is not significantly different from the expected 3:1 ratio ($chi^2$-test=0.38).

Linkage analysis was performed with MapQTL 6.0. First, interval mapping was performed to identify regions or markers linked to the trait. Second, co-factors were selected after which (as a third step) MQM-mapping was performed.

The coverage of chromosome 8 by polymorphic markers is rather low, as only five markers were identified. As the interval in which the trait is mapped is considerably large (at least 12 cM), analysis of the population with more markers was necessary for fine-mapping of the trait. However, given the fact that many markers appeared to be non-polymorphic on chromosome 8 in this cross, that might need additional initial effort in marker selection.

Example 4

Elucidation of Modified Slmyc2 Gene of the Invention

Besides the QTL that was mapped as described in Example 3, it was investigated whether the gene underlying the trait of the invention could be identified.

Whole genome sequencing (WGS) of the plant of the invention and of the non-mutant background was performed. As in example 3 it was shown that chromosome 8 comprised the modified Slmyc2 gene of the invention, all 25 homozygous SNP markers generated on this chromosome were taken into account. Of these 25 markers, 4 markers were found non-discriminatory, so no difference between the plant of the invention and the non-mutant background was observed.

A total of 227 plants from multiple F4 populations was phenotyped and 80 individuals showed the phenotype of the invention. Remarkably, one out the 21 markers, was 100% predictive for all 80 plants of the invention. For 21 of these plants, marker SL06992 gave an unique positive score. This SNP marker, designated SL06992 (SEQ ID No. 4) was blasted and found to localize on the same place on chromosome 8 as the AUGUSTUS predicted gene SL2_40ch08.g6 was annotated. In this annotation, the nucleotide at position 4124 of the genomic sequence is changed from G to T in plants of the invention. This corresponds with the same position in SEQ ID No. 8, representing the wild type sequence. Said nucleotide change results in a stop codon at position 493 of the amino acid, thereby creating a truncated version of the protein.

Example 5

Determining Terpene Levels in Plants of the Invention

In order to measure terpene levels in plants of the invention, i.e. plants that comprise the modified Slmyc2 gene, already topped *Solanum lycopersicum* plants were used. Samples were taken from the first, second and third leaf from the top of the plant. A total of five leaf discs of 0.71 $cm^2$ were collected. They were stored in a 10 ml vial and 1.0 ml of the solvent dichloromethane was added.

Subsequently, the leaf discs were mildly shaken. After 45-90 minutes, the solvent was transferred in another vial. Solvent extracts were stored at −20° C. until analysis.

In performing the analysis, 200 μl of the solvent comprising volatiles was mixed with 5 μl of the internal standard nonylacetate. Of this mixture, 1 μl was injected in the gas chromatography-mass spectrometry (GC-MS) instrument.

In order to show the ratio of volatile amounts for plants of the invention and heterozygous and wild type plants, the results are shown in arbitrary units. The values given in FIGS. 4A-B are normalized for the internal standard, nonylacetate.

From the results, it becomes clear that both the mono- and sesquiterpenes are absent in the plant of the invention, whereas in plants not comprising the modified Slmyc2 of the invention the presence of terpenes was shown to be significant ($P<0.05$).

Example 6

Determining Expression Levels of Terpene Synthase (TPS) Genes in Plant of the Invention In order to determine whether the absence of certain terpenes is related to expression of TPS genes, a qPCR experiment was designed. The three top leaves of plants of the invention were sampled, pooled and RNA was isolated using the RNeasy kit (Qiagen), using 100 mg of plant tissue. cDNA was synthesized using a Maxima cDNA synthesis kit (Thermo Scientific) starting from a total of 1000 ng RNA. Primer combinations to detect expression of TPS genes in tomato were derived from Falara et al. (Plant. Phys. 157, 770-789 (2011). A qPCR run was executed using the Rotor-Gene Q PCR cycler (Qiagen).

For 12 TPS genes the fold change regulation in plants of the invention containing the mutation homozygously or heterozygously and the non-mutant background was detected, which is shown in FIG. 7. Three types of expression patterns could be identified. For the genes TPS16, TPS17 and TPS33 expression was detected in the wild type plants whereas no expression was detected in both the homozygous as well as the heterozygous plants of the invention, as the fluorescence signal threshold level was not reached. The expression of TPS21 and TPS41 was detected and clearly down regulated in both homozygous as well as heterozygous mutant plants of the invention. For the other TPS genes no expression was detected for the homozygous mutant plants, as the fluorescence signal threshold level was not reached. For the heterozygous plants down regulation was observed when compared to the wild type expression pattern.

Example 7

Evaluation of the Effects of Plants that Comprise the Modified Slmyc2 Gene on the Establishment and Effectiveness of *Amblyseius swirskii* Against *Aculops lycopersici,*

The experiment was carried out in a multi-tunnel greenhouse located in Vicar (Almeria, Andalusia, Spain). This experiment was performed in a greenhouse comprising a total of 16 walk-in (experimental) cages of 5×3.5×4 m (l×w×h).

Two factors were evaluated, plant variety and predator, in a split plot design with four replicates. There were four main plots (group of four cages) of both plant varieties (plants comprising the modified Slmyc2 gene and Razymo), each divided into two subplots (experimental cages), each designated at random for each of the following treatments: 0 or 75 *A. swirskii*/plant.

*Amblyseius swirskii* was obtained from Koppert Biological Systems in bottles containing 50,000 mites of different stages and eggs mixed with a prey mite and a carrying material (SWIRSKI-MITE™). *Aculops lycopersici* (tomato russet mite, TRM) to infest the plants was obtained from a rearing colony maintained on tomato for several months before the starting of the experiment and originally collected on tomato plants from different locations within the region of Murcia (Spain)

Seeds of tomato cv. Razymo and plants comprising the modified Slmyc2 gene were sown into peat moss root cubes. When seedlings reached the five-leaves stage, they were transplanted into 25 l coco peat fibre bags placed inside the designated walk-in cage, at 10 seedlings per cage. Each tomato plant was inoculated with ca. 250 mobile stages of TRM two weeks after transplanting. Mites were counted under a stereomicroscope to select pieces of leaflets containing ca. 50 mites and five of these pieces were deposed onto a different leaf of each plant. All mites to infest plants were collected simultaneously and from the same part of the plant to assure homogeneity in age and sex-ratio. Predators were released at once in the designated cages four weeks after the tomato russet mite release. *A. swirskii* was distributed by sprinkling the carrying material over all plants at a rate of 75 predatory mites/plant. Quantity of mites per gram of substrate was used to calculate the amount to release.

Evaluations started just before the predator release and continued weekly thereafter until the end of the experiment. To evaluate the density of TRM, in each sampling, four plants were randomly selected in each walk-in cage and 3 leaf-disks (3.5 cm 0) were taken from 3 different leaves (one disk per leaf) of each selected plant. One leaf was selected at random from the upper, one from the middle, and one form the bottom third of the plants. Leaf-disc samples were brought to the laboratory into a refrigerated cold-box and then the number of TRM (mobile stages) were counted using a stereoscopic microscope. Predator populations were assessed in situ by counting the number of predatory mites (mobile forms) present in the same above-mentioned leaves, but before picking the leaf-disks to count the number of TRM.

The results from this experiment are visualized in FIG. 8. Numbers of TRM increased progressively over the entire experimental period and averaged at similar numbers in all plots with the exception of those containing the plants comprising the modified Slmyc2 gene and receiving *A. swirskii*, where TRM averaged always at values under 7.5 mites per 3.5 cm 0 leaflet, nearly 20 times lower than in the other treatments at the end of the experiment. Abundance of TRM was therefore lower in response to *A. swirskii* on plants comprising the modified Slmyc2 gene ($F_{3,45}$=17.640; P<0.001).

Example 8

Evaluation of the Effectiveness of *Ambleyseius Swirskii* and *Amblydromalus limonicus* Against *Bemisia tabaci* (Whitefly) on Plants Comprising the Modified Slmyc2 Gene.

Experiments were carried out in a multi-tunnel greenhouse located in Vicar (Almeria, Andalusia, Spain). This experiment was performed in a greenhouse comprising a total of 16 walk-in (experimental) cages of 5×3.5×4 m (l×w×h).

During the summer and winter experiments, three treatments were compared in a complete randomized block design with 4 replicates in each experiment. The treatments were: 1) *B. tabaci;* 2) *B. tabaci+A. swirskii* and 3) *B. tabaci+A. limonicus.*

In both experiments, *B. tabaci* adults to infest the plants were collected from a mass-rearing colony maintained on tobacco plants. *A. swirskii* was provided by Koppert Biological Systems in bottles containing 50,000 predatory mites from different stages and eggs mixed with a prey mite and a carrying material (SWIRSKI-MITE™). *A. limonicus* was obtained from Koppert Biological Systems in bottles containing 10,000 mites of different stages and eggs mixed with a prey mite and a carrying material (LIMONICA™).

Seeds of tomato plants comprising the modified Slmyc2 gene were sown into peat moss root cubes. When seedlings reached the five-leaves stage, they were transplanted into 25 l coco peat fibre bags placed inside the designated walk-in cages, at 10 seedlings per cage. Adult pests were cooled briefly in a cold room at 8° C. for counting, then released into all cages at a rate of 10 adults/plant and 5 females/plant per week over three consecutive weeks for a total of 30 whitefly adults/plant. The first whitefly adults were released just after transplanting. This release schedule was used to simulate a gradual but heavy immigration of the pest into the greenhouse. For weekly infestations of all cages, adult whiteflies were simultaneously collected from the mass rearing and belonged to the same cohort to assure homogeneity in age and sex ratio. *A. swirskii* and *A. limonicus* were released one week after the first adult pests release by sprinkling the carrying material over all plants at a rate of 75 predatory mites/plant. Quantity of mites per gram of substrate was used to calculate the amount to release.

In the experiments, in each weekly sampling four plants were randomly selected in each experimental cage and three leaves were sampled from each of the four randomly selected plants. One leaf was selected at random from the upper, one from the middle, and one from the bottom third of the plant. On each leaf, whitefly nymphs and adults and the immature stages (larvae, protonymphs, and deutonymphs) and adults of phytoseiid mites were counted.

The results for the whitefly infestation experiments are shown in FIG. 9. The population of whitefly nymphs was similarly suppressed by *A. swirskii* and *A. limonicus*. Moreover, numbers of whitefly nymphs per leaf remained nearly constant and never exceeded 15 nymphs per leaf during the entire experiment in plots receiving the predators.

Example 9

Evaluation of the Effectiveness of *Ambleyseius swirskii* and *Amblydromalus limonicus* Against *Frankliniella occidentalis* (Thrips) Under Summer and Winter Conditions on Plants Comprising the Modified Slmyc2 Gene.

Experiments were carried out in a multi-tunnel greenhouse located in Vicar (Almeria, Andalusia, Spain). This experiment was performed in a greenhouse comprising a total of 16 walk-in (experimental) cages of 5×3.5×4 m (l×w×h).

During the summer and winter experiments, three treatments were compared in a complete randomized block design with 4 replicates in each experiment. The treatments were: 1) *F. occidentalis;* 2) *F. occidentalis+A. swirskii* and 3) *F. occidentalis+A. limonicus.*

In both experiments, *F. occidentalis* adults to infest the plants were obtained from a rearing colony maintained at Koppert Biological Systems on green bean pods. *A. swirskii* was provided by Koppert Biological Systems in bottles containing 50,000 predatory mites from different stages and eggs mixed with a prey mite and a carrying material (SWIRSKI-MITE™). *A. limonicus* was obtained from Koppert Biological Systems in bottles containing 10,000 mites of different stages and eggs mixed with a prey mite and a carrying material (LIMONICA™).

Procedures were the same for both the Summer and Winter experiments. Seeds of tomato plants comprising the modified Slmyc2 gene were sown into peat moss root cubes (Summer: Jul. 1, 2014; Winter: Sep. 22, 2014). When seedlings reached the five-leaves stage, they were transplanted into 25 l coco peat fibre bags placed inside the designated walk-in cages, at 10 seedlings per cage (Summer: Aug. 5, 2014; Winter: Oct. 28, 2014). Adult pests were cooled briefly in a cold room at 8° C. for counting, then released into all cages at a rate of 10 adults/plant and 5 females/plant per week over three consecutive weeks for a total of 15 thrips females/plant. The first thrips adults were released just after transplanting. This release schedule was used to simulate a gradual but heavy immigration of both pests into the greenhouse. Newly emerged adult thrips were used for the experiment, which were collected prior to each weekly release from a single cohort, to assure the homogeneity in age. Thrips females were mixed with an unknown number of males. *A. swirskii* and *A. limonicus* were released one week after the first adult pests release (Summer: Aug. 12, 2014; Winter: Nov. 4, 2014) by sprinkling the carrying material over all plants at a rate of 75 predatory mites/plant. Quantity of mites per gram of substrate was used to calculate the amount to release.

In the Summer and Winter experiments, in each weekly sampling four plants were randomly selected in each experimental cage and three leaves were sampled from each of the four randomly selected plants. One leaf was selected at random from the upper, one from the middle, and one from the bottom third of the plant. On each leaf, adults and mobile forms of thrips and adults of phytoseiid mites were counted.

The results for the thrips infestation experiments are shown in FIGS. 10A-B. *A. limonicus* and *A. swirskii* were able to significantly reduce thrips populations either during summer or winter, although *A. limonicus* resulted more effective in winter compared to *A. swirskii* (Summer: $F_{2,31}$=21.632; P<0.001; Winter: $F_{2,45}$=48.789; P<0.001; FIGS. 10A-B). During summer, in cages receiving the predators numbers of thrips per leaf decreased progressively throughout the experimental period with almost no thrips being recorded at the end (FIG. 10A). During winter, both predators reduced similarly pest populations during the first weeks, but halfway through the experiment (approximately when average daily temperatures were under 20° C.) thrips density increased rapidly in plots treated with *A. swirskii* reaching similar densities than in untreated cages at the end of the experiment, reflecting no control of the pest by the predator (FIG. 10B). It is known that *A. swirskii* is less active at temperatures below 20° C. Contrary, in cages receiving *A. limonicus, thrips* density remained again constant and always averaged under 3, approximately 6 times lower compared to cages receiving *A. swirskii. A. limonicus* can thus still be successfully used at temperatures at which *A. swirskii* is less active.

The invention is further described by the following numbered paragraphs:

1. Modified Slmyc2 gene, comprising at least one modification as compared to the wild type sequence of SEQ ID No. 5, which modification leads to the reduction or absence of SlMYC2 protein activity, wherein the modified Slmyc2 gene is capable of conferring an aberrant glandular hair phenotype to a *Solanum lycopersicum* plant.
2. Modified Slmyc2 gene of paragraph 1, wherein the modification is selected from a modification that decreases the mRNA level of the Slmyc2 gene, a modification that decreases the level of the SlMYC2 protein and/or a modification that decreases the activity of the SlMYC2 protein, as compared to the wild type Slmyc2 gene of SEQ ID No. 5.
3. Modified Slmyc2 gene of paragraph 1 or 2, wherein the modification results in the presence of a premature stop codon within the coding sequence.
4. Modified Slmyc2 gene of paragraph 3, wherein the modification comprises a SNP on position 1477 of SEQ ID No. 2, in particular from nucleotide G (wild type) to T.
5. Modified Slmyc2 gene of any of the paragraphs 1 to 4, wherein the aberrant glandular hair phenotype is characterized by the reduction and preferably absence of terpenes, in particular α-pinene, myrcene, carene, α-phellandrene, β-phellandrene, p-cymene, limonene, 6-elemene, β-caryophyllene and/or α-humulene, and/or is characterized by deformed glandular hairs.
6. A *Solanum lycopersicum* plant comprising a modified Slmyc2 gene of any of the paragraphs 1 to 5.
7. A *Solanum lycopersicum* plant of paragraph 6, wherein the plant exhibits an aberrant glandular hair phenotype which allows for the establishment of predatory mites, in particular *Amblyseius swirskii* and/or *Amblydromalus limonicus*, on said *Solanum lycopersicum* plant.
8. A *Solanum lycopersicum* seed comprising the modified Slmyc2 gene of any of the paragraphs 1 to 5, wherein the plant that can be grown from the seed shows the aberrant glandular hair phenotype.
9. Progeny plant of a *Solanum lycopersicum* plant of paragraph 6 or 7, wherein the progeny plant comprises the modified Slmyc2 gene, of any of the paragraphs 1 to 5.
10. Propagation material capable of developing into and/or being derived from a *Solanum lycopersicum* plant of paragraph 6 or 7, wherein the propagation material comprises the modified Slmyc2 gene of any of the paragraphs 1 to 5 and wherein the propagation material is selected from a group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts and cells, or a tissue culture thereof.
11. Use of a modified Slmyc2 gene of any of the paragraphs 1 to 5 for the development of a *Solanum lycopersicum* plant on which predatory mites, in particular *Amblyseius swirskii* and/or *Amblydromalus limonicus* can establish.
12. Use of paragraph 11, wherein the establishment of predatory mites, in particular *Amblyseius swirskii* and/or *Amblydromalus limonicus*, is allowed by an aberrant glandular hair phenotype.
13. Use of paragraph 12, wherein the aberrant glandular hair phenotype is characterized by the reduction and preferably absence of terpenes, in particular α-pinene, myrcene, carene, α-phellandrene, β-phellandrene, p-cymene, limonene, δ-elemene, β-caryophyllene and/or α-humulene, and/or is characterized by deformed glandular hairs.
14. Use of a *Solanum lycopersicum* plant of paragraph 6 or paragraph 7, for the cultivation and preservation of predatory mites, or a colony therefrom.
15. Method for obtaining a *Solanum lycopersicum* plant which exhibits an aberrant glandular hair phenotype, that allows for the establishment of mites, in particular the predatory mites *Amblyseius swirskii* and/or *Amblydromalus limonicus*, comprising reducing the endogenous level of SlMYC2 protein in the plant by mutation of the Slmyc2 gene of the plant.
16. Modified myc2 gene, which when expressed in a plant leads to the reduction and preferably absence of terpenes in said plant, and/or which is preferably capable of conferring an aberrant glandular hair phenotype to said plant, which gene comprises a modification that leads to reduction or absence of MYC2 protein activity, and wherein the modification is selected from a modification that decreases the mRNA level of the myc2 gene, a modification that decreases the level of the MYC2 protein and/or a modification that decreases the activity of the MYC2 protein, as compared to a non-modified wild type myc2 gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

```
<110>    Rijk Zwaan Zaadteelt en Zaadhandel B.V.

<120>    TOMATO PLANTS ALLOWING THE ESTABLISHMENT OF MITES

<130>    L/2SC79/KK/261

<140>    EPPCT/EP2015/068860

<141>    2015-08-17

<150>    EP141813063
```

-continued

SEQUENCE LISTING

<151> 2014-08-18

<160> 20

<170> BiSSAP 1.2

<210> 1

<211> 8000

<212> DNA

<213> *Solanum lycopersicum*

<220>

<221> source

<222> 1..8000

<223> iorganism = "*Solanum lycopersicum*"
/mol_type = "unassigned DNA"

<400> 1
attcaataat taattgtaat tgtctggcat tgttatggtg gttcacatgt caagttgctt 60
ttatattatt tgttattaaa ataaaaatag aaaaatcaat gttattttca cgttcagcat 120
ccaccaaaac gtgctattaa taatttaatg tctaaaacat atctacaaat tatattatat 180
tagtataata tactttatga tatcttgaac aaagacaatt acaagtagga ccaatcaaaa 240
tgattccaca acgtgacgcc aacgcgtaca aataaggatt ttcctttatt ataactttat 300
aataattaac tcaccgtaat taatttgtat gattataatg aaatgactga aactttttcg 360
ctcttaacaa gaaatctcga tcgaacttta gccatgaaat aaaaataatt gtgttgagag 420
tagaatttcc aaaaatagat tttatagtgt gtaaaattat atttattaat ttttaatatg 480
attatcaaaa taccgaatcg aagaaagtaa gtaaatttta aggaatgtaa tatgtatgtg 540
gtctcaccct tacatgcatt gaatatgtaa agagtgtttt cgaaggacaa ggattttttt 600
gtttttacta ttaatgtatt ttaaaaactt aagacaaaat tatttactca aaatttacat 660
gcgatattgt actaaaacga tttacaatta ttgtaggtac cttaattact ctgatagtgc 720
atggccttta attacaaggg ataccaataa caaaaaagtc catatttgtg atgaatatgt 780
cttatcacaa aaattgagag gaatattatg atagatttaa tgaaaaattt taatatggac 840
aaaagaatat tatgatagat ttaaagaaaa aatttaatat ggacaaaatt tgtgatggac 900
taataaattt actttttca ttacgaattt ttggagcctc acgttgaaga tccaatgact 960
tgttttcaaa ttagtttcaa agaatggctg agaatagtct ttctaaaaaa gcatcttcaa 1020
tcgatggctt gaatttaatt attaaaagaa ttattatatt tgataatgta ttgattagat 1080
gcacgttatg aatttaaaat ttcattttag acatgaacct aatatttaaa tagacaccaa 1140
cacaagtata tgacgcgaac aagtgatatt taagttatga gttcaaaatt tatgaatcat 1200
tagtcataac taaaaatgtg atactttagg ggataaggat agaagagcaa atttaaattt 1260
tacgtgaacc tttttattt aaatagaaaa taatagagcg ataaattcat tatttatcga 1320
gtttcaaatc attaaaaata caatatataa tatacgaatt agatgtatat acacatttga 1380
attcaatggt ggactatata atttgatatt taagtaagca aaagtagata aggagttcaa 1440
gtttaaattt gtaaacatag aatttcctat tttagagttt aaggtaaatt tatgtatatt 1500
ttatcgtttg gaatctcatt ttacgatgct acgctaaata ttagaaattg ctaaaaataa 1560

SEQUENCE LISTING

```
ttgttgttat tgtaatataa tatcaaaatc aacatgattt catttatttt ctttccatat     1620
atgaattatt tccataaagc ctacatgtag gagatatgct aatttaatat ttcctggaaa     1680
tagttaactt agttgaaaca ttgaagtatt agatatttta ttaatataag cactttaaca     1740
aatatggtta taaaaaaaaa tcttcttctt ttcaattcct ttaacattca ttgaaaatct     1800
tcttatttaa caatattttt ccaattagtt caataactcg tcttcaatca tcgaagatat     1860
ttaatgttac tttttttgaa gtaatgaaat ttacttctaa taatcttgtc tttttttaa      1920
attggaaatg ggaatagaaa atgataagac gaaattaaat cctcacctac aagataaaag     1980
tttagataag ttttgatagt taattaaatg aatttcaaat tttttaatac ttaaatactt     2040
ctcattaata attgtaaaga tatctacttt tttcattcac tttttacttc aaaaataaat     2100
caaattatgt cacactttca ctgtaataaa ttatatatat ataataaaaa aaaagaaaaa     2160
tcttctacct atataagtac gactctctaa tggtgttaag taaaaagaaa aatttagtat     2220
aaagtcctag gtagttaaaa agtaaaaagt agaactaatg ccggctttcc ttatcctacg     2280
tataattttc ccataaatcg cccaccttaa tttttttttt ctgatttttc atttggcatc     2340
gaagcttata ttagaattta aacttacgtt aaaatttttt ataatggcac taaaattttt     2400
actaacataa ataattatcc catcctaata aaaatttaaa taaaaaatat ttgattaaaa     2460
atacttaccg tttttctcgg aaccctcttc tctttgtcca ctcactttcc tcactcattt     2520
atttttgagc tcacaatatt tttattatat atatatatat atccacaaaa atctctactc     2580
tcatttctca cctaacaaac aaaatctctc attttctgtt ttttgtaaaa ttcttcaatt     2640
taattgaatg acggactata gattatggag taataccaat actactaata catgtgatga     2700
tactatgatg atggattctt ttttatcttc cgatccatcc tctttttggc ctgcttccac     2760
tcccaatcgt ccgactccgg tgaacggagt cggagaaacg atgccgtttt tcaatcaaga     2820
gtcactacag caaaggcttc aggctttaat tgacggtgct cgtgaatcat gggcatatgc     2880
tattttctgg caatcgtcag ttgttgattt tgcgagccaa actgtattgg gttggggaga     2940
tgggtattat aaaggagaag aagataagaa taaacggaga gggtcgtcta gttcagcagc     3000
taattttgtt gctgagcaag agcatagaaa gaaggtgctt cgggagctga attcattaat     3060
atccggtgta caagcttccg ccggaaacgg aactgatgat gcagtggatg aggaagtgac     3120
ggatactgaa tggtttttttc tgatttcaat gacccaatcg tttgttaacg gtaacgggct    3180
tccgggcttg gcgatgtaca gttcaagccc aatttgggtt actggaacag agaaattagc     3240
tgcttctcaa tgtgaacggg ccaggcaagc ccaaggtttc gggcttcaga cgattgtgtg     3300
tattccttca gctaacggtg tagtggagct tggttcgact gagctgatat tccaaagctc     3360
ggatttgatg aacaaggtta agtatttgtt taacttcaat attgatatgg ggtctgttac     3420
aggctcaggt tcgggctcag gctcttgtgc tgtgcatcct gagcccgatc cttcggccct     3480
ttggcttacg gatccatctt cctcggttgt ggaacctaag gattcgttaa ttcatagtag     3540
tagtagggat gttcaacttg tgtatggaaa tgagaattct gaaaatcagc agcagcattg     3600
tcaaggattt ttcacaaagg agttgaattt ttcgggttat ggatttgatg gaagtagtaa     3660
taggaataaa actggaattt cttgtaagcc ggagtccagg gagatattga attttggtga     3720
tagtagtaag agattttcag ggcaatcaca gttgggtcct gggcctgggc tcatggagga     3780
gaacaagaac aagaacaaga acaagaaaag gtcacttgga tcaaggggaa acaatgaaga     3840
```

-continued

SEQUENCE LISTING

```
aggaatgctt tcgtttgttt cgggtgtgat cttgccaact tcaacaatgg ggaagtccgg     3900
ggattctgat cactcagatc tcgaagcctc agtggtgaag gaggccgttg tagaacctga     3960
aaagaagccg aggaagcgag ggaggaaacc agccaatgga agggaggagc cattgaatca     4020
cgtggaagcg gagagacaga ggagggagaa attgaatcaa agattctacg cgctcagagc     4080
cgtagtccca aatgtgtcta aaatggataa ggcatcactt cttagagatg caattgcata     4140
catcaatgag ttgaaatcaa aagttcaaaa ttcagattta gataaagagg agttgaggag     4200
ccaaattgaa tgtttaagga aggaattaac caacaaggga tcatcaaact attccgcctc     4260
ccctccattg aatcaagatg tcaagattgt cgatatggac attgacgtta aggtgattgg     4320
atgggatgct atgattcgta tacaatgtag taaaaagaac catccagctg ccaggctaat     4380
ggcagccctc aaggacttgg acctagacgt gcaccacgct agtgtttccg tggtgaatga     4440
tttgatgatc caacaagcca cagtcaaaat ggggagccgg ctttatgctc aagaacagct     4500
taggatagca ttgacatcaa aaattgctga atcgcgatga aattatgtcc ctagtgagct     4560
atgtataatg ttatcttcta atgagcgaga attttcttct ctgtatataa atgtgatgaa     4620
accaatacta gagatctcga gttgaggctt tttagttcat gtaagattag atatatatat     4680
atgatgcagc ttcatccttt tgtattcttc atccaggaaa taaatgagaa accaataatt     4740
ggtggctgat gatcaacttc atgttattac taattctcgt tccctcttct tttgggatac     4800
aacacttgtc attttacatt aggcaaatta gaagaaaata ctaagcattt tttaattgaa     4860
cgtaacatgt catgtgtgaa ctagagtcac aagttcaatt catgtaacaa acaatcacct     4920
ttgcatttta gtggagaagg atgcattgag tttcaacttg tacactaact agtcataaga     4980
gattactttg ttataaaaaa aaaaacaatt tttgaccttg ttgtgtatat aatatatgat     5040
tcgagtttgg acgaaagttt ttatttaatt atgatggata tattagttat ggagtacaca     5100
attgccttta ctataaaact tattactttt taataataaa tatttttttta atgtaaatat     5160
ataaatataa tcaaaactta atataaatgg atgtattact aatcagttgc ttgttttagt     5220
ctagaagaaa gcaccaaaca aaggggtagg gctgcatttt catttataga gaattcattg     5280
aatttggtca aatcatagct gtattcattg gactaggaaa tatttaaaaa gtatatatat     5340
tattgtttat aataaatataa tgtcatgagt atcatttgag tttgaagtga cacaagccct     5400
ttaaatgcag ttgatttagg cacaaacttt gttattattc ccgccgtcca aatagttgtt     5460
acatttggct tcctaaaaat taatttaact aatttttaaa tttaatttta tattttgaaa     5520
aattaaagtt tataaataca aaaattattt taatttctta catataatta aaaaatatat     5580
ataaaattta tataatttag cgctggaaaa ttattttgaa aacagaggaa gtattattat     5640
tattttggtc ttatgaattg tgtgataaac agtttatatc tgttaatcaa atagacagag     5700
attgatagat gtgacaaaga ttcgtttttt gtttgaggtt ttataaaagg aaaattgtat     5760
aaaatagcaa actaataact taaattaaat ggaatagcta gggtttgatt taattgtgct     5820
ccatagcaaa cgttggcaaa aatttaccag aagtctcgct cgccactctc ccattctcgc     5880
ctctctcgct ttatacatag aagtgtataa tttatgtttc tgttttgtat aaagcgagag     5940
aaaattgtat atacacatgc aaaaatgtat atctttgtgt tatacactta attatataat     6000
ttacaaacat tttacttcaa atattgcagc gaaaaaggcc aaagaattat acaatcgtga     6060
attatataat tgcagtgaaa tacaattttt tctagcttta tacaacagaa gtgtatatat     6120
tgtatttctg tttttgtata aagcgagaaa aacatatatc ttcttgctat acacttataa     6180
```

-continued

SEQUENCE LISTING

```
ttatgcaata tacatacatt ttaattcgat taaactgtat acaaaactaa ttatacaatt     6240
gcagcgaaat ggcgaattat acaatttagg ccagcgaatt atacactttt atatgtatag     6300
cgaattatac agtttttata tttgctatgg agcgcatata ttatacaaat atgatttttt     6360
tgtttgctat atgtgaaagt tgccctttta taaaagcttt tatgtatagt ttgatttgtt     6420
tttttaaaaa ataaaatatg acaactttag tatcaaaata gattaaattt atatacaata     6480
aatagttata ttttacagcc agccatttat ctttcttttt tttcaagcca caaaatcacc     6540
ttgtagaaag ttattttgtt cgatatttta ttgctaatat ataaaaatat tattataaaa     6600
agcatgtaat atatatataa aaatttgatt tcaaagaata ctttgatcat tataatgata     6660
tgttaatata aataataatt attatagatt aatctgatcg tatattttca gtatacatta     6720
atatatacat ctaaaatatg actgtattaa atatgaacaa aatcatttac atcaccctat     6780
ataatatttt aattaaaaag atgtataaag aagaataaaa aacgctgaag tttaaagcga     6840
atgttattga ccagatcaaa ttgacttgaa gaccaaaatt gaattgttga atacaattaa     6900
ttaatttaaa aatgaccatg ttttacatgt gaaattcatt tatatatata tatatatatc     6960
atatattatt atagtattca cattttgttg tttacactga tggttccgtt aagtgttcac     7020
atttctttgt ttaacactaa actttggagg gaaggatgtg aaaataaaaa atttgggtag     7080
aaaattaatc gataatttaa tattgtctaa tttatcttat gtatattatg atcattactc     7140
ccttattatc tttgtatttt tttaatcttg attatcatat tatttagtat tttttttatcc     7200
ttaattttga tatgttttac ttgagtcaaa aatctataga aaataatttt tctattttta     7260
caagataagg gtaaagatgt gcgaacacaa attttttgaa gccccactta tgaaattaca     7320
ctgaacatat tgttgtagta actgtacgaa ctcttttttc tttctatata aacaaatgta     7380
taactaaagt atttagtaaa ataaaaatat aattctattt agttcatgaa tgagaccaca     7440
atatgaatgt atagagctgg ggatattttt tgtttttgtg tagatggata ttaatcgaag     7500
atgtattggt tcttaatagt aagaataaca atagccatta ccctaaagat tgattcacct     7560
ttattttagg gtataaacca aaaaagaatg gacattatta acacgagacc tttagcattt     7620
ccaaaaaaaa tgggagaatt ttgttattta tttaaaaaga aaaaaaaaaa gaacacaccc     7680
ttaacctcaa tatcctcaaa aattcaacca tcaatatcat tattttattt tcatatccta     7740
tgcatttttt attagcttgt aaacttttaa ttttcttcct attcttttat acaacaatga     7800
ctctcaattg tttaacctgc caagctctaa aaagaacaga ttcacatgag gaactaaggg     7860
aaacactgaa tcatgttaat gataagtcga attttcgtct tttttcagtg ggaatggaga     7920
ggaactggtc agggaacttg gttgaaagac ggaaatatga aaaaacgagg ggtcgaacca     7980
taatgggaaa agaaaataat                                                 8000
```

<210> 2

<211> 1893

<212> DNA

<213> *Solanum lycopersicum*

<220>

<221> source

<222> 1..1893

-continued

SEQUENCE LISTING

<223> /organism = "*Solanum lycopersicum*"
/mol_type = "unassigned DNA"

<400> 2

```
atgacggact atagattatg gagtaatacc aatactacta atacatgtga tgatactatg      60
atgatggatt ctttttatc ttccgatcca tcctcttttt ggcctgcttc cactcccaat      120
cgtccgactc cggtgaacgg agtcggagaa acgatgccgt ttttcaatca agagtcacta     180
cagcaaaggc ttcaggcttt aattgacggt gctcgtgaat catgggcata tgctattttc     240
tggcaatcgt cagttgttga ttttgcgagc caaactgtat tgggttgggg agatgggtat     300
tataaaggag aagaagataa gaataaacgg agagggtcgt ctagttcagc agctaatttt     360
gttgctgagc aagagcatag aaagaaggtg cttcgggagc tgaattcatt aatatccggt     420
gtacaagctt ccgccggaaa cggaactgat gatgcagtgg atgaggaagt gacggatact     480
gaatggtttt ttctgatttc aatgacccaa tcgtttgtta acggtaacgg gcttccgggc     540
ttggcgatgt acagttcaag cccaatttgg gttactggaa cagagaaatt agctgcttct     600
caatgtgaac gggccaggca agcccaaggt ttcgggcttc agacgattgt gtgtattcct     660
tcagctaacg gtgtagtgga gcttggttcg actgagctga tattccaaag ctcggatttg     720
atgaacaagg ttaagtattt gtttaacttc aatattgata tggggtctgt tacaggctca     780
ggttcgggct caggctcttg tgctgtgcat cctgagcccg atccttcggc cctttggctt     840
acggatccat cttcctcggt tgtggaacct aaggattcgt taattcatag tagtagtagg     900
gatgttcaac ttgtgtatgg aaatgagaat tctgaaaatc agcagcagca ttgtcaagga     960
tttttcacaa aggagttgaa tttttcgggt tatggatttg atggaagtag taataggaat    1020
aaaactggaa tttcttgtaa gccggagtcc agggagatat tgaattttgg tgatagtagt    1080
aagagatttt cagggcaatc acagttgggt cctgggcctg ggctcatgga ggagaacaag    1140
aacaagaaca agaacaagaa aaggtcactt ggatcaaggg gaaacaatga agaaggaatg    1200
ctttcgtttg tttcgggtgt gatcttgcca acttcaacaa tggggaagtc cggggattct    1260
gatcactcag atctcgaagc ctcagtggtg aaggaggccg ttgtagaacc tgaaaagaag    1320
ccgaggaagc gagggaggaa accagccaat ggaagggagg agccattgaa tcacgtggaa    1380
gcggagagac agaggaggga gaaattgaat caaagattct acgcgctcag agccgtagtc    1440
ccaaatgtgt ctaaaatgga taaggcatca cttcttagag atgcaattgc atacatcaat    1500
gagttgaaat caaaagttca aaattcagat ttagataaag aggagttgag gagccaaatt    1560
gaatgtttaa ggaaggaatt aaccaacaag ggatcatcaa actattccgc ctcccctcca    1620
ttgaatcaag atgtcaagat tgtcgatatg gacattgacg ttaaggtgat tggatgggat    1680
gctatgattc gtatacaatg tagtaaaaag aaccatccag ctgccaggct aatggcagcc    1740
ctcaaggact tggacctaga cgtgcaccac gctagtgttt ccgtggtgaa tgatttgatg    1800
atccaacaag ccacagtcaa aatggggagc cggctttatg ctcaagaaca gcttaggata    1860
gcattgacat caaaaattgc tgaatcgcga tga                                 1893
```

<210> 3

<211> 630

<212> PRT

-continued

SEQUENCE LISTING

<213> *Solanum lycopersicum*

<220>

<221> SITE

<222> 493

<223> site of stop codon

<400> 3

```
Met Thr Asp Tyr Arg Leu Trp Ser Asn Thr Asn Thr Thr Asn Thr Cys
1               5                   10                  15

Asp Asp Thr Met Met Met Asp Ser Phe Leu Ser Ser Asp Pro Ser Ser
            20                  25                  30

Phe Trp Pro Ala Ser Thr Pro Asn Arg Pro Thr Pro Val Asn Gly Val
        35                  40                  45

Gly Glu Thr Met Pro Phe Phe Asn Gln Glu Ser Leu Gln Gln Arg Leu
    50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95

Gly Asp Gly Tyr Tyr Lys Gly Glu Glu Asp Lys Asn Lys Arg Arg Gly
            100                 105                 110

Ser Ser Ser Ser Ala Ala Asn Phe Val Ala Glu Gln Glu His Arg Lys
        115                 120                 125

Lys Val Leu Arg Glu Leu Asn Ser Leu Ile Ser Gly Val Gln Ala Ser
    130                 135                 140

Ala Gly Asn Gly Thr Asp Asp Ala Val Asp Glu Glu Val Thr Asp Thr
145                 150                 155                 160

Glu Trp Phe Phe Leu Ile Ser Met Thr Gln Ser Phe Val Asn Gly Asn
                165                 170                 175

Gly Leu Pro Gly Leu Ala Met Tyr Ser Ser Ser Pro Ile Trp Val Thr
            180                 185                 190

Gly Thr Glu Lys Leu Ala Ala Ser Gln Cys Glu Arg Ala Arg Gln Ala
        195                 200                 205

Gln Gly Phe Gly Leu Gln Thr Ile Val Cys Ile Pro Ser Ala Asn Gly
    210                 215                 220

Val Val Glu Leu Gly Ser Thr Glu Leu Ile Phe Gln Ser Ser Asp Leu
225                 230                 235                 240

Met Asn Lys Val Lys Tyr Leu Phe Asn Phe Asn Ile Asp Met Gly Ser
                245                 250                 255

Val Thr Gly Ser Gly Ser Gly Ser Gly Ser Cys Ala Val His Pro Glu
            260                 265                 270

Pro Asp Pro Ser Ala Leu Trp Leu Thr Asp Pro Ser Ser Ser Val Val
        275                 280                 285

Glu Pro Lys Asp Ser Leu Ile His Ser Ser Ser Arg Asp Val Gln Leu
    290                 295                 300

Val Tyr Gly Asn Glu Asn Ser Glu Asn Gln Gln Gln His Cys Gln Gly
305                 310                 315                 320

Phe Phe Thr Lys Glu Leu Asn Phe Ser Gly Tyr Gly Phe Asp Gly Ser
                325                 330                 335

Ser Asn Arg Asn Lys Thr Gly Ile Ser Cys Lys Pro Glu Ser Arg Glu
            340                 345                 350
```

SEQUENCE LISTING

```
Ile Leu Asn Phe Gly Asp Ser Ser Lys Arg Phe Ser Gly Gln Ser Gln
        355                 360                 365

Leu Gly Pro Gly Pro Gly Leu Met Glu Glu Asn Lys Asn Lys Asn Lys
    370                 375                 380

Asn Lys Lys Arg Ser Leu Gly Ser Arg Gly Asn Asn Glu Glu Gly Met
385                 390                 395                 400

Leu Ser Phe Val Ser Gly Val Ile Leu Pro Thr Ser Thr Met Gly Lys
                405                 410                 415

Ser Gly Asp Ser Asp His Ser Asp Leu Glu Ala Ser Val Val Lys Glu
            420                 425                 430

Ala Val Val Glu Pro Glu Lys Lys Pro Arg Lys Arg Gly Arg Lys Pro
        435                 440                 445

Ala Asn Gly Arg Glu Glu Pro Leu Asn His Val Glu Ala Glu Arg Gln
    450                 455                 460

Arg Arg Glu Lys Leu Asn Gln Arg Phe Tyr Ala Leu Arg Ala Val Val
465                 470                 475                 480

Pro Asn Val Ser Lys Met Asp Lys Ala Ser Leu Leu Xaa Asp Ala Ile
                485                 490                 495

Ala Tyr Ile Asn Glu Leu Lys Ser Lys Val Gln Asn Ser Asp Leu Asp
            500                 505                 510

Lys Glu Glu Leu Arg Ser Gln Ile Glu Cys Leu Arg Lys Glu Leu Thr
        515                 520                 525

Asn Lys Gly Ser Ser Asn Tyr Ser Ala Ser Pro Pro Leu Asn Gln Asp
    530                 535                 540

Val Lys Ile Val Asp Met Asp Ile Asp Val Lys Val Ile Gly Trp Asp
545                 550                 555                 560

Ala Met Ile Arg Ile Gln Cys Ser Lys Lys Asn His Pro Ala Ala Arg
                565                 570                 575

Leu Met Ala Ala Leu Lys Asp Leu Asp Leu Asp Val His His Ala Ser
            580                 585                 590

Val Ser Val Val Asn Asp Leu Met Ile Gln Gln Ala Thr Val Lys Met
        595                 600                 605

Gly Ser Arg Leu Tyr Ala Gln Glu Gln Leu Arg Ile Ala Leu Thr Ser
    610                 615                 620

Lys Ile Ala Glu Ser Arg
625                 630

<210>    4

<211>    201

<212>    DNA

<213>    Solanum lycopersicum

<220>

<221>    source

<222>    1..201

<223>    /organism = "Solanum lycopersicum"
         /mol_type = "unassigned DNA"

<400>    4

ggaagcggag agacagagga gggagaaatt gaatcaaaga ttctacgcgc tcagagccgt        60

agtcccaaat gtgtctaaaa tggataaggc atcacttctt tgagatgcaa ttgcatacat       120
```

-continued

SEQUENCE LISTING caatgagttg aaatcaaaag ttcaaaattc agatttagat aaagaggagt tgaggagcca 180
aattgaatgt ttaaggaagg a 201

<210> 5

<211> 8000

<212> DNA

<213> *Solanum lycopersicum*

<220>

<221> source

<222> 1..8000

<223> /organism = "*Solanum lycopersicum*"
/mol_type = "unassigned DNA"

<400> 5
attcaataat taattgtaat tgtctggcat tgttatggtg gttcacatgt caagttgctt 60
ttatattatt tgttattaaa ataaaaatag aaaaatcaat gttattttca cgttcagcat 120
ccaccaaaac gtgctattaa taatttaatg tctaaaacat atctacaaat tatattatat 180
tagtataata tactttatga tatcttgaac aaagacaatt acaagtagga ccaatcaaaa 240
tgattccaca acgtgacgcc aacgcgtaca aataaggatt ttcctttatt ataactttat 300
aataattaac tcaccgtaat taatttgtat gattataatg aaatgactga aacttttttcg 360 ctcttaacaa gaaatctcga tcgaacttta gccatgaaat aaaaataatt gtgttgagag 420
tagaatttcc aaaaatagat tttatagtgt gtaaaattat atttattaat ttttaatatg 480
attatcaaaa taccgaatcg aagaaagtaa gtaaatttta aggaatgtaa tatgtatgtg 540
gtctcaccct tacatgcatt gaatatgtaa agagtgtttt cgaaggacaa ggattttttt 600
gtttttacta ttaatgtatt ttaaaaactt aagacaaaat tatttactca aaatttacat 660
gcgatattgt actaaaacga tttacaatta ttgtaggtac cttaattact ctgatagtgc 720
atggccttta attacaaggg ataccaataa caaaaaagtc catatttgtg atgaatatgt 780
cttatcacaa aaattgagag gaatattatg atagatttaa tgaaaaattt taatatggac 840
aaaagaatat tatgatagat ttaaagaaaa aatttaatat ggacaaaatt tgtgatggac 900
taataaattt acttttttca ttacgaattt ttggagcctc acgttgaaga tccaatgact 960
tgttttcaaa ttagtttcaa agaatggctg agaatagtct ttctaaaaaa gcatcttcaa 1020
tcgatggctt gaatttaatt attaaaagaa ttattatatt tgataatgta ttgattagat 1080
gcacgttatg aatttaaaat ttcattttag acatgaacct aatatttaaa tagacaccaa 1140
cacaagtata tgacgcgaac aagtgatatt taagttatga gttcaaaatt tatgaatcat 1200
tagtcataac taaaaatgtg atactttagg ggataaggat agaagagcaa atttaaattt 1260
tacgtgaacc tttttttattt aaatagaaaa taatagagcg ataaattcat tatttatcga 1320
gtttcaaatc attaaaaata caatatataa tatacgaatt agatgtatat acacatttga 1380
attcaatggt ggactatata atttgatatt taagtaagca aaagtagata aggagttcaa 1440
gtttaaattt gtaaacatag aatttcctat tttagagttt aaggtaaatt tatgtatatt 1500
ttatcgtttg gaatctcatt ttacgatgct acgctaaata ttagaaattg ctaaaaataa 1560
ttgttgttat tgtaatataa tatcaaaatc aacatgattt catttatttt ctttccatat 1620

-continued

SEQUENCE LISTING atgaattatt tccataaagc ctacatgtag gagatatgct aatttaatat ttcctggaaa 1680
tagttaactt agttgaaaca ttgaagtatt agatatttta ttaatataag cactttaaca 1740
aatatggtta taaaaaaaaa tcttcttctt ttcaattcct ttaacattca ttgaaaatct 1800
tcttatttaa caatattttt ccaattagtt caataactcg tcttcaatca tcgaagatat 1860
ttaatgttac tttttttgaa gtaatgaaat ttacttctaa taatcttgtc ttttttttaa 1920
attggaaatg ggaatagaaa atgataagac gaaattaaat cctcacctac aagataaaag 1980
tttagataag ttttgatagt taattaaatg aatttcaaat tttttaatac ttaaatactt 2040
ctcattaata attgtaaaga tatctacttt tttcattcac tttttacttc aaaaataaat 2100
caaattatgt cacactttca ctgtaataaa ttatatatat ataataaaaa aaaagaaaaa 2160
tcttctacct atataagtac gactctctaa tggtgttaag taaaaagaaa aatttagtat 2220
aaagtcctag gtagttaaaa agtaaaaagt agaactaatg ccggctttcc ttatcctacg 2280
tataattttc ccataaatcg cccaccttaa tttttttttt ctgatttttc atttggcatc 2340
gaagcttata ttagaattta aacttacgtt aaaatttttt ataatggcac taaaattttt 2400
actaacataa ataattatcc catcctaata aaaatttaaa taaaaaatat ttgattaaaa 2460
atacttaccg tttttctcgg aaccctcttc tctttgtcca ctcactttcc tcactcattt 2520
atttttgagc tcacaatatt tttattatat atatatatat atccacaaaa atctctactc 2580
tcatttctca cctaacaaac aaaatctctc attttctgtt ttttgtaaaa ttcttcaatt 2640
taattgaatg acggactata gattatggag taataccaat actactaata catgtgatga 2700
tactatgatg atggattctt ttttatcttc cgatccatcc tctttttggc ctgcttccac 2760
tcccaatcgt ccgactccgg tgaacggagt cggagaaacg atgccgtttt tcaatcaaga 2820
gtcactacag caaaggcttc aggctttaat tgacggtgct cgtgaatcat gggcatatgc 2880
tattttctgg caatcgtcag ttgttgattt tgcgagccaa actgtattgg gttggggaga 2940
tgggtattat aaaggagaag aagataagaa taaacggaga gggtcgtcta gttcagcagc 3000
taattttgtt gctgagcaag agcatagaaa gaaggtgctt cgggagctga attcattaat 3060
atccggtgta caagcttccg ccggaaacgg aactgatgat gcagtggatg aggaagtgac 3120
ggatactgaa tggttttttc tgatttcaat gacccaatcg tttgttaacg gtaacgggct 3180
tccgggcttg gcgatgtaca gttcaagccc aatttgggtt actggaacag agaaattagc 3240
tgcttctcaa tgtgaacggg ccaggcaagc ccaaggtttc gggcttcaga cgattgtgtg 3300
tattccttca gctaacggtg tagtggagct tggttcgact gagctgatat tccaaagctc 3360
ggatttgatg aacaaggtta agtatttgtt taacttcaat attgatatgg ggtctgttac 3420
aggctcaggt tcgggctcag gctcttgtgc tgtgcatcct gagcccgatc cttcggccct 3480
ttggcttacg gatccatctt cctcggttgt ggaacctaag gattcgttaa ttcatagtag 3540
tagtagggat gttcaacttg tgtatggaaa tgagaattct gaaaatcagc agcagcattg 3600
tcaaggattt ttcacaaagg agttgaattt ttcgggttat ggatttgatg gaagtagtaa 3660
taggaataaa actggaattt cttgtaagcc ggagtccagg gagatattga attttggtga 3720
tagtagtaag agattttcag ggcaatcaca gttgggtcct gggcctgggc tcatggagga 3780
gaacaagaac aagaacaaga acaagaaaag gtcacttgga tcaaggggaa acaatgaaga 3840
aggaatgctt tcgtttgttt cgggtgtgat cttgccaact tcaacaatgg ggaagtccgg 3900

-continued

SEQUENCE LISTING

```
ggattctgat cactcagatc tcgaagcctc agtggtgaag gaggccgttg tagaacctga 3960
aaagaagccg aggaagcgag ggaggaaacc agccaatgga agggaggagc cattgaatca 4020
cgtggaagcg gagagacaga ggagggagaa attgaatcaa agattctacg cgctcagagc 4080
cgtagtccca aatgtgtcta aaatggataa ggcatcactt cttggagatg caattgcata 4140
catcaatgag ttgaaatcaa aagttcaaaa ttcagattta gataaagagg agttgaggag 4200
ccaaattgaa tgtttaagga aggaattaac caacaaggga tcatcaaact attccgcctc 4260
ccctccattg aatcaagatg tcaagattgt cgatatggac attgacgtta aggtgattgg 4320
atgggatgct atgattcgta tacaatgtag taaaaagaac catccagctg ccaggctaat 4380
ggcagccctc aaggacttgg acctagacgt gcaccacgct agtgtttccg tggtgaatga 4440
tttgatgatc caacaagcca cagtcaaaat ggggagccgg ctttatgctc aagaacagct 4500
taggatagca ttgacatcaa aaattgctga atcgcgatga aattatgtcc ctagtgagct 4560
atgtataatg ttatcttcta atgagcgaga attttcttct ctgtatataa atgtgatgaa 4620
accaatacta gagatctcga gttgaggctt tttagttcat gtaagattag atatatatat 4680
atgatgcagc ttcatccttt tgtattcttc atccaggaaa taaatgagaa accaataatt 4740
ggtggctgat gatcaacttc atgttattac taattctcgt tccctcttct tttgggatac 4800
aacacttgtc attttacatt aggcaaatta gaagaaaata ctaagcattt tttaattgaa 4860
cgtaacatgt catgtgtgaa ctagagtcac aagttcaatt catgtaacaa acaatcacct 4920
ttgcatttta gtggagaagg atgcattgag tttcaacttg tacactaact agtcataaga 4980
gattactttg ttataaaaaa aaaaacaatt tttgaccttg ttgtgtatat aatatatgat 5040
tcgagtttgg acgaaagttt ttatttaatt atgatggata tattagttat ggagtacaca 5100
attgccttta ctataaaact tattactttt taataataaa tatttttta atgtaaatat 5160
ataaatataa tcaaaactta atataaatgg atgtattact aatcagttgc ttgttttagt 5220
ctagaagaaa gcaccaaaca aaggggtagg gctgcatttt catttataga gaattcattg 5280
aatttggtca aatcatagct gtattcattg gactaggaaa tatttaaaaa gtatatatat 5340
tattgtttat aataatataa tgtcatgagt atcatttgag tttgaagtga cacaagccct 5400
ttaaatgcag ttgatttagg cacaaacttt gttattattc ccgccgtcca aatagttgtt 5460
acatttggct tcctaaaaat taatttaact aatttttaaa tttaatttta tattttgaaa 5520
aattaaagtt tataaataca aaaattattt taatttctta catataatta aaaaatatat 5580
ataaaattta tataatttag cgctggaaaa ttattttgaa aacagaggaa gtattattat 5640
tattttggtc ttatgaattg tgtgataaac agtttatatc tgttaatcaa atagacagag 5700
attgatagat gtgacaaaga ttcgtttttt gtttgaggtt ttataaaagg aaaattgtat 5760
aaaatagcaa actaataact taaattaaat ggaatagcta gggtttgatt taattgtgct 5820
ccatagcaaa cgttggcaaa aatttaccag aagtctcgct cgccactctc ccattctcgc 5880
ctctctcgct ttatacatag aagtgtataa tttatgtttc tgttttgtat aaagcgagag 5940
aaaattgtat atacacatgc aaaaatgtat atctttgtgt tatacactta attatataat 6000
ttacaaacat tttacttcaa atattgcagc gaaaaaggcc aaagaattat acaatcgtga 6060
attatataat tgcagtgaaa tacaattttt tctagcttta tacaacagaa gtgtatatat 6120
tgtatttctg tttttgtata aagcgagaaa aacatatatc ttcttgctat acacttataa 6180
ttatgcaata tacatacatt ttaattcgat taaactgtat acaaaactaa ttatacaatt 6240
```

-continued

SEQUENCE LISTING gcagcgaaat ggcgaattat acaatttagg ccagcgaatt atacactttt atatgtatag 6300
cgaattatac agtttttata tttgctatgg agcgcatata ttatacaaat atgatttttt 6360
tgtttgctat atgtgaaagt tgccctttta taaaagcttt tatgtatagt ttgatttgtt 6420
tttttaaaaa ataaaatatg acaactttag tatcaaaata gattaaattt atatacaata 6480
aatagttata ttttacagcc agccatttat ctttcttttt tttcaagcca caaaatcacc 6540
ttgtagaaag ttattttgtt cgatatttta ttgctaatat ataaaaatat tattataaaa 6600
agcatgtaat atatatataa aaatttgatt tcaaagaata ctttgatcat tataatgata 6660
tgttaatata aataataatt attatagatt aatctgatcg tatattttca gtatacatta 6720
atatatacat ctaaaatatg actgtattaa atatgaacaa aatcatttac atcaccctat 6780
ataatatttt aattaaaaag atgtataaag aagaataaaa aacgctgaag tttaaagcga 6840
atgttattga ccagatcaaa ttgacttgaa gaccaaaatt gaattgttga atacaattaa 6900
ttaatttaaa aatgaccatg ttttacatgt gaaattcatt tatatatata tatatatatc 6960
atatattatt atagtattca cattttgttg tttacactga tggttccgtt aagtgttcac 7020
atttctttgt ttaacactaa actttggagg gaaggatgtg aaaataaaaa atttgggtag 7080
aaaattaatc gataatttaa tattgtctaa tttatcttat gtatattatg atcattactc 7140
ccttattatc tttgtatttt tttaatcttg attatcatat tatttagtat ttttttatcc 7200
ttaattttga tatgttttac ttgagtcaaa aatctataga aaataatttt tctattttta 7260
caagataagg gtaaagatgt gcgaacacaa ctttttttgaa gccccactta tgaaattaca 7320
ctgaacatat tgttgtagta actgtacgaa ctcttttttc tttctatata aacaaatgta 7380
taactaaagt atttagtaaa ataaaaatat aattctattt agttcatgaa tgagaccaca 7440
atatgaatgt atagagctgg ggatattttt tgtttttgtg tagatggata ttaatcgaag 7500
atgtattggt tcttaatagt aagaataaca atagccatta ccctaaagat tgattcacct 7560
ttattttagg gtataaacca aaaaagaatg gacattatta acacgagacc tttagcattt 7620
ccaaaaaaaa tgggagaatt ttgttattta tttaaaaaga aaaaaaaaaa gaacacaccc 7680
ttaacctcaa tatcctcaaa aattcaacca tcaatatcat tattttattt tcatatccta 7740
tgcatttttt attagcttgt aaacttttaa ttttcttcct attcttttat acaacaatga 7800
ctctcaattg tttaacctgc caagctctaa aaagaacaga ttcacatgag gaactaaggg 7860
aaacactgaa tcatgttaat gataagtcga attttcgtct tttttcagtg ggaatggaga 7920
ggaactggtc agggaacttg gttgaaagac ggaaatatga aaaaacgagg ggtcgaacca 7980
taatgggaaa agaaaataat 8000

<210> 6

<211> 1893

<212> DNA

<213> *Solanum lycopersicum*

<220>

<221> source

<222> 1..1893

-continued

SEQUENCE LISTING

<223> /organism = "*Solanum lycopersicum*"
/mol_type = "unassigned DNA"

<400> 6

```
atgacggact atagattatg gagtaatacc aatactacta atacatgtga tgatactatg      60
atgatggatt ctttttttatc ttccgatcca tcctcttttt ggcctgcttc cactcccaat     120
cgtccgactc cggtgaacgg agtcggagaa acgatgccgt tttcaatca agagtcacta      180
cagcaaaggc ttcaggcttt aattgacggt gctcgtgaat catgggcata tgctattttc     240
tggcaatcgt cagttgttga ttttgcgagc caaactgtat tgggttgggg agatgggtat     300
tataaaggag aagaagataa gaataaacgg agagggtcgt ctagttcagc agctaatttt     360
gttgctgagc aagagcatag aaagaaggtg cttcgggagc tgaattcatt aatatccggt     420
gtacaagctt ccgccggaaa cggaactgat gatgcagtgg atgaggaagt gacggatact     480
gaatggtttt ttctgatttc aatgacccaa tcgtttgtta acggtaacgg gcttccgggc     540
ttggcgatgt acagttcaag cccaatttgg gttactggaa cagagaaatt agctgcttct     600
caatgtgaac gggccaggca agcccaaggt ttcgggcttc agacgattgt gtgtattcct     660
tcagctaacg gtgtagtgga gcttggttcg actgagctga tattccaaag ctcggatttg     720
atgaacaagg ttaagtattt gtttaacttc aatattgata tggggtctgt tacaggctca     780
ggttcgggct caggctcttg tgctgtgcat cctgagcccg atccttcggc cctttggctt     840
acggatccat cttcctcggt tgtggaacct aaggattcgt taattcatag tagtagtagg     900
gatgttcaac ttgtgtatgg aaatgagaat tctgaaaatc agcagcagca ttgtcaagga     960
tttttcacaa aggagttgaa tttttcgggt tatggatttg atggaagtag taataggaat    1020
aaaactggaa tttcttgtaa gccggagtcc agggagatat tgaattttgg tgatagtagt    1080
aagagatttt cagggcaatc acagttgggt cctgggcctg ggctcatgga ggagaacaag    1140
aacaagaaca agaacaagaa aaggtcactt ggatcaaggg gaaacaatga agaaggaatg    1200
ctttcgtttg tttcgggtgt gatcttgcca acttcaacaa tggggaagtc cggggattct    1260
gatcactcag atctcgaagc ctcagtggtg aaggaggccg ttgtagaacc tgaaaagaag    1320
ccgaggaagc gagggaggaa accagccaat ggaagggagg agccattgaa tcacgtggaa    1380
gcggagagac agaggaggga gaaattgaat caaagattct acgcgctcag agccgtagtc    1440
ccaaatgtgt ctaaaatgga taaggcatca cttcttggag atgcaattgc atacatcaat    1500
gagttgaaat caaaagttca aaattcagat ttagataaag aggagttgag gagccaaatt    1560
gaatgtttaa ggaaggaatt aaccaacaag ggatcatcaa actattccgc ctcccctcca    1620
ttgaatcaag atgtcaagat tgtcgatatg gacattgacg ttaaggtgat tggatgggat    1680
gctatgattc gtatacaatg tagtaaaaag aaccatccag ctgccaggct aatggcagcc    1740
ctcaaggact tggacctaga cgtgcaccac gctagtgttt ccgtggtgaa tgatttgatg    1800
atccaacaag ccacagtcaa aatggggagc cggctttatg ctcaagaaca gcttaggata    1860
gcattgacat caaaaattgc tgaatcgcga tga                                 1893
```

<210> 7

<211> 630

<212> PRT

-continued

SEQUENCE LISTING

<213> *Solanum lycopersicum*

<400> 7

```
Met Thr Asp Tyr Arg Leu Trp Ser Asn Thr Asn Thr Thr Asn Thr Cys
1               5                   10                  15

Asp Asp Thr Met Met Met Asp Ser Phe Leu Ser Ser Asp Pro Ser Ser
            20                  25                  30

Phe Trp Pro Ala Ser Thr Pro Asn Arg Pro Thr Pro Val Asn Gly Val
        35                  40                  45

Gly Glu Thr Met Pro Phe Phe Asn Gln Glu Ser Leu Gln Gln Arg Leu
    50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95

Gly Asp Gly Tyr Tyr Lys Gly Glu Glu Asp Lys Asn Lys Arg Arg Gly
            100                 105                 110

Ser Ser Ser Ser Ala Ala Asn Phe Val Ala Glu Gln Glu His Arg Lys
        115                 120                 125

Lys Val Leu Arg Glu Leu Asn Ser Leu Ile Ser Gly Val Gln Ala Ser
    130                 135                 140

Ala Gly Asn Gly Thr Asp Asp Ala Val Asp Glu Glu Val Thr Asp Thr
145                 150                 155                 160

Glu Trp Phe Phe Leu Ile Ser Met Thr Gln Ser Phe Val Asn Gly Asn
                165                 170                 175

Gly Leu Pro Gly Leu Ala Met Tyr Ser Ser Ser Pro Ile Trp Val Thr
            180                 185                 190

Gly Thr Glu Lys Leu Ala Ala Ser Gln Cys Glu Arg Ala Arg Gln Ala
        195                 200                 205

Gln Gly Phe Gly Leu Gln Thr Ile Val Cys Ile Pro Ser Ala Asn Gly
    210                 215                 220

Val Val Glu Leu Gly Ser Thr Glu Leu Ile Phe Gln Ser Ser Asp Leu
225                 230                 235                 240

Met Asn Lys Val Lys Tyr Leu Phe Asn Phe Asn Ile Asp Met Gly Ser
                245                 250                 255

Val Thr Gly Ser Gly Ser Gly Ser Gly Ser Cys Ala Val His Pro Glu
            260                 265                 270

Pro Asp Pro Ser Ala Leu Trp Leu Thr Asp Pro Ser Ser Ser Val Val
        275                 280                 285

Glu Pro Lys Asp Ser Leu Ile His Ser Ser Ser Arg Asp Val Gln Leu
    290                 295                 300

Val Tyr Gly Asn Glu Asn Ser Glu Asn Gln Gln Gln His Cys Gln Gly
305                 310                 315                 32

Phe Phe Thr Lys Glu Leu Asn Phe Ser Gly Tyr Gly Phe Asp Gly Ser
                325                 330                 335

Ser Asn Arg Asn Lys Thr Gly Ile Ser Cys Lys Pro Glu Ser Arg Glu
            340                 345                 350

Ile Leu Asn Phe Gly Asp Ser Ser Lys Arg Phe Ser Gly Gln Ser Gln
        355                 360                 365

Leu Gly Pro Gly Pro Gly Leu Met Glu Glu Asn Lys Asn Lys Asn Lys
    370                 375                 380
```

-continued

SEQUENCE LISTING

```
Asn Lys Lys Arg Ser Leu Gly Ser Arg Gly Asn Asn Glu Glu Gly Met
385                 390                 395                 400

Leu Ser Phe Val Ser Gly Val Ile Leu Pro Thr Ser Thr Met Gly Lys
                405                 410                 415

Ser Gly Asp Ser Asp His Ser Asp Leu Glu Ala Ser Val Val Lys Glu
            420                 425                 430

Ala Val Val Glu Pro Glu Lys Lys Pro Arg Lys Arg Gly Arg Lys Pro
        435                 440                 445

Ala Asn Gly Arg Glu Glu Pro Leu Asn His Val Glu Ala Glu Arg Gln
    450                 455                 460

Arg Arg Glu Lys Leu Asn Gln Arg Phe Tyr Ala Leu Arg Ala Val Val
465                 470                 475                 480

Pro Asn Val Ser Lys Met Asp Lys Ala Ser Leu Leu Gly Asp Ala Ile
                485                 490                 495

Ala Tyr Ile Asn Glu Leu Lys Ser Lys Val Gln Asn Ser Asp Leu Asp
            500                 505                 510

Lys Glu Glu Leu Arg Ser Gln Ile Glu Cys Leu Arg Lys Glu Leu Thr
        515                 520                 525

Asn Lys Gly Ser Ser Asn Tyr Ser Ala Ser Pro Pro Leu Asn Gln Asp
    530                 535                 540

Val Lys Ile Val Asp Met Asp Ile Asp Val Lys Val Ile Gly Trp Asp
545                 550                 555                 560

Ala Met Ile Arg Ile Gln Cys Ser Lys Lys Asn His Pro Ala Ala Arg
                565                 570                 575

Leu Met Ala Ala Leu Lys Asp Leu Asp Leu Asp Val His His Ala Ser
            580                 585                 590

Val Ser Val Val Asn Asp Leu Met Ile Gln Gln Ala Thr Val Lys Met
        595                 600                 605

Gly Ser Arg Leu Tyr Ala Gln Glu Gln Leu Arg Ile Ala Leu Thr Ser
    610                 615                 620

Lys Ile Ala Glu Ser Arg
625                 630
```

<210> 8

<211> 201

<212> DNA

<213> *Solanum lycopersicum*

<220>

<221> source

<222> 1..201

<223> /organism = "*Solanum lycopersicum*"
/mol_type = "unassigned DNA"

<400> 8

```
ggaagcggag agacagagga gggagaaatt gaatcaaaga ttctacgcgc tcagagccgt      60

agtcccaaat gtgtctaaaa tggataaggc atcacttctt ggagatgcaa ttgcatacat     120

caatgagttg aaatcaaaag ttcaaaattc agatttagat aaagaggagt tgaggagcca     180

aattgaatgt ttaaggaagg a                                               201
```

-continued

SEQUENCE LISTING

<210> 9

<211> 6700

<212> DNA

<213> *Capsicum annuum*

<220>

<221> source

<222> 1..6700

<223> /organism = "*Capsicum annuum*"
/mol_type = "unassigned DNA"

<400> 9

```
ctctaaatat gtaaaatgaa ttaggaataa atgcacatat tttccttcgc agaaagagat     60
agcaacatgg acctcaaaca gcctcttggc atattattta cttaactatc aaaatggtta    120
aatgtgtatt ttataataac taaaagctta aacaataaag taataaatct tattagtata    180
ttttatttct atctgtatca tcgactcctt catatgtcta taattaatac tttttgctaa    240
acataacatt atttcttttt ataagttgaa acactgaatt atcacacttt catattatat    300
aaactcgtaa ctgaaaatgt ttcaaaaata gttatagata atatcttttc aattcctaaa    360
ttcaactcct caacccaagg aaagaatgga aatggattca tatacgttga tttctcattc    420
tttttctatc atttcattta ccttcctatt gagagggaaa tggaatcaag aaaatgatca    480
accacattat tagatactca cttcgttagt gttatttgtt aaatattgac ttgatacact    540
gcacctttgg gtgtggttga gttggtttga ggggtgactt tcaaagcgaa ggtcgcggta    600
tcaattccct ctaatgcttt ttcaatctag ctcgtcacac taggtttacc tagtgcggtt    660
tacatctcct gtgtggttta cgagtgatta tacagtgagg ggtttaccca atacacacaa    720
agtgctcacc cgaagggcag aggctagtgg ctgggtaaac ccgaagggca gaggctagtg    780
gctgcggggt ttacccagtg cgcacaaagt gctcacccga ctttcctgaa gtttcaaaaa    840
atatatatat atatatatat tgacttgata catttcttaa agagcaaaat aaattaaaaa    900
ttaaataata actcaactct acattttctt aattgaacag aaaaataagt aactatgttt    960
tggtacagtg aataaataga agtggtcgaa aaagtatttt ctccattcta gaagtacacc   1020
aagcttctaa taagagtcaa cacacctaag tttaaacgta attcaaacat caatttctta   1080
gtttttaaaa ctaaattatg gatattaaaa aattataaga aaaacaaatg atactcctta   1140
caatttattt ggttatcaga ttacaactga ttcgacttgt caaataataa tgattgaaat   1200
atatgatagg atatgtcgca gtaagagatt tgaatcataa taggtgagga taaacgctat   1260
tgcaaaaaaa gtttttaatt ttcaccaaat attgggaaac tacttcaaat atactccatc   1320
aatttacatt taaagaataa ataattaata ttaaggataa aagatttttt tttttaatct   1380
tatttttgat atatcaaaat gataagtata aataaaaatt caattaaaga aataatgtaa   1440
cgtaaaagtg aacagaggga atccttttta gtagacattt atatttagtt gaagtttaaa   1500
aatcccaaat aattcaaatt aaagttgact ttcataaaca cttattaaaa aaatcagcca   1560
aagataatac atttataaaa atgtaatttt caaatgaatt aactagacgt aaattttttt   1620
tttttcaaaa gtaatttttt aataagttat tttaataaaa aagcttctca aaataagaaa   1680
tttttatagc cacttgacca aacaagtctc ccaaacatga atttgaatta atttttaaaa   1740
```

-continued

SEQUENCE LISTING

```
aaatttcgca agtaaaaact aaaaagactt cttaaaatgt gtttttcaaa atttaaattc   1800
tattcaagtt tgatattatc ctaaaattat tgaccatatt agaaatgttt gattgaaatt   1860
atttcttgaa aattagaaaa aaaatgaggt tctttgatat tttttgaag cagtggtatg   1920
gccatataag aatacactca ttatatgtta ttgattggtt gctgattaaa gaagttcgtc   1980
tttttaattt tttattcgat atttatattg aaactttgat taccttactg taagatgtga   2040
catttctaac aaaattatat ttatattaaa aattttaaaa ttaaaacatt taattaaggg   2100
tgagccagat ccactaccgc accgtagccg cgacccatat ggtacaagag gagtagtagt   2160
gatgttggcg attaattggc gggtccttcg tggaacccgc cagtctcttt cctcattctc   2220
ccaaattcag ctcaaattca cctcaaataa aacccaaact caaattccac tcttattaac   2280
caaacccaat atttctctct catttttctc cgccacaccc ctctatcctc attctctctc   2340
tctctacaca ccattttcac ctgttttctg ctgtgtgttt tatggaatga ctgattacag   2400
cttgcccacc atgaatctct ggaataacag tactactgat gacaacgttt ctatgatgga   2460
ggcttttatg tcttccgatc tttctttttg gggtggtact actacttcta gtgctactgc   2520
tactgctgct gctcttgcta atcccaatta tacttcaact gtttaccctc ctcctggcgc   2580
ttcttgtgca tcttccgtaa cggctacagc tgctgctgtg actgttgatg cgtcaaaaac   2640
catgccattt ttcaaccagg agacgctaca gcagcgtctt cagaccctaa tagacggtgc   2700
tcgtgagacg tggacgtatg ctatcttctg gcagtcgtct gatttagatt tctcgagtcc   2760
gtctgtgttg ggttggggtg atggttatta caaaggggag gaggataaaa acaagaggaa   2820
attatctgtt tcttctccgg cttatattgc tgagcaggaa catcggaaga aggttcttag   2880
agagctgaat tcgttgattt cagggacaca aactggtaca gacgatgctg ttgatgaaga   2940
agttaccgat accgaatggt tetttettat ctccatgact caatcttttg tcaacgggaa   3000
cgggcttccg ggccaggcta tgtgcagttc cagcccgatt tgggttgccg gagtagagaa   3060
attggctgct tctcactgtg aacgggctcg gcaggcccaa gggttcgggc ttcagacgat   3120
ggtgtgtatc ccttcagcta acggtgttgt tgaattgggt tcgacggagt tgattatcca   3180
gagttctgat ctgatgaata aggttagagt actgttcaat ttcaataatg atttggggtc   3240
aggttcatgg gctgtgcagc cggagagcga tccgtcagcg ctttggttga cggagccatc   3300
ttcctcaggt atggaagtta gagagtcttt aaatacagtt caaacaagtt caattccatc   3360
aagtaatagt aataagcaaa ttgcgtatgg aaatgagaac aatgatcatc catctggaaa   3420
tgggaatggt catagttctt ataatcagca gcatcctcat caacaaacac aaggattttt   3480
cacgaaggag ttaaactttt cggactttgg gttcgatgga agtagtaata ggaacgggaa   3540
ttcatcgctc tcttgcaagc ctgagtctgg ggaaatcttg aattttggtg atagtacgaa   3600
gaaaagtgct tgtagtgcaa atgggaactt gttttcgggc cattcccaat ttggggcagg   3660
tgaggagaac aagaacaaga ccaagaaaag gtcagctact tccaggggaa gcaatgaaga   3720
aggaatgctt tcatttgttt cgggtacagt tttgccttct tccggtatga agtcaggcgg   3780
aggcgaagac tctgaccatt cagatcttga agcttcggtg gtgaaagaag ctgatagtag   3840
tagagttgta gaaccggaaa agaagccaag gaagcgagga aggaagcctg ctaatggaag   3900
ggaggaacct ttgaatcatg ttgaggcaga gaggcaaagg agggagaaat tgaaccaaag   3960
attctacgcg cttagagctg ttgtaccgaa tgtgtctaag atggacaagg catcacttct   4020
```

-continued

SEQUENCE LISTING tggagatgca atttcataca taaatgagtt gaaatcgaag cttcacaata cagagtcaga 4080
taaagaagac ttgaagagcc aaatagagga tttgaagaaa gaattagcta gtaaagaatc 4140
aaggcgccct ggtcaaccac caccaaacca agatctcaag atgtctagcc acaccggaac 4200
caagattgta gacgcggaga tagacattaa gataatggga tgggatgtta tgattcgtgt 4260
acaatctaat aaaaagaatc atccagccgc aaggtttatg gcggccctca tggaactaga 4320
cctagatgtg aaccatgcca gtgtttcatt ggtgaacgag ttgatgatcc agcaagccac 4380
agtgaaaatg agtagccgtc attacactga agagcagctt aggatagcat tgatgtcaag 4440
aattgctgaa acgcgctaaa aaagacccta gaaagtagat agaactcaaa gaaagcatgt 4500
gggctttgat ggcgctctgg ttgctgcagc tctatgtaat gtttttgtta tgaattagag 4560
atttcatcag gctatcttcg tgttattttt cgaacttgta ccttaggtgg ttgtcgaaat 4620
attcttgtac ataaatgtta ttacccgaaa actcaacata atcgggcttt agctcatgta 4680
attaaacata tattccaact ccgtcttgtc tgttagattg catctatcat tatgtattct 4740
ttgtccatgc ataaatgaag aaatttgatg gcaggtgaat ttgattttga agcaaatgtg 4800
atttactgtc gtgctgctta ttcttatacc caatttttga gctgcattag gattgtgtga 4860
agtactttaa gctattcatt catgagaaaa atgtgaaaga gatcatcatt tcagaaatat 4920
gcactatttc tccaattcaa acttcatgtt caaattgtat taaataattg tattggaggt 4980
cattgcttac gacctttatg catcacattt tgactaaaaa caataacgga ttatttcatg 5040
agaatatttg gatttacata tacacctcag aaaaactatc atctttcatt tgagtttttt 5100
aatgtcatac tccatccgac tcaatttaat ttgcgccgaa gaatgccaaa aaagtttcac 5160
atttatggtc aatagatgag taatctcctt ataaggcttg gattatcctc tttcctaatg 5220
ctcaaaaggt gtaagtttag ccatgaccta attttatata tacttttttt ttgacatttc 5280
tttaatctta atttttcata cgacatattt aagattataa aattaaataa tattttaata 5340
cattctatct tgtgtcaagt taaatgagac aaacaaatta taacaaagga agcatcaaat 5400
aaaataggaa agaaggaaaa agggatttcg taaaagagcg ataagataag gtgatagttt 5460
gatagactag attggactag atgcaacagc aaaatagaac aggaaactac aaggaactag 5520
tccatttatt catttggctg cttgctcgtt tatattgtga attgtatatc tccacatatt 5580
ttattctaat aaagatatca ggaagaaggc atgtgtctta ttattttcct ttaggagaat 5640
acactgaact tggttcttct tttggtccct attgtctact atagaccaat gtatattttc 5700
cataatagta ttggcataac atgctaaagt attttccata atagtattgg caagaaacgc 5760
catgaatatc atgtaggttg aaactgacag caacgtttca aattcacttc atttgaactt 5820
tcacttcacc caagtacagt ctccccgtcc gaagcaggat tttcatcaaa gagatgcaac 5880
atttaccata aataaatttt ctcccccccca tccctctctc tctatatatt agtaactttg 5940
gatccagatg aaccctttc cgcctcacaa gtttcaccca agttccaagt atatgttact 6000
ctagaagttt taactttctt tttagtaatt ctttgttaat atgttgtccc tatactagta 6060
tctggacatg ccactactga aaaattcaaa atttaccttc attctttaag gtaatttaca 6120
attcaatctt taaggttttt atattgacct tattatattt taaagttatg aatttatatt 6180
tattattatt actttctata tttttaaata agtgacattt tagtcttttc attttatttc 6240
taaataactt ggtgttttag ataattaaga agatattaat gatgttatta taagtttacc 6300
actttttaaa taaagaaagt tttacatgac ttaaggagta ctaagaatta catcatttcc 6360

-continued

SEQUENCE LISTING

```
aaagaaatat taagaataag ttggtaaaaa tactatttat ttaaaaataa aaaaaaataa   6420
ttttaacaaa ctaatacata taaatttata tttcctattg aaaatacaat tcatactaat   6480
ctcaacgccg ctcggtaaaa ttagatccgc ttcactttaa ctgctaatta ttgaataaag   6540
tgtagggaca aatttgatgt aaataaaatc atctactcca ctaatatatt aatttgtttt   6600
taatttaata tatatttttc atacactaga caacaaagaa ttgtgacgtg acgcaaattt   6660
ggtggaagtg gacatgcaga caaaaaagat catgtgttac                         6700

<210>   10
<211>   2073
<212>   DNA
<213>   Capsicum annuum
<220>
<221>   source
<222>   1..2073
<223>   /organism = "Capsicum annuum"
        /mol_type = "unassigned DNA"

<400>   10

atgactgatt acagcttgcc caccatgaat ctctggaata acagtactac tgatgacaac     60
gtttctatga tggaggcttt tatgtcttcc gatctttctt tttggggtgg tactactact    120
tctagtgcta ctgctactgc tgctgctctt gctaatccca attatacttc aactgtttac    180
cctcctcctg gcgcttcttg tgcatcttcc gtaacggcta cagctgctgc tgtgactgtt    240
gatgcgtcaa aaaccatgcc atttttcaac caggagacgc tacagcagcg tcttcagacc    300
ctaatagacg gtgctcgtga gacgtggacg tatgctatct tctggcagtc gtctgattta    360
gatttctcga gtccgtctgt gttgggttgg ggtgatggtt attacaaagg ggaggaggat    420
aaaaacaaga ggaaattatc tgtttcttct ccggcttata ttgctgagca ggaacatcgg    480
aagaaggttc ttagagagct gaattcgttg atttcaggga cacaaactgg tacagacgat    540
gctgttgatg aagaagttac cgataccgaa tggttctttc ttatctccat gactcaatct    600
tttgtcaacg ggaacgggct tccgggccag gctatgtgca gttccagccc gatttgggtt    660
gccggagtag agaaattggc tgcttctcac tgtgaacggg ctcggcaggc ccaagggttc    720
gggcttcaga cgatggtgtg tatcccttca gctaacggtg ttgttgaatt gggttcgacg    780
gagttgatta tccagagttc tgatctgatg aataaggtta gagtactgtt caatttcaat    840
aatgatttgg ggtcaggttc atgggctgtg cagccggaga gcgatccgtc agcgctttgg    900
ttgacggagc catcttcctc aggtatggaa gttagagagt ctttaaatac agttcaaaca    960
agttcaattc catcaagtaa tagtaataag caaattgcgt atggaaatga gaacaatgat   1020
catccatctg gaaatgggaa tggtcatagt tcttataatc agcagcatcc tcatcaacaa   1080
acacaaggat ttttcacgaa ggagttaaac ttttcggact ttgggttcga tggaagtagt   1140
aataggaacg ggaattcatc gctctcttgc aagcctgagt ctggggaaat cttgaatttt   1200
ggtgatagta cgaagaaaag tgcttgtagt gcaaatggga acttgttttc gggccattcc   1260
caatttgggg caggtgagga gaacaagaac aagaccaaga aaaggtcagc tacttccagg   1320
ggaagcaatg aagaaggaat gctttcattt gtttcgggta cagttttgcc ttcttccggt   1380
```

-continued

SEQUENCE LISTING atgaagtcag gcggaggcga agactctgac cattcagatc ttgaagcttc ggtggtgaaa 1440
gaagctgata gtagtagagt tgtagaaccg gaaaagaagc caaggaagcg aggaaggaag 1500
cctgctaatg gaagggagga acctttgaat catgttgagg cagagaggca aaggagggag 1560
aaattgaacc aaagattcta cgcgcttaga gctgttgtac cgaatgtgtc taagatggac 1620
aaggcatcac ttcttggaga tgcaatttca tacataaatg agttgaaatc gaagcttcac 1680
aatacagagt cagataaaga agacttgaag agccaaatag aggatttgaa gaaagaatta 1740
gctagtaaag aatcaaggcg ccctggtcaa ccaccaccaa accaagatct caagatgtct 1800
agccacaccg gaaccaagat tgtagacgcg gagatagaca ttaagataat gggatgggat 1860
gttatgattc gtgtacaatc taataaaaag aatcatccag ccgcaaggtt tatggcggcc 1920
ctcatggaac tagacctaga tgtgaaccat gccagtgttt cattggtgaa cgagttgatg 1980
atccagcaag ccacagtgaa aatgagtagc cgtcattaca ctgaagagca gcttaggata 2040
gcattgatgt caagaattgc tgaaacgcgc taa 2073

<210> 11

<211> 690

<212> PRT

<213> *Capsicum annuum*

<400> 11

Met Thr Asp Tyr Ser Leu Pro Thr Met Asn Leu Trp Asn Asn Ser Thr
1 5 10 15

Thr Asp Asp Asn Val Ser Met Met Glu Ala Phe Met Ser Ser Asp Leu
20 25 30

Ser Phe Trp Gly Gly Thr Thr Thr Ser Ser Ala Thr Ala Thr Ala Ala
35 40 45

Ala Leu Ala Asn Pro Asn Tyr Thr Ser Thr Val Tyr Pro Pro Pro Gly
50 55 60

Ala Ser Cys Ala Ser Ser Val Thr Ala Thr Ala Ala Ala Val Thr Val
65 70 75 80

Asp Ala Ser Lys Thr Met Pro Phe Phe Asn Gln Glu Thr Leu Gln Gln
85 90 95

Arg Leu Gln Thr Leu Ile Asp Gly Ala Arg Glu Thr Trp Thr Tyr Ala
100 105 110

Ile Phe Trp Gln Ser Ser Asp Leu Asp Phe Ser Ser Pro Ser Val Leu
115 120 125

Gly Trp Gly Asp Gly Tyr Tyr Lys Gly Glu Glu Asp Lys Asn Lys Arg
130 135 140

Lys Leu Ser Val Ser Ser Pro Ala Tyr Ile Ala Glu Gln Glu His Arg
145 150 155 160

Lys Lys Val Leu Arg Glu Leu Asn Ser Leu Ile Ser Gly Thr Gln Thr
165 170 175

Gly Thr Asp Asp Ala Val Asp Glu Glu Val Thr Asp Thr Glu Trp Phe
180 185 190

Phe Leu Ile Ser Met Thr Gln Ser Phe Val Asn Gly Asn Gly Leu Pro
195 200 205

Gly Gln Ala Met Cys Ser Ser Ser Pro Ile Trp Val Ala Gly Val Glu
210 215 220

-continued

SEQUENCE LISTING

```
Lys Leu Ala Ala Ser His Cys Glu Arg Ala Arg Gln Ala Gln Gly Phe
225                 230                 235                 240

Gly Leu Gln Thr Met Val Cys Ile Pro Ser Ala Asn Gly Val Val Glu
                245                 250                 255

Leu Gly Ser Thr Glu Leu Ile Ile Gln Ser Ser Asp Leu Met Asn Lys
            260                 265                 270

Val Arg Val Leu Phe Asn Phe Asn Asn Asp Leu Gly Ser Gly Ser Trp
        275                 280                 285

Ala Val Gln Pro Glu Ser Asp Pro Ser Ala Leu Trp Leu Thr Glu Pro
    290                 295                 300

Ser Ser Ser Gly Met Glu Val Arg Glu Ser Leu Asn Thr Val Gln Thr
305                 310                 315                 320

Ser Ser Ile Pro Ser Ser Asn Ser Asn Lys Gln Ile Ala Tyr Gly Asn
                325                 330                 335

Glu Asn Asn Asp His Pro Ser Gly Asn Gly Asn Gly His Ser Ser Tyr
            340                 345                 350

Asn Gln Gln His Pro His Gln Gln Thr Gln Gly Phe Phe Thr Lys Glu
        355                 360                 365

Leu Asn Phe Ser Asp Phe Gly Phe Asp Gly Ser Ser Asn Arg Asn Gly
    370                 375                 380

Asn Ser Ser Leu Ser Cys Lys Pro Glu Ser Gly Glu Ile Leu Asn Phe
385                 390                 395                 400

Gly Asp Ser Thr Lys Lys Ser Ala Cys Ser Ala Asn Gly Asn Leu Phe
                405                 410                 415

Ser Gly His Ser Gln Phe Gly Ala Gly Glu Glu Asn Lys Asn Lys Thr
            420                 425                 430

Lys Lys Arg Ser Ala Thr Ser Arg Gly Ser Asn Glu Glu Gly Met Leu
        435                 440                 445

Ser Phe Val Ser Gly Thr Val Leu Pro Ser Ser Gly Met Lys Ser Gly
    450                 455                 460

Gly Gly Glu Asp Ser Asp His Ser Asp Leu Glu Ala Ser Val Val Lys
465                 470                 475                 480

Glu Ala Asp Ser Ser Arg Val Val Glu Pro Glu Lys Lys Pro Arg Lys
                485                 490                 495

Arg Gly Arg Lys Pro Ala Asn Gly Arg Glu Glu Pro Leu Asn His Val
            500                 505                 510

Glu Ala Glu Arg Gln Arg Arg Glu Lys Leu Asn Gln Arg Phe Tyr Ala
        515                 520                 525

Leu Arg Ala Val Val Pro Asn Val Ser Lys Met Asp Lys Ala Ser Leu
    530                 535                 540

Leu Gly Asp Ala Ile Ser Tyr Ile Asn Glu Leu Lys Ser Lys Leu His
545                 550                 555                 560

Asn Thr Glu Ser Asp Lys Glu Asp Leu Lys Ser Gln Ile Glu Asp Leu
                565                 570                 575

Lys Lys Glu Leu Ala Ser Lys Glu Ser Arg Arg Pro Gly Gln Pro Pro
            580                 585                 590

Pro Asn Gln Asp Leu Lys Met Ser Ser His Thr Gly Thr Lys Ile Val
        595                 600                 605

Asp Ala Glu Ile Asp Ile Lys Ile Met Gly Trp Asp Val Met Ile Arg
    610                 615                 620

Val Gln Ser Asn Lys Lys Asn His Pro Ala Ala Arg Phe Met Ala Ala
625                 630                 635                 640
```

-continued

SEQUENCE LISTING

```
Leu Met Glu Leu Asp Leu Asp Val Asn His Ala Ser Val Ser Leu Val
                645                 650                 655

Asn Glu Leu Met Ile Gln Gln Ala Thr Val Lys Met Ser Ser Arg His
            660                 665                 670

Tyr Thr Glu Glu Gln Leu Arg Ile Ala Leu Met Ser Arg Ile Ala Glu
        675                 680                 685

Thr Arg
    690

<210>     12

<211>     5200

<212>     DNA

<213>     Cucumis sativus

<220>

<221>     source

<222>     1..5200

<223>     /organism = "Cucumis sativus"
          /mol_type = "unassigned DNA"

<400>     12

ttttaaattt gaggcgtcat aaagttagtt tatatgtgag aggtatcttg ttgaattttt        60

taagttttta aaatttttta ttcaataaag ttctaaaatt tgctctattt tfttctgtt        120

tggcatccaa ctgtagacat actttttcaa aattttaaca ctcggtttgg tatttgaatt       180

taattaaata aagctatact caacaaaaaa atatattgtt ttttaaagta gttaattaag       240

ttggttaata ccataaagta agcacaaagc aatatgtgac aaataagtga taaataagta       300

atttgtctta cgggtatttg tgacaaataa gtttataagg ataactcaac catcttagac       360

aacctatcaa catcaacttg cctaaggtga atgttaatat tgattgttag gggtgagtgt       420

cacttgccat tgaagttgat tatcaaaggt gattttcatt gcagtttatc atataagcag       480

tagttggagt ctgaaattga aggtggttat cgaagttgat aatcaaaaag tgattttctc       540

aaagtttgta gtcatagctt ggaattcatc gtgtaaacgt ggtcatcaaa gttggctttt       600

tttggagttt cctattggag atagttacca tagcccaaaa ttagttgttg gaggtggtca       660

cataaaggta tctagtcgtt aggtcagttt gtcatcgaag gtggttgcca gaccttgaaa       720

tcgatcatca aagttggtta tctgagtgtg gtaatggtaa ttgatcgttg aatctattag       780

aaaaactgga gagagcttca tcaacctata aagttagtgg accaaagaga actcaaactc       840

aacttatatt ttgatgtgtt aactccccta aaataaaaca aacgaaacaa aaaaaaaaaa       900

tcataaagac aaaaatgaaa aaatggagta ccatcattgt actaaaaaaa tatattttaa       960

caaaagaaaa aatcaatgac tacaaataaa ttttaaaaca ctagatttaa aaaaaaaaat      1020

caaagaacaa aaatagaaga tatttatata tatatatatt taaaaaagaa aattaataga      1080

tattataatg aggcttagta ttttcaaaat cctgttttag ggcaaaaaaa agaggggaaa      1140

aataaaacaa cttccgtctt tgattcacaa acaagagacg tgtcatgttc tcattagcta      1200

aaaccggaaa aaaagcgatg agtaaaaaag tcataaaaac ggttaaccct caacgcctct      1260

caagggttct tcacgtgcca gtcacgtgga aggaagggaa gcgaaccggg tctaagaaaa      1320

ccgcactatc tggggtaagt actattagta taattgtact ataagcgcgg agttgagaaa      1380
```

-continued

SEQUENCE LISTING

```
gacgccggct ttttgaacga tttaatcggc gatctaaaga agaagcctct tggttccttc      1440
ttctectett cgcttctctg ttaaatgttc atcacaaata aatcccatac caatcgcccg      1500
acatttctct cactccacaa tcggagacca aagattattc ctttttcccc atttctattt      1560
cttccaatct caatcgcatg acggattatc gtttgtcgac gatgaatctc tggactgacg      1620
agaacgcgtc ggttatggac gctttcatga attccgatct gtcttcctac tgggctccgt      1680
cagccgcctc ctctcactct cttcaccacc caccgccacc tcagtcctcc gcctccacat      1740
ccactccccc gccggacgca cctaagtccc tccccgtttt caatcaggag actctgcagc      1800
agcggctcca ggcgctgatc gacggtgcta gggagagttg gacttatgcg attttctggc      1860
agtcgtctta tgattattct ggtgggtctg ttttggggtg ggtgatgggg tattacaaag      1920
gagaggaaga taaaggaaag ggaaaagcga aaatggtgtc gtcagcggcg gagcaggctc      1980
accggaagaa ggttttacgg gagcttaact ctttgatttc tggctctgcc gccggacctg      2040
acgatgcggt ggatgaggag gttacggata cggagtggtt ctttttggtt tcgatgactc      2100
agtcgtttgt taatggtgtt gggttaccga gtcaagcgtt ttaccactcg acgccgattt      2160
gggtctctgg tgccgatcgg ctgtcggcgt ctgcctgtga acgagctaga caggggaggg      2220
tttttgggtt acagacgatg gtctgtattc catcgcctaa cggtgttgtg gaaatgggtt      2280
cgacggaatt gattcatcga acgtcggatt tgatgaataa ggtcaagatt ctgttcaatt      2340
tcaacaatct cgaaacgagt tcttggattt cgggaactac cgccgccgca tccgctgccg      2400
acgaagggga aaacgacccg tcgtcgatgt ggatcagtga gccatcgagt acaatcgaga      2460
tgaaggattc aatcaccacc actgttcctt ccagcaacgt tccggcaaag ccaatccgtt      2520
cggaaaatcc cagtacaagt agcttaacgg aaaatatgag cacgattcaa caatcccatc      2580
ataaacagag ccaaagcttc ttaaatttct ccgattacgg cttcgaatca aatcccacaa      2640
agaacaccac cgctaccgcc accgcaacca ccagcaccac cccatcattc aagccggaat      2700
ccggcgggat gctgaatttc ggcaacggga gcctcttctc cggccattca cagtacgtaa      2760
caaacgaaca gaacgagaaa aagagatccc ctgcttctcg aagtagcaac gacgaaggga      2820
tcctctcttt cacctccggc gtgatcttac cctcttccgg taaggtaaaa tccggtgatt      2880
cagaccattc agatctcgaa gcatcagcga tcagagaagt ggatagctgt acaaaatcat      2940
tagaacccga aaaacgtcca agaaaaagag gtagaaaacc agcaaacgga agagaagagc      3000
cattgaatca cgtagaagca gagagacaac ggcgagagaa attaaaccag aaattctacg      3060
ctctccgagc tgtagttcca aacgtatcta agatggacaa agcctcacta ctaggtgacg      3120
cggtttcgta cataaacgag ctcaaatcga agctccaaat ggcagaatcg gagaaaacag      3180
atatgggaaa acatctagaa ttgctgaaga aggagatggg aggaaaagat ttaggatgtt      3240
actcaaaccc aaatgatgaa gatctgaaaa cagggaaaag aaaggtaatg gatatggaga      3300
ttgaagttaa aatcatgggt tgggatgcga tgataaggat tcaaagcaac aagaagaatc      3360
atccggcggc gaggttgatg acggcgttta aggatttgga tttagaaatg cttcacgcga      3420
gtgtttctgt agtgaatgat ttgatgattc aacaagcaac agtgaagatg gggagcagat      3480
tttacacaca agagcagctt aaaatggctc ttgtcgcccg agtcggcggt ggtggaagtg      3540
gaggcggcgg tggaatcatg taaatggggt taggggacat ttttgaagct cccaattagt      3600
agagtttagt tgagggaatc tgatttagta ttgtgtaata taaatgttgg taaattattt      3660
```

-continued

SEQUENCE LISTING

```
ttgataattc tcttgttgtt catcttttgt tgttagagta atttgggagt tcttctatat      3720

gtagtttttg tttattaaat atgaaatcta atagaagtaa agatcaaaga ccttcaaact      3780

ttgtgtttga tcatttcaat tctccttctt tccttttttt tttttttttt tgtttttgtt      3840

tttgttttta gggttttgtt tgaactagta ggtctagttt agggaaaatc taggtttgat      3900

cggaaattaa ggactaacct taacctttct tggtacaaac tttagttaaa cctacatgtc      3960

aatagactta aaagatttag tattaaggtc caaactttcc cacggttgag atcgaaagcc      4020

cctgatataa gaacaactca taaaatttga catttgatta ggttattaag tggatttcaa      4080

tggggatcga gacctactct cttaggtcaa catttttcat aaatacataa gttggttagt      4140

ctagatttgt aaattttaat tgggtttagt tgtttatgta tggagatagg taattgaact      4200

tctcatattg agttatatac tcctacaagt aaagggagaa actcccaata gatattggtt      4260

gtgttggaaa ggttatgaat cgattaataa gtcaattacc attatcttga ttttgaacgc      4320

caatgcatca catgcatata tatatatata tattgtcggc tagtacacga ccaattaatg      4380

tttggataaa gttctttcca gaatcatcct attttcaaga ctcactaaaa tccttcagat      4440

atatggttcc acaattggtc ctatgtacaa cagtgtattg aactacttca acacgatgtt      4500

cgtacaacaa tacccacaac tcatttttgc actccatagc aaaaaataat atattatgtt      4560

aaggacaacc ccttaggtaa attgctttga atgagttaat caatcattta tccttgtgga      4620

tctaacatta atcctctcat acctactaat tggtatgctt gagatgcatt ttctcgagca      4680

cctatagaag acgttatata tagactggat taaaagggac actcatccta aaattaggat      4740

tcatttcttg tagcaaatat tcacttgtag catacgatat ctaaagggac tggcgtaagt      4800

tttctactgc gggtacgttt ccataatgat ggtgtctttt caatatcaaa ctttactgtt      4860

caccatcttg aactagccat cctttagaga gtattgttaa aagatatcaa ttcctaatga      4920

aatggatgtc gcagtggccc actaaaagtc tttaattgat attacaatct ttatgctagt      4980

tgagctatgc tcgatttatc attttgtata caataagctc taacaagtta gttaggttcc      5040

atcctttata tatagtttgt acacattatt atttttagat gcatgccaca tgcctaaacc      5100

ttcaaatgat tggttactat attggagagt ttaagctacc tctcatacat agaaatgtta      5160

agtagattca atgaagttta gaaattttaa ttttgaaaat                            5200
```

<210> 13

<211> 1986

<212> DNA

<213> *Cucumis sativus*

<220>

<221> source

<222> 1..1986

<223> /organism = "*Cucumis sativus*"
/mol_type = "unassigned DNA"

<400> 13

```
atgacggatt atcgtttgtc gacgatgaat ctctggactg acgagaacgc gtcggttatg      60

gacgctttca tgaattccga tctgtcttcc tactgggctc cgtcagccgc ctcctctcac     120

tctcttcacc acccaccgcc acctcagtcc tccgcctcca catccactcc cccgccggac     180
```

SEQUENCE LISTING

```
gcacctaagt ccctccccgt tttcaatcag gagactctgc agcagcggct ccaggcgctg     240
atcgacggtg ctagggagag ttggacttat gcgattttct ggcagtcgtc ttatgattat     300
tctggtgggt ctgttttggg gtggggtgat gggtattaca aaggagagga agataaagga     360
aagggaaaag cgaaaatggt gtcgtcagcg gcggagcagg ctcaccggaa gaaggtttta     420
cgggagctta actctttgat ttctggctct gccgccggac ctgacgatgc ggtggatgag     480
gaggttacgg atacggagtg gttctttttg gtttcgatga ctcagtcgtt tgttaatggt     540
gttgggttac cgagtcaagc gttttaccac tcgacgccga tttgggtctc tggtgccgat     600
cggctgtcgg cgtctgcctg tgaacgagct agacagggga gggtttttgg gttacagacg     660
atggtctgta ttccatcgcc taacggtgtt gtggaaatgg gttcgacgga attgattcat     720
cgaacgtcgg atttgatgaa taaggtcaag attctgttca atttcaacaa tctcgaaacg     780
agttcttgga tttcgggaac taccgccgcc gcatccgctg ccgacgaagg ggaaaacgac     840
ccgtcgtcga tgtggatcag tgagccatcg agtacaatcg agatgaagga ttcaatcacc     900
accactgttc cttccagcaa cgttccggca aagccaatcc gttcggaaaa tcccagtaca     960
agtagcttaa cggaaaatat gagcacgatt caacaatccc atcataaaca gagccaaagc    1020
ttcttaaatt tctccgatta cggcttcgaa tcaaatccca caaagaacac caccgctacc    1080
gccaccgcaa ccaccagcac caccccatca ttcaagccgg aatccggcgg gatgctgaat    1140
ttcggcaacg ggagcctctt ctccggccat tcacagtacg taacaaacga acagaacgag    1200
aaaaagagat cccctgcttc tcgaagtagc aacgacgaag ggatcctctc tttcacctcc    1260
ggcgtgatct taccctcttc cggtaaggta aaatccggtg attcagacca ttcagatctc    1320
gaagcatcag cgatcagaga agtggatagc tgtacaaaat cattagaacc cgaaaaacgt    1380
ccaagaaaaa gaggtagaaa accagcaaac ggaagagaag agccattgaa tcacgtagaa    1440
gcagagagac aacggcgaga gaaattaaac cagaaattct acgctctccg agctgtagtt    1500
ccaaacgtat ctaagatgga caaagcctca ctactaggtg acgcggtttc gtacataaac    1560
gagctcaaat cgaagctcca aatggcagaa tcggagaaaa cagatatggg aaaacatcta    1620
gaattgctga agaaggagat gggaggaaaa gatttaggat gttactcaaa cccaaatgat    1680
gaagatctga aaacagggaa aagaaaggta atggatatgg agattgaagt taaaatcatg    1740
ggttgggatg cgatgataag gattcaaagc aacaagaaga atcatccggc ggcgaggttg    1800
atgacggcgt ttaaggattt ggatttagaa atgcttcacg cgagtgtttc tgtagtgaat    1860
gatttgatga ttcaacaagc aacagtgaag atggggagca gattttacac acaagagcag    1920
cttaaaatgg ctcttgtcgc ccgagtcggc ggtggtggaa gtggaggcgg cggtggaatc    1980
atgtaa                                                               1986
```

<210> 14

<211> 661

<212> PRT

<213> *Cucumis sativus*

<400> 14

```
Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
            20                  25                  30
```

SEQUENCE LISTING

```
Ala Pro Ser Ala Ala Ser Ser His Ser Leu His His Pro Pro Pro Pro
        35                  40                  45

Gln Ser Ser Ala Ser Thr Ser Thr Pro Pro Pro Asp Ala Pro Lys Ser
    50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Gly Ser Val Leu Gly Trp Gly Asp Gly Tyr
            100                 105                 110

Tyr Lys Gly Glu Glu Asp Lys Gly Lys Gly Lys Ala Lys Met Val Ser
        115                 120                 125

Ser Ala Ala Glu Gln Ala His Arg Lys Lys Val Leu Arg Glu Leu Asn
    130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Val Asn Gly Val Gly Leu Pro Ser Gln Ala Phe Tyr His Ser Thr
            180                 185                 190

Pro Ile Trp Val Ser Gly Ala Asp Arg Leu Ser Ala Ser Ala Cys Glu
        195                 200                 205

Arg Ala Arg Gln Gly Arg Val Phe Gly Leu Gln Thr Met Val Cys Ile
    210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
                245                 250                 255

Asn Leu Glu Thr Ser Ser Trp Ile Ser Gly Thr Thr Ala Ala Ala Ser
            260                 265                 270

Ala Ala Asp Glu Gly Glu Asn Asp Pro Ser Ser Met Trp Ile Ser Glu
        275                 280                 285

Pro Ser Ser Thr Ile Glu Met Lys Asp Ser Ile Thr Thr Thr Val Pro
    290                 295                 300

Ser Ser Asn Val Pro Ala Lys Pro Ile Arg Ser Glu Asn Pro Ser Thr
305                 310                 315                 320

Ser Ser Leu Thr Glu Asn Met Ser Thr Ile Gln Gln Ser His His Lys
                325                 330                 335

Gln Ser Gln Ser Phe Leu Asn Phe Ser Asp Tyr Gly Phe Glu Ser Asn
            340                 345                 350

Pro Thr Lys Asn Thr Thr Ala Thr Ala Thr Ala Thr Thr Ser Thr Thr
        355                 360                 365

Pro Ser Phe Lys Pro Glu Ser Gly Gly Met Leu Asn Phe Gly Asn Gly
    370                 375                 380

Ser Leu Phe Ser Gly His Ser Gln Tyr Val Thr Asn Glu Gln Asn Glu
385                 390                 395                 400

Lys Lys Arg Ser Pro Ala Ser Arg Ser Ser Asn Asp Glu Gly Ile Leu
                405                 410                 415

Ser Phe Thr Ser Gly Val Ile Leu Pro Ser Ser Gly Lys Val Lys Ser
            420                 425                 430
```

-continued

SEQUENCE LISTING

```
Gly Asp Ser Asp His Ser Asp Leu Glu Ala Ser Ala Ile Arg Glu Val
        435                 440                 445

Asp Ser Cys Thr Lys Ser Leu Glu Pro Glu Lys Arg Pro Arg Lys Arg
    450                 455                 460

Gly Arg Lys Pro Ala Asn Gly Arg Glu Glu Pro Leu Asn His Val Glu
465                 470                 475                 480

Ala Glu Arg Gln Arg Arg Glu Lys Leu Asn Gln Lys Phe Tyr Ala Leu
                485                 490                 495

Arg Ala Val Val Pro Asn Val Ser Lys Met Asp Lys Ala Ser Leu Leu
            500                 505                 510

Gly Asp Ala Val Ser Tyr Ile Asn Glu Leu Lys Ser Lys Leu Gln Met
        515                 520                 525

Ala Glu Ser Glu Lys Thr Asp Met Gly Lys His Leu Glu Leu Leu Lys
    530                 535                 540

Lys Glu Met Gly Gly Lys Asp Leu Gly Cys Tyr Ser Asn Pro Asn Asp
545                 550                 555                 560

Glu Asp Leu Lys Thr Gly Lys Arg Lys Val Met Asp Met Glu Ile Glu
                565                 570                 575

Val Lys Ile Met Gly Trp Asp Ala Met Ile Arg Ile Gln Ser Asn Lys
            580                 585                 590

Lys Asn His Pro Ala Ala Arg Leu Met Thr Ala Phe Lys Asp Leu Asp
        595                 600                 605

Leu Glu Met Leu His Ala Ser Val Ser Val Val Asn Asp Leu Met Ile
    610                 615                 620

Gln Gln Ala Thr Val Lys Met Gly Ser Arg Phe Tyr Thr Gln Glu Gln
625                 630                 635                 640

Leu Lys Met Ala Leu Val Ala Arg Val Gly Gly Gly Gly Ser Gly Gly
                645                 650                 655

Gly Gly Gly Ile Met
            660
```

<210> 15

<211> 6400

<212> DNA

<213> *Cucumis melo*

<220>

<221> source

<222> 1..6400

<223> /organism = "*Cucumis melo*"
/mol_type = "unassigned DNA"

<220>

<221> unsure

<222> 5198..5369

<223> /note = "n" is unknown base"

<400> 15

```
ttcctgtcct aaggttgcag taattttaga ttttactttg agataaaaat tgtaaaaatt      60

aaatgggttt agtattacaa taatcgattt aactataaaa ttcttaaata ataaattaat     120
```

SEQUENCE LISTING

```
atattttaat tatattatgt aagttaggct ttgtaagtta tttattctct tacattaatt      180
atagtatgtg ttttttttata tgatttgaat ttcaattcat tttattgtat ttaaattatc      240
tgataaaagt ttaggatttt ttaataaaat taaatcaatt actatagaag attaaaaata      300
ttttaattta aaaatgagtt attttgaaaa aagaaataaa ggatatatat atatacatat      360
tgaaataagt gagagtatta ctttattttg agtaaagtgg gaaaataaat ttttgcgtag      420
aaaatttgct aactttcaaa aaagcatttg tcgtcttttc tctttcttct atttttgtaa      480
ttttgttgtt tttttccct ctcattcctt aatcatttta ttgcaatgtt tttcccttaa      540
aaagaagcat agctcaattt tttaaatatt ttgataatgt gtagaattga ataatcaaat      600
ctctaatatt catgctaacc attttaacta tttttgata gggttgaaag tatgttaggt      660
ttttatgagt atttactata tattaacaat tgggctcaat ttttataaat ttgtaatttg      720
atggtttgag ttttaaaagg aaagaaatgg ttggaatgtt aataatcaat atggtttaga      780
ttaaagtaat cgatttcaca aaagttggag ttgagctagg gatatgacat gcattcaacc      840
cacctaggct tgaggggaga cgagagtttg gaccaaatgt ccaaatatga accgatcaat      900
ttttaccttg gtcgagacat acccacactt ttgattaaat aggcatgtta aacgtgtagg      960
acaacatatt gagtttgaga aaaagcctaa tctaactcca aaaccctaat ttaaatgtct     1020
taggtcataa gtaagttaac tatatcatcc aaactcttgc gagttgcgac aacttaaaga     1080
gtttaattag ttacaatcat tattgtaatt tttttaaatt tgaggcatca tatgttgtta     1140
ctcgatgagg ctgtttaggg cgttgagttg atgtagggtg ttgttaagaa gcaaagtaat     1200
atgtcttatg gatacttgtg acaaataagt ttataaggat gatccaacca atcttagaca     1260
acttctcaac atcaaattgc cttaggtgaa tgttagtata tattgattgt tagaggtagt     1320
tgtcactatt tgtcattgaa gttgattatc aaaggtgatt ctcgttgaag tttatcatag     1380
aggtgggttg ttggagccca aagttaaagg tggttttcga agttgataat caaaggcgat     1440
tttcgctaaa gtttgtagtc atagcttgga attcatcgca tggacgtagt catcaaagtt     1500
ggctttcgtt ggatttgtta tcagagatga ttacaggctc gaaattagtg gttggaggtg     1560
gtcgtgcaaa ggtaatctag ttgtcatagt ttttcatcga aggtggttgt aggaccctga     1620
aatcgattgt caaagttgga ggtgtgaaag tggctgttgt cggagtcgga tcctagagtt     1680
tggtaatggg taattgtcat aatggtaatc gatcgtcgaa tccattgaaa acattggaaa     1740
gaactccacc aacatgtaaa gttggtaggc caaacgaaac tcaaacccat cttatattga     1800
tgtgcaaaac atctctagga taaaacaaac caaactaata aatcataaag acaaaaatga     1860
aaaatgagag taccaaaaaa aaaaaaaaaa gagcaataac ttcaaataag ttttaaaaca     1920
ctagatttaa aaaaaaaatc aaagaacaaa aatagaagat attttaatct ctacaaaaaa     1980
aaaaaaaaag aaaaaaagaa aattatagat attaataatt gtaatgaggc ttagtatttt     2040
caaaatcctc atttagagga aaaaaaaagg gagaaaataa actaacttcc gtctttgttt     2100
cacaaacaag acacgcgtca tattctcatt agctaaaacc gcaaaaaaag caatcagtca     2160
aaaagtctta aaaacggtta acactctaaa cgcctctcaa gaattcttca cgtgtcagtc     2220
acatggaaaa gaaaccggcc gaaccgggtc gaagtaaacc gcgttatctg gcgaagtaca     2280
aagtataata gtactataac cgcggagttg aaaaagacgc cggctttttg aacgattaaa     2340
tcggcgatct aaagaagaag gctcttggtt ccttcttcct ctgtgttcgc tectttetta     2400
aatgttcatc acaaataaat cccaatccaa tcgcccgaca tttctctcac tccacaatcg     2460
```

-continued

SEQUENCE LISTING

```
gagacagaag attattcctt ttttccgatt tctgtttctt ccaatctcaa tcgcatgacg     2520
gattatcgtt tgtcgacgat gaatctctgg actgacgaga acgcgtcggt gatggacgct     2580
ttcatgaatt ccgatctctc ttcctactgg gctccatcag ccgcctcctc tcactctctt     2640
caccatccac caccacctca gtcctccgcc tcaacgtcca ctcccccgcc ggacccacct     2700
aagtccctcc ccgttttcaa tcaggagact ctgcagcagc ggctccaggc gctgattgac     2760
ggtgctaggg agagttggac ttatgcgatt ttctggcagt catcttatga ttattccggt     2820
gggtctgttt tggggtgggg tgatgggtat tacaaaggag aggaagataa aggaaagggg     2880
aaagcgaaaa tggtgtcgtc agcggcagag caggctcacc ggaagaaggt tttacgggag     2940
cttaactctt tgatttctgg ctctgccgct ggaccggacg atgcggtgga tgaggaggtt     3000
acggatacag agtggttctt tttggtttcg atgactcagt cgtttgttaa tggtgttggg     3060
ttaccgagtc aggcgtttta ccactcgacg ccgatttggg tctctggtgc cgatcggctg     3120
tcggcgtctg cctgtgaacg agctagacag gggagggttt ttgggttaca gacgatggtc     3180
tgtattccat cgcctaacgg tgttgtggaa atgggttcga cggaattgat tcatcgaaca     3240
tcggatttga tgaataaggt caaaattctg ttcaatttca acaatctcga gacgagttct     3300
tggatttcgg gaactaccgc cgccgcatcc gctgcagacg aaggggaaaa cgacccgtcg     3360
tcgatgtgga tcagtgagcc atctagtaca atcgagatga aggattcaat taccaccacc     3420
gtcccttcca gcaacgttcc ggcaaagcca atccgatccg aaaatcccag ttcaagtagc     3480
ttaacggaaa atatgagcac gattcaacaa tcccatcata aacagagcca aagcttctta     3540
aatttctccg attacggctt cgagtcaaat ccctcaaaga acaccaccgc caccgccacc     3600
gtaaccacca gcaccactcc atcattcaag ccggaatccg gcgggatgct gaattttgga     3660
aacggaagcc tcttctccgg ccattcacag tacgtaacaa acgaacagaa cgaagaaaag     3720
agatcccctg cttctcgaag tagcaacgac gaagggatcc tctctttcac ctccggcgtg     3780
atcttaccct cttccggtaa ggtaaaatca ggcgattcgg accactcaga tctcgaagca     3840
tcagtgatca gagaagtaga tagctgtaca aaatcattag aacccgaaaa acgtccaaga     3900
aaaagaggta gaaaaccagc aaacggaaga gaagagccat tgaatcacgt agaagcagag     3960
agacaacggc gagagaaatt aaaccagaaa ttctacgctc tacgagctgt agttccaaac     4020
gtatctaaaa tggacaaagc ctcactactc ggtgacgccg tttcgtacat aaacgagctg     4080
aaatcgaagc tccaaatggc agaatcggag aaaacagata tgggaaaaca tctagaattg     4140
ctgaagaagg agatgggagg gaaagatgta ggatgttaca caaacccaaa tgatgaagat     4200
ctgaaaatag ggaaaagaaa ggtaatggat atggagattg aagttaaaat catgggttgg     4260
gatgcgatga tcagaattca aagcaacaag aagaatcatc cggcggcgag gttgatgacg     4320
gcgtttaagg atttggattt agaaatgctt cacgccagtg tttctgtagt gaatgatttg     4380
atgattcaac aagcaacagt gaagatgggg agcagatttt acacacaaga gcagcttaaa     4440
atggctcttg tggcccgagt cggtggtggt ggtggaggcg gaagcggcgg tggaatgatg     4500
taaatggggt taggggacat ttttgaagct cccaagtagt agagattagt tgagggaata     4560
taaatctgat ttagtattgt gtaatattaa tgttggtaaa ttatttttga taattttgtt     4620
gttcatcttt tgttgttaga gtaatttggg agttcttctt ctatatatat gtagtttttg     4680
ttgattaaat atcaaatcta atagaagtga agatcaaaga ccttcaaact ttgtgtttga     4740
```

-continued

SEQUENCE LISTING tgatttcagt tctctttcct ttgtttttag ggttttgttt gaagtaaaaa tctaggtttg 4800
attggaaatt taggactaac cttaacctcc cagctcagta caaaccttag ttaaacctaa 4860
atgtcaatgg acctaagatt tggtattggg tccacatttc gtgtggttga gatagaaaac 4920
cccaactttc atataagaac aacccatata aaattcgtca tttgattagg ttattcgata 4980
agtggatttc aaaagggatc gggagaataa ctagtctctt aagtcaacat ttttcatata 5040
tacataagtt ggtcgatcta gatttctaaa ttttaagttg ggtttagttg tttttgtaca 5100
atagggaacg tgcgtgtgcg tgtgcgcgtg cgtgtgtgtg tggttgtgtg tgtgtgtgtg 5160
tcgctagttg tgtgtgtgtg tgtggttcgc taatacannn nnnnnnnnnn nnnnnnnnnn 5220
nnnnnnnnnn nnnnnnnnnn nnnnnnnnnn nnnnnnnnnn nnnnnnnnnn nnnnnnnnnn 5280
nnnnnnnnnn nnnnnnnnnn nnnnnnnnnn nnnnnnnnnn nnnnnnnnnn nnnnnnnnnn 5340
nnnnnnnnnn nnnnnnnnnn nnnnnnnnnt caatggactg acgtatttat ttactaggtc 5400
ataatgatgg tgtttttcca aaatcaaact ttgctgttca atatcttaga ctagccatcc 5460
tttagaggag attgttaaaa aatcatcaat tactaataaa aaaaagacta ttgcagtggc 5520
ccactggaag tctttagttg atactacaat ctttatgcta gttaagctac gctcaatttg 5580
tccgtttgta tacaatgaac tctagcaaat tagcttacat catttataca tactttaaat 5640
gattggttac tgtctatcgg ggagagttta acctagctct tatacataga aattttaagc 5700
aggtttaacg aaagttgaag tttagaaaat ttaattttga aaataatcat ataaacatgc 5760
atgtcacaca tgtttattga tatgctaagt caatgagcta tagagagtta ggttcatagc 5820
cacataaata aaacctataa ctcttagttt tatgttttcg aaatttatgg ccgtttctta 5880
ctatttaaac ttttctaaaa gaaaaaattt gaactcatta aattctaaca acaaaaacat 5940
gtttttgaaa acgaaataaa aatagataat aaaacacaaa aaacttatag atgaaaatag 6000
tgtttataag gttacttaaa aaaaaaccaa acaatcatca aatacgaagt ttttgaaatt 6060
tgatttagat ttattcgatg tgtggttaat aattgggatg tagaaagata agctatggat 6120
gatagtgaag aattgaaggt gaccttacac ttcatatatg gacataaaaa aggaccattt 6180
tcatagaatc ttcaagaaga tattgatgga gataattttc tctcttttg tgaccccttc 6240 ttcatataaa gtaattccat tgttgaagtt aaatggtaaa aaagaaaaaa aaaaaagaac 6300
tttttattat tgtataaaac aatgatttag attttgaatt ttatttgtga caatttggtc 6360
attttgaata tctaaactac gttggttatt ttatcgtcac 6400

<210> 16

<211> 1989

<212> DNA

<213> *Cucumis melo*

<220>

<221> source

<222> 1..1989

SEQUENCE LISTING

<223> /organism = "*Cucumis melo*"
/mol_type = "unassigned DNA"

<400> 16
atgacggatt atcgtttgtc gacgatgaat ctctggactg acgagaacgc gtcggtgatg 60
gacgctttca tgaattccga tctctcttcc tactgggctc catcagccgc ctcctctcac 120
tctcttcacc atccaccacc acctcagtcc tccgcctcaa cgtccactcc cccgccggac 180
ccacctaagt ccctccccgt tttcaatcag gagactctgc agcagcggct ccaggcgctg 240
attgacggtg ctagggagag ttggacttat gcgattttct ggcagtcatc ttatgattat 300
tccggtgggt ctgttttggg gtggggtgat gggtattaca aaggagagga agataaagga 360
aaggggaaag cgaaaatggt gtcgtcagcg gcagagcagg ctcaccggaa gaaggtttta 420
cgggagctta actctttgat ttctggctct gccgctggac cggacgatgc ggtggatgag 480
gaggttacgg atacagagtg gttctttttg gtttcgatga ctcagtcgtt tgttaatggt 540
gttgggttac cgagtcaggc gttttaccac tcgacgccga tttgggtctc tggtgccgat 600
cggctgtcgg cgtctgcctg tgaacgagct agacagggga gggtttttgg gttacagacg 660
atggtctgta ttccatcgcc taacggtgtt gtggaaatgg gttcgacgga attgattcat 720
cgaacatcgg atttgatgaa taaggtcaaa attctgttca atttcaacaa tctcgagacg 780
agttcttgga tttcgggaac taccgccgcc gcatccgctg cagacgaagg ggaaaacgac 840
ccgtcgtcga tgtggatcag tgagccatct agtacaatcg agatgaagga ttcaattacc 900
accaccgtcc cttccagcaa cgttccggca aagccaatcc gatccgaaaa tcccagttca 960
agtagcttaa cggaaaatat gagcacgatt caacaatccc atcataaaca gagccaaagc 1020
ttcttaaatt tctccgatta cggcttcgag tcaaatccct caaagaacac caccgccacc 1080
gccaccgtaa ccaccagcac cactccatca ttcaagccgg aatccggcgg gatgctgaat 1140
tttggaaacg gaagcctctt ctccggccat tcacagtacg taacaaacga acagaacgaa 1200
gaaaagagat cccctgcttc tcgaagtagc aacgacgaag ggatcctctc tttcacctcc 1260
ggcgtgatct taccctcttc cggtaaggta aaatcaggcg attcggacca ctcagatctc 1320
gaagcatcag tgatcagaga agtagatagc tgtacaaaat cattagaacc cgaaaaacgt 1380
ccaagaaaaa gaggtagaaa accagcaaac ggaagagaag agccattgaa tcacgtagaa 1440
gcagagagac aacggcgaga gaaattaaac cagaaattct acgctctacg agctgtagtt 1500
ccaaacgtat ctaaaatgga caaagcctca ctactcggtg acgccgtttc gtacataaac 1560
gagctgaaat cgaagctcca aatggcagaa tcggagaaaa cagatatggg aaaacatcta 1620
gaattgctga agaaggagat gggagggaaa gatgtaggat gttacacaaa cccaaatgat 1680
gaagatctga aaatagggaa aagaaaggta atggatatgg agattgaagt taaaatcatg 1740
ggttgggatg cgatgatcag aattcaaagc aacaagaaga atcatccggc ggcgaggttg 1800
atgacggcgt ttaaggattt ggatttagaa atgcttcacg ccagtgtttc tgtagtgaat 1860
gatttgatga ttcaacaagc aacagtgaag atggggagca gattttacac acaagagcag 1920
cttaaaatgg ctcttgtggc ccgagtcggt ggtggtggtg gaggcggaag cggcggtgga 1980
atgatgtaa 1989

<210> 17

<211> 662

-continued

SEQUENCE LISTING

<212> PRT

<213> *Cucumis melo*

<400> 17

Met Thr Asp Tyr Arg Leu Ser Thr Met Asn Leu Trp Thr Asp Glu Asn
1 5 10 15

Ala Ser Val Met Asp Ala Phe Met Asn Ser Asp Leu Ser Ser Tyr Trp
20 25 30

Ala Pro Ser Ala Ala Ser Ser His Ser Leu His His Pro Pro Pro Pro
35 40 45

Gln Ser Ser Ala Ser Thr Ser Thr Pro Pro Pro Asp Pro Pro Lys Ser
50 55 60

Leu Pro Val Phe Asn Gln Glu Thr Leu Gln Gln Arg Leu Gln Ala Leu
65 70 75 80

Ile Asp Gly Ala Arg Glu Ser Trp Thr Tyr Ala Ile Phe Trp Gln Ser
85 90 95

Ser Tyr Asp Tyr Ser Gly Gly Ser Val Leu Gly Trp Gly Asp Gly Tyr
100 105 110

Tyr Lys Gly Glu Glu Asp Lys Gly Lys Gly Lys Ala Lys Met Val Ser
115 120 125

Ser Ala Ala Glu Gln Ala His Arg Lys Lys Val Leu Arg Glu Leu Asn
130 135 140

Ser Leu Ile Ser Gly Ser Ala Ala Gly Pro Asp Asp Ala Val Asp Glu
145 150 155 160

Glu Val Thr Asp Thr Glu Trp Phe Phe Leu Val Ser Met Thr Gln Ser
165 170 175

Phe Val Asn Gly Val Gly Leu Pro Ser Gln Ala Phe Tyr His Ser Thr
180 185 190

Pro Ile Trp Val Ser Gly Ala Asp Arg Leu Ser Ala Ser Ala Cys Glu
195 200 205

Arg Ala Arg Gln Gly Arg Val Phe Gly Leu Gln Thr Met Val Cys Ile
210 215 220

Pro Ser Pro Asn Gly Val Val Glu Met Gly Ser Thr Glu Leu Ile His
225 230 235 240

Arg Thr Ser Asp Leu Met Asn Lys Val Lys Ile Leu Phe Asn Phe Asn
245 250 255

Asn Leu Glu Thr Ser Ser Trp Ile Ser Gly Thr Thr Ala Ala Ala Ser
260 265 270

Ala Ala Asp Glu Gly Glu Asn Asp Pro Ser Ser Met Trp Ile Ser Glu
275 280 285

Pro Ser Ser Thr Ile Glu Met Lys Asp Ser Ile Thr Thr Thr Val Pro
290 295 300

Ser Ser Asn Val Pro Ala Lys Pro Ile Arg Ser Glu Asn Pro Ser Ser
305 310 315 320

Ser Ser Leu Thr Glu Asn Met Ser Thr Ile Gln Gln Ser His His Lys
325 330 335

Gln Ser Gln Ser Phe Leu Asn Phe Ser Asp Tyr Gly Phe Glu Ser Asn
340 345 350

Pro Ser Lys Asn Thr Thr Ala Thr Ala Thr Val Thr Thr Ser Thr Thr
355 360 365

SEQUENCE LISTING

Pro Ser Phe Lys Pro Glu Ser Gly Gly Met Leu Asn Phe Gly Asn Gly
    370                 375                 380

Ser Leu Phe Ser Gly His Ser Gln Tyr Val Thr Asn Glu Gln Asn Glu
385                 390                 395                 400

Glu Lys Arg Ser Pro Ala Ser Arg Ser Ser Asn Asp Glu Gly Ile Leu
            405                 410                 415

Ser Phe Thr Ser Gly Val Ile Leu Pro Ser Ser Gly Lys Val Lys Ser
        420                 425                 430

Gly Asp Ser Asp His Ser Asp Leu Glu Ala Ser Val Ile Arg Glu Val
    435                 440                 445

Asp Ser Cys Thr Lys Ser Leu Glu Pro Glu Lys Arg Pro Arg Lys Arg
    450                 455                 460

Gly Arg Lys Pro Ala Asn Gly Arg Glu Glu Pro Leu Asn His Val Glu
465                 470                 475                 480

Ala Glu Arg Gln Arg Arg Glu Lys Leu Asn Gln Lys Phe Tyr Ala Leu
            485                 490                 495

Arg Ala Val Val Pro Asn Val Ser Lys Met Asp Lys Ala Ser Leu Leu
        500                 505                 510

Gly Asp Ala Val Ser Tyr Ile Asn Glu Leu Lys Ser Lys Leu Gln Met
    515                 520                 525

Ala Glu Ser Glu Lys Thr Asp Met Gly Lys His Leu Glu Leu Leu Lys
    530                 535                 540

Lys Glu Met Gly Gly Lys Asp Val Gly Cys Tyr Thr Asn Pro Asn Asp
545                 550                 555                 560

Glu Asp Leu Lys Ile Gly Lys Arg Lys Val Met Asp Met Glu Ile Glu
            565                 570                 575

Val Lys Ile Met Gly Trp Asp Ala Met Ile Arg Ile Gln Ser Asn Lys
        580                 585                 590

Lys Asn His Pro Ala Ala Arg Leu Met Thr Ala Phe Lys Asp Leu Asp
    595                 600                 605

Leu Glu Met Leu His Ala Ser Val Ser Val Val Asn Asp Leu Met Ile
    610                 615                 620

Gln Gln Ala Thr Val Lys Met Gly Ser Arg Phe Tyr Thr Gln Glu Gln
625                 630                 635                 640

Leu Lys Met Ala Leu Val Ala Arg Val Gly Gly Gly Gly Gly Gly Gly
            645                 650                 655

Ser Gly Gly Gly Met Met
        660

<210> 18

<211> 6400

<212> DNA

<213> *citrillus lanatus*

<220>

<221> source

<222> 1..6400

-continued

SEQUENCE LISTING

<223> /organism = "*citrillus lanatus*"
/mol_type = "unassigned DNA"

<400> 18

```
ttttatataa atactaaatt gttataaatt aaactacgtt attactttgt ttttatttca      60
tctgcaaaca ttcaaaattg aaatccttct agtcacaagt taaaaaaatt gggagactat     120
accaggtgta cagtgaaagg aaaattacaa ggagtaaaaa aattaatatt gaattttata     180
aactatctta acattttatt ttttattttt tattttgcca actacaacaa ataagagaaa     240
ttatgttaaa ttgcaaaact gctaaaaata tttaaaatca atagcaaaat acaccgtcta     300
catgcgaatg tgggatcaaa tctcccctgt ttgaagtgaa aaaagttaaa ggagcatttg     360
actaaattaa caaagaaatt tttgttttca accaaaacaa atgttactct gttactttgt     420
tttgagtgaa ttgtgaaagt aagctaatgt gtagaaaatg tgataacttt caaaaaagca     480
ttcgtcgcct tttatatttc tacaatattg tttcgtttca tttttttttt tatttttttca     540
tcccctcctt ccttaatata actattgcaa atttcttaaa tgagtttaac aacctttcaa     600
tgcaagtttt tttctttttt tttttttta caatctgtga agttgaaaaa attgatacta     660
tcaccttata ttggcagtat taaccttatg ccatatgagt tatatttatt ttgataaata     720
cttacaatat gttaatgatt aagttcaatt tttatgtagt gtaaatttaa atttttaaat     780
ttaatttaat gaatattctg cttcctgaaa caacatgttg gtcccacggg tggtatcagg     840
tggaggttgt ctttggattg acaagcattg gaagatttaa aagctcttcg ttttccattc     900
gggattgtca ttctgtcact tttggtggaa tctgattatg ttgaagtgat cacgtccctt     960
tgcaagattg atagtgatct ttcgaatatt acatttgttt tttgttgtgt tttaaagcta    1020
gatgaagaat ttgggaacat ccattttgct aagtgttcga ggtttagtaa ttatttggct    1080
gcacactcgc tagctagatt ggttgtgtct cctttttttga attctttttt aggctcgaat   1140
ttgacttcct cctccttgga aaggttttaa ttttagttca tggggttcta atgtccctaa    1200
gttgttagtt gctgttattg gtgaggttga ttgtcagttg gggaaaaaaa attttaatag    1260
tttagaccta gttttacacc tcatttggta actatttggt ttttttgaat gattttgctg    1320
gttgagagag ataagtgaaa tttttatata tttgtaaata gtttgatatt tttttcattt    1380
ataataattt ctcttcaaaa ttcaatcaaa tttttaaagt ataaattaaa agaaagggat    1440
cataacaaat cactcatcca tttgaaatac aaaaataaat tttgcactat atatatataa    1500
actcaacatc tcttataaga taaagcaaaa taactaaata aaataaattg ttttcaaata    1560
taagaaaatg aacaaaaaca tttataacta caatcaaatt ttactgtcta tttgcgatag    1620
atctcgatct attgtagata gattgtaata ttttgttatt tttttaaata tattctgcaa    1680
ctttatcatt taaaataatt tttcaaataa aaatttagaa acaaaattgt tgattgcaag    1740
taagtacata gactaaaaat atttgttaac aaaaaaaaaa aaaaaaaaac aatcaaagac    1800
tttaaataat ttttaaaata aaaattgcag agagattaga aaaaaaatca aagaacagaa    1860
atggtagata tttttagctt tttttaaaaa aagaaaaata atagatattt taatatggcg    1920
tagtattttc aaaagcgatt tatttggagc aaaaaaagga aagaataaaa ccacttcagt    1980
ctttgattaa caaatcagac acgtgtcaac ctctcattag tggaaaatgc aaacaaaccg    2040
atcagtcaaa agtcttaaaa acggttaccc cccaaagctc acaaacgaaa cgccccccgat   2100
gatccttcac gtgcccgtca cgtggaaaga aacgaaccga accgggtcta aatgagccgc    2160
```

-continued

SEQUENCE LISTING

```
actctctggc aggagtacta gtatagtact acaagcgcgg agttgaaaac gacgccggct     2220
ttttgaacga ttaaatcggc gatccaaaga agaagcctct tggttccttc ttcccctgtt     2280
cgctcctctg taaatgttca tcacaaataa atcccaatcc aatcgcccga catttctctc     2340
actccacaat tggagaccca gaattattct ctttttccca ttctgtttct tctcgaatcc     2400
caatcgcatg acggattatc gtttgtcgac gatgaatctc tggactgacg aaaacgcgtc     2460
ggtgatggac gctttcatga actccgatct gtcctcttac tgggctccat ctgccgcctc     2520
ctctcactct cttcaccacc caccgccgcc tcagtcctcc gcctccacct ccactccccc     2580
accggacccg cccaagtccc tgcctgtttt caatcaggag actctgcagc agcggctcca     2640
ggcgctgatc gatggcgcta gggagagttg gacttacgcg attttctggc agtcgtccta     2700
tgattattcc ggtgcgtcgg ttttagggtg gggagatggg tattacaaag gggaggagga     2760
taaagggaag ggaaaagcga aaatggtgtc gtcggcggca gagcaggctc atcggaagaa     2820
ggttttacgg gagcttaact ctttaatttc tggctccgct gccggaccgg acgatgcggt     2880
ggatgaggag gttacggata cggagtggtt ctttttggtt tcgatgactc agtcttttga     2940
taatggagtt tggttaccga gtcaggcgtt ttacaactcg acgccgattt gggtttctgg     3000
cgccgatcgg ctgtcggcgt ctgcctgtga acgggccaga caggggaggg tttttgggtt     3060
acagacgatg gtctgtattc catcgccaaa cggagttgtg gaaatgggtt cgacggaatt     3120
gattcatcga acgtcggatt tgatgaacaa ggtcaagatt ctgttcaatt tcaacaatct     3180
cgaaacgagt tcttggatat cggaaccac cgccgccgat gaaggggaaa acgacccgtc     3240
gtcgatgtgg atcagtgagc cgtcgagtac tatcgagatg aaggattcca ttaccaccac     3300
cgtcccttcc ggcaacgtcc cggcaaagcc aatccattcg gaaaatccca gttccagcag     3360
cttaacggaa aatatcagcg cgatccaaca accatcccat caaaaacaaa gccaaagctt     3420
cttaaatttc tccgattacg gcttcgaatc aaatccctca aagaacacca ccgcggccgc     3480
aacaaccacc accgccaccc catcattcaa gccggaatcc ggcgggatgc tgaatttcgg     3540
caacggaaac ctcttctcta gccattcaca gtatgtaaca aacgaacaga acgagaaaaa     3600
gagatcccct gcttctcgga gtagcaacga cgaagggatc ctctctttca cctctggcgt     3660
gatcttaccc tcctccggta aggtaaaatc cggggactca gaccactcag atctcgaagc     3720
atcggtgatc agagaagtgg atagctgtac aaaatcatta gaacccgaaa aacgtccaag     3780
aaaaagaggt agaaaaccag caaacggaag agaagagcca ttgaatcatg tagaagcaga     3840
gagacaacgg cgagagaagt tgaaccagaa attctacgct ctccgagctg tagttccaaa     3900
cgtatctaaa atggacaagg cctcactact gggagacgcg gtttcttaca tcaacgagct     3960
caaatcaaag ctccaaatag cggaaacgga gaaaacagag atgggaaaac atttagaatt     4020
gctgaagaag gagatgggag ggaaagattt cgggaattac ccgaacccaa atgatgaaga     4080
tctgaaaata gggaaaagaa aggtaatgga tatggagatc gaagttaaaa tcatgggttg     4140
ggatgcgatg ataaggattc aaagcagcaa gaaaaatcat ccggcggcaa ggctgatggc     4200
ggcgtttaag gatttagatt tagaaatgct tcatgcgagt gtttctgtag tgaatgattt     4260
gatgattcaa caggcaacgg tgaagatggg gagcagattt tacacacagg agcagcttaa     4320
aatggctctc gtcgcccgag tcgggggcgg cggcggcagc agccatggaa tgatgtaaat     4380
gggttgtgta attacaagtg ggaggggaca tttttgaggg ctcccaagta gagattagct     4440
```

-continued

SEQUENCE LISTING

```
gagggaatct gattagtatg tgtaagataa aatgttggta aattattttg atcattttgt     4500
tgttgtttca tcttttttg gttgttagag taatttggga agttctttgt gtagtttttg     4560
ttaaatatca aatctaatag aacagaagat gaaagacctt caaactttgt gatgggttgc     4620
tgtcttcaaa aatacccatt gcgtttctct ctttttggt agaagtttag tcggtaggta     4680
cttcttccac taaaccttaa cctcacatag tatccacacg agttaagtct agagttctca     4740
atagccatga gttgggccca aaggccgaga agcccaactt tcgtatctca aatcagatta     4800
ggtttaagac ttaagtcatc ctcaatttgt ctgtttgtat aataatatct atctattatg     4860
cttattaatg agctattata aggtaaggta ggttacatca tttatattta tagttagata     4920
atcactcaaa gttaatttta gatgcatgcc gcacgtctaa acttgcaaat gattggttac     4980
catatttggg aggagttcat aaaaatgtta aagtgaaaat atcatataca acatgttgat     5040
gccacatgtt tgtttcatat gctaattcag tgtgagctat ggtcagtttg gttgagagtt     5100
acactttata aaaactattt ttttaaggca gtgtcttata acaaatttca tttttaattt     5160
tatgattttt caaattttg aaatttattt ccttctaatt ctaatttttc tattatggtg     5220
ttcacatgtc tacatgaaac tcttgaattc cttgtcaaat tctaataaca aaaacatgtt     5280
tttggaaact acatatttta gtttttttc tttaacaaaa catggaaact taggatgaaa     5340
gtagtgttta taaggttatt tttcaaaaac aaaatatcaa atgattatca aatgagacct     5400
taattcttaa aatttggcta cgattttgaa atattattaa aaagtatata acaaaacaaa     5460
aacaaagaat gtcacgagta aattttgttt ctataaattt aaattaaaaa aaatttaaaa     5520
atagagatca aataatcata aaaaagagcc tatgtgtgat tggcatgtaa aaagataagg     5580
tttttgagcc attgatgata gtggaagctt gtgaagaatt aaagatgacc ttacacttca     5640
tgtatggaca taaaatgtca tcttcataga atattcaaga agattttgat aaatataatt     5700
tttcactctt tgtgacttct ataaagtagt tcaattgttg aagtaaaatg gcaaaaaatg     5760
gttttatgaa ctttcataaa attgataatc ctcaccccaa ttccatttgt ttgtttttag     5820
tttttaaaa ttaaacctat tttttctatt tcttgtaatg atttacatct ttcttaggtg     5880
taatcgttga attcgtagtc aaattctaaa atgaaaaact aattttttta gttttcaaaa     5940
tttggcttga cttttaaacc attggtaaaa aaattagata acaaaggcaa aaatttggaa     6000
ttggaagtag tctctataaa cttaattttc aaaaacaaaa aaaagaccaa aaaccaaatg     6060
gttaccaaac gggatagtaa tttttgaatt gatttgtaca atttagttct tcttttgtaa     6120
taattaagtg tgtcaattct taatacgtaa taactaactt aatatttgta gctaataaaa     6180
taatattttt tgtctttaat tagtttataa gatgtgactg taagaaattc tattaaatgt     6240
ttttttttca ccatagaagt taaattgtta aataattgaa agtttatgga ttaaacttta     6300
cataattgtt taaaaattaa attattacaa aactagaaaa tttagaggtt aaaagtgttt     6360
ttttttttt tttttttaa cttaaaaggt tttatttgga                             6400
```

<210> 19

<211> 1971

<212> DNA

-continued

SEQUENCE LISTING

<213> *citrillus lanatus*

<220>

<221> source

<222> 1..1971

<223> /organism = "*citrillus lanatus*"
/mol_type = "unassigned DNA"

<400> 19

```
atgacggatt atcgtttgtc gacgatgaat ctctggactg acgaaaacgc gtcggtgatg      60
gacgctttca tgaactccga tctgtcctct tactgggctc catctgccgc ctcctctcac     120
tctcttcacc acccaccgcc gcctcagtcc tccgcctcca cctccactcc cccaccggac     180
ccgcccaagt ccctgcctgt tttcaatcag gagactctgc agcagcggct ccaggcgctg     240
atcgatggcg ctagggagag ttggacttac gcgattttct ggcagtcgtc ctatgattat     300
tccggtgcgt cggttttagg gtggggagat gggtattaca aaggggagga ggataaaggg     360
aagggaaaag cgaaaatggt gtcgtcggcg gcagagcagg ctcatcggaa gaaggtttta     420
cgggagctta actctttaat ttctggctcc gctgccggac cggacgatgc ggtggatgag     480
gaggttacgg atacggagtg gttctttttg gtttcgatga ctcagtcttt tgataatgga     540
gtttggttac cgagtcaggc gttttacaac tcgacgccga tttgggtttc tggcgccgat     600
cggctgtcgg cgtctgcctg tgaacgggcc agacagggga gggtttttgg gttacagacg     660
atggtctgta ttccatcgcc aaacggagtt gtggaaatgg gttcgacgga attgattcat     720
cgaacgtcgg atttgatgaa caaggtcaag attctgttca atttcaacaa tctcgaaacg     780
agttcttgga tatcgggaac caccgccgcc gatgaagggg aaaacgaccc gtcgtcgatg     840
tggatcagtg agccgtcgag tactatcgag atgaaggatt ccattaccac caccgtccct     900
tccggcaacg tcccggcaaa gccaatccat tcggaaaatc ccagttccag cagcttaacg     960
gaaaatatca gcgcgatcca acaaccatcc catcaaaaac aaagccaaag cttcttaaat    1020
ttctccgatt acggcttcga atcaaatccc tcaaagaaca ccaccgcggc cgcaacaacc    1080
accaccgcca ccccatcatt caagccggaa tccggcggga tgctgaattt cggcaacgga    1140
aacctcttct ctagccattc acagtatgta acaaacgaac agaacgagaa aaagagatcc    1200
cctgcttctc ggagtagcaa cgacgaaggg atcctctctt tcacctctgg cgtgatctta    1260
ccctcctccg gtaaggtaaa atccggggac tcagaccact cagatctcga agcatcggtg    1320
atcagagaag tggatagctg tacaaaatca ttagaacccg aaaaacgtcc aagaaaaaga    1380
ggtagaaaac cagcaaacgg aagagaagag ccattgaatc atgtagaagc agagagacaa    1440
cggcgagaga agttgaacca gaaattctac gctctccgag ctgtagttcc aaacgtatct    1500
aaaatggaca aggcctcact actgggagac gcggtttctt acatcaacga gctcaaatca    1560
aagctccaaa tagcggaaac ggagaaaaca gagatgggaa aacatttaga attgctgaag    1620
aaggagatgg gagggaaaga tttcgggaat tacccgaacc caaatgatga agatctgaaa    1680
atagggaaaa gaaaggtaat ggatatggag atcgaagtta aaatcatggg ttgggatgcg    1740
atgataagga ttcaaagcag caagaaaaat catccggcgg caaggctgat ggcggcgttt    1800
aaggatttag atttagaaat gcttcatgcg agtgtttctg tagtgaatga tttgatgatt    1860
```

-continued

SEQUENCE LISTING caacaggcaa cggtgaagat ggggagcaga ttttacacac aggagcagct taaaatggct 1920
ctcgtcgccc gagtcggggg cggcggcggc agcagccatg gaatgatgta a 1971

<210> 20

<211> 656

<212> PRT

<213> *citrillus lanatus*

<400> 20

```
Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
            20                  25                  30

Ala Pro Ser Ala Ala Ser Ser His Ser Leu His His Pro Pro Pro Pro
        35                  40                  45

Gln Ser Ser Ala Ser Thr Ser Thr Pro Pro Pro Asp Pro Pro Lys Ser
    50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Ala Ser Val Leu Gly Trp Gly Asp Gly Tyr
            100                 105                 110

Tyr Lys Gly Glu Glu Asp Lys Gly Lys Gly Lys Ala Lys Met Val Ser
        115                 120                 125

Ser Ala Ala Glu Gln Ala His Arg Lys Lys Val Leu Arg Glu Leu Asn
    130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Asp Asn Gly Val Trp Leu Pro Ser Gln Ala Phe Tyr Asn Ser Thr
            180                 185                 190

Pro Ile Trp Val Ser Gly Ala Asp Arg Leu Ser Ala Ser Ala Cys Glu
        195                 200                 205

Arg Ala Arg Gln Gly Arg Val Phe Gly Leu Gln Thr Met Val Cys Ile
    210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
                245                 250                 255

Asn Leu Glu Thr Ser Ser Trp Ile Ser Gly Thr Thr Ala Ala Asp Glu
            260                 265                 270

Gly Glu Asn Asp Pro Ser Ser Met Trp Ile Ser Glu Pro Ser Ser Thr
        275                 280                 285

Ile Glu Met Lys Asp Ser Ile Thr Thr Thr Val Pro Ser Gly Asn Val
    290                 295                 300

Pro Ala Lys Pro Ile His Ser Glu Asn Pro Ser Ser Ser Ser Leu Thr
305                 310                 315                 320

Glu Asn Ile Ser Ala Ile Gln Gln Pro Ser His Gln Lys Gln Ser Gln
                325                 330                 335
```

-continued

SEQUENCE LISTING

```
Ser Phe Leu Asn Phe Ser Asp Tyr Gly Phe Glu Ser Asn Pro Ser Lys
            340                 345                 350

Asn Thr Thr Ala Ala Ala Thr Thr Thr Thr Ala Thr Pro Ser Phe Lys
        355                 360                 365

Pro Glu Ser Gly Gly Met Leu Asn Phe Gly Asn Gly Asn Leu Phe Ser
    370                 375                 380

Ser His Ser Gln Tyr Val Thr Asn Glu Gln Asn Glu Lys Lys Arg Ser
385                 390                 395                 400

Pro Ala Ser Arg Ser Ser Asn Asp Glu Gly Ile Leu Ser Phe Thr Ser
                405                 410                 415

Gly Val Ile Leu Pro Ser Ser Gly Lys Val Lys Ser Gly Asp Ser Asp
            420                 425                 430

His Ser Asp Leu Glu Ala Ser Val Ile Arg Glu Val Asp Ser Cys Thr
        435                 440                 445

Lys Ser Leu Glu Pro Glu Lys Arg Pro Arg Lys Arg Gly Arg Lys Pro
    450                 455                 460

Ala Asn Gly Arg Glu Glu Pro Leu Asn His Val Glu Ala Glu Arg Gln
465                 470                 475                 480

Arg Arg Glu Lys Leu Asn Gln Lys Phe Tyr Ala Leu Arg Ala Val Val
                485                 490                 495

Pro Asn Val Ser Lys Met Asp Lys Ala Ser Leu Leu Gly Asp Ala Val
            500                 505                 510

Ser Tyr Ile Asn Glu Leu Lys Ser Lys Leu Gln Ile Ala Glu Thr Glu
        515                 520                 525

Lys Thr Glu Met Gly Lys His Leu Glu Leu Leu Lys Lys Glu Met Gly
    530                 535                 540

Gly Lys Asp Phe Gly Asn Tyr Pro Asn Pro Asn Asp Glu Asp Leu Lys
545                 550                 555                 560

Ile Gly Lys Arg Lys Val Met Asp Met Glu Ile Glu Val Lys Ile Met
                565                 570                 575

Gly Trp Asp Ala Met Ile Arg Ile Gln Ser Ser Lys Lys Asn His Pro
            580                 585                 590

Ala Ala Arg Leu Met Ala Ala Phe Lys Asp Leu Asp Leu Glu Met Leu
        595                 600                 605

His Ala Ser Val Ser Val Val Asn Asp Leu Met Ile Gln Gln Ala Thr
    610                 615                 620

Val Lys Met Gly Ser Arg Phe Tyr Thr Gln Glu Gln Leu Lys Met Ala
625                 630                 635                 640

Leu Val Ala Arg Val Gly Gly Gly Gly Gly Ser Ser His Gly Met Met
                645                 650                 655
```

SEQUENCE LISTING

<160> NUMBER OF SEQ ID NOS: 20

<210> SEQ ID NO 1
<211> LENGTH: 8000
<212> TYPE: DNA
<213> ORGANISM: Solanum lycopersicum

<400> SEQUENCE: 1
attcaataat taattgtaat tgtctggcat tgttatggtg gttcacatgt caagttgctt 60

-continued

```
ttatattatt tgttattaaa ataaaaatag aaaaatcaat gttattttca cgttcagcat    120
ccaccaaaac gtgctattaa taatttaatg tctaaaacat atctacaaat tatattatat    180
tagtataata tactttatga tatcttgaac aaagacaatt acaagtagga ccaatcaaaa    240
tgattccaca acgtgacgcc aacgcgtaca aataaggatt ttcctttatt ataactttat    300
aataattaac tcaccgtaat taatttgtat gattataatg aaatgactga aactttttcg    360
ctcttaacaa gaaatctcga tcgaacttta gccatgaaat aaaaataatt gtgttgagag    420
tagaatttcc aaaaatagat tttatagtgt gtaaaattat atttattaat ttttaatatg    480
attatcaaaa taccgaatcg aagaaagtaa gtaaatttta aggaatgtaa tatgtatgtg    540
gtctcaccct tacatgcatt gaatatgtaa agagtgtttt cgaaggacaa ggattttttt    600
gtttttacta ttaatgtatt ttaaaaactt aagacaaaat tatttactca aaatttacat    660
gcgatattgt actaaaacga tttacaatta ttgtaggtac cttaattact ctgatagtgc    720
atggccttta attacaaggg ataccaataa caaaaaagtc catatttgtg atgaatatgt    780
cttatcacaa aaattgagag gaatattatg atagatttaa tgaaaaattt taatatggac    840
aaaagaatat tatgatagat ttaaagaaaa aatttaatat ggacaaaatt tgtgatggac    900
taataaattt actttttca ttacgaattt ttggagcctc acgttgaaga tccaatgact    960
tgttttcaaa ttagtttcaa agaatggctg agaatagtct ttctaaaaaa gcatcttcaa   1020
tcgatggctt gaatttaatt attaaaagaa ttattatatt tgataatgta ttgattagat   1080
gcacgttatg aatttaaaat ttcattttag acatgaacct aatatttaaa tagacaccaa   1140
cacaagtata tgacgcgaac aagtgatatt taagttatga gttcaaaatt tatgaatcat   1200
tagtcataac taaaaatgtg atactttagg ggataaggat agaagagcaa atttaaattt   1260
tacgtgaacc tttttatatt aaatagaaaa taatagagcg ataaattcat tatttatcga   1320
gtttcaaatc attaaaaata caatatataa tatacgaatt agatgtatat acacatttga   1380
attcaatggt ggactatata atttgatatt taagtaagca aaagtagata aggagttcaa   1440
gtttaaattt gtaaacatag aatttcctat tttagagttt aaggtaaatt tatgtatatt   1500
ttatcgtttg gaatctcatt ttacgatgct acgctaaata ttagaaattg ctaaaaataa   1560
ttgttgttat tgtaatataa tatcaaaatc aacatgattt catttatttt ctttccatat   1620
atgaattatt tccataaagc ctacatgtag gagatatgct aatttaatat ttcctggaaa   1680
tagttaactt agttgaaaca ttgaagtatt agatatttta ttaatataag cactttaaca   1740
aatatggtta taaaaaaaaa tcttcttctt ttcaattcct ttaacattca ttgaaaatct   1800
tcttatttaa caatattttt ccaattagtt caataactcg tcttcaatca tcgaagatat   1860
ttaatgttac ttttttgaa gtaatgaaat ttacttctaa taatcttgtc ttttttttaa   1920
attggaaatg ggaatagaaa atgataagac gaaattaaat cctcacctac aagataaaag   1980
tttagataag ttttgatagt taattaaatg aatttcaaat tttttaatac ttaaatactt   2040
ctcattaata attgtaaaga tatctacttt tttcattcac tttttacttc aaaaataaat   2100
caaattatgt cacactttca ctgtaataaa ttatatatat ataataaaaa aaaagaaaaa   2160
tcttctacct atataagtac gactctctaa tggtgttaag taaaaagaaa aatttagtat   2220
aaagtcctag gtagttaaaa agtaaaaagt agaactaatg ccggctttcc ttatcctacg   2280
tataattttc ccataaatcg cccaccttaa ttttttttt ctgatttttc atttggcatc   2340
gaagcttata ttagaattta aacttacgtt aaaattttt ataatggcac taaaattttt   2400
```

-continued

```
actaacataa ataattatcc catcctaata aaaatttaaa taaaaaatat ttgattaaaa   2460
atacttaccg tttttctcgg aaccctcttc tctttgtcca ctcactttcc tcactcattt   2520
atttttgagc tcacaatatt tttattatat atatatatat atccacaaaa atctctactc   2580
tcatttctca cctaacaaac aaaatctctc attttctgtt ttttgtaaaa ttcttcaatt   2640
taattgaatg acggactata gattatggag taataccaat actactaata catgtgatga   2700
tactatgatg atggattctt ttttatcttc cgatccatcc tctttttggc ctgcttccac   2760
tcccaatcgt ccgactccgg tgaacggagt cggagaaacg atgccgtttt tcaatcaaga   2820
gtcactacag caaaggcttc aggctttaat tgacggtgct cgtgaatcat gggcatatgc   2880
tattttctgg caatcgtcag ttgttgattt tgcgagccaa actgtattgg gttggggaga   2940
tgggtattat aaaggagaag aagataagaa taaacggaga gggtcgtcta gttcagcagc   3000
taattttgtt gctgagcaag agcatagaaa gaaggtgctt cgggagctga attcattaat   3060
atccggtgta caagcttccg ccggaaacgg aactgatgat gcagtggatg aggaagtgac   3120
ggatactgaa tggttttttc tgatttcaat gacccaatcg tttgttaacg gtaacgggct   3180
tccgggcttg gcgatgtaca gttcaagccc aatttgggtt actggaacag agaaattagc   3240
tgcttctcaa tgtgaacggg ccaggcaagc ccaaggtttc gggcttcaga cgattgtgtg   3300
tattccttca gctaacggtg tagtggagct tggttcgact gagctgatat tccaaagctc   3360
ggatttgatg aacaaggtta agtatttgtt taacttcaat attgatatgg ggtctgttac   3420
aggctcaggt tcgggctcag gctcttgtgc tgtgcatcct gagcccgatc cttcggccct   3480
ttggcttacg gatccatctt cctcggttgt ggaacctaag gattcgttaa ttcatagtag   3540
tagtagggat gttcaacttg tgtatggaaa tgagaattct gaaaatcagc agcagcattg   3600
tcaaggattt ttcacaaagg agttgaattt ttcgggttat ggatttgatg gaagtagtaa   3660
taggaataaa actggaattt cttgtaagcc ggagtccagg gagatattga attttggtga   3720
tagtagtaag agattttcag ggcaatcaca gttgggtcct gggcctgggc tcatggagga   3780
gaacaagaac aagaacaaga acaagaaaag gtcacttgga tcaaggggaa acaatgaaga   3840
aggaatgctt tcgtttgttt cgggtgtgat cttgccaact tcaacaatgg ggaagtccgg   3900
ggattctgat cactcagatc tcgaagcctc agtggtgaag gaggccgttg tagaacctga   3960
aaagaagccg aggaagcgag ggaggaaacc agccaatgga agggaggagc cattgaatca   4020
cgtggaagcg gagagacaga ggagggagaa attgaatcaa agattctacg cgctcagagc   4080
cgtagtccca aatgtgtcta aaatggataa ggcatcactt ctttgagatg caattgcata   4140
catcaatgag ttgaaatcaa aagttcaaaa ttcagattta gataaagagg agttgaggag   4200
ccaaattgaa tgtttaagga aggaattaac caacaaggga tcatcaaact attccgcctc   4260
ccctccattg aatcaagatg tcaagattgt cgatatggac attgacgtta aggtgattgg   4320
atgggatgct atgattcgta tacaatgtag taaaaagaac catccagctg ccaggctaat   4380
ggcagccctc aaggacttgg acctagacgt gcaccacgct agtgtttccg tggtgaatga   4440
tttgatgatc caacaagcca cagtcaaaat ggggagccgg ctttatgctc aagaacagct   4500
taggatagca ttgacatcaa aaattgctga atcgcgatga aattatgtcc ctagtgagct   4560
atgtataatg ttatcttcta atgagcgaga attttcttct ctgtatataa atgtgatgaa   4620
accaatacta gagatctcga gttgaggctt tttagttcat gtaagattag atatatatat   4680
atgatgcagc ttcatccttt tgtattcttc atccaggaaa taaatgagaa accaataatt   4740
ggtggctgat gatcaacttc atgttattac taattctcgt tccctcttct tttgggatac   4800
```

-continued

```
aacacttgtc attttacatt aggcaaatta gaagaaaata ctaagcattt tttaattgaa   4860
cgtaacatgt catgtgtgaa ctagagtcac aagttcaatt catgtaacaa acaatcacct   4920
ttgcatttta gtggagaagg atgcattgag tttcaacttg tacactaact agtcataaga   4980
gattactttg ttataaaaaa aaaaacaatt tttgaccttg ttgtgtatat aatatatgat   5040
tcgagtttgg acgaaagttt ttatttaatt atgatggata tattagttat ggagtacaca   5100
attgccttta ctataaaact tattactttt taataataaa tattttttta atgtaaatat   5160
ataaatataa tcaaaactta atataaatgg atgtattact aatcagttgc ttgttttagt   5220
ctagaagaaa gcaccaaaca aaggggtagg gctgcatttt catttataga gaattcattg   5280
aatttggtca aatcatagct gtattcattg gactaggaaa tatttaaaaa gtatatatat   5340
tattgtttat aataaatataa tgtcatgagt atcatttgag tttgaagtga cacaagccct   5400
ttaaatgcag ttgatttagg cacaaacttt gttattattc ccgccgtcca aatagttgtt   5460
acatttggct tcctaaaaat taatttaact aatttttaaa tttaatttta tattttgaaa   5520
aattaaagtt tataaataca aaaattattt taatttctta catataatta aaaaatatat   5580
ataaaattta tataatttag cgctggaaaa ttattttgaa aacagaggaa gtattattat   5640
tattttggtc ttatgaattg tgtgataaac agtttatatc tgttaatcaa atagacagag   5700
attgatagat gtgacaaaga ttcgtttttt gtttgaggtt ttataaaagg aaaattgtat   5760
aaaatagcaa actaataact taaattaaat ggaatagcta gggtttgatt taattgtgct   5820
ccatagcaaa cgttggcaaa aatttaccag aagtctcgct cgccactctc ccattctcgc   5880
ctctctcgct ttatacatag aagtgtataa tttatgtttc tgttttgtat aaagcgagag   5940
aaaattgtat atacacatgc aaaaatgtat atctttgtgt tatacactta attatataat   6000
ttacaaacat tttacttcaa atattgcagc gaaaaaggcc aaagaattat acaatcgtga   6060
attatataat tgcagtgaaa tacaattttt tctagcttta tacaacagaa gtgtatatat   6120
tgtatttctg tttttgtata aagcgagaaa aacatatatc ttcttgctat acacttataa   6180
ttatgcaata tacatacatt ttaattcgat taaactgtat acaaaactaa ttatacaatt   6240
gcagcgaaat ggcgaattat acaatttagg ccagcgaatt atacactttt atatgtatag   6300
cgaattatac agtttttata tttgctatgg agcgcatata ttatacaaat atgatttttt   6360
tgtttgctat atgtgaaagt tgccctttta taaaagcttt tatgtatagt ttgatttgtt   6420
tttttaaaaa ataaaatatg acaactttag tatcaaaata gattaaattt atatacaata   6480
aatagttata ttttacagcc agccatttat ctttcttttt tttcaagcca caaaatcacc   6540
ttgtagaaag ttattttgtt cgatatttta ttgctaatat ataaaaatat tattataaaa   6600
agcatgtaat atatatataa aaatttgatt tcaaagaata ctttgatcat tataatgata   6660
tgttaatata aataataatt attatagatt aatctgatcg tatattttca gtatacatta   6720
atatatacat ctaaaatatg actgtattaa atatgaacaa aatcatttac atcaccctat   6780
ataatatttt aattaaaaag atgtataaag aagaataaaa aacgctgaag tttaaagcga   6840
atgttattga ccagatcaaa ttgacttgaa gaccaaaatt gaattgttga atacaattaa   6900
ttaatttaaa aatgaccatg ttttacatgt gaaattcatt tatatatata tatatatatc   6960
atatattatt atagtattca cattttgttg tttacactga tggttccgtt aagtgttcac   7020
atttctttgt ttaacactaa actttggagg gaaggatgtg aaaataaaaa atttgggtag   7080
aaaattaatc gataatttaa tattgtctaa tttatcttat gtatattatg atcattactc   7140
```

-continued

```
ccttattatc tttgtatttt tttaatcttg attatcatat tatttagtat ttttttatcc   7200
ttaattttga tatgttttac ttgagtcaaa aatctataga aaataatttt tctattttta   7260
caagataagg gtaaagatgt gcgaacacaa ctttttttgaa gccccactta tgaaattaca   7320
ctgaacatat tgttgtagta actgtacgaa ctctttttttc tttctatata aacaaatgta   7380
taactaaagt atttagtaaa ataaaaatat aattctattt agttcatgaa tgagaccaca   7440
atatgaatgt atagagctgg ggatattttt tgtttttgtg tagatggata ttaatcgaag   7500
atgtattggt tcttaatagt aagaataaca atagccatta ccctaaagat tgattcacct   7560
ttattttagg gtataaacca aaaaagaatg gacattatta acacgagacc tttagcattt   7620
ccaaaaaaaa tgggagaatt ttgttattta tttaaaaaga aaaaaaaaaa gaacacaccc   7680
ttaacctcaa tatcctcaaa aattcaacca tcaatatcat tattttattt tcatatccta   7740
tgcatttttt attagcttgt aaacttttaa ttttcttcct attcttttat acaacaatga   7800
ctctcaattg tttaacctgc caagctctaa aaagaacaga ttcacatgag gaactaaggg   7860
aaacactgaa tcatgttaat gataagtcga attttcgtct tttttcagtg ggaatggaga   7920
ggaactggtc agggaacttg gttgaaagac ggaaatatga aaaaacgagg ggtcgaacca   7980
taatgggaaa agaaaataat                                               8000
```

<210> SEQ ID NO 2
<211> LENGTH: 1893
<212> TYPE: DNA
<213> ORGANISM: Solanum lycopersicum

<400> SEQUENCE: 2

```
atgacggact atagattatg gagtaatacc aatactacta atacatgtga tgatactatg     60
atgatggatt cttttttatc ttccgatcca tcctcttttt ggcctgcttc cactcccaat    120
cgtccgactc cggtgaacgg agtcggagaa acgatgccgt tttttcaatca agagtcacta    180
cagcaaaggc ttcaggcttt aattgacggt gctcgtgaat catgggcata tgctattttc    240
tggcaatcgt cagttgttga ttttgcgagc caaactgtat tgggttgggg agatgggtat    300
tataaaggag aagaagataa gaataaacgg agagggtcgt ctagttcagc agctaatttt    360
gttgctgagc aagagcatag aaagaaggtg cttcgggagc tgaattcatt aatatccggt    420
gtacaagctt ccgccggaaa cggaactgat gatgcagtgg atgaggaagt gacggatact    480
gaatggtttt ttctgatttc aatgacccaa tcgtttgtta acggtaacgg gcttccgggc    540
ttggcgatgt acagttcaag cccaatttgg gttactggaa cagagaaatt agctgcttct    600
caatgtgaac gggccaggca agcccaaggt ttcgggcttc agacgattgt gtgtattcct    660
tcagctaacg gtgtagtgga gcttggttcg actgagctga tattccaaag ctcggatttg    720
atgaacaagg ttaagtattt gtttaacttc aatattgata tggggtctgt tacaggctca    780
ggttcgggct caggctcttg tgctgtgcat cctgagcccg atccttcggc cctttggctt    840
acggatccat cttcctcggt tgtggaacct aaggattcgt taattcatag tagtagtagg    900
gatgttcaac ttgtgtatgg aaatgagaat tctgaaaatc agcagcagca ttgtcaagga    960
tttttcacaa aggagttgaa tttttcgggt tatggatttg atggaagtag taataggaat   1020
aaaactggaa tttcttgtaa gccggagtcc agggagatat tgaattttgg tgatagtagt   1080
aagagatttt cagggcaatc acagttgggt cctgggcctg ggctcatgga ggagaacaag   1140
aacaagaaca agaacaagaa aaggtcactt ggatcaaggg gaaacaatga agaaggaatg   1200
ctttcgtttg tttcgggtgt gatcttgcca acttcaacaa tggggaagtc cggggattct   1260
```

```
gatcactcag atctcgaagc ctcagtggtg aaggaggccg ttgtagaacc tgaaaagaag   1320

ccgaggaagc gagggaggaa accagccaat ggaagggagg agccattgaa tcacgtggaa   1380

gcggagagac agaggaggga gaaattgaat caaagattct acgcgctcag agccgtagtc   1440

ccaaatgtgt ctaaaatgga taaggcatca cttctttgag atgcaattgc atacatcaat   1500

gagttgaaat caaaagttca aaattcagat ttagataaag aggagttgag gagccaaatt   1560

gaatgtttaa ggaaggaatt aaccaacaag ggatcatcaa actattccgc ctcccctcca   1620

ttgaatcaag atgtcaagat tgtcgatatg gacattgacg ttaaggtgat tggatgggat   1680

gctatgattc gtatacaatg tagtaaaaag aaccatccag ctgccaggct aatggcagcc   1740

ctcaaggact tggacctaga cgtgcaccac gctagtgttt ccgtggtgaa tgatttgatg   1800

atccaacaag ccacagtcaa aatggggagc cggctttatg ctcaagaaca gcttaggata   1860

gcattgacat caaaaattgc tgaatcgcga tga                                1893
```

<210> SEQ ID NO 3
<211> LENGTH: 630
<212> TYPE: PRT
<213> ORGANISM: Solanum lycopersicum
<220> FEATURE:
<221> NAME/KEY: SITE
<222> LOCATION: 493
<223> OTHER INFORMATION: site of stop codon

<400> SEQUENCE: 3

```
Met Thr Asp Tyr Arg Leu Trp Ser Asn Thr Asn Thr Thr Asn Thr Cys
1               5                   10                  15

Asp Asp Thr Met Met Met Asp Ser Phe Leu Ser Ser Asp Pro Ser Ser
            20                  25                  30

Phe Trp Pro Ala Ser Thr Pro Asn Arg Pro Thr Pro Val Asn Gly Val
        35                  40                  45

Gly Glu Thr Met Pro Phe Phe Asn Gln Glu Ser Leu Gln Gln Arg Leu
    50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95

Gly Asp Gly Tyr Tyr Lys Gly Glu Glu Asp Lys Asn Lys Arg Arg Gly
            100                 105                 110

Ser Ser Ser Ser Ala Ala Asn Phe Val Ala Glu Gln Glu His Arg Lys
        115                 120                 125

Lys Val Leu Arg Glu Leu Asn Ser Leu Ile Ser Gly Val Gln Ala Ser
    130                 135                 140

Ala Gly Asn Gly Thr Asp Asp Ala Val Asp Glu Glu Val Thr Asp Thr
145                 150                 155                 160

Glu Trp Phe Phe Leu Ile Ser Met Thr Gln Ser Phe Val Asn Gly Asn
                165                 170                 175

Gly Leu Pro Gly Leu Ala Met Tyr Ser Ser Ser Pro Ile Trp Val Thr
            180                 185                 190

Gly Thr Glu Lys Leu Ala Ala Ser Gln Cys Glu Arg Ala Arg Gln Ala
        195                 200                 205

Gln Gly Phe Gly Leu Gln Thr Ile Val Cys Ile Pro Ser Ala Asn Gly
    210                 215                 220

Val Val Glu Leu Gly Ser Thr Glu Leu Ile Phe Gln Ser Ser Asp Leu
225                 230                 235                 240
```

```
Met Asn Lys Val Lys Tyr Leu Phe Asn Phe Asn Ile Asp Met Gly Ser
                245                 250                 255

Val Thr Gly Ser Gly Ser Gly Ser Gly Ser Cys Ala Val His Pro Glu
            260                 265                 270

Pro Asp Pro Ser Ala Leu Trp Leu Thr Asp Pro Ser Ser Ser Val Val
        275                 280                 285

Glu Pro Lys Asp Ser Leu Ile His Ser Ser Ser Arg Asp Val Gln Leu
    290                 295                 300

Val Tyr Gly Asn Glu Asn Ser Glu Asn Gln Gln Gln His Cys Gln Gly
305                 310                 315                 320

Phe Phe Thr Lys Glu Leu Asn Phe Ser Gly Tyr Gly Phe Asp Gly Ser
                325                 330                 335

Ser Asn Arg Asn Lys Thr Gly Ile Ser Cys Lys Pro Glu Ser Arg Glu
            340                 345                 350

Ile Leu Asn Phe Gly Asp Ser Ser Lys Arg Phe Ser Gly Gln Ser Gln
        355                 360                 365

Leu Gly Pro Gly Pro Gly Leu Met Glu Glu Asn Lys Asn Lys Asn Lys
    370                 375                 380

Asn Lys Lys Arg Ser Leu Gly Ser Arg Gly Asn Asn Glu Glu Gly Met
385                 390                 395                 400

Leu Ser Phe Val Ser Gly Val Ile Leu Pro Thr Ser Thr Met Gly Lys
                405                 410                 415

Ser Gly Asp Ser Asp His Ser Asp Leu Glu Ala Ser Val Val Lys Glu
            420                 425                 430

Ala Val Val Glu Pro Glu Lys Lys Pro Arg Lys Arg Gly Arg Lys Pro
        435                 440                 445

Ala Asn Gly Arg Glu Glu Pro Leu Asn His Val Glu Ala Glu Arg Gln
    450                 455                 460

Arg Arg Glu Lys Leu Asn Gln Arg Phe Tyr Ala Leu Arg Ala Val Val
465                 470                 475                 480

Pro Asn Val Ser Lys Met Asp Lys Ala Ser Leu Leu Xaa Asp Ala Ile
                485                 490                 495

Ala Tyr Ile Asn Glu Leu Lys Ser Lys Val Gln Asn Ser Asp Leu Asp
            500                 505                 510

Lys Glu Glu Leu Arg Ser Gln Ile Glu Cys Leu Arg Lys Glu Leu Thr
        515                 520                 525

Asn Lys Gly Ser Ser Asn Tyr Ser Ala Ser Pro Pro Leu Asn Gln Asp
    530                 535                 540

Val Lys Ile Val Asp Met Asp Ile Asp Val Lys Val Ile Gly Trp Asp
545                 550                 555                 560

Ala Met Ile Arg Ile Gln Cys Ser Lys Lys Asn His Pro Ala Ala Arg
                565                 570                 575

Leu Met Ala Ala Leu Lys Asp Leu Asp Leu Asp Val His His Ala Ser
            580                 585                 590

Val Ser Val Val Asn Asp Leu Met Ile Gln Gln Ala Thr Val Lys Met
        595                 600                 605

Gly Ser Arg Leu Tyr Ala Gln Glu Gln Leu Arg Ile Ala Leu Thr Ser
    610                 615                 620

Lys Ile Ala Glu Ser Arg
625                 630
```

<210> SEQ ID NO 4
<211> LENGTH: 201

```
<212> TYPE: DNA
<213> ORGANISM: Solanum lycopersicum

<400> SEQUENCE: 4

ggaagcggag agacagagga gggagaaatt gaatcaaaga ttctacgcgc tcagagccgt     60

agtcccaaat gtgtctaaaa tggataaggc atcacttctt tgagatgcaa ttgcatacat    120

caatgagttg aaatcaaaag ttcaaaattc agatttagat aaagaggagt tgaggagcca    180

aattgaatgt ttaaggaagg a                                              201


<210> SEQ ID NO 5
<211> LENGTH: 8000
<212> TYPE: DNA
<213> ORGANISM: Solanum lycopersicum

<400> SEQUENCE: 5

attcaataat taattgtaat tgtctggcat tgttatggtg gttcacatgt caagttgctt     60

ttatattatt tgttattaaa ataaaaatag aaaaatcaat gttattttca cgttcagcat    120

ccaccaaaac gtgctattaa taatttaatg tctaaaacat atctacaaat tatattatat    180

tagtataata tactttatga tatcttgaac aaagacaatt acaagtagga ccaatcaaaa    240

tgattccaca acgtgacgcc aacgcgtaca aataaggatt ttcctttatt ataactttat    300

aataattaac tcaccgtaat taatttgtat gattataatg aaatgactga aactttttcg    360

ctcttaacaa gaaatctcga tcgaacttta gccatgaaat aaaaataatt gtgttgagag    420

tagaatttcc aaaaatagat tttatagtgt gtaaaattat atttattaat ttttaatatg    480

attatcaaaa taccgaatcg aagaaagtaa gtaaatttta aggaatgtaa tatgtatgtg    540

gtctcaccct tacatgcatt gaatatgtaa agagtgtttt cgaaggacaa ggattttttt    600

gtttttacta ttaatgtatt ttaaaaactt aagacaaaat tatttactca aaatttacat    660

gcgatattgt actaaaacga tttacaatta ttgtaggtac cttaattact ctgatagtgc    720

atggccttta attacaaggg ataccaataa caaaaaagtc catatttgtg atgaatatgt    780

cttatcacaa aaattgagag gaatattatg atagatttaa tgaaaaattt taatatggac    840

aaaagaatat tatgatagat ttaaagaaaa aatttaatat ggacaaaatt tgtgatggac    900

taataaattt actttttca ttacgaattt ttggagcctc acgttgaaga tccaatgact    960

tgttttcaaa ttagtttcaa agaatggctg agaatagtct ttctaaaaaa gcatcttcaa   1020

tcgatggctt gaatttaatt attaaaagaa ttattatatt tgataatgta ttgattagat   1080

gcacgttatg aatttaaaat ttcattttag acatgaacct aatatttaaa tagacaccaa   1140

cacaagtata tgacgcgaac aagtgatatt taagttatga gttcaaaatt tatgaatcat   1200

tagtcataac taaaaatgtg atactttagg ggataaggat agaagagcaa atttaaattt   1260

tacgtgaacc ttttttattt aaatagaaaa taatagagcg ataaattcat tatttatcga   1320

gtttcaaatc attaaaaata caatatataa tatacgaatt agatgtatat acacatttga   1380

attcaatggt ggactatata atttgatatt taagtaagca aaagtagata aggagttcaa   1440

gtttaaattt gtaaacatag aatttcctat tttagagttt aaggtaaatt tatgtatatt   1500

ttatcgtttg gaatctcatt ttacgatgct acgctaaata ttagaaattg ctaaaaataa   1560

ttgttgttat tgtaatataa tatcaaaatc aacatgattt catttatttt ctttccatat   1620

atgaattatt tccataaagc ctacatgtag gagatatgct aatttaatat ttcctggaaa   1680

tagttaactt agttgaaaca ttgaagtatt agatatttta ttaatataag cactttaaca   1740
```

-continued

```
aatatggtta taaaaaaaaa tcttcttctt ttcaattcct ttaacattca ttgaaaatct   1800
tcttatttaa caatattttt ccaattagtt caataactcg tcttcaatca tcgaagatat   1860
ttaatgttac ttttttgaa gtaatgaaat ttacttctaa taatcttgtc ttttttttaa   1920
attggaaatg ggaatagaaa atgataagac gaaattaaat cctcacctac aagataaaag   1980
tttagataag ttttgatagt taattaaatg aatttcaaat tttttaatac ttaaatactt   2040
ctcattaata attgtaaaga tatctacttt tttcattcac tttttacttc aaaaataaat   2100
caaattatgt cacactttca ctgtaataaa ttatatatat ataataaaaa aaaagaaaaa   2160
tcttctacct atataagtac gactctctaa tggtgttaag taaaaagaaa aatttagtat   2220
aaagtcctag gtagttaaaa agtaaaaagt agaactaatg ccggctttcc ttatcctacg   2280
tataattttc ccataaatcg cccaccttaa tttttttttt ctgatttttc atttggcatc   2340
gaagcttata ttagaattta aacttacgtt aaaatttttt ataatggcac taaaattttt   2400
actaacataa ataattatcc catcctaata aaaatttaaa taaaaaatat ttgattaaaa   2460
atacttaccg tttttctcgg aaccctcttc tctttgtcca ctcactttcc tcactcattt   2520
atttttgagc tcacaatatt tttattatat atatatatat atccacaaaa atctctactc   2580
tcatttctca cctaacaaac aaaatctctc attttctgtt ttttgtaaaa ttcttcaatt   2640
taattgaatg acggactata gattatggag taataccaat actactaata catgtgatga   2700
tactatgatg atggattctt ttttatcttc cgatccatcc tctttttggc ctgcttccac   2760
tcccaatcgt ccgactccgg tgaacggagt cggagaaacg atgccgtttt tcaatcaaga   2820
gtcactacag caaaggcttc aggctttaat tgacggtgct cgtgaatcat gggcatatgc   2880
tattttctgg caatcgtcag ttgttgattt tgcgagccaa actgtattgg gttggggaga   2940
tgggtattat aaaggagaag aagataagaa taaacggaga gggtcgtcta gttcagcagc   3000
taattttgtt gctgagcaag agcatagaaa gaaggtgctt cgggagctga attcattaat   3060
atccggtgta caagcttccg ccggaaacgg aactgatgat gcagtggatg aggaagtgac   3120
ggatactgaa tggtttttttc tgatttcaat gacccaatcg tttgttaacg gtaacgggct   3180
tccgggcttg gcgatgtaca gttcaagccc aatttgggtt actggaacag agaaattagc   3240
tgcttctcaa tgtgaacggg ccaggcaagc ccaaggtttc gggcttcaga cgattgtgtg   3300
tattccttca gctaacggtg tagtggagct tggttcgact gagctgatat tccaaagctc   3360
ggatttgatg aacaaggtta agtatttgtt taacttcaat attgatatgg ggtctgttac   3420
aggctcaggt tcgggctcag gctcttgtgc tgtgcatcct gagcccgatc cttcggccct   3480
ttggcttacg gatccatctt cctcggttgt ggaacctaag gattcgttaa ttcatagtag   3540
tagtagggat gttcaacttg tgtatggaaa tgagaattct gaaaatcagc agcagcattg   3600
tcaaggattt ttcacaaagg agttgaattt ttcgggttat ggatttgatg gaagtagtaa   3660
taggaataaa actggaattt cttgtaagcc ggagtccagg gagatattga attttggtga   3720
tagtagtaag agattttcag ggcaatcaca gttgggtcct gggcctgggc tcatggagga   3780
gaacaagaac aagaacaaga acaagaaaag gtcacttgga tcaaggggaa acaatgaaga   3840
aggaatgctt tcgtttgttt cgggtgtgat cttgccaact tcaacaatgg ggaagtccgg   3900
ggattctgat cactcagatc tcgaagcctc agtggtgaag gaggccgttg tagaacctga   3960
aaagaagccg aggaagcgag ggaggaaacc agccaatgga agggaggagc cattgaatca   4020
cgtggaagcg gagagacaga ggagggagaa attgaatcaa agattctacg cgctcagagc   4080
cgtagtccca aatgtgtcta aaatggataa ggcatcactt cttggagatg caattgcata   4140
```

-continued

```
catcaatgag ttgaaatcaa aagttcaaaa ttcagattta gataaagagg agttgaggag   4200
ccaaattgaa tgtttaagga aggaattaac caacaaggga tcatcaaact attccgcctc   4260
ccctccattg aatcaagatg tcaagattgt cgatatggac attgacgtta aggtgattgg   4320
atgggatgct atgattcgta tacaatgtag taaaaagaac catccagctg ccaggctaat   4380
ggcagccctc aaggacttgg acctagacgt gcaccacgct agtgtttccg tggtgaatga   4440
tttgatgatc caacaagcca cagtcaaaat ggggagccgg ctttatgctc aagaacagct   4500
taggatagca ttgacatcaa aaattgctga atcgcgatga aattatgtcc ctagtgagct   4560
atgtataatg ttatcttcta atgagcgaga attttcttct ctgtatataa atgtgatgaa   4620
accaatacta gagatctcga gttgaggctt tttagttcat gtaagattag atatatatat   4680
atgatgcagc ttcatccttt tgtattcttc atccaggaaa taaatgagaa accaataatt   4740
ggtggctgat gatcaacttc atgttattac taattctcgt tccctcttct tttgggatac   4800
aacacttgtc attttacatt aggcaaatta gaagaaaata ctaagcattt tttaattgaa   4860
cgtaacatgt catgtgtgaa ctagagtcac aagttcaatt catgtaacaa acaatcacct   4920
ttgcatttta gtggagaagg atgcattgag tttcaacttg tacactaact agtcataaga   4980
gattactttg ttataaaaaa aaaaacaatt tttgaccttg ttgtgtatat aatatatgat   5040
tcgagtttgg acgaaagttt ttatttaatt atgatggata tattagttat ggagtacaca   5100
attgccttta ctataaaact tattactttt taataataaa tattttttta atgtaaatat   5160
ataaatataa tcaaaactta atataaatgg atgtattact aatcagttgc ttgttttagt   5220
ctagaagaaa gcaccaaaca aaggggtagg gctgcatttt catttataga gaattcattg   5280
aatttggtca aatcatagct gtattcattg gactaggaaa tatttaaaaa gtatatatat   5340
tattgtttat aataaatataa tgtcatgagt atcatttgag tttgaagtga cacaagccct   5400
ttaaatgcag ttgatttagg cacaaacttt gttattattc ccgccgtcca aatagttgtt   5460
acatttggct tcctaaaaat taatttaact aatttttaaa tttaatttta tattttgaaa   5520
aattaaagtt tataaataca aaaattattt taatttctta catataatta aaaaatatat   5580
ataaaattta tataatttag cgctggaaaa ttattttgaa aacagaggaa gtattattat   5640
tattttggtc ttatgaattg tgtgataaac agtttatatc tgttaatcaa atagacagag   5700
attgatagat gtgacaaaga ttcgtttttt gtttgaggtt ttataaaagg aaaattgtat   5760
aaaatagcaa actaataact taaattaaat ggaatagcta gggtttgatt taattgtgct   5820
ccatagcaaa cgttggcaaa aatttaccag aagtctcgct cgccactctc ccattctcgc   5880
ctctctcgct ttatacatag aagtgtataa tttatgtttc tgttttgtat aaagcgagag   5940
aaaattgtat atacacatgc aaaaatgtat atctttgtgt tatacactta attatataat   6000
ttacaaacat tttacttcaa atattgcagc gaaaaaggcc aaagaattat acaatcgtga   6060
attatataat tgcagtgaaa tacaattttt tctagcttta tacaacagaa gtgtatatat   6120
tgtatttctg tttttgtata aagcgagaaa aacatatatc ttcttgctat acacttataa   6180
ttatgcaata tacatacatt ttaattcgat taaactgtat acaaaactaa ttatacaatt   6240
gcagcgaaat ggcgaattat acaatttagg ccagcgaatt atacactttt atatgtatag   6300
cgaattatac agtttttata tttgctatgg agcgcatata ttatacaaat atgatttttt   6360
tgtttgctat atgtgaaagt tgccctttta taaaagcttt tatgtatagt ttgatttgtt   6420
tttttaaaaa ataaaatatg acaactttag tatcaaaata gattaaattt atatacaata   6480
```

aatagttata ttttacagcc agccatttat ctttcttttt tttcaagcca caaaatcacc 6540
ttgtagaaag ttattttgtt cgatatttta ttgctaatat ataaaaatat tattataaaa 6600
agcatgtaat atatatataa aaatttgatt tcaaagaata ctttgatcat tataatgata 6660
tgttaatata aataataatt attatagatt aatctgatcg tatattttca gtatacatta 6720
atatatacat ctaaaatatg actgtattaa atatgaacaa aatcatttac atcaccctat 6780
ataatatttt aattaaaaag atgtataaag aagaataaaa aacgctgaag tttaaagcga 6840
atgttattga ccagatcaaa ttgacttgaa gaccaaaatt gaattgttga atacaattaa 6900
ttaatttaaa aatgaccatg ttttacatgt gaaattcatt tatatatata tatatatatc 6960
atatattatt atagtattca cattttgttg tttacactga tggttccgtt aagtgttcac 7020
atttctttgt ttaacactaa actttggagg gaaggatgtg aaaataaaaa atttgggtag 7080
aaaattaatc gataatttaa tattgtctaa tttatcttat gtatattatg atcattactc 7140
ccttattatc tttgtatttt tttaatcttg attatcatat tatttagtat tttttttatcc 7200 ttaatttga tatgttttac ttgagtcaaa aatctataga aaataatttt tctattttta 7260
caagataagg gtaaagatgt gcgaacacaa ctttttttgaa gccccactta tgaaattaca 7320
ctgaacatat tgttgtagta actgtacgaa ctctttttttc tttctatata aacaaatgta 7380
taactaaagt atttagtaaa ataaaaatat aattctattt agttcatgaa tgagaccaca 7440
atatgaatgt atagagctgg ggatattttt tgtttttgtg tagatggata ttaatcgaag 7500
atgtattggt tcttaatagt aagaataaca atagccatta ccctaaagat tgattcacct 7560
ttattttagg gtataaacca aaaaagaatg gacattatta acacgagacc tttagcattt 7620
ccaaaaaaaa tgggagaatt ttgttattta tttaaaaaga aaaaaaaaaa gaacacaccc 7680
ttaacctcaa tatcctcaaa aattcaacca tcaatatcat tattttattt tcatatccta 7740
tgcatttttt attagcttgt aaacttttaa ttttcttcct attcttttat acaacaatga 7800
ctctcaattg tttaacctgc caagctctaa aaagaacaga ttcacatgag gaactaaggg 7860
aaacactgaa tcatgttaat gataagtcga attttcgtct tttttcagtg ggaatggaga 7920
ggaactggtc agggaacttg gttgaaagac ggaaatatga aaaaacgagg ggtcgaacca 7980
taatgggaaa agaaaataat 8000

<210> SEQ ID NO 6
<211> LENGTH: 1893
<212> TYPE: DNA
<213> ORGANISM: Solanum lycopersicum

<400> SEQUENCE: 6
atgacggact atagattatg gagtaatacc aatactacta atacatgtga tgatactatg 60
atgatggatt cttttttatc ttccgatcca tcctcttttt ggcctgcttc cactcccaat 120
cgtccgactc cggtgaacgg agtcggagaa acgatgccgt ttttcaatca agagtcacta 180
cagcaaaggc ttcaggcttt aattgacggt gctcgtgaat catgggcata tgctattttc 240
tggcaatcgt cagttgttga ttttgcgagc caaactgtat tgggttgggg agatgggtat 300
tataaaggag aagaagataa gaataaacgg agagggtcgt ctagttcagc agctaatttt 360
gttgctgagc aagagcatag aaagaaggtg cttcgggagc tgaattcatt aatatccggt 420
gtacaagctt ccgccggaaa cggaactgat gatgcagtgg atgaggaagt gacggatact 480
gaatggtttt ttctgatttc aatgacccaa tcgtttgtta acggtaacgg gcttccgggc 540
ttggcgatgt acagttcaag cccaatttgg gttactggaa cagagaaatt agctgcttct 600

```
caatgtgaac gggccaggca agcccaaggt ttcgggcttc agacgattgt gtgtattcct    660

tcagctaacg gtgtagtgga gcttggttcg actgagctga tattccaaag ctcggatttg    720

atgaacaagg ttaagtattt gtttaacttc aatattgata tggggtctgt tacaggctca    780

ggttcgggct caggctcttg tgctgtgcat cctgagcccg atccttcggc cctttggctt    840

acggatccat cttcctcggt tgtggaacct aaggattcgt taattcatag tagtagtagg    900

gatgttcaac ttgtgtatgg aaatgagaat tctgaaaatc agcagcagca ttgtcaagga    960

tttttcacaa aggagttgaa tttttcgggt tatggatttg atggaagtag taataggaat   1020

aaaactggaa tttcttgtaa gccggagtcc agggagatat tgaattttgg tgatagtagt   1080

aagagatttt cagggcaatc acagttgggt cctgggcctg ggctcatgga ggagaacaag   1140

aacaagaaca agaacaagaa aaggtcactt ggatcaaggg gaaacaatga agaaggaatg   1200

ctttcgtttg tttcgggtgt gatcttgcca acttcaacaa tggggaagtc cggggattct   1260

gatcactcag atctcgaagc ctcagtggtg aaggaggccg ttgtagaacc tgaaaagaag   1320

ccgaggaagc gagggaggaa accagccaat ggaagggagg agccattgaa tcacgtggaa   1380

gcggagagac agaggaggga gaaattgaat caaagattct acgcgctcag agccgtagtc   1440

ccaaatgtgt ctaaaatgga taaggcatca cttcttggag atgcaattgc atacatcaat   1500

gagttgaaat caaaagttca aaattcagat ttagataaag aggagttgag gagccaaatt   1560

gaatgtttaa ggaaggaatt aaccaacaag ggatcatcaa actattccgc ctcccctcca   1620

ttgaatcaag atgtcaagat tgtcgatatg gacattgacg ttaaggtgat tggatgggat   1680

gctatgattc gtatacaatg tagtaaaaag aaccatccag ctgccaggct aatggcagcc   1740

ctcaaggact tggacctaga cgtgcaccac gctagtgttt ccgtggtgaa tgatttgatg   1800

atccaacaag ccacagtcaa aatggggagc cggctttatg ctcaagaaca gcttaggata   1860

gcattgacat caaaaattgc tgaatcgcga tga                                1893
```

<210> SEQ ID NO 7
<211> LENGTH: 630
<212> TYPE: PRT
<213> ORGANISM: Solanum lycopersicum

<400> SEQUENCE: 7

```
Met Thr Asp Tyr Arg Leu Trp Ser Asn Thr Asn Thr Thr Asn Thr Cys
1               5                   10                  15

Asp Asp Thr Met Met Met Asp Ser Phe Leu Ser Ser Asp Pro Ser Ser
            20                  25                  30

Phe Trp Pro Ala Ser Thr Pro Asn Arg Pro Thr Pro Val Asn Gly Val
        35                  40                  45

Gly Glu Thr Met Pro Phe Phe Asn Gln Glu Ser Leu Gln Gln Arg Leu
    50                  55                  60

Gln Ala Leu Ile Asp Gly Ala Arg Glu Ser Trp Ala Tyr Ala Ile Phe
65                  70                  75                  80

Trp Gln Ser Ser Val Val Asp Phe Ala Ser Gln Thr Val Leu Gly Trp
                85                  90                  95

Gly Asp Gly Tyr Tyr Lys Gly Glu Glu Asp Lys Asn Lys Arg Arg Gly
            100                 105                 110

Ser Ser Ser Ser Ala Ala Asn Phe Val Ala Glu Gln Glu His Arg Lys
        115                 120                 125

Lys Val Leu Arg Glu Leu Asn Ser Leu Ile Ser Gly Val Gln Ala Ser
    130                 135                 140
```

-continued

```
Ala Gly Asn Gly Thr Asp Asp Ala Val Asp Glu Glu Val Thr Asp Thr
145                 150                 155                 160

Glu Trp Phe Phe Leu Ile Ser Met Thr Gln Ser Phe Val Asn Gly Asn
                165                 170                 175

Gly Leu Pro Gly Leu Ala Met Tyr Ser Ser Ser Pro Ile Trp Val Thr
            180                 185                 190

Gly Thr Glu Lys Leu Ala Ala Ser Gln Cys Glu Arg Ala Arg Gln Ala
        195                 200                 205

Gln Gly Phe Gly Leu Gln Thr Ile Val Cys Ile Pro Ser Ala Asn Gly
    210                 215                 220

Val Val Glu Leu Gly Ser Thr Glu Leu Ile Phe Gln Ser Ser Asp Leu
225                 230                 235                 240

Met Asn Lys Val Lys Tyr Leu Phe Asn Phe Asn Ile Asp Met Gly Ser
                245                 250                 255

Val Thr Gly Ser Gly Ser Gly Ser Gly Ser Cys Ala Val His Pro Glu
            260                 265                 270

Pro Asp Pro Ser Ala Leu Trp Leu Thr Asp Pro Ser Ser Ser Val Val
        275                 280                 285

Glu Pro Lys Asp Ser Leu Ile His Ser Ser Ser Arg Asp Val Gln Leu
    290                 295                 300

Val Tyr Gly Asn Glu Asn Ser Glu Asn Gln Gln Gln His Cys Gln Gly
305                 310                 315                 320

Phe Phe Thr Lys Glu Leu Asn Phe Ser Gly Tyr Gly Phe Asp Gly Ser
                325                 330                 335

Ser Asn Arg Asn Lys Thr Gly Ile Ser Cys Lys Pro Glu Ser Arg Glu
            340                 345                 350

Ile Leu Asn Phe Gly Asp Ser Ser Lys Arg Phe Ser Gly Gln Ser Gln
        355                 360                 365

Leu Gly Pro Gly Pro Gly Leu Met Glu Glu Asn Lys Asn Lys Asn Lys
    370                 375                 380

Asn Lys Lys Arg Ser Leu Gly Ser Arg Gly Asn Asn Glu Glu Gly Met
385                 390                 395                 400

Leu Ser Phe Val Ser Gly Val Ile Leu Pro Thr Ser Thr Met Gly Lys
                405                 410                 415

Ser Gly Asp Ser Asp His Ser Asp Leu Glu Ala Ser Val Val Lys Glu
            420                 425                 430

Ala Val Val Glu Pro Glu Lys Lys Pro Arg Lys Arg Gly Arg Lys Pro
        435                 440                 445

Ala Asn Gly Arg Glu Glu Pro Leu Asn His Val Glu Ala Glu Arg Gln
    450                 455                 460

Arg Arg Glu Lys Leu Asn Gln Arg Phe Tyr Ala Leu Arg Ala Val Val
465                 470                 475                 480

Pro Asn Val Ser Lys Met Asp Lys Ala Ser Leu Leu Gly Asp Ala Ile
                485                 490                 495

Ala Tyr Ile Asn Glu Leu Lys Ser Lys Val Gln Asn Ser Asp Leu Asp
            500                 505                 510

Lys Glu Glu Leu Arg Ser Gln Ile Glu Cys Leu Arg Lys Glu Leu Thr
        515                 520                 525

Asn Lys Gly Ser Ser Asn Tyr Ser Ala Ser Pro Pro Leu Asn Gln Asp
    530                 535                 540

Val Lys Ile Val Asp Met Asp Ile Asp Val Lys Val Ile Gly Trp Asp
545                 550                 555                 560
```

-continued

```
Ala Met Ile Arg Ile Gln Cys Ser Lys Lys Asn His Pro Ala Ala Arg
                565                 570                 575

Leu Met Ala Ala Leu Lys Asp Leu Asp Leu Asp Val His His Ala Ser
            580                 585                 590

Val Ser Val Val Asn Asp Leu Met Ile Gln Gln Ala Thr Val Lys Met
        595                 600                 605

Gly Ser Arg Leu Tyr Ala Gln Glu Gln Leu Arg Ile Ala Leu Thr Ser
    610                 615                 620

Lys Ile Ala Glu Ser Arg
625                 630


<210> SEQ ID NO 8
<211> LENGTH: 201
<212> TYPE: DNA
<213> ORGANISM: Solanum lycopersicum

<400> SEQUENCE: 8

ggaagcggag agacagagga gggagaaatt gaatcaaaga ttctacgcgc tcagagccgt      60

agtcccaaat gtgtctaaaa tggataaggc atcacttctt ggagatgcaa ttgcatacat     120

caatgagttg aaatcaaaag ttcaaaattc agatttagat aaagaggagt tgaggagcca     180

aattgaatgt ttaaggaagg a                                               201


<210> SEQ ID NO 9
<211> LENGTH: 6700
<212> TYPE: DNA
<213> ORGANISM: Capsicum annuum

<400> SEQUENCE: 9

ctctaaatat gtaaaatgaa ttaggaataa atgcacatat tttccttcgc agaaagagat      60

agcaacatgg acctcaaaca gcctcttggc atattattta cttaactatc aaaatggtta     120

aatgtgtatt ttataataac taaaagctta aacaataaag taataaatct tattagtata     180

ttttatttct atctgtatca tcgactcctt catatgtcta taattaatac tttttgctaa     240

acataacatt atttcttttt ataagttgaa acactgaatt atcacacttt catattatat     300

aaactcgtaa ctgaaaatgt ttcaaaaata gttatagata atatcttttc aattcctaaa     360

ttcaactcct caacccaagg aaagaatgga aatggattca tatacgttga tttctcattc     420

tttttctatc atttcattta ccttcctatt gagagggaaa tggaatcaag aaaatgatca     480

accacattat tagatactca cttcgttagt gttatttgtt aaatattgac ttgatacact     540

gcacctttgg gtgtggttga gttggtttga ggggtgactt tcaaagcgaa ggtcgcggta     600

tcaattccct ctaatgcttt ttcaatctag ctcgtcacac taggtttacc tagtgcggtt     660

tacatctcct gtgtggttta cgagtgatta tacagtgagg ggtttaccca atacacacaa     720

agtgctcacc cgaagggcag aggctagtgg ctgggtaaac ccgaagggca gaggctagtg     780

gctgcggggt ttacccagtg cgcacaaagt gctcacccga ctttcctgaa gtttcaaaaa     840

atatatatat atatatatat tgacttgata catttcttaa agagcaaaat aaattaaaaa     900

ttaaataata actcaactct acattttctt aattgaacag aaaaataagt aactatgttt     960

tggtacagtg aataaataga agtggtcgaa aaagtatttt ctccattcta gaagtacacc    1020

aagcttctaa taagagtcaa cacacctaag tttaaacgta attcaaacat caatttctta    1080

gtttttaaaa ctaaattatg gatattaaaa aattataaga aaaacaaatg atactcctta    1140

caatttattt ggttatcaga ttacaactga ttcgacttgt caaataataa tgattgaaat    1200
```

-continued

```
atatgatagg atatgtcgca gtaagagatt tgaatcataa taggtgagga taaacgctat   1260
tgcaaaaaaa gtttttaatt ttcaccaaat attgggaaac tacttcaaat atactccatc   1320
aatttacatt taaagaataa ataattaata ttaaggataa aagatttttt tttttaatct   1380
tatttttgat atatcaaaat gataagtata aataaaaatt caattaaaga aataatgtaa   1440
cgtaaaagtg aacagaggga atccttttta gtagacattt atatttagtt gaagtttaaa   1500
aatcccaaat aattcaaatt aaagttgact ttcataaaca cttattaaaa aaatcagcca   1560
aagataatac atttataaaa atgtaatttt caaatgaatt aactagacgt aaattttttt   1620
tttttcaaaa gtaatttttt aataagttat tttaataaaa aagcttctca aaataagaaa   1680
tttttatagc cacttgacca aacaagtctc ccaaacatga atttgaatta atttttaaaa   1740
aaatttcgca agtaaaaact aaaaagactt cttaaaatgt gtttttcaaa atttaaattc   1800
tattcaagtt tgatattatc ctaaaattat tgaccatatt agaaatgttt gattgaaatt   1860
atttcttgaa aattagaaaa aaaatgaggt tctttgatat ttttttgaag cagtggtatg   1920
gccatataag aatacactca ttatatgtta ttgattggtt gctgattaaa gaagttcgtc   1980
tttttaattt tttattcgat atttatattg aaactttgat taccttactg taagatgtga   2040
catttctaac aaaattatat ttatattaaa aattttaaaa ttaaaacatt taattaaggg   2100
tgagccagat ccactaccgc accgtagccg cgacccatat ggtacaagag gagtagtagt   2160
gatgttggcg attaattggc gggtccttcg tggaacccgc cagtctcttt cctcattctc   2220
ccaaattcag ctcaaattca cctcaaataa aacccaaact caaattccac tcttattaac   2280
caaacccaat atttctctct cattttctc cgccacaccc ctctatcctc attctctctc   2340
tctctacaca ccattttcac ctgttttctg ctgtgtgttt tatggaatga ctgattacag   2400
cttgcccacc atgaatctct ggaataacag tactactgat gacaacgttt ctatgatgga   2460
ggcttttatg tcttccgatc tttctttttg gggtggtact actacttcta gtgctactgc   2520
tactgctgct gctcttgcta atcccaatta tacttcaact gtttaccctc ctcctggcgc   2580
ttcttgtgca tcttccgtaa cggctacagc tgctgctgtg actgttgatg cgtcaaaaac   2640
catgccattt ttcaaccagg agacgctaca gcagcgtctt cagaccctaa tagacggtgc   2700
tcgtgagacg tggacgtatg ctatcttctg gcagtcgtct gatttagatt tctcgagtcc   2760
gtctgtgttg ggttggggtg atggttatta caaaggggag gaggataaaa acaagaggaa   2820
attatctgtt tcttctccgg cttatattgc tgagcaggaa catcggaaga aggttcttag   2880
agagctgaat tcgttgattt cagggacaca aactggtaca gacgatgctg ttgatgaaga   2940
agttaccgat accgaatggt tctttcttat ctccatgact caatcttttg tcaacgggaa   3000
cgggcttccg ggccaggcta tgtgcagttc cagcccgatt tgggttgccg gagtagagaa   3060
attggctgct tctcactgtg aacgggctcg gcaggcccaa gggttcgggc ttcagacgat   3120
ggtgtgtatc ccttcagcta acggtgttgt tgaattgggt tcgacggagt tgattatcca   3180
gagttctgat ctgatgaata aggttagagt actgttcaat ttcaataatg atttggggtc   3240
aggttcatgg gctgtgcagc cggagagcga tccgtcagcg ctttggttga cggagccatc   3300
ttcctcaggt atggaagtta gagagtcttt aaatacagtt caaacaagtt caattccatc   3360
aagtaatagt aataagcaaa ttgcgtatgg aaatgagaac aatgatcatc catctggaaa   3420
tgggaatggt catagttctt ataatcagca gcatcctcat caacaaacac aaggattttt   3480
cacgaaggag ttaaactttt cggactttgg gttcgatgga agtagtaata ggaacgggaa   3540
ttcatcgctc tcttgcaagc ctgagtctgg ggaaatcttg aattttggtg atagtacgaa   3600
```

gaaaagtgct tgtagtgcaa atgggaactt gttttcgggc cattcccaat ttggggcagg 3660
tgaggagaac aagaacaaga ccaagaaaag gtcagctact tccaggggaa gcaatgaaga 3720
aggaatgctt tcatttgttt cgggtacagt tttgccttct tccggtatga agtcaggcgg 3780
aggcgaagac tctgaccatt cagatcttga agcttcggtg gtgaaagaag ctgatagtag 3840
tagagttgta gaaccggaaa agaagccaag gaagcgagga aggaagcctg ctaatggaag 3900
ggaggaacct ttgaatcatg ttgaggcaga gaggcaaagg agggagaaat tgaaccaaag 3960
attctacgcg cttagagctg ttgtaccgaa tgtgtctaag atggacaagg catcacttct 4020
tggagatgca atttcataca taaatgagtt gaaatcgaag cttcacaata cagagtcaga 4080
taaagaagac ttgaagagcc aaatagagga tttgaagaaa gaattagcta gtaaagaatc 4140
aaggcgccct ggtcaaccac caccaaacca agatctcaag atgtctagcc acaccggaac 4200
caagattgta gacgcggaga tagacattaa gataatggga tgggatgtta tgattcgtgt 4260
acaatctaat aaaaagaatc atccagccgc aaggtttatg gcggccctca tggaactaga 4320
cctagatgtg aaccatgcca gtgtttcatt ggtgaacgag ttgatgatcc agcaagccac 4380
agtgaaaatg agtagccgtc attacactga agagcagctt aggatagcat tgatgtcaag 4440
aattgctgaa acgcgctaaa aaagacccta gaaagtagat agaactcaaa gaaagcatgt 4500
gggctttgat ggcgctctgg ttgctgcagc tctatgtaat gtttttgtta tgaattagag 4560
atttcatcag gctatcttcg tgttattttt cgaacttgta ccttaggtgg ttgtcgaaat 4620
attcttgtac ataaatgtta ttacccgaaa actcaacata atcgggcttt agctcatgta 4680
attaaacata tattccaact ccgtcttgtc tgttagattg catctatcat tatgtattct 4740
ttgtccatgc ataaatgaag aaatttgatg gcaggtgaat ttgattttga agcaaatgtg 4800
atttactgtc gtgctgctta ttcttatacc caatttttga gctgcattag gattgtgtga 4860
agtactttaa gctattcatt catgagaaaa atgtgaaaga gatcatcatt tcagaaatat 4920
gcactatttc tccaattcaa acttcatgtt caaattgtat taaataattg tattggaggt 4980
cattgcttac gacctttatg catcacattt tgactaaaaa caataacgga ttatttcatg 5040
agaatatttg gatttacata tacacctcag aaaaactatc atctttcatt tgagtttttt 5100
aatgtcatac tccatccgac tcaatttaat ttgcgccgaa gaatgccaaa aaagtttcac 5160
atttatggtc aatagatgag taatctcctt ataaggcttg gattatcctc tttcctaatg 5220
ctcaaaaggt gtaagtttag ccatgaccta attttatata tacttttttt ttgacatttc 5280
tttaatctta atttttcata cgacatattt aagattataa aattaaataa tattttaata 5340
cattctatct tgtgtcaagt taaatgagac aaacaaatta taacaaagga agcatcaaat 5400
aaaataggaa agaaggaaaa agggatttcg taaaagagcg ataagataag gtgatagttt 5460
gatagactag attggactag atgcaacagc aaaatagaac aggaaactac aaggaactag 5520
tccatttatt catttggctg cttgctcgtt tatattgtga attgtatatc tccacatatt 5580
ttattctaat aaagatatca ggaagaaggc atgtgtctta ttattttcct ttaggagaat 5640
acactgaact tggttcttct tttggtccct attgtctact atagaccaat gtatattttc 5700
cataatagta ttggcataac atgctaaagt attttccata atagtattgg caagaaacgc 5760
catgaatatc atgtaggttg aaactgacag caacgtttca aattcacttc atttgaactt 5820
tcacttcacc caagtacagt ctccccgtcc gaagcaggat tttcatcaaa gagatgcaac 5880
atttaccata aataaatttt ctcccccccca tccctctctc tctatatatt agtaactttg 5940

```
gatccagatg aacccttttc cgcctcacaa gtttcaccca agttccaagt atatgttact   6000

ctagaagttt taactttctt tttagtaatt ctttgttaat atgttgtccc tatactagta   6060

tctggacatg ccactactga aaaattcaaa atttaccttc attctttaag gtaatttaca   6120

attcaatctt taaggttttt atattgacct tattatattt taaagttatg aatttatatt   6180

tattattatt actttctata tttttaaata agtgacattt tagtcttttc attttatttc   6240

taaataactt ggtgttttag ataattaaga agatattaat gatgttatta taagtttacc   6300

actttttaaa taaagaaagt tttacatgac ttaaggagta ctaagaatta catcatttcc   6360

aaagaaatat taagaataag ttggtaaaaa tactatttat ttaaaaataa aaaaaaataa   6420

ttttaacaaa ctaatacata taaatttata tttcctattg aaaatacaat tcatactaat   6480

ctcaacgccg ctcggtaaaa ttagatccgc ttcactttaa ctgctaatta ttgaataaag   6540

tgtagggaca aatttgatgt aaataaaatc atctactcca ctaatatatt aatttgtttt   6600

taatttaata tatattttc atacactaga caacaaagaa ttgtgacgtg acgcaaattt   6660

ggtggaagtg gacatgcaga caaaaaagat catgtgttac                         6700
```

<210> SEQ ID NO 10
<211> LENGTH: 2073
<212> TYPE: DNA
<213> ORGANISM: Capsicum annuum

<400> SEQUENCE: 10

```
atgactgatt acagcttgcc caccatgaat ctctggaata acagtactac tgatgacaac     60

gtttctatga tggaggcttt tatgtcttcc gatctttctt tttggggtgg tactactact    120

tctagtgcta ctgctactgc tgctgctctt gctaatccca attatacttc aactgtttac    180

cctcctcctg gcgcttcttg tgcatcttcc gtaacggcta cagctgctgc tgtgactgtt    240

gatgcgtcaa aaaccatgcc atttttcaac caggagacgc tacagcagcg tcttcagacc    300

ctaatagacg gtgctcgtga gacgtggacg tatgctatct tctggcagtc gtctgattta    360

gatttctcga gtccgtctgt gttgggttgg ggtgatggtt attacaaagg ggaggaggat    420

aaaaacaaga ggaaattatc tgtttcttct ccggcttata ttgctgagca ggaacatcgg    480

aagaaggttc ttagagagct gaattcgttg atttcaggga cacaaactgg tacagacgat    540

gctgttgatg aagaagttac cgataccgaa tggttctttc ttatctccat gactcaatct    600

tttgtcaacg ggaacgggct tccgggccag gctatgtgca gttccagccc gatttgggtt    660

gccggagtag agaaattggc tgcttctcac tgtgaacggg ctcggcaggc ccaagggttc    720

gggcttcaga cgatggtgtg tatcccttca gctaacggtg ttgttgaatt gggttcgacg    780

gagttgatta tccagagttc tgatctgatg aataaggtta gagtactgtt caatttcaat    840

aatgatttgg ggtcaggttc atgggctgtg cagccggaga gcgatccgtc agcgctttgg    900

ttgacggagc catcttcctc aggtatggaa gttagagagt ctttaaatac agttcaaaca    960

agttcaattc catcaagtaa tagtaataag caaattgcgt atggaaatga gaacaatgat   1020

catccatctg gaaatgggaa tggtcatagt tcttataatc agcagcatcc tcatcaacaa   1080

acacaaggat ttttcacgaa ggagttaaac ttttcggact ttgggttcga tggaagtagt   1140

aataggaacg ggaattcatc gctctcttgc aagcctgagt ctggggaaat cttgaatttt   1200

ggtgatagta cgaagaaaag tgcttgtagt gcaaatggga acttgttttc gggccattcc   1260

caatttgggg caggtgagga gaacaagaac aagaccaaga aaaggtcagc tacttccagg   1320

ggaagcaatg aagaaggaat gctttcattt gtttcgggta cagttttgcc ttcttccggt   1380
```

-continued

```
atgaagtcag gcggaggcga agactctgac cattcagatc ttgaagcttc ggtggtgaaa   1440

gaagctgata gtagtagagt tgtagaaccg gaaaagaagc caaggaagcg aggaaggaag   1500

cctgctaatg gaagggagga acctttgaat catgttgagg cagagaggca aaggagggag   1560

aaattgaacc aaagattcta cgcgcttaga gctgttgtac cgaatgtgtc taagatggac   1620

aaggcatcac ttcttggaga tgcaatttca tacataaatg agttgaaatc gaagcttcac   1680

aatacagagt cagataaaga agacttgaag agccaaatag aggatttgaa gaaagaatta   1740

gctagtaaag aatcaaggcg ccctggtcaa ccaccaccaa accaagatct caagatgtct   1800

agccacaccg gaaccaagat tgtagacgcg gagatagaca ttaagataat gggatgggat   1860

gttatgattc gtgtacaatc taataaaaag aatcatccag ccgcaaggtt tatggcggcc   1920

ctcatggaac tagacctaga tgtgaaccat gccagtgttt cattggtgaa cgagttgatg   1980

atccagcaag ccacagtgaa aatgagtagc cgtcattaca ctgaagagca gcttaggata   2040

gcattgatgt caagaattgc tgaaacgcgc taa                                2073
```

<210> SEQ ID NO 11
<211> LENGTH: 690
<212> TYPE: PRT
<213> ORGANISM: Capsicum annuum

<400> SEQUENCE: 11

```
Met Thr Asp Tyr Ser Leu Pro Thr Met Asn Leu Trp Asn Asn Ser Thr
1               5                   10                  15

Thr Asp Asp Asn Val Ser Met Met Glu Ala Phe Met Ser Ser Asp Leu
            20                  25                  30

Ser Phe Trp Gly Gly Thr Thr Thr Ser Ser Ala Thr Ala Thr Ala Ala
        35                  40                  45

Ala Leu Ala Asn Pro Asn Tyr Thr Ser Thr Val Tyr Pro Pro Pro Gly
    50                  55                  60

Ala Ser Cys Ala Ser Ser Val Thr Ala Thr Ala Ala Ala Val Thr Val
65                  70                  75                  80

Asp Ala Ser Lys Thr Met Pro Phe Phe Asn Gln Glu Thr Leu Gln Gln
                85                  90                  95

Arg Leu Gln Thr Leu Ile Asp Gly Ala Arg Glu Thr Trp Thr Tyr Ala
            100                 105                 110

Ile Phe Trp Gln Ser Ser Asp Leu Asp Phe Ser Ser Pro Ser Val Leu
        115                 120                 125

Gly Trp Gly Asp Gly Tyr Tyr Lys Gly Glu Glu Asp Lys Asn Lys Arg
    130                 135                 140

Lys Leu Ser Val Ser Ser Pro Ala Tyr Ile Ala Glu Gln Glu His Arg
145                 150                 155                 160

Lys Lys Val Leu Arg Glu Leu Asn Ser Leu Ile Ser Gly Thr Gln Thr
                165                 170                 175

Gly Thr Asp Asp Ala Val Asp Glu Glu Val Thr Asp Thr Glu Trp Phe
            180                 185                 190

Phe Leu Ile Ser Met Thr Gln Ser Phe Val Asn Gly Asn Gly Leu Pro
        195                 200                 205

Gly Gln Ala Met Cys Ser Ser Ser Pro Ile Trp Val Ala Gly Val Glu
    210                 215                 220

Lys Leu Ala Ala Ser His Cys Glu Arg Ala Arg Gln Ala Gln Gly Phe
225                 230                 235                 240

Gly Leu Gln Thr Met Val Cys Ile Pro Ser Ala Asn Gly Val Val Glu
```

```
                245                 250                 255

Leu Gly Ser Thr Glu Leu Ile Ile Gln Ser Ser Asp Leu Met Asn Lys
            260                 265                 270

Val Arg Val Leu Phe Asn Phe Asn Asn Asp Leu Gly Ser Gly Ser Trp
        275                 280                 285

Ala Val Gln Pro Glu Ser Asp Pro Ser Ala Leu Trp Leu Thr Glu Pro
    290                 295                 300

Ser Ser Ser Gly Met Glu Val Arg Glu Ser Leu Asn Thr Val Gln Thr
305                 310                 315                 320

Ser Ser Ile Pro Ser Ser Asn Ser Asn Lys Gln Ile Ala Tyr Gly Asn
                325                 330                 335

Glu Asn Asn Asp His Pro Ser Gly Asn Gly Asn Gly His Ser Ser Tyr
            340                 345                 350

Asn Gln Gln His Pro His Gln Gln Thr Gln Gly Phe Phe Thr Lys Glu
        355                 360                 365

Leu Asn Phe Ser Asp Phe Gly Phe Asp Gly Ser Ser Asn Arg Asn Gly
    370                 375                 380

Asn Ser Ser Leu Ser Cys Lys Pro Glu Ser Gly Glu Ile Leu Asn Phe
385                 390                 395                 400

Gly Asp Ser Thr Lys Lys Ser Ala Cys Ser Ala Asn Gly Asn Leu Phe
                405                 410                 415

Ser Gly His Ser Gln Phe Gly Ala Gly Glu Glu Asn Lys Asn Lys Thr
            420                 425                 430

Lys Lys Arg Ser Ala Thr Ser Arg Gly Ser Asn Glu Glu Gly Met Leu
        435                 440                 445

Ser Phe Val Ser Gly Thr Val Leu Pro Ser Ser Gly Met Lys Ser Gly
    450                 455                 460

Gly Gly Glu Asp Ser Asp His Ser Asp Leu Glu Ala Ser Val Val Lys
465                 470                 475                 480

Glu Ala Asp Ser Ser Arg Val Val Glu Pro Glu Lys Lys Pro Arg Lys
                485                 490                 495

Arg Gly Arg Lys Pro Ala Asn Gly Arg Glu Glu Pro Leu Asn His Val
            500                 505                 510

Glu Ala Glu Arg Gln Arg Arg Glu Lys Leu Asn Gln Arg Phe Tyr Ala
        515                 520                 525

Leu Arg Ala Val Val Pro Asn Val Ser Lys Met Asp Lys Ala Ser Leu
    530                 535                 540

Leu Gly Asp Ala Ile Ser Tyr Ile Asn Glu Leu Lys Ser Lys Leu His
545                 550                 555                 560

Asn Thr Glu Ser Asp Lys Glu Asp Leu Lys Ser Gln Ile Glu Asp Leu
                565                 570                 575

Lys Lys Glu Leu Ala Ser Lys Glu Ser Arg Arg Pro Gly Gln Pro Pro
            580                 585                 590

Pro Asn Gln Asp Leu Lys Met Ser Ser His Thr Gly Thr Lys Ile Val
        595                 600                 605

Asp Ala Glu Ile Asp Ile Lys Ile Met Gly Trp Asp Val Met Ile Arg
    610                 615                 620

Val Gln Ser Asn Lys Lys Asn His Pro Ala Ala Arg Phe Met Ala Ala
625                 630                 635                 640

Leu Met Glu Leu Asp Leu Asp Val Asn His Ala Ser Val Ser Leu Val
                645                 650                 655

Asn Glu Leu Met Ile Gln Gln Ala Thr Val Lys Met Ser Ser Arg His
            660                 665                 670
```

```
Tyr Thr Glu Glu Gln Leu Arg Ile Ala Leu Met Ser Arg Ile Ala Glu
        675                 680                 685

Thr Arg
    690


<210> SEQ ID NO 12
<211> LENGTH: 5200
<212> TYPE: DNA
<213> ORGANISM: Cucumis sativus

<400> SEQUENCE: 12

ttttaaattt gaggcgtcat aaagttagtt tatatgtgag aggtatcttg ttgaattttt     60

taagttttta aaatttttta ttcaataaag ttctaaaatt tgctctattt tttttctgtt    120

tggcatccaa ctgtagacat actttttcaa aattttaaca ctcggtttgg tatttgaatt    180

taattaaata aagctatact caacaaaaaa atatattgtt ttttaaagta gttaattaag    240

ttggttaata ccataaagta agcacaaagc aatatgtgac aaataagtga taaataagta    300

atttgtctta cgggtatttg tgacaaataa gtttataagg ataactcaac catcttagac    360

aacctatcaa catcaacttg cctaaggtga atgttaatat tgattgttag gggtgagtgt    420

cacttgccat tgaagttgat tatcaaaggt gattttcatt gcagtttatc atataagcag    480

tagttggagt ctgaaattga aggtggttat cgaagttgat aatcaaaaag tgattttctc    540

aaagtttgta gtcatagctt ggaattcatc gtgtaaacgt ggtcatcaaa gttggctttt    600

tttggagttt cctattggag atagttacca tagcccaaaa ttagttgttg gaggtggtca    660

cataaaggta tctagtcgtt aggtcagttt gtcatcgaag gtggttgcca gaccttgaaa    720

tcgatcatca aagttggtta tctgagtgtg gtaatggtaa ttgatcgttg aatctattag    780

aaaaactgga gagagcttca tcaacctata aagttagtgg accaaagaga actcaaactc    840

aacttatatt ttgatgtgtt aactccccta aaataaaaca aacgaaacaa aaaaaaaaaa    900

tcataaagac aaaaaatgaaa aaatggagta ccatcattgt actaaaaaaa tatattttaa    960

caaaagaaaa aatcaatgac tacaaataaa ttttaaaaca ctagatttaa aaaaaaaaat   1020

caaagaacaa aaatagaaga tatttatata tatatatatt taaaaaagaa aattaataga   1080

tattataatg aggcttagta ttttcaaaat cctgttttag ggcaaaaaaa agaggggaaa   1140

aataaaacaa cttccgtctt tgattcacaa acaagagacg tgtcatgttc tcattagcta   1200

aaaccggaaa aaaagcgatg agtaaaaaag tcataaaaac ggttaaccct caacgcctct   1260

caagggttct tcacgtgcca gtcacgtgga aggaagggaa gcgaaccggg tctaagaaaa   1320

ccgcactatc tggggtaagt actattagta taattgtact ataagcgcgg agttgagaaa   1380

gacgccggct ttttgaacga tttaatcggc gatctaaaga agaagcctct tggttccttc   1440

ttctcctctt cgcttctctg ttaaatgttc atcacaaata aatcccatac caatcgcccg   1500

acatttctct cactccacaa tcggagacca aagattattc cttttttccc atttctattt   1560

cttccaatct caatcgcatg acggattatc gtttgtcgac gatgaatctc tggactgacg   1620

agaacgcgtc ggttatggac gctttcatga attccgatct gtcttcctac tgggctccgt   1680

cagccgcctc ctctcactct cttcaccacc caccgccacc tcagtcctcc gcctccacat   1740

ccactccccc gccggacgca cctaagtccc tccccgtttt caatcaggag actctgcagc   1800

agcggctcca ggcgctgatc gacggtgcta gggagagttg gacttatgcg attttctggc   1860

agtcgtctta tgattattct ggtgggtctg ttttggggtg gggtgatggg tattacaaag   1920
```

-continued

```
gagaggaaga taaaggaaag ggaaaagcga aaatggtgtc gtcagcggcg gagcaggctc   1980
accggaagaa ggttttacgg gagcttaact ctttgatttc tggctctgcc gccggacctg   2040
acgatgcggt ggatgaggag gttacggata cggagtggtt ctttttggtt tcgatgactc   2100
agtcgtttgt taatggtgtt gggttaccga gtcaagcgtt ttaccactcg acgccgattt   2160
gggtctctgg tgccgatcgg ctgtcggcgt ctgcctgtga acgagctaga caggggaggg   2220
tttttgggtt acagacgatg gtctgtattc catcgcctaa cggtgttgtg gaaatgggtt   2280
cgacggaatt gattcatcga acgtcggatt tgatgaataa ggtcaagatt ctgttcaatt   2340
tcaacaatct cgaaacgagt tcttggattt cgggaactac cgccgccgca tccgctgccg   2400
acgaagggga aaacgacccg tcgtcgatgt ggatcagtga gccatcgagt acaatcgaga   2460
tgaaggattc aatcaccacc actgttcctt ccagcaacgt tccggcaaag ccaatccgtt   2520
cggaaaatcc cagtacaagt agcttaacgg aaaatatgag cacgattcaa caatcccatc   2580
ataaacagag ccaaagcttc ttaaatttct ccgattacgg cttcgaatca aatcccacaa   2640
agaacaccac cgctaccgcc accgcaacca ccagcaccac cccatcattc aagccggaat   2700
ccggcgggat gctgaatttc ggcaacggga gcctcttctc cggccattca cagtacgtaa   2760
caaacgaaca gaacgagaaa aagagatccc ctgcttctcg aagtagcaac gacgaaggga   2820
tcctctcttt cacctccggc gtgatcttac cctcttccgg taaggtaaaa tccggtgatt   2880
cagaccattc agatctcgaa gcatcagcga tcagagaagt ggatagctgt acaaaatcat   2940
tagaacccga aaaacgtcca agaaaaagag gtagaaaacc agcaaacgga agagaagagc   3000
cattgaatca cgtagaagca gagagacaac ggcgagagaa attaaaccag aaattctacg   3060
ctctccgagc tgtagttcca aacgtatcta agatggacaa agcctcacta ctaggtgacg   3120
cggtttcgta cataaacgag ctcaaatcga agctccaaat ggcagaatcg gagaaaacag   3180
atatgggaaa acatctagaa ttgctgaaga aggagatggg aggaaaagat ttaggatgtt   3240
actcaaaccc aaatgatgaa gatctgaaaa cagggaaaag aaaggtaatg gatatggaga   3300
ttgaagttaa aatcatgggt tgggatgcga tgataaggat tcaaagcaac aagaagaatc   3360
atccggcggc gaggttgatg acggcgttta aggatttgga tttagaaatg cttcacgcga   3420
gtgtttctgt agtgaatgat ttgatgattc aacaagcaac agtgaagatg gggagcagat   3480
tttacacaca agagcagctt aaaatggctc ttgtcgcccg agtcggcggt ggtggaagtg   3540
gaggcggcgg tggaatcatg taaatggggt taggggacat tttgaagct cccaattagt   3600
agagtttagt tgagggaatc tgatttagta ttgtgtaata taaatgttgg taaattattt   3660
ttgataattc tcttgttgtt catcttttgt tgttagagta atttgggagt tcttctatat   3720
gtagtttttg tttattaaat atgaaatcta atagaagtaa agatcaaaga ccttcaaact   3780
ttgtgtttga tcatttcaat tctccttctt tcctttttt ttttttttt tgtttttgtt   3840
tttgttttta gggttttgtt tgaactagta ggtctagttt agggaaaatc taggtttgat   3900
cggaaattaa ggactaacct taacctttct tggtacaaac tttagttaaa cctacatgtc   3960
aatagactta aaagatttag tattaaggtc caaactttcc cacggttgag atcgaaagcc   4020
cctgatataa gaacaactca taaaatttga catttgatta ggttattaag tggatttcaa   4080
tggggatcga gacctactct cttaggtcaa catttttcat aaatacataa gttggttagt   4140
ctagatttgt aaattttaat tgggtttagt tgtttatgta tggagatagg taattgaact   4200
tctcatattg agttatatac tcctacaagt aaagggagaa actcccaata gatattggtt   4260
gtgttggaaa ggttatgaat cgattaataa gtcaattacc attatcttga ttttgaacgc   4320
```

-continued

```
caatgcatca catgcatata tatatatata tattgtcggc tagtacacga ccaattaatg   4380

tttggataaa gttctttcca gaatcatcct attttcaaga ctcactaaaa tccttcagat   4440

atatggttcc acaattggtc ctatgtacaa cagtgtattg aactacttca acacgatgtt   4500

cgtacaacaa tacccacaac tcatttttgc actccatagc aaaaaataat atattatgtt   4560

aaggacaacc ccttaggtaa attgctttga atgagttaat caatcattta tccttgtgga   4620

tctaacatta atcctctcat acctactaat tggtatgctt gagatgcatt ttctcgagca   4680

cctatagaag acgttatata tagactggat taaaagggac actcatccta aaattaggat   4740

tcatttcttg tagcaaatat tcacttgtag catacgatat ctaaagggac tggcgtaagt   4800

tttctactgc gggtacgttt ccataatgat ggtgtctttt caatatcaaa ctttactgtt   4860

caccatcttg aactagccat cctttagaga gtattgttaa aagatatcaa ttcctaatga   4920

aatggatgtc gcagtggccc actaaaagtc tttaattgat attacaatct ttatgctagt   4980

tgagctatgc tcgatttatc attttgtata caataagctc taacaagtta gttaggttcc   5040

atcctttata tatagtttgt acacattatt atttttagat gcatgccaca tgcctaaacc   5100

ttcaaatgat tggttactat attggagagt ttaagctacc tctcatacat agaaatgtta   5160

agtagattca atgaagttta gaaattttaa ttttgaaaat                         5200
```

<210> SEQ ID NO 13
<211> LENGTH: 1986
<212> TYPE: DNA
<213> ORGANISM: Cucumis sativus

<400> SEQUENCE: 13

```
atgacggatt atcgtttgtc gacgatgaat ctctggactg acgagaacgc gtcggttatg     60

gacgctttca tgaattccga tctgtcttcc tactgggctc cgtcagccgc ctcctctcac    120

tctcttcacc acccaccgcc acctcagtcc tccgcctcca catccactcc cccgccggac    180

gcacctaagt ccctccccgt tttcaatcag gagactctgc agcagcggct ccaggcgctg    240

atcgacggtg ctagggagag ttggacttat gcgattttct ggcagtcgtc ttatgattat    300

tctggtgggt ctgttttggg gtggggtgat gggtattaca aaggagagga agataaagga    360

aagggaaaag cgaaaatggt gtcgtcagcg gcggagcagg ctcaccggaa gaaggtttta    420

cgggagctta actctttgat ttctggctct gccgccggac ctgacgatgc ggtggatgag    480

gaggttacgg atacggagtg gttctttttg gtttcgatga ctcagtcgtt tgttaatggt    540

gttgggttac cgagtcaagc gttttaccac tcgacgccga tttgggtctc tggtgccgat    600

cggctgtcgg cgtctgcctg tgaacgagct agacagggga gggtttttgg gttacagacg    660

atggtctgta ttccatcgcc taacggtgtt gtggaaatgg gttcgacgga attgattcat    720

cgaacgtcgg atttgatgaa taaggtcaag attctgttca atttcaacaa tctcgaaacg    780

agttcttgga tttcgggaac taccgccgcc gcatccgctg ccgacgaagg ggaaaacgac    840

ccgtcgtcga tgtggatcag tgagccatcg agtacaatcg agatgaagga ttcaatcacc    900

accactgttc cttccagcaa cgttccggca aagccaatcc gttcggaaaa tcccagtaca    960

agtagcttaa cggaaaatat gagcacgatt caacaatccc atcataaaca gagccaaagc   1020

ttcttaaatt tctccgatta cggcttcgaa tcaaatccca caaagaacac caccgctacc   1080

gccaccgcaa ccaccagcac caccccatca ttcaagccgg aatccggcgg gatgctgaat   1140

ttcggcaacg ggagcctctt ctccggccat tcacagtacg taacaaacga acagaacgag   1200
```

```
aaaaagagat cccctgcttc tcgaagtagc aacgacgaag ggatcctctc tttcacctcc   1260

ggcgtgatct taccctcttc cggtaaggta aaatccggtg attcagacca ttcagatctc   1320

gaagcatcag cgatcagaga agtggatagc tgtacaaaat cattagaacc cgaaaaacgt   1380

ccaagaaaaa gaggtagaaa accagcaaac ggaagagaag agccattgaa tcacgtagaa   1440

gcagagagac aacggcgaga gaaattaaac cagaaattct acgctctccg agctgtagtt   1500

ccaaacgtat ctaagatgga caaagcctca ctactaggtg acgcggtttc gtacataaac   1560

gagctcaaat cgaagctcca aatggcagaa tcggagaaaa cagatatggg aaaacatcta   1620

gaattgctga agaaggagat gggaggaaaa gatttaggat gttactcaaa cccaaatgat   1680

gaagatctga aaacagggaa aagaaaggta atggatatgg agattgaagt taaaatcatg   1740

ggttgggatg cgatgataag gattcaaagc aacaagaaga atcatccggc ggcgaggttg   1800

atgacggcgt ttaaggattt ggatttagaa atgcttcacg cgagtgtttc tgtagtgaat   1860

gatttgatga ttcaacaagc aacagtgaag atggggagca gattttacac acaagagcag   1920

cttaaaatgg ctcttgtcgc ccgagtcggc ggtggtggaa gtggaggcgg cggtggaatc   1980

atgtaa                                                              1986
```

<210> SEQ ID NO 14
<211> LENGTH: 661
<212> TYPE: PRT
<213> ORGANISM: Cucumis sativus

<400> SEQUENCE: 14

```
Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
            20                  25                  30

Ala Pro Ser Ala Ala Ser Ser His Ser Leu His His Pro Pro Pro Pro
        35                  40                  45

Gln Ser Ser Ala Ser Thr Ser Thr Pro Pro Pro Asp Ala Pro Lys Ser
    50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Gly Ser Val Leu Gly Trp Gly Asp Gly Tyr
            100                 105                 110

Tyr Lys Gly Glu Glu Asp Lys Gly Lys Gly Lys Ala Lys Met Val Ser
        115                 120                 125

Ser Ala Ala Glu Gln Ala His Arg Lys Lys Val Leu Arg Glu Leu Asn
    130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Val Asn Gly Val Gly Leu Pro Ser Gln Ala Phe Tyr His Ser Thr
            180                 185                 190

Pro Ile Trp Val Ser Gly Ala Asp Arg Leu Ser Ala Ser Ala Cys Glu
        195                 200                 205

Arg Ala Arg Gln Gly Arg Val Phe Gly Leu Gln Thr Met Val Cys Ile
    210                 215                 220

Pro Ser Pro Asn Gly Val Val Glu Met Gly Ser Thr Glu Leu Ile His
```

-continued

```
225                 230                 235                 240

Arg Thr Ser Asp Leu Met Asn Lys Val Lys Ile Leu Phe Asn Phe Asn
                245                 250                 255

Asn Leu Glu Thr Ser Ser Trp Ile Ser Gly Thr Thr Ala Ala Ala Ser
            260                 265                 270

Ala Ala Asp Glu Gly Glu Asn Asp Pro Ser Ser Met Trp Ile Ser Glu
        275                 280                 285

Pro Ser Ser Thr Ile Glu Met Lys Asp Ser Ile Thr Thr Thr Val Pro
    290                 295                 300

Ser Ser Asn Val Pro Ala Lys Pro Ile Arg Ser Glu Asn Pro Ser Thr
305                 310                 315                 320

Ser Ser Leu Thr Glu Asn Met Ser Thr Ile Gln Gln Ser His His Lys
                325                 330                 335

Gln Ser Gln Ser Phe Leu Asn Phe Ser Asp Tyr Gly Phe Glu Ser Asn
            340                 345                 350

Pro Thr Lys Asn Thr Thr Ala Thr Ala Thr Ala Thr Thr Ser Thr Thr
        355                 360                 365

Pro Ser Phe Lys Pro Glu Ser Gly Gly Met Leu Asn Phe Gly Asn Gly
    370                 375                 380

Ser Leu Phe Ser Gly His Ser Gln Tyr Val Thr Asn Glu Gln Asn Glu
385                 390                 395                 400

Lys Lys Arg Ser Pro Ala Ser Arg Ser Ser Asn Asp Glu Gly Ile Leu
                405                 410                 415

Ser Phe Thr Ser Gly Val Ile Leu Pro Ser Ser Gly Lys Val Lys Ser
            420                 425                 430

Gly Asp Ser Asp His Ser Asp Leu Glu Ala Ser Ala Ile Arg Glu Val
        435                 440                 445

Asp Ser Cys Thr Lys Ser Leu Glu Pro Glu Lys Arg Pro Arg Lys Arg
    450                 455                 460

Gly Arg Lys Pro Ala Asn Gly Arg Glu Glu Pro Leu Asn His Val Glu
465                 470                 475                 480

Ala Glu Arg Gln Arg Arg Glu Lys Leu Asn Gln Lys Phe Tyr Ala Leu
                485                 490                 495

Arg Ala Val Val Pro Asn Val Ser Lys Met Asp Lys Ala Ser Leu Leu
            500                 505                 510

Gly Asp Ala Val Ser Tyr Ile Asn Glu Leu Lys Ser Lys Leu Gln Met
        515                 520                 525

Ala Glu Ser Glu Lys Thr Asp Met Gly Lys His Leu Glu Leu Leu Lys
    530                 535                 540

Lys Glu Met Gly Gly Lys Asp Leu Gly Cys Tyr Ser Asn Pro Asn Asp
545                 550                 555                 560

Glu Asp Leu Lys Thr Gly Lys Arg Lys Val Met Asp Met Glu Ile Glu
                565                 570                 575

Val Lys Ile Met Gly Trp Asp Ala Met Ile Arg Ile Gln Ser Asn Lys
            580                 585                 590

Lys Asn His Pro Ala Ala Arg Leu Met Thr Ala Phe Lys Asp Leu Asp
        595                 600                 605

Leu Glu Met Leu His Ala Ser Val Ser Val Val Asn Asp Leu Met Ile
    610                 615                 620

Gln Gln Ala Thr Val Lys Met Gly Ser Arg Phe Tyr Thr Gln Glu Gln
625                 630                 635                 640

Leu Lys Met Ala Leu Val Ala Arg Val Gly Gly Gly Gly Ser Gly Gly
                645                 650                 655
```

```
Gly Gly Gly Ile Met
            660


<210> SEQ ID NO 15
<211> LENGTH: 6400
<212> TYPE: DNA
<213> ORGANISM: Cucumis melo
<220> FEATURE:
<221> NAME/KEY: misc_feature
<222> LOCATION: 5198..5369
<223> OTHER INFORMATION: /note="n = a or c or t or g"

<400> SEQUENCE: 15

ttcctgtcct aaggttgcag taattttaga ttttactttg agataaaaat tgtaaaaatt     60

aaatgggttt agtattacaa taatcgattt aactataaaa ttcttaaata ataaattaat    120

atattttaat tatattatgt aagttaggct ttgtaagtta tttattctct tacattaatt    180

atagtatgtg tttttttata tgatttgaat ttcaattcat tttattgtat ttaaattatc    240

tgataaaagt ttaggatttt ttaataaaat taaatcaatt actatagaag attaaaaata    300

ttttaattta aaaatgagtt attttgaaaa aagaaataaa ggatatatat atatacatat    360

tgaaataagt gagagtatta ctttattttg agtaaagtgg gaaaataaat ttttgcgtag    420

aaaatttgct aactttcaaa aaagcatttg tcgtcttttc tctttcttct atttttgtaa    480

ttttgttgtt ttttttccct ctcattcctt aatcatttta ttgcaatgtt tttcccttaa    540

aaagaagcat agctcaattt tttaaatatt ttgataatgt gtagaattga ataatcaaat    600

ctctaatatt catgctaacc attttaacta ttttttgata gggttgaaag tatgttaggt    660

ttttatgagt atttactata tattaacaat tgggctcaat ttttataaat ttgtaatttg    720

atggtttgag ttttaaaagg aaagaaatgg ttggaatgtt aataatcaat atggtttaga    780

ttaaagtaat cgatttcaca aaagttggag ttgagctagg gatatgacat gcattcaacc    840

cacctaggct tgaggggaga cgagagtttg gaccaaatgt ccaaatatga accgatcaat    900

ttttaccttg gtcgagacat acccacactt ttgattaaat aggcatgtta aacgtgtagg    960

acaacatatt gagtttgaga aaaagcctaa tctaactcca aaaccctaat ttaaatgtct   1020

taggtcataa gtaagttaac tatatcatcc aaactcttgc gagttgcgac aacttaaaga   1080

gtttaattag ttacaatcat tattgtaatt tttttaaatt tgaggcatca tatgttgtta   1140

ctcgatgagg ctgtttaggg cgttgagttg atgtagggtg ttgttaagaa gcaaagtaat   1200

atgtcttatg gatacttgtg acaaataagt ttataaggat gatccaacca atcttagaca   1260

acttctcaac atcaaattgc cttaggtgaa tgttagtata tattgattgt tagaggtagt   1320

tgtcactatt tgtcattgaa gttgattatc aaaggtgatt ctcgttgaag tttatcatag   1380

aggtgggttg ttggagccca aagttaaagg tggttttcga agttgataat caaaggcgat   1440

tttcgctaaa gtttgtagtc atagcttgga attcatcgca tggacgtagt catcaaagtt   1500

ggctttcgtt ggatttgtta tcagagatga ttacaggctc gaaattagtg gttggaggtg   1560

gtcgtgcaaa ggtaatctag ttgtcatagt ttttcatcga aggtggttgt aggaccctga   1620

aatcgattgt caaagttgga ggtgtgaaag tggctgttgt cggagtcgga tcctagagtt   1680

tggtaatggg taattgtcat aatggtaatc gatcgtcgaa tccattgaaa acattggaaa   1740

gaactccacc aacatgtaaa gttggtaggc caaacgaaac tcaaacccat cttatattga   1800

tgtgcaaaac atctctagga taaaacaaac caaactaata aatcataaag acaaaaatga   1860

aaaatgagag taccaaaaaa aaaaaaaaaa gagcaataac ttcaaataag ttttaaaaca   1920
```

-continued

```
ctagatttaa aaaaaaaatc aaagaacaaa aatagaagat attttaatct ctacaaaaaa   1980
aaaaaaaaag aaaaaaagaa aattatagat attaataatt gtaatgaggc ttagtatttt   2040
caaaatcctc atttagagga aaaaaaaagg gagaaaataa actaacttcc gtctttgttt   2100
cacaaacaag acacgcgtca tattctcatt agctaaaacc gcaaaaaaag caatcagtca   2160
aaaagtctta aaaacggtta acactctaaa cgcctctcaa gaattcttca cgtgtcagtc   2220
acatggaaaa gaaaccggcc gaaccgggtc gaagtaaacc gcgttatctg gcgaagtaca   2280
aagtataata gtactataac cgcggagttg aaaaagacgc cggctttttg aacgattaaa   2340
tcggcgatct aaagaagaag gctcttggtt ccttcttcct ctgtgttcgc tcctttctta   2400
aatgttcatc acaaataaat cccaatccaa tcgcccgaca tttctctcac tccacaatcg   2460
gagacagaag attattcctt ttttccgatt tctgtttctt ccaatctcaa tcgcatgacg   2520
gattatcgtt tgtcgacgat gaatctctgg actgacgaga acgcgtcggt gatggacgct   2580
ttcatgaatt ccgatctctc ttcctactgg gctccatcag ccgcctcctc tcactctctt   2640
caccatccac caccacctca gtcctccgcc tcaacgtcca ctcccccgcc ggacccacct   2700
aagtccctcc ccgttttcaa tcaggagact ctgcagcagc ggctccaggc gctgattgac   2760
ggtgctaggg agagttggac ttatgcgatt ttctggcagt catcttatga ttattccggt   2820
gggtctgttt tggggtgggg tgatgggtat tacaaaggag aggaagataa aggaaagggg   2880
aaagcgaaaa tggtgtcgtc agcggcagag caggctcacc ggaagaaggt tttacgggag   2940
cttaactctt tgatttctgg ctctgccgct ggaccggacg atgcggtgga tgaggaggtt   3000
acggatacag agtggttctt tttggtttcg atgactcagt cgtttgttaa tggtgttggg   3060
ttaccgagtc aggcgtttta ccactcgacg ccgatttggg tctctggtgc cgatcggctg   3120
tcggcgtctg cctgtgaacg agctagacag ggagagggttt ttgggttaca gacgatggtc   3180
tgtattccat cgcctaacgg tgttgtggaa atgggttcga cggaattgat tcatcgaaca   3240
tcggatttga tgaataaggt caaaattctg ttcaatttca acaatctcga gacgagttct   3300
tggatttcgg gaactaccgc cgccgcatcc gctgcagacg aaggggaaaa cgacccgtcg   3360
tcgatgtgga tcagtgagcc atctagtaca atcgagatga aggattcaat taccaccacc   3420
gtcccttcca gcaacgttcc ggcaaagcca atccgatccg aaaatcccag ttcaagtagc   3480
ttaacggaaa atatgagcac gattcaacaa tcccatcata aacagagcca aagcttctta   3540
aatttctccg attacggctt cgagtcaaat ccctcaaaga acaccaccgc caccgccacc   3600
gtaaccacca gcaccactcc atcattcaag ccggaatccg gcgggatgct gaattttgga   3660
aacggaagcc tcttctccgg ccattcacag tacgtaacaa acgaacagaa cgaagaaaag   3720
agatcccctg cttctcgaag tagcaacgac gaagggatcc tctctttcac ctccggcgtg   3780
atcttaccct cttccggtaa ggtaaaatca ggcgattcgg accactcaga tctcgaagca   3840
tcagtgatca gagaagtaga tagctgtaca aaatcattag aacccgaaaa acgtccaaga   3900
aaaagaggta gaaaaccagc aaacggaaga gaagagccat tgaatcacgt agaagcagag   3960
agacaacggc gagagaaatt aaaccagaaa ttctacgctc tacgagctgt agttccaaac   4020
gtatctaaaa tggacaaagc ctcactactc ggtgacgccg tttcgtacat aaacgagctg   4080
aaatcgaagc tccaaatggc agaatcggag aaaacagata tgggaaaaca tctagaattg   4140
ctgaagaagg agatgggagg gaaagatgta ggatgttaca caaacccaaa tgatgaagat   4200
ctgaaaatag ggaaaagaaa ggtaatggat atggagattg aagttaaaat catgggttgg   4260
```

-continued

```
gatgcgatga tcagaattca aagcaacaag aagaatcatc cggcggcgag gttgatgacg   4320
gcgtttaagg atttggattt agaaatgctt cacgccagtg tttctgtagt gaatgatttg   4380
atgattcaac aagcaacagt gaagatgggg agcagatttt acacacaaga gcagcttaaa   4440
atggctcttg tggcccgagt cggtggtggt ggtggaggcg gaagcggcgg tggaatgatg   4500
taaatggggt taggggacat ttttgaagct cccaagtagt agagattagt tgagggaata   4560
taaatctgat ttagtattgt gtaatattaa tgttggtaaa ttatttttga taattttgtt   4620
gttcatcttt tgttgttaga gtaatttggg agttcttctt ctatatatat gtagtttttg   4680
ttgattaaat atcaaatcta atagaagtga agatcaaaga ccttcaaact ttgtgtttga   4740
tgatttcagt tctctttcct ttgtttttag ggttttgttt gaagtaaaaa tctaggtttg   4800
attggaaatt taggactaac cttaacctcc cagctcagta caaaccttag ttaaacctaa   4860
atgtcaatgg acctaagatt tggtattggg tccacatttc gtgtggttga gatagaaaac   4920
cccaactttc atataagaac aacccatata aaattcgtca tttgattagg ttattcgata   4980
agtggatttc aaaagggatc gggagaataa ctagtctctt aagtcaacat ttttcatata   5040
tacataagtt ggtcgatcta gatttctaaa ttttaagttg ggtttagttg tttttgtaca   5100
atagggaacg tgcgtgtgcg tgtgcgcgtg cgtgtgtgtg tggttgtgtg tgtgtgtgtg   5160
tcgctagttg tgtgtgtgtg tgtggttcgc taatacannn nnnnnnnnnn nnnnnnnnnn   5220
nnnnnnnnnn nnnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnnnnnnnnn nnnnnnnnnt caatggactg acgtatttat ttactaggtc   5400
ataatgatgg tgtttttcca aaatcaaact ttgctgttca atatcttaga ctagccatcc   5460
tttagaggag attgttaaaa aatcatcaat tactaataaa aaaaagacta ttgcagtggc   5520
ccactggaag tctttagttg atactacaat ctttatgcta gttaagctac gctcaatttg   5580
tccgtttgta tacaatgaac tctagcaaat tagcttacat catttataca tactttaaat   5640
gattggttac tgtctatcgg ggagagttta acctagctct tatacataga aattttaagc   5700
aggtttaacg aaagttgaag tttagaaaat ttaattttga aaataatcat ataaacatgc   5760
atgtcacaca tgtttattga tatgctaagt caatgagcta tagagagtta ggttcatagc   5820
cacataaata aaacctataa ctcttagttt tatgttttcg aaatttatgg ccgtttctta   5880
ctatttaaac ttttctaaaa gaaaaaattt gaactcatta aattctaaca acaaaaacat   5940
gtttttgaaa acgaaataaa aatagataat aaaacacaaa aaacttatag atgaaaatag   6000
tgtttataag gttacttaaa aaaaaaccaa acaatcatca aatacgaagt ttttgaaatt   6060
tgatttagat ttattcgatg tgtggttaat aattgggatg tagaaagata agctatggat   6120
gatagtgaag aattgaaggt gaccttacac ttcatatatg gacataaaaa aggaccattt   6180
tcatagaatc ttcaagaaga tattgatgga gataattttc tctctttttg tgaccccttc   6240
ttcatataaa gtaattccat tgttgaagtt aaatggtaaa aaagaaaaaa aaaaaagaac   6300
tttttattat tgtataaaac aatgatttag attttgaatt ttatttgtga caatttggtc   6360
attttgaata tctaaactac gttggttatt ttatcgtcac                         6400
```

<210> SEQ ID NO 16
<211> LENGTH: 1989
<212> TYPE: DNA
<213> ORGANISM: Cucumis melo

<400> SEQUENCE: 16

```
atgacggatt atcgtttgtc gacgatgaat ctctggactg acgagaacgc gtcggtgatg     60
gacgctttca tgaattccga tctctcttcc tactgggctc catcagccgc ctcctctcac    120
tctcttcacc atccaccacc acctcagtcc tccgcctcaa cgtccactcc cccgccggac    180
ccacctaagt ccctccccgt tttcaatcag gagactctgc agcagcggct ccaggcgctg    240
attgacggtg ctagggagag ttggacttat gcgattttct ggcagtcatc ttatgattat    300
tccggtgggt ctgttttggg gtggggtgat gggtattaca aaggagagga agataaagga    360
aaggggaaag cgaaaatggt gtcgtcagcg gcagagcagg ctcaccggaa gaaggtttta    420
cgggagctta actctttgat ttctggctct gccgctggac cggacgatgc ggtggatgag    480
gaggttacgg atacagagtg gttctttttg gtttcgatga ctcagtcgtt tgttaatggt    540
gttgggttac cgagtcaggc gttttaccac tcgacgccga tttgggtctc tggtgccgat    600
cggctgtcgg cgtctgcctg tgaacgagct agacagggga gggtttttgg gttacagacg    660
atggtctgta ttccatcgcc taacggtgtt gtggaaatgg gttcgacgga attgattcat    720
cgaacatcgg atttgatgaa taaggtcaaa attctgttca atttcaacaa tctcgagacg    780
agttcttgga tttcgggaac taccgccgcc gcatccgctg cagacgaagg ggaaaacgac    840
ccgtcgtcga tgtggatcag tgagccatct agtacaatcg agatgaagga ttcaattacc    900
accaccgtcc cttccagcaa cgttccggca aagccaatcc gatccgaaaa tcccagttca    960
agtagcttaa cggaaaatat gagcacgatt caacaatccc atcataaaca gagccaaagc   1020
ttcttaaatt tctccgatta cggcttcgag tcaaatccct caaagaacac caccgccacc   1080
gccaccgtaa ccaccagcac cactccatca ttcaagccgg aatccggcgg gatgctgaat   1140
tttggaaacg gaagcctctt ctccggccat tcacagtacg taacaaacga acagaacgaa   1200
gaaaagagat cccctgcttc tcgaagtagc aacgacgaag ggatcctctc tttcacctcc   1260
ggcgtgatct taccctcttc cggtaaggta aaatcaggcg attcggacca ctcagatctc   1320
gaagcatcag tgatcagaga agtagatagc tgtacaaaat cattagaacc cgaaaaacgt   1380
ccaagaaaaa gaggtagaaa accagcaaac ggaagagaag agccattgaa tcacgtagaa   1440
gcagagagac aacggcgaga gaaattaaac cagaaattct acgctctacg agctgtagtt   1500
ccaaacgtat ctaaaatgga caaagcctca ctactcggtg acgccgtttc gtacataaac   1560
gagctgaaat cgaagctcca aatggcagaa tcggagaaaa cagatatggg aaaacatcta   1620
gaattgctga agaaggagat gggagggaaa gatgtaggat gttacacaaa cccaaatgat   1680
gaagatctga aaatagggaa aagaaaggta atggatatgg agattgaagt taaaatcatg   1740
ggttgggatg cgatgatcag aattcaaagc aacaagaaga atcatccggc ggcgaggttg   1800
atgacggcgt ttaaggattt ggatttagaa atgcttcacg ccagtgtttc tgtagtgaat   1860
gatttgatga ttcaacaagc aacagtgaag atggggagca gattttacac acaagagcag   1920
cttaaaatgg ctcttgtggc ccgagtcggt ggtggtggtg gaggcggaag cggcggtgga   1980
atgatgtaa                                                           1989
```

<210> SEQ ID NO 17
<211> LENGTH: 662
<212> TYPE: PRT
<213> ORGANISM: Cucumis melo

<400> SEQUENCE: 17

```
Met Thr Asp Tyr Arg Leu Ser Thr Met Asn Leu Trp Thr Asp Glu Asn
1               5                   10                  15
```

-continued

```
Ala Ser Val Met Asp Ala Phe Met Asn Ser Asp Leu Ser Ser Tyr Trp
            20                  25                  30

Ala Pro Ser Ala Ala Ser Ser His Ser Leu His His Pro Pro Pro Pro
        35                  40                  45

Gln Ser Ser Ala Ser Thr Ser Thr Pro Pro Pro Asp Pro Pro Lys Ser
    50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Gly Ser Val Leu Gly Trp Gly Asp Gly Tyr
            100                 105                 110

Tyr Lys Gly Glu Glu Asp Lys Gly Lys Gly Lys Ala Lys Met Val Ser
        115                 120                 125

Ser Ala Ala Glu Gln Ala His Arg Lys Lys Val Leu Arg Glu Leu Asn
    130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Val Asn Gly Val Gly Leu Pro Ser Gln Ala Phe Tyr His Ser Thr
            180                 185                 190

Pro Ile Trp Val Ser Gly Ala Asp Arg Leu Ser Ala Ser Ala Cys Glu
        195                 200                 205

Arg Ala Arg Gln Gly Arg Val Phe Gly Leu Gln Thr Met Val Cys Ile
    210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
                245                 250                 255

Asn Leu Glu Thr Ser Ser Trp Ile Ser Gly Thr Thr Ala Ala Ala Ser
            260                 265                 270

Ala Ala Asp Glu Gly Glu Asn Asp Pro Ser Ser Met Trp Ile Ser Glu
        275                 280                 285

Pro Ser Ser Thr Ile Glu Met Lys Asp Ser Ile Thr Thr Thr Val Pro
    290                 295                 300

Ser Ser Asn Val Pro Ala Lys Pro Ile Arg Ser Glu Asn Pro Ser Ser
305                 310                 315                 320

Ser Ser Leu Thr Glu Asn Met Ser Thr Ile Gln Gln Ser His His Lys
                325                 330                 335

Gln Ser Gln Ser Phe Leu Asn Phe Ser Asp Tyr Gly Phe Glu Ser Asn
            340                 345                 350

Pro Ser Lys Asn Thr Thr Ala Thr Ala Thr Val Thr Thr Ser Thr Thr
        355                 360                 365

Pro Ser Phe Lys Pro Glu Ser Gly Gly Met Leu Asn Phe Gly Asn Gly
    370                 375                 380

Ser Leu Phe Ser Gly His Ser Gln Tyr Val Thr Asn Glu Gln Asn Glu
385                 390                 395                 400

Glu Lys Arg Ser Pro Ala Ser Arg Ser Ser Asn Asp Glu Gly Ile Leu
                405                 410                 415

Ser Phe Thr Ser Gly Val Ile Leu Pro Ser Ser Gly Lys Val Lys Ser
            420                 425                 430
```

-continued

```
Gly Asp Ser Asp His Ser Asp Leu Glu Ala Ser Val Ile Arg Glu Val
        435                 440                 445

Asp Ser Cys Thr Lys Ser Leu Glu Pro Glu Lys Arg Pro Arg Lys Arg
    450                 455                 460

Gly Arg Lys Pro Ala Asn Gly Arg Glu Glu Pro Leu Asn His Val Glu
465                 470                 475                 480

Ala Glu Arg Gln Arg Arg Glu Lys Leu Asn Gln Lys Phe Tyr Ala Leu
                485                 490                 495

Arg Ala Val Val Pro Asn Val Ser Lys Met Asp Lys Ala Ser Leu Leu
            500                 505                 510

Gly Asp Ala Val Ser Tyr Ile Asn Glu Leu Lys Ser Lys Leu Gln Met
        515                 520                 525

Ala Glu Ser Glu Lys Thr Asp Met Gly Lys His Leu Glu Leu Leu Lys
    530                 535                 540

Lys Glu Met Gly Gly Lys Asp Val Gly Cys Tyr Thr Asn Pro Asn Asp
545                 550                 555                 560

Glu Asp Leu Lys Ile Gly Lys Arg Lys Val Met Asp Met Glu Ile Glu
                565                 570                 575

Val Lys Ile Met Gly Trp Asp Ala Met Ile Arg Ile Gln Ser Asn Lys
            580                 585                 590

Lys Asn His Pro Ala Ala Arg Leu Met Thr Ala Phe Lys Asp Leu Asp
        595                 600                 605

Leu Glu Met Leu His Ala Ser Val Ser Val Val Asn Asp Leu Met Ile
    610                 615                 620

Gln Gln Ala Thr Val Lys Met Gly Ser Arg Phe Tyr Thr Gln Glu Gln
625                 630                 635                 640

Leu Lys Met Ala Leu Val Ala Arg Val Gly Gly Gly Gly Gly Gly Gly
                645                 650                 655

Ser Gly Gly Gly Met Met
            660


<210> SEQ ID NO 18
<211> LENGTH: 6400
<212> TYPE: DNA
<213> ORGANISM: Citrullus lanatus

<400> SEQUENCE: 18

ttttatataa atactaaatt gttataaatt aaactacgtt attactttgt ttttatttca      60

tctgcaaaca ttcaaaattg aaatccttct agtcacaagt taaaaaaatt gggagactat     120

accaggtgta cagtgaaagg aaaattacaa ggagtaaaaa aattaatatt gaattttata     180

aactatctta acattttatt ttttattttt tattttgcca actacaacaa ataagagaaa     240

ttatgttaaa ttgcaaaact gctaaaaata tttaaaatca atagcaaaat acaccgtcta     300

catgcgaatg tgggatcaaa tctcccctgt ttgaagtgaa aaaagttaaa ggagcatttg     360

actaaattaa caaagaaatt tttgttttca accaaaacaa atgttactct gttactttgt     420

tttgagtgaa ttgtgaaagt aagctaatgt gtagaaaatg tgataacttt caaaaaagca     480

ttcgtcgcct tttatatttc tacaatattg tttcgtttca ttttttattt tattttttca     540

tcccctcctt ccttaatata actattgcaa atttcttaaa tgagtttaac aacctttcaa     600

tgcaagtttt tttctttttt ttttttttta caatctgtga agttgaaaaa attgatacta     660

tcaccttata ttggcagtat taaccttatg ccatatgagt tatatttatt ttgataaata     720

cttacaatat gttaatgatt aagttcaatt tttatgtagt gtaaatttaa atttttaaat     780
```

-continued

```
ttaatttaat gaatattctg cttcctgaaa caacatgttg gtcccacggg tggtatcagg     840
tggaggttgt ctttggattg acaagcattg gaagatttaa aagctcttcg ttttccattc     900
gggattgtca ttctgtcact tttggtggaa tctgattatg ttgaagtgat cacgtccctt     960
tgcaagattg atagtgatct ttcgaatatt acatttgttt tttgttgtgt tttaaagcta    1020
gatgaagaat ttgggaacat ccattttgct aagtgttcga ggtttagtaa ttatttggct    1080
gcacactcgc tagctagatt ggttgtgtct cctttttga attcttttt aggctcgaat     1140
ttgacttcct cctccttgga aaggttttaa ttttagttca tggggttcta atgtccctaa    1200
gttgttagtt gctgttattg gtgaggttga ttgtcagttg gggaaaaaaa attttaatag    1260
tttagaccta gttttacacc tcatttggta actatttggt tttttgaat gattttgctg     1320
gttgagagag ataagtgaaa tttttatata tttgtaaata gtttgatatt tttttcattt    1380
ataataattt ctcttcaaaa ttcaatcaaa tttttaaagt ataaattaaa agaaagggat    1440
cataacaaat cactcatcca tttgaaatac aaaaataaat tttgcactat atatatataa    1500
actcaacatc tcttataaga taaagcaaaa taactaaata aaataaattg ttttcaaata    1560
taagaaaatg aacaaaaaca tttataacta caatcaaatt ttactgtcta tttgcgatag    1620
atctcgatct attgtagata gattgtaata ttttgttatt tttttaaata tattctgcaa    1680
ctttatcatt taaaataatt tttcaaataa aaatttagaa acaaaattgt tgattgcaag    1740
taagtacata gactaaaaat atttgttaac aaaaaaaaaa aaaaaaaaac aatcaaagac    1800
tttaaataat ttttaaaata aaaattgcag agagattaga aaaaaaatca aagaacagaa    1860
atggtagata tttttagctt tttttaaaaa aagaaaaata atagatattt taatatggcg    1920
tagtattttc aaaagcgatt tatttggagc aaaaaaagga aagaataaaa ccacttcagt    1980
ctttgattaa caaatcagac acgtgtcaac ctctcattag tggaaaatgc aaacaaaccg    2040
atcagtcaaa agtcttaaaa acggttaccc cccaaagctc acaaacgaaa cgccccccgat   2100
gatccttcac gtgcccgtca cgtggaaaga aacgaaccga accgggtcta aatgagccgc    2160
actctctggc aggagtacta gtatagtact acaagcgcgg agttgaaaac gacgccggct    2220
ttttgaacga ttaaatcggc gatccaaaga agaagcctct tggttccttc ttcccctgtt    2280
cgctcctctg taaatgttca tcacaaataa atcccaatcc aatcgcccga catttctctc    2340
actccacaat tggagaccca gaattattct ctttttccca ttctgtttct tctcgaatcc    2400
caatcgcatg acggattatc gtttgtcgac gatgaatctc tggactgacg aaaacgcgtc    2460
ggtgatggac gctttcatga actccgatct gtcctcttac tgggctccat ctgccgcctc    2520
ctctcactct cttcaccacc caccgccgcc tcagtcctcc gcctccacct ccactccccc    2580
accggacccg cccaagtccc tgcctgtttt caatcaggag actctgcagc agcggctcca    2640
ggcgctgatc gatggcgcta gggagagttg gacttacgcg attttctggc agtcgtccta    2700
tgattattcc ggtgcgtcgg ttttagggtg gggagatggg tattacaaag gggaggagga    2760
taaagggaag ggaaaagcga aaatggtgtc gtcggcggca gagcaggctc atcggaagaa    2820
ggttttacgg gagcttaact ctttaatttc tggctccgct gccggaccgg acgatgcggt    2880
ggatgaggag gttacggata cggagtggtt ctttttggtt tcgatgactc agtcttttga    2940
taatggagtt tggttaccga gtcaggcgtt ttacaactcg acgccgattt gggtttctgg    3000
cgccgatcgg ctgtcggcgt ctgcctgtga acgggccaga caggggaggg tttttgggtt    3060
acagacgatg gtctgtattc catcgccaaa cggagttgtg gaaatgggtt cgacggaatt    3120
gattcatcga acgtcggatt tgatgaacaa ggtcaagatt ctgttcaatt tcaacaatct    3180
```

```
cgaaacgagt tcttggatat cgggaaccac cgccgccgat gaaggggaaa acgacccgtc   3240
gtcgatgtgg atcagtgagc cgtcgagtac tatcgagatg aaggattcca ttaccaccac   3300
cgtcccttcc ggcaacgtcc cggcaaagcc aatccattcg gaaaatccca gttccagcag   3360
cttaacggaa aatatcagcg cgatccaaca accatcccat caaaaacaaa gccaaagctt   3420
cttaaatttc tccgattacg gcttcgaatc aaatccctca aagaacacca ccgcggccgc   3480
aacaaccacc accgccaccc catcattcaa gccggaatcc ggcgggatgc tgaatttcgg   3540
caacggaaac ctcttctcta gccattcaca gtatgtaaca aacgaacaga acgagaaaaa   3600
gagatcccct gcttctcgga gtagcaacga cgaagggatc ctctctttca cctctggcgt   3660
gatcttaccc tcctccggta aggtaaaatc cggggactca gaccactcag atctcgaagc   3720
atcggtgatc agagaagtgg atagctgtac aaaatcatta gaacccgaaa aacgtccaag   3780
aaaaagaggt agaaaaccag caaacggaag agaagagcca ttgaatcatg tagaagcaga   3840
gagacaacgg cgagagaagt tgaaccagaa attctacgct ctccgagctg tagttccaaa   3900
cgtatctaaa atggacaagg cctcactact gggagacgcg gtttcttaca tcaacgagct   3960
caaatcaaag ctccaaatag cggaaacgga gaaaacagag atgggaaaac atttagaatt   4020
gctgaagaag gagatgggag ggaaagattt cgggaattac ccgaacccaa atgatgaaga   4080
tctgaaaata gggaaaagaa aggtaatgga tatggagatc gaagttaaaa tcatgggttg   4140
ggatgcgatg ataaggattc aaagcagcaa gaaaaatcat ccggcggcaa ggctgatggc   4200
ggcgtttaag gatttagatt tagaaatgct tcatgcgagt gtttctgtag tgaatgattt   4260
gatgattcaa caggcaacgg tgaagatggg gagcagattt tacacacagg agcagcttaa   4320
aatggctctc gtcgcccgag tcgggggcgg cggcggcagc agccatggaa tgatgtaaat   4380
gggttgtgta attacaagtg ggaggggaca tttttgaggg ctcccaagta gagattagct   4440
gagggaatct gattagtatg tgtaagataa aatgttggta aattattttg atcattttgt   4500
tgttgtttca tctttttttg gttgttagag taatttggga agttctttgt gtagtttttg   4560
ttaaatatca aatctaatag aacagaagat gaaagacctt caaactttgt gatgggttgc   4620
tgtcttcaaa aatacccatt gcgtttctct ctttttttggt agaagtttag tcggtaggta   4680
cttcttccac taaaccttaa cctcacatag tatccacacg agttaagtct agagttctca   4740
atagccatga gttgggccca aaggccgaga agcccaactt tcgtatctca aatcagatta   4800
ggtttaagac ttaagtcatc ctcaatttgt ctgtttgtat aataatatct atctattatg   4860
cttattaatg agctattata aggtaaggta ggttacatca tttatattta tagttagata   4920
atcactcaaa gttaatttta gatgcatgcc gcacgtctaa acttgcaaat gattggttac   4980
catatttggg aggagttcat aaaaatgtta aagtgaaaat atcatataca acatgttgat   5040
gccacatgtt tgtttcatat gctaattcag tgtgagctat ggtcagtttg gttgagagtt   5100
acactttata aaaactattt ttttaaggca gtgtcttata acaaatttca tttttaattt   5160
tatgattttt caaatttttg aaatttattt ccttctaatt ctaatttttc tattatggtg   5220
ttcacatgtc tacatgaaac tcttgaattc cttgtcaaat tctaataaca aaaacatgtt   5280
tttggaaact acatatttta gttttttttc tttaacaaaa catggaaact taggatgaaa   5340
gtagtgttta taaggttatt tttcaaaaac aaaatatcaa atgattatca aatgagacct   5400
taattcttaa aatttggcta cgattttgaa atattattaa aaagtatata acaaaacaaa   5460
aacaaagaat gtcacgagta aattttgttt ctataaattt aaattaaaaa aaatttaaaa   5520
```

```
atagagatca aataatcata aaaaagagcc tatgtgtgat tggcatgtaa aaagataagg   5580
tttttgagcc attgatgata gtggaagctt gtgaagaatt aaagatgacc ttacacttca   5640
tgtatggaca taaaatgtca tcttcataga atattcaaga agattttgat aaatataatt   5700
tttcactctt tgtgacttct ataaagtagt tcaattgttg aagtaaaatg gcaaaaaatg   5760
gttttatgaa ctttcataaa attgataatc ctcaccccaa ttccatttgt ttgtttttag   5820
ttttttaaaa ttaaacctat tttttctatt tcttgtaatg atttacatct ttcttaggtg   5880
taatcgttga attcgtagtc aaattctaaa atgaaaaact aattttttta gttttcaaaa   5940
tttggcttga cttttaaacc attggtaaaa aaattagata acaaaggcaa aaatttggaa   6000
ttggaagtag tctctataaa cttaattttc aaaaacaaaa aaaagaccaa aaaccaaatg   6060
gttaccaaac gggatagtaa tttttgaatt gatttgtaca atttagttct tcttttgtaa   6120
taattaagtg tgtcaattct taatacgtaa taactaactt aatatttgta gctaataaaa   6180
taatattttt tgtctttaat tagtttataa gatgtgactg taagaaattc tattaaatgt   6240
tttttttca ccatagaagt taaattgtta aataattgaa agtttatgga ttaaacttta   6300
cataattgtt taaaaattaa attattacaa aactagaaaa tttagaggtt aaaagtgttt   6360
ttttttttt tttttttaa cttaaaaggt tttatttgga                          6400
```

<210> SEQ ID NO 19
<211> LENGTH: 1971
<212> TYPE: DNA
<213> ORGANISM: Citrullus lanatus

<400> SEQUENCE: 19

```
atgacggatt atcgtttgtc gacgatgaat ctctggactg acgaaaacgc gtcggtgatg     60
gacgctttca tgaactccga tctgtcctct tactgggctc catctgccgc ctcctctcac    120
tctcttcacc acccaccgcc gcctcagtcc tccgcctcca cctccactcc cccaccggac    180
ccgcccaagt ccctgcctgt tttcaatcag gagactctgc agcagcggct ccaggcgctg    240
atcgatggcg ctagggagag ttggacttac gcgattttct ggcagtcgtc ctatgattat    300
tccggtgcgt cggttttagg gtggggagat gggtattaca aaggggagga ggataaaggg    360
aagggaaaag cgaaaatggt gtcgtcggcg gcagagcagg ctcatcggaa gaaggtttta    420
cgggagctta actctttaat ttctggctcc gctgccggac cggacgatgc ggtggatgag    480
gaggttacgg atacggagtg gttctttttg gtttcgatga ctcagtcttt tgataatgga    540
gtttggttac cgagtcaggc gttttacaac tcgacgccga tttgggtttc tggcgccgat    600
cggctgtcgg cgtctgcctg tgaacgggcc agacagggga gggtttttgg gttacagacg    660
atggtctgta ttccatcgcc aaacggagtt gtggaaatgg gttcgacgga attgattcat    720
cgaacgtcgg atttgatgaa caaggtcaag attctgttca atttcaacaa tctcgaaacg    780
agttcttgga tatcgggaac caccgccgcc gatgaagggg aaaacgaccc gtcgtcgatg    840
tggatcagtg agccgtcgag tactatcgag atgaaggatt ccattaccac caccgtccct    900
tccggcaacg tcccggcaaa gccaatccat tcggaaaatc ccagttccag cagcttaacg    960
gaaaatatca gcgcgatcca acaaccatcc catcaaaaac aaagccaaag cttcttaaat   1020
ttctccgatt acggcttcga atcaaatccc tcaaagaaca ccaccgcggc cgcaacaacc   1080
accaccgcca ccccatcatt caagccggaa tccggcggga tgctgaattt cggcaacgga   1140
aacctcttct ctagccattc acagtatgta acaaacgaac agaacgagaa aaagagatcc   1200
cctgcttctc ggagtagcaa cgacgaaggg atcctctctt tcacctctgg cgtgatctta   1260
```

```
ccctcctccg gtaaggtaaa atccggggac tcagaccact cagatctcga agcatcggtg   1320

atcagagaag tggatagctg tacaaaatca ttagaacccg aaaaacgtcc aagaaaaaga   1380

ggtagaaaac cagcaaacgg aagagaagag ccattgaatc atgtagaagc agagagacaa   1440

cggcgagaga agttgaacca gaaattctac gctctccgag ctgtagttcc aaacgtatct   1500

aaaatggaca aggcctcact actgggagac gcggtttctt acatcaacga gctcaaatca   1560

aagctccaaa tagcggaaac ggagaaaaca gagatgggaa aacatttaga attgctgaag   1620

aaggagatgg gagggaaaga tttcgggaat tacccgaacc caaatgatga agatctgaaa   1680

atagggaaaa gaaaggtaat ggatatggag atcgaagtta aaatcatggg ttgggatgcg   1740

atgataagga ttcaaagcag caagaaaaat catccggcgg caaggctgat ggcggcgttt   1800

aaggatttag atttagaaat gcttcatgcg agtgtttctg tagtgaatga tttgatgatt   1860

caacaggcaa cggtgaagat ggggagcaga ttttacacac aggagcagct taaaatggct   1920

ctcgtcgccc gagtcggggg cggcggcggc agcagccatg gaatgatgta a            1971
```

<210> SEQ ID NO 20
<211> LENGTH: 656
<212> TYPE: PRT
<213> ORGANISM: Citrullus lanatus

<400> SEQUENCE: 20

```
Met Thr Asp Tyr Arg Leu Ser Thr Met Asn Leu Trp Thr Asp Glu Asn
1               5                   10                  15

Ala Ser Val Met Asp Ala Phe Met Asn Ser Asp Leu Ser Ser Tyr Trp
            20                  25                  30

Ala Pro Ser Ala Ala Ser Ser His Ser Leu His His Pro Pro Pro Pro
        35                  40                  45

Gln Ser Ser Ala Ser Thr Ser Thr Pro Pro Pro Asp Pro Pro Lys Ser
    50                  55                  60

Leu Pro Val Phe Asn Gln Glu Thr Leu Gln Gln Arg Leu Gln Ala Leu
65                  70                  75                  80

Ile Asp Gly Ala Arg Glu Ser Trp Thr Tyr Ala Ile Phe Trp Gln Ser
                85                  90                  95

Ser Tyr Asp Tyr Ser Gly Ala Ser Val Leu Gly Trp Gly Asp Gly Tyr
            100                 105                 110

Tyr Lys Gly Glu Glu Asp Lys Gly Lys Gly Lys Ala Lys Met Val Ser
        115                 120                 125

Ser Ala Ala Glu Gln Ala His Arg Lys Lys Val Leu Arg Glu Leu Asn
    130                 135                 140

Ser Leu Ile Ser Gly Ser Ala Ala Gly Pro Asp Asp Ala Val Asp Glu
145                 150                 155                 160

Glu Val Thr Asp Thr Glu Trp Phe Phe Leu Val Ser Met Thr Gln Ser
                165                 170                 175

Phe Asp Asn Gly Val Trp Leu Pro Ser Gln Ala Phe Tyr Asn Ser Thr
            180                 185                 190

Pro Ile Trp Val Ser Gly Ala Asp Arg Leu Ser Ala Ser Ala Cys Glu
        195                 200                 205

Arg Ala Arg Gln Gly Arg Val Phe Gly Leu Gln Thr Met Val Cys Ile
    210                 215                 220

Pro Ser Pro Asn Gly Val Val Glu Met Gly Ser Thr Glu Leu Ile His
225                 230                 235                 240

Arg Thr Ser Asp Leu Met Asn Lys Val Lys Ile Leu Phe Asn Phe Asn
```

```
                245                 250                 255

Asn Leu Glu Thr Ser Ser Trp Ile Ser Gly Thr Thr Ala Ala Asp Glu
            260                 265                 270

Gly Glu Asn Asp Pro Ser Ser Met Trp Ile Ser Glu Pro Ser Ser Thr
        275                 280                 285

Ile Glu Met Lys Asp Ser Ile Thr Thr Thr Val Pro Ser Gly Asn Val
    290                 295                 300

Pro Ala Lys Pro Ile His Ser Glu Asn Pro Ser Ser Ser Ser Leu Thr
305                 310                 315                 320

Glu Asn Ile Ser Ala Ile Gln Gln Pro Ser His Gln Lys Gln Ser Gln
                325                 330                 335

Ser Phe Leu Asn Phe Ser Asp Tyr Gly Phe Glu Ser Asn Pro Ser Lys
            340                 345                 350

Asn Thr Thr Ala Ala Ala Thr Thr Thr Thr Ala Thr Pro Ser Phe Lys
        355                 360                 365

Pro Glu Ser Gly Gly Met Leu Asn Phe Gly Asn Gly Asn Leu Phe Ser
    370                 375                 380

Ser His Ser Gln Tyr Val Thr Asn Glu Gln Asn Glu Lys Lys Arg Ser
385                 390                 395                 400

Pro Ala Ser Arg Ser Ser Asn Asp Glu Gly Ile Leu Ser Phe Thr Ser
                405                 410                 415

Gly Val Ile Leu Pro Ser Ser Gly Lys Val Lys Ser Gly Asp Ser Asp
            420                 425                 430

His Ser Asp Leu Glu Ala Ser Val Ile Arg Glu Val Asp Ser Cys Thr
        435                 440                 445

Lys Ser Leu Glu Pro Glu Lys Arg Pro Arg Lys Arg Gly Arg Lys Pro
    450                 455                 460

Ala Asn Gly Arg Glu Glu Pro Leu Asn His Val Glu Ala Glu Arg Gln
465                 470                 475                 480

Arg Arg Glu Lys Leu Asn Gln Lys Phe Tyr Ala Leu Arg Ala Val Val
                485                 490                 495

Pro Asn Val Ser Lys Met Asp Lys Ala Ser Leu Leu Gly Asp Ala Val
            500                 505                 510

Ser Tyr Ile Asn Glu Leu Lys Ser Lys Leu Gln Ile Ala Glu Thr Glu
        515                 520                 525

Lys Thr Glu Met Gly Lys His Leu Glu Leu Leu Lys Lys Glu Met Gly
    530                 535                 540

Gly Lys Asp Phe Gly Asn Tyr Pro Asn Pro Asn Asp Glu Asp Leu Lys
545                 550                 555                 560

Ile Gly Lys Arg Lys Val Met Asp Met Glu Ile Glu Val Lys Ile Met
                565                 570                 575

Gly Trp Asp Ala Met Ile Arg Ile Gln Ser Ser Lys Lys Asn His Pro
            580                 585                 590

Ala Ala Arg Leu Met Ala Ala Phe Lys Asp Leu Asp Leu Glu Met Leu
        595                 600                 605

His Ala Ser Val Ser Val Val Asn Asp Leu Met Ile Gln Gln Ala Thr
    610                 615                 620

Val Lys Met Gly Ser Arg Phe Tyr Thr Gln Glu Gln Leu Lys Met Ala
625                 630                 635                 640

Leu Val Ala Arg Val Gly Gly Gly Gly Gly Ser Ser His Gly Met Met
                645                 650                 655
```

What is claimed is:

1. A non-naturally occurring *Solanum lycopersicum* plant having homozygously a non-naturally occurring mutated gene comprising a mutation, wherein the mutation comprises a single nucleotide polymorphism on or before position 1477, with reference to SEQ ID NO: 2 or 6, that results in a stop codon, wherein the protein expressed from the non-naturally occurring mutated gene terminates at or before amino acid 493, with reference to SEQ ID NO: 7, and wherein the mutation confers an aberrant type VI glandular hair phenotype that allows for the establishment of predatory mites on the plant and/or a reduction or absence of terpenes in glandular hair.

2. The non-naturally occurring *Solanum lycopersicum* plant of claim 1, wherein the reduced or absent terpenes comprise α-pinene, myrcene, carene, α-phellandrene, β-phellandrene, p-cymene, limonene, δ-elemene, β-caryophyllene and/or α-humulene.

3. The non-naturally occurring *Solanum lycopersicum* plant of claim 1, wherein monoterpenes and sesquiterpenes are absent in the glandular hair.

4. A propagation material from the non-naturally occurring *Solanum lycopersicum* plant of claim 1.

5. The propagation material of claim 4 comprising a microspore, pollen, ovary, ovule, embryo, embryo sac, egg cell, cutting, root, root tip, hypocotyl, cotyledon, stem, leaf, flower, anther, seed, meristematic cell, protoplast, cell, or a tissue culture.

6. The non-naturally occurring *Solanum lycopersicum* plant of claim 1, wherein the predatory mites comprise *Amblyseius swirskii* and/or *Amblydromalus limonicus.*

7. A seed from non-naturally occurring *Solanum lycopersicum* plant of claim 1, comprising the non-naturally occurring mutated gene, homozygously.

8. A progeny plant from the plant of claim 1, wherein the progeny plant comprises the non-naturally occurring mutated gene, homozygously.

9. A non-naturally occurring *Solanum lycopersicum* seed having homozygously a non-naturally occurring mutated gene comprising a mutation, wherein the mutation comprises a single nucleotide polymorphism on or before position 1477, with reference to SEQ ID NO: 2 or 6, that results in a stop codon, wherein the protein expressed from the non-naturally occurring mutated gene terminates at or before amino acid 493, with reference to SEQ ID NO: 7, and wherein the mutation confers on a plant grown from the seed an aberrant type VI glandular hair phenotype that allows for the establishment of predatory mites on the plant and/or a reduction or absence of terpenes in glandular hair.

10. The non-naturally occurring *Solanum lycopersicum* seed of claim 9, wherein in the plant grown from the seed, the reduced or absent terpenes comprise α-pinene, myrcene, carene, α-phellandrene, β-phellandrene, p-cymene, limonene, δ-elemene, β-caryophyllene and/or α-humulene.

11. The non-naturally occurring *Solanum lycopersicum* seed of claim 9, wherein monoterpenes and sesquiterpenes are absent in the glandular hair in the plant grown from the seed.

12. The non-naturally occurring *Solanum lycopersicum* plant of claim 1, wherein the mutation comprises a G>T mutation at position 1477, with reference to SEQ ID NO: 2, that results in a stop codon, wherein the protein expressed from the non-naturally occurring mutated gene terminates at amino acid 493, with reference to SEQ ID NO: 7.

13. The non-naturally occurring *Solanum lycopersicum* plant of claim 1, wherein the mutation comprises a nonsense mutation in SEQ ID NO: 6 that results in the presence of a premature stop codon within that coding sequence.

14. The non-naturally occurring *Solanum lycopersicum* plant of claim 13, wherein there is a premature stop codon before amino acid position 493 of SEQ ID NO: 7.

15. The non-naturally occurring *Solanum lycopersicum* seed of claim 9, wherein the mutation comprises a G>T mutation at position 1477, with reference to SEQ ID NO: 2, that results in a stop codon, wherein the protein expressed from the non-naturally occurring mutated gene terminates at amino acid 493, with reference to SEQ ID NO: 7.

16. The non-naturally occurring *Solanum lycopersicum* seed of claim 9, wherein the mutation comprises a missense mutation in SEQ ID NO: 6.

17. The non-naturally occurring *Solanum lycopersicum* seed of claim 9, wherein the mutation comprises a nonsense mutation in SEQ ID NO: 6 that results in the presence of a premature stop codon within that coding sequence.

18. The non-naturally occurring *Solanum lycopersicum* seed of claim 17, wherein there is a premature stop codon before amino acid position 493 of SEQ ID NO: 7.

* * * * *